(12) United States Patent
Yoon et al.

(10) Patent No.: US 12,250,882 B2
(45) Date of Patent: Mar. 11, 2025

(54) DEUTERIUM-CONTAINING COMPOUND, AND ORGANIC LIGHT-EMITTING DEVICE COMPRISING SAME

(71) Applicant: LG CHEM, LTD., Seoul (KR)

(72) Inventors: Hongsik Yoon, Daejeon (KR); Wanpyo Hong, Daejeon (KR); Jin Joo Kim, Daejeon (KR); Dong Hoon Lee, Daejeon (KR); Moung Gon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 990 days.

(21) Appl. No.: 17/262,592

(22) PCT Filed: Oct. 25, 2019

(86) PCT No.: PCT/KR2019/014147
§ 371 (c)(1),
(2) Date: Jun. 24, 2021

(87) PCT Pub. No.: WO2020/085842
PCT Pub. Date: Apr. 30, 2020

(65) Prior Publication Data
US 2022/0271233 A1    Aug. 25, 2022

(30) Foreign Application Priority Data

Oct. 26, 2018    (KR) .................. 10-2018-0128593

(51) Int. Cl.
| | |
|---|---|
| H01L 51/00 | (2006.01) |
| C07D 209/86 | (2006.01) |
| C07D 403/10 | (2006.01) |
| C07D 403/14 | (2006.01) |
| C07D 409/14 | (2006.01) |
| C07D 487/04 | (2006.01) |
| C09K 11/06 | (2006.01) |
| H10K 85/60 | (2023.01) |
| H10K 50/11 | (2023.01) |
| H10K 101/10 | (2023.01) |
| H10K 101/30 | (2023.01) |

(52) U.S. Cl.
CPC ....... *H10K 85/6572* (2023.02); *C07D 209/86* (2013.01); *C07D 403/10* (2013.01); *C07D 403/14* (2013.01); *C07D 409/14* (2013.01); *C07D 487/04* (2013.01); *C09K 11/06* (2013.01); *H10K 85/654* (2023.02); *H10K 85/6574* (2023.02); *H10K 85/6576* (2023.02); *C07B 2200/05* (2013.01); *C09K 2211/1018* (2013.01); *H10K 50/11* (2023.02); *H10K 2101/10* (2023.02); *H10K 2101/30* (2023.02)

(58) Field of Classification Search
CPC ............ H01L 51/0072; H01L 51/0067; H01L 51/0074; H01L 51/0073; H01L 51/5012; C07D 209/86; C07D 403/10; C07D 409/14; C07D 487/04; C09K 11/06
See application file for complete search history.

(56) References Cited

U.S. PATENT DOCUMENTS

| | | | |
|---|---|---|---|
| 2015/0105564 A1 | 4/2015 | Adachi et al. | |
| 2016/0072076 A1 | 3/2016 | Stoessel et al. | |
| 2017/0352816 A1 | 12/2017 | Jeon et al. | |
| 2018/0010040 A1* | 1/2018 | Pan ................. | C07D 209/86 |

FOREIGN PATENT DOCUMENTS

| | | |
|---|---|---|
| KR | 10-2011-0077930 A | 7/2011 |
| KR | 10-2012-0013173 A | 2/2012 |
| KR | 10-2014-0078144 A | 6/2014 |
| KR | 10-2015-0005583 A | 1/2015 |
| KR | 10-2015-0132872 A | 11/2015 |
| KR | 10-2017-0136256 A | 12/2017 |
| KR | 10-2018-0047306 A | 5/2018 |

* cited by examiner

*Primary Examiner* — Robert D Harlan
(74) *Attorney, Agent, or Firm* — Bryan Cave Leighton Paisner LLP

(57) ABSTRACT

The present specification provides a compound represented by Formula 1 and an organic light emitting device including the same. The compound contains a deuterium and is used as a material of a light emitting layer of the organic light emitting device

[Formula 1]

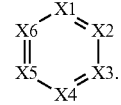

10 Claims, 1 Drawing Sheet

[Figure 1]
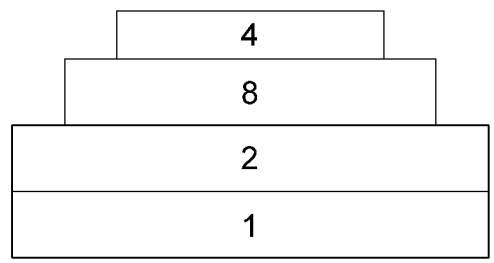
[Figure 2]
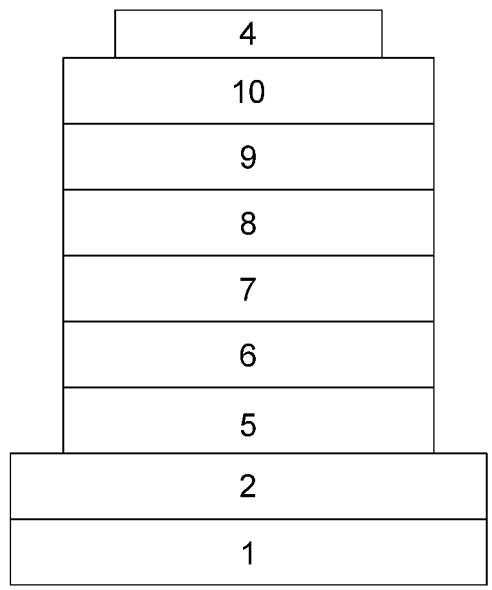

DEUTERIUM-CONTAINING COMPOUND, AND ORGANIC LIGHT-EMITTING DEVICE COMPRISING SAME

This application is a National Phase entry pursuant to 35 U.S.C. § 371 of International Application No. PCT/KR2019/014147, filed on Oct. 25, 2019, and claims priority to and claims priority to and the benefit of Korean Patent Application No. 10-2018-0128593 filed in the Korean Intellectual Property Office on Oct. 26, 2018, the entire contents of which are incorporated herein by reference.

TECHNICAL FIELD

The present invention relates to a deuterium-containing compound and an organic light emitting device including the same.

BACKGROUND ART

The present disclosure relates to a novel organic compound which may be advantageously used for an organic light emitting device. More particularly, the present disclosure relates to a thermally activated delayed fluorescence (TADF) material with which deuterium is substituted and a use of the same for an OLED.

Fluorescence light emitting materials using a phenomenon thermally activated delayed fluorescence is also referred to as thermally excited delayed fluorescence (Thermally Activated Delayed Fluorescence, hereinafter appropriately abbreviated as "TADF") using a phenomenon in which the reverse intersystem crossing (hereinafter, appropriately abbreviated as "RISC") from triplet excitons to singlet excitons occurs, and the applicability of the same for an organic EL device have been reported. When delayed fluorescence is used by the TADF mechanism, even in a fluorescence emission by electric field excitation, a 100% internal quantum efficiency equivalent to the phosphorescence emission is also possible theoretically.

In order to exhibit the TADF phenomenon, a reverse intersystem crossing from 75% triplet excitons to singlet excitons produced by excitation of an electric field excitation at room temperature or a temperature of a light emitting layer in a light emitting device needs to occur. Further, the singlet excitons produced by the reverse intersystem crossing emit fluorescence similarly to 25% singlet excitons produced by the direct excitation, so that 100% internal quantum efficiency is theoretically possible. In order for the reverse intersystem crossing to occur, the difference ($\Delta ST$) between the singlet energy level (S1) and the triplet energy level (T1) is required to be small.

For example, to exhibit the TADF phenomenon, it is effective to decrease the $\Delta ST$ of an organic compound, and to decrease the $\Delta ST$, it is advantageous to clearly separate the highest occupied molecular orbital (HOMO) and the lowest unoccupied molecular orbital (LUMO) in the molecule without mixing the HOMO and the LUMO.

However, when the highest occupied molecular orbital (HOMO) and the lowest unoccupied molecular orbital (LUMO) in the molecule are clearly separated without mixing the HOMO and the LUMO, the n conjugated system in the molecule is reduced or cut off, and thus it is difficult to allow the reverse intersystem crossing to be compatible with stability, and as a result, the service life of the light emitting device is shortened.

Accordingly, there is a need for a new way for increasing the TADF lifetime.

DETAILED DESCRIPTION OF THE INVENTION

Technical Problem

The present invention has been made in an effort to provide a compound which has a small difference ($\Delta ST_D$) between the singlet energy level ($S1_D$) and the triplet energy level ($T1_D$), and thus has high efficiency and good service life characteristics of an organic light emitting device when included in a light emitting layer of the device; and an organic light emitting device including the same.

Technical Solution

An exemplary embodiment of the present specification provides a compound represented by the following Formula 1.

[Formula 1]

In Formula 1,

X1 to X6 are the same as or different from each other, and are each independently N, C(A1), C(A2), C(A3), C(A4), C—H, C-D, or C—R', and R' is an aryl group, wherein (1) three of X1 to X6 are C-D, one thereof is C(A2), one thereof is C(A4), and one thereof is N, C(A2), C(A4), C—H, C-D, or C—R', or (2) at least one of X1 to X6 is C(A1) or C(A2), at least one thereof is C(A3) or C(A4), and at least one of X1 to X6 is C(A1) or C(A3), A1 is any one of the following a-1 to a-4, and when there are two or more A1's, A1's are the same as or different from each other,

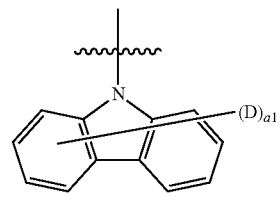

(a-1)

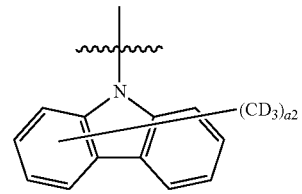

(a-2)

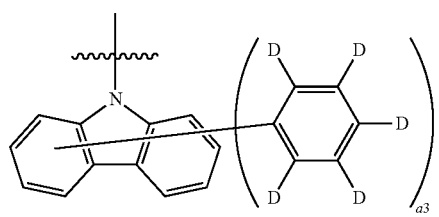
(a-3)

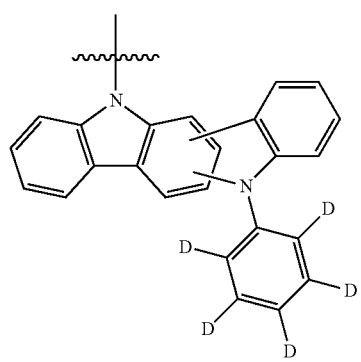
(a-4)

in a-1 to a-3, a1 is an integer from 1 to 4, a2 is an integer from 1 to 8, and a3 is an integer from 1 to 8, A2 is the following b-1 or b-2, and when there are two or more A2's, A2's are the same as or different from each other,

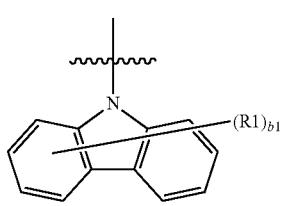
(b-1)

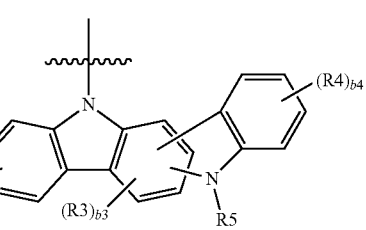
(b-2)

A3 is the following c-1 or c-2, and when there are two or more A3's, A3's are the same as or different from each other,

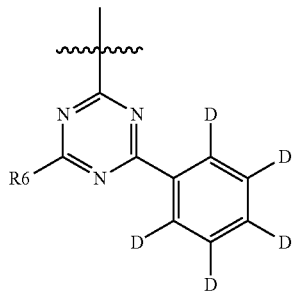
(c-1)

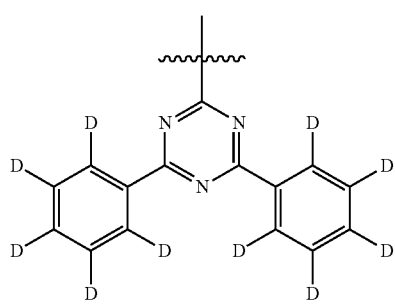
(c-2)

A4 is the following d-1 or d-2, and when there are two or more A4's, A4's are the same as or different from each other,

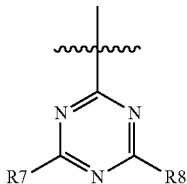
(d-1)

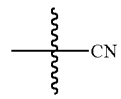
(d-2)

in b-1, b-2, c-1, and d-1,

R1 to R8 are the same as or different from each other, and are each independently any one group selected from the group consisting of hydrogen; an alkyl group; an aryl group; and a heteroaryl group, or a group to which two or more groups selected from the group are linked, b1 is an integer from 0 to 8, and when b1 is 2 or higher, R1's are the same as or different from each other, b2 is an integer from 0 to 4, and when b2 is 2 or higher, R2's are the same as or different from each other, b3 is an integer from 0 to 2, and when b3 is 2, R3's are the same as or different from each other, and b4 is an integer from 0 to 4, and when b4 is 2 or higher, R4's are the same as or different from each other.

Further, an exemplary embodiment of the present specification provides an organic light emitting device including: a first electrode; a second electrode provided to face the first electrode; and a light emitting layer provided between the first electrode and the second electrode, in which the light emitting layer includes the compound represented by Formula 1.

Advantageous Effects

In some exemplary embodiments, the organic light emitting device including the compound of the present invention has high efficiency or excellent service life characteristics.

In an exemplary embodiment, the compound represented by Formula 1 can be used for a light emitting layer of the organic light emitting device.

BRIEF DESCRIPTION OF DRAWINGS

FIG. 1 illustrates an example of an organic light emitting device composed of a substrate 1, a positive electrode 2, a light emitting layer 8, and a negative electrode 4.

FIG. 2 illustrates an example of an organic light emitting device composed of a substrate 1, a positive electrode 2, a hole injection layer 5, a hole transport layer 6, a hole adjusting layer 7, a light emitting layer 8, an electron transport layer 9, an electron injection layer 10, and a negative electrode 4.

EXPLANATION OF REFERENCE NUMERALS AND SYMBOLS

1: Substrate
2: Positive electrode
4: Negative electrode
5: Hole injection layer
6: Hole transport layer
7: Hole adjusting layer
8: Light emitting layer
9: Electron transport layer
10: Electron injection layer

BEST MODE

Hereinafter, the present invention will be described in more detail.

In the present specification,

means a moiety bonded to another substituent or a bonding portion.

In an exemplary embodiment, the term "substitution" means that a hydrogen atom bonded to a carbon atom of a compound is changed into another substituent. A position at which the substituent is substituted is not limited as long as the position is a position at which a hydrogen atom is substituted, that is, a position at which a substituent can be substituted. When there are two or more substituents, the two or more substituents may be the same as or different from each other.

In the present specification, "energy level" means a size of energy. Accordingly, even when the energy level is expressed in the negative (−) direction from the vacuum level, it is interpreted that the energy level means an absolute value of the corresponding energy value. For example, a large energy level means that the absolute value increases in the negative direction from the vacuum level. Further, in the present specification, an expression that the energy level is 'deep' or 'high' has the same meaning as an expression that the energy level is large.

In the present specification, the triplet energy level can be measured by using a spectroscopic instrument capable of measuring fluorescence and phosphorescence. Specifically, the triplet energy level may be confirmed by preparing a solution at a concentration of $10^{-6}$ M with toluene or tetrahydrofuran (THF) as a solvent in an extremely low temperature state using liquid nitrogen, irradiating the solution with a light source at an absorption wavelength band of a material, and then excluding the light emission at the singlet energy level from the light emission spectrum, and analyzing the spectrum emitted at the triplet energy level. When electrons are excited from the light source, two components can be separated from each other in the extremely low temperature state because the time for electrons to stay at the triplet energy level is much longer than the time for the electrons to stay at the singlet energy level. In the present specification, the singlet energy level is measured by using a fluorescence instrument, and may be measured by irradiating the solution with the light source at room temperature unlike the above-described method for measuring the triplet energy level.

In the present specification, when one part "includes" one constituent element in the present specification, unless otherwise specifically described, this does not mean that another constituent element is excluded, but means that another constituent element may be further included.

In the present specification, when one member is disposed "on" another member, this includes not only a case where the one member is brought into contact with another member, but also a case where still another member is present between the two members.

Examples of the substituents of the present specification will be described below, but are not limited thereto.

In the present specification, an alkyl group means a straight-chained or branched saturated hydrocarbon. The number of the carbon atoms of the alkyl group is not particularly limited, but is 1 to 40; 1 to 20; 1 to 10; or 1 to 6. The alkyl group may be chained or cyclic.

Specific examples of the chained alkyl group include methyl, ethyl, n-propyl, isopropyl, n-butyl, isobutyl, tert-butyl, sec-butyl, 1-methylbutyl, 1-ethylbutyl, n-pentyl, isopentyl, neopentyl, tert-pentyl, n-hexyl, 1-methylpentyl, 2-methylpentyl, 4-methylpentyl, 3,3-dimethylbutyl, 2-ethylbutyl, n-heptyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl, and the like, but are not limited thereto.

The number of the carbon atoms of the cyclic alkyl group (cycloalkyl group) is not particularly limited, but is 3 to 40; 3 to 24; 3 to 14; or 3 to 8. Specific examples of the cycloalkyl group include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group means a fully or partially unsaturated substituted or unsubstituted monocyclic or polycyclic aryl group. The number of the carbon atoms thereof is not particularly limited, but is 6 to 60; 6 to 40; or 6 to 30. The aryl group may be a monocyclic aryl group or a polycyclic aryl group. Examples of the monocyclic aryl group include a phenyl group, a biphenyl group, a terphenyl group, and the like, but are not limited thereto. Examples of the polycyclic aryl group include a naphthyl group, an anthracenyl group, a phenanthrenyl group, a perylenyl group, a fluoranthenyl group, a triphenylenyl group, a phenalenyl group, a pyrenyl group, a tetracenyl group, a chrysenyl group, a pentacenyl group, a fluorenyl group, an indenyl group, an acenaphthylenyl group, a benzofluorenyl group, a spirofluorenyl group, and the like, but are not limited thereto.

In the present specification, when it is said that a fluorenyl group may be substituted, the substituted fluorenyl group includes all the compounds in which substituents of a pentagonal ring of a fluorenyl group are spiro-bonded to each other to form an aromatic hydrocarbon. Examples of the substituted fluorene include 9,9'-spirobifluorene, spiro[cyclopentane-1,9'-fluorene], spiro[benzo[c]fluorene-7,9-fluorene], and the like, but are not limited thereto.

In the present specification, a heteroaryl group is a cyclic group including one or more of N, O, and S as a heteroatom, and the number of carbon atoms thereof is not particularly limited, but is 2 to 40; 2 to 30; or 2 to 20. Examples of the heteroaryl group include a thiophenyl group, a furanyl group, a pyrrolyl group, an imidazolyl group, a triazolyl group, an oxazolyl group, an oxadiazolyl group, a triazolyl group, a pyridinyl group, a bipyridinyl group, a pyrimidinyl group, a triazinyl group, a triazolyl group, an acridinyl group, a carbolinyl group, an acenaphthoquinoxalinyl group, an indenoquinazolinyl group, an indenoisoquinolinyl group, an indenoquinolinyl group, a pyridoindole group, a pyridazinyl group, a pyrazinyl group, a qinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthrolinyl group, a thiazolyl group, an isoxazolyl group, an oxadiazolyl group, a thiadiazolyl group, a benzothiazolyl group, a phenoxazinyl group, a phenothiazinyl group, a dibenzofuranyl group, and the like, but are not limited thereto. The heteroaryl group includes an aliphatic heteroaryl group and an aromatic heteroaryl group.

Hereinafter, various exemplary embodiments of the present invention will be described in more detail.

An exemplary embodiment of the present specification provides a compound represented by the following Formula 1.

[Formula 1]

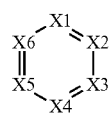

In Formula 1,

X1 to X6 are the same as or different from each other, and are each independently N, C(A1), C(A2), C(A3), C(A4), C—H, C-D, or C—R', and R' is an aryl group, wherein (1) three of X1 to X6 are C-D, one thereof is C(A2), one thereof is C(A4), and one thereof is N, C(A2), C(A4), C—H, C-D, or C—R', or (2) at least one of X1 to X6 is C(A1) or C(A2), at least one thereof is C(A3) or C(A4), and at least one of X1 to X6 is C(A1) or C(A3).

The compound represented by Formula 1 includes both carbazole or indolocarbazole which serves as an electron donor and triazine or a cyano group which serves as an electron acceptor. Accordingly, the compound represented by Formula 1 may have delayed fluorescence characteristics because the orbital form of the highest occupied molecular orbital (HOMO) and the lowest unoccupied molecular orbital (LUMO) in the molecule is separated by 50% or more.

Since a structure further including a cyano group or triazine like the compound represented by Formula 1 has a smaller difference between the triplet energy level and the singlet energy level than a structure including only indolocarbazole or carbazole, delayed fluorescence characteristics through reverse intersystem crossing (RISC) are better.

In an exemplary embodiment, at least one of X1 to X6 is C(A4), and A4 is d-2. When A4 is d-2, —CN is directly bonded to a central core including X1. When —CN is linked to the core including X1 through an aryl group, the LUMO (lowest unoccupied molecular orbital) energy level is lowered by the expansion of conjugation, so that the difference between the triplet energy level and the singlet energy level becomes larger, and thus, the delayed fluorescence characteristics are reduced.

A nitrogen of carbazole or indolocarbazole included in the compound represented by Formula 1 is bonded to a ring which includes X1. Thus, the compound represented by Formula 1 has a smaller difference between the singlet energy level and the triplet energy level than that of a structure in which carbon of carbazole or indolocarbazole is bonded to a ring including X1, and thus has better delayed fluorescence characteristics.

The compound represented by Formula 1 is a deuterium-containing compound including at least one deuterium. When some or all of the hydrogens present in a compound are substituted with deuterium, most of the chemical properties do not change. However, since the atomic weight of deuterium is twice the atomic weight of hydrogen, when the hydrogen of the compound is substituted with deuterium, the vibration mode of the compound becomes small, so that the vibration energy level becomes low. Accordingly, when the hydrogen atom present in a compound is substituted with deuterium, the intermolecular van der Waals force is reduced, so that it is possible to prevent a decrease in quantum efficiency due to the collision caused by the intermolecular vibration. In addition, C-D bonds improve the stability of the compound.

In an exemplary embodiment, the compound represented by Formula 1 is in a form in which any one of X1 to X6 is C-D, C(A1), or C(A3), and includes deuterium.

In an exemplary embodiment, A1 is any one of the following a-1 to a-4.

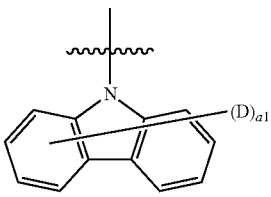

(a-1)

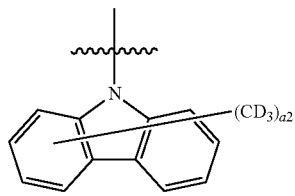

(a-2)

-continued

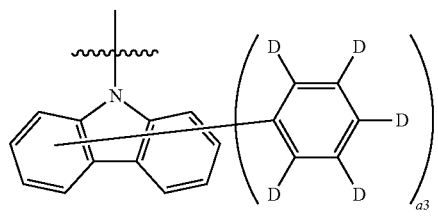
(a-3)

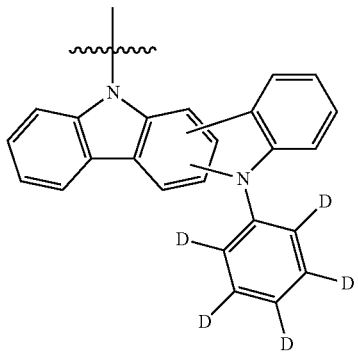
(a-4)

In a-1 to a-3, a1 is an integer from 1 to 4, a2 is an integer from 1 to 8, and a3 is an integer from 1 to 8.

In an exemplary embodiment, A3 is the following c-1 or c-2.

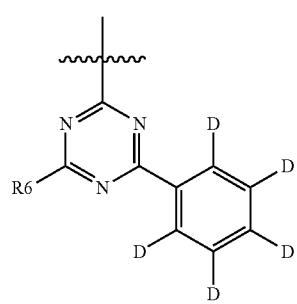
(c-1)

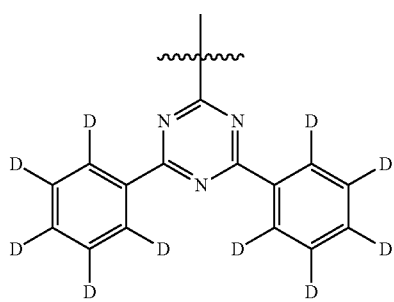
(c-2)

In an exemplary embodiment, the compound represented by Formula 1 includes a carbazole represented by a-1 and in which one to four deuteriums are substituted. The reaction rate of a chemical process of a compound including C-D bonds may be slower than that of a compound including only C—H bonds due to the kinetic isotope effect. When the chemical decomposition of a luminescent compound is accompanied by the breaking of C—H bonds, the stability of the compound is improved due to the stronger C-D bonds.

In an exemplary embodiment, a1 is 1.
In an exemplary embodiment, a1 is 2.
In an exemplary embodiment, a1 is 4.

In an exemplary embodiment, a-1 is any one of the following a-11 to a-15.

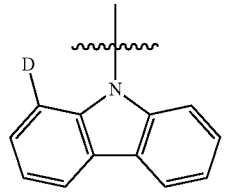
(a-11)

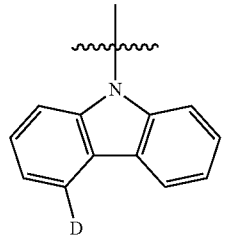
(a-12)

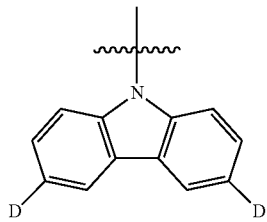
(a-13)

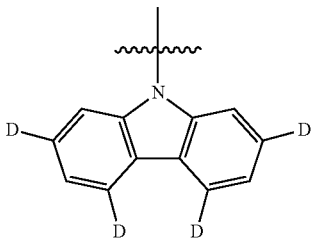
(a-14)

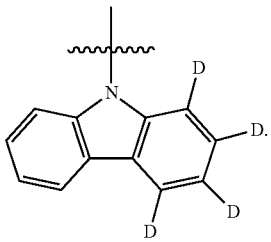
(a-15)

In an exemplary embodiment, the compound of Formula 1 includes a carbazole represented by a-2 and in which —CD$_3$ is substituted.

When —CH$_3$ is substituted with a benzene ring of the carbazole, a benzylic proton may be particularly reactive, so that the chemical decomposition may be facilitated in a luminescent compound. In this case, when hydrogen in —CH$_3$ is substituted with deuterium, the stability of the compound may be increased. Since the van der Waals radius of C-D is smaller than that of C—H, —CD$_3$ is a substituent with less steric hindrance than —CH$_3$. Thus, when the compound has —CD$_3$ in benzene ring of the carbazole as a substituent, the twist on the aromatic ring is small, so that the conjugation of the compound may be improved, and the efficiency and service life of the device can be improved.

In an exemplary embodiment, a2 is 1.

In an exemplary embodiment, a2 is 2.

In an exemplary embodiment, a-2 is the following a-21 or a-22.

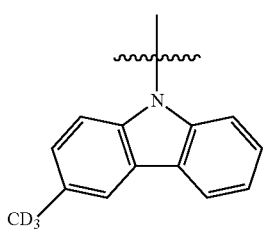
(a-21)

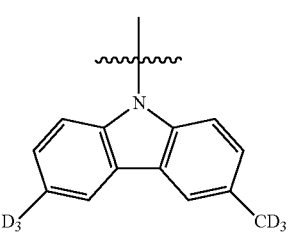
(a-22)

In an exemplary embodiment, the compound of Formula 1 includes a carbazole represented by a-3 and in which —C$_6$D$_5$ is substituted.

When a phenyl group is substituted with a carbazole, the distribution of the HOMO (highest occupied molecular orbital) may be broadened through a phenyl group, and when hydrogen of the phenyl group is substituted with deuterium, C-D bonds may improve the stability of the compound. Accordingly, the efficiency and service life of the device can be improved.

In an exemplary embodiment, a3 is 1.

In an exemplary embodiment, a-3 is any one of the following a-31 to a-33.

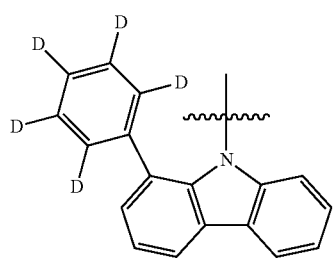
(a-31)

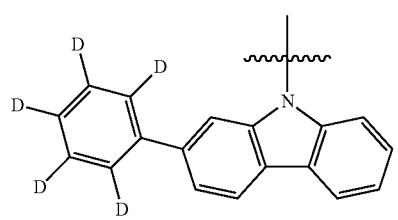
(a-32)

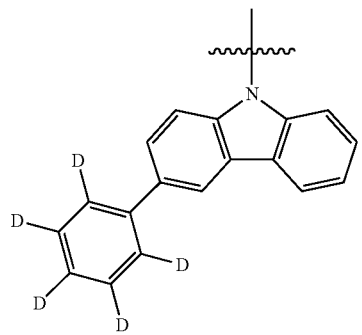
(a-33)

In an exemplary embodiment, A2 is the following b-1 or b-2, and when there are two or more A2's, A2's are the same as or different from each other,

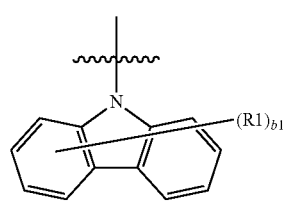
(b-1)

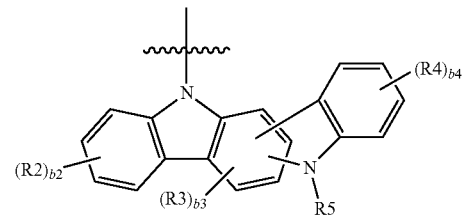
(b-2)

A4 is the following d-1 or d-2, and when there are two or more A4's, A4's are the same as or different from each other,

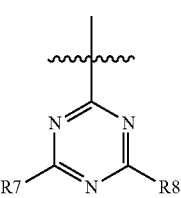
(d-1)

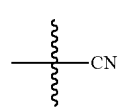
(d-2)

in b-1, b-2, and d-1,

R1 to R5, R7, and R8 are the same as or different from each other, and are each independently any one group selected from the group consisting of hydrogen; an alkyl group; an aryl group; and a heteroaryl group, or a group to which two or more groups selected from the group are linked, b1 is an integer from 0 to 8, and when b1 is 2 or more, R1's are the same as or different from each other, b2 is an integer from 0 to 4, and when b2 is 2 or higher, R2's are the same as or different from each other, b3 is an integer from 0 to 2, and when b3 is 2, R3's are the same as or different from each other, and b4 is an integer from 0 to 4, and when b4 is 2 or higher, R4's are the same as or different from each other.

In an exemplary embodiment, Formula 1 is represented by the following Formula 1-1 or 1-2.

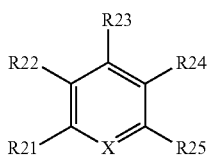

[Formula 1-1]

In Formula 1-1,

X is N or CR26, and R26 is A1, A2, A3, A4, H, D, or an aryl group,

R21 to R25 are the same as or different from each other, and are each independently A1, A2, A3, A4, H, D, or an aryl group, wherein at least one of R21 to R25 is A1 or A2, at least one thereof is A3 or A4, and at least one of R21 to R25 is A1 or A3,

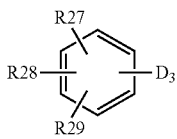

[Formula 1-2]

in Formula 1-2,

R27 is A2, R28 is A4, and R29 is A2, A4, H, D, or an aryl group, and in Formulae 1-1 and 1-2, the definitions of A1, A2, A3, and A4 are the same as those defined in Formula 1.

In an exemplary embodiment, R1 to R8 are the same as or different from each other, and are each independently any one group selected from the group consisting of hydrogen; a C1-C10 alkyl group; a C6-C30 aryl group; and a C2-C30 heteroaryl group, or a group to which two or more groups selected from the group are linked.

In an exemplary embodiment, R1 to R8 are the same as or different from each other, and are each independently any one group selected from the group consisting of hydrogen; a C1-C6 alkyl group; a C6-C25 aryl group; and a C2-C25 heteroaryl group, or a group to which two or more groups selected from the group are linked.

In an exemplary embodiment, R1 to R8 are the same as or different from each other, and are each independently any one group selected from the group consisting of hydrogen; a C1-C4 alkyl group; a C6-C18 aryl group; and a C2-C18 heteroaryl group, or a group to which two or more groups selected from the group are linked.

In an exemplary embodiment, R1 to R8 are the same as or different from each other, and are each independently hydrogen; a methyl group; an aryl group which is unsubstituted or substituted with an alkyl group; or a heteroaryl group which is unsubstituted or substituted with an aryl group.

In an exemplary embodiment, R1 to R8 are the same as or different from each other, and are each independently hydrogen; a methyl group; a phenyl group; a naphthyl group; a dimethylfluorenyl group; a dibenzofuranyl group; a dibenzothiophenyl group; or a carbazolyl group which is substituted with a phenyl group.

In an exemplary embodiment, R1 is a methyl group; a phenyl group; or a carbazolyl group which is substituted with a phenyl group.

In an exemplary embodiment, R2 to R5 are the same as or different from each other, and are each independently hydrogen; a phenyl group; a dimethylfluorenyl group; a naphthyl group; a dibenzofuranyl group; or a dibenzothiophenyl group.

In an exemplary embodiment, R2 to R6 are the same as or different from each other, and are each independently hydrogen; a phenyl group; a dimethylfluorenyl group; a naphthyl group; a dibenzofuranyl group; or a dibenzothiophenyl group.

In an exemplary embodiment, R6 to R8 are the same as or different from each other, and are each independently hydrogen; a phenyl group; a dibenzofuranyl group; a dibenzothiophenyl group; or a carbazolyl group which is substituted with a phenyl group.

In an exemplary embodiment, R5 to R8 are the same as or different from each other, and are each independently hydrogen; a phenyl group; a dibenzofuranyl group; a dibenzothiophenyl group; or a carbazolyl group which is substituted with a phenyl group.

In an exemplary embodiment, R' is a C6-C36 aryl group; a C6-C30 aryl group; or a C6-C25 aryl group.

In an exemplary embodiment, R' is a phenyl group.

In an exemplary embodiment, three of X1 to X6 are C-D, one thereof is C(A2), one thereof is C(A4), and one thereof is C(A2), C(A4), C—H, C-D, or C—R'.

In an exemplary embodiment, three of X1 to X6 are C-D, one thereof is C(A2), one thereof is C(A4), and one thereof is C(A2) or C(A4).

In an exemplary embodiment, at least one of X1 to X6 is C(A1).

In an exemplary embodiment, at least one of X1 to X6 is C(A3).

In an exemplary embodiment, 0 or one of X1 to X6 is N.

In an exemplary embodiment, at least one of X1 to X6 is C(A4), and A4 is d-2.

In an exemplary embodiment, at least two of X1 to X6 are C(A4), and two A4's are each d-2.

In an exemplary embodiment, Formula 1-2 is represented by the following Formula 2.

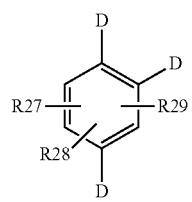

[Formula 2]

In Formula 2, the definitions of R27 to R29 are the same as those defined in Formula 1-2.

In an exemplary embodiment, the compound represented by Formula 1 is any one selected from the following compounds.

-continued
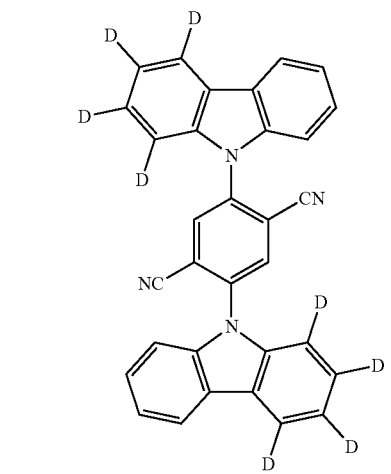
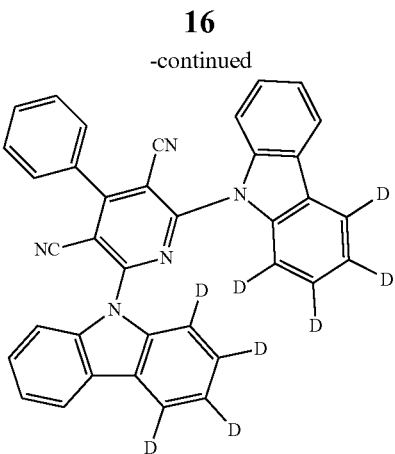
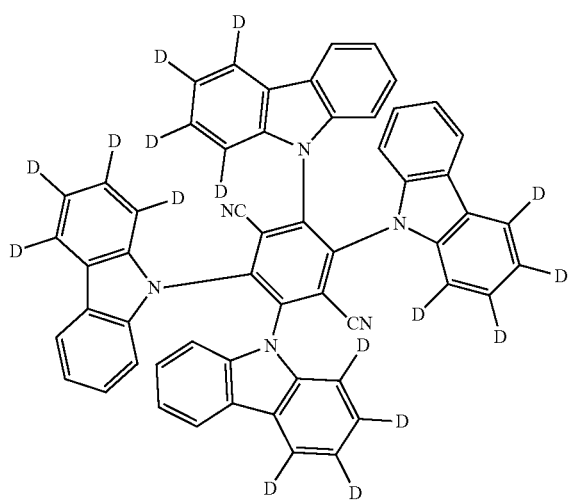
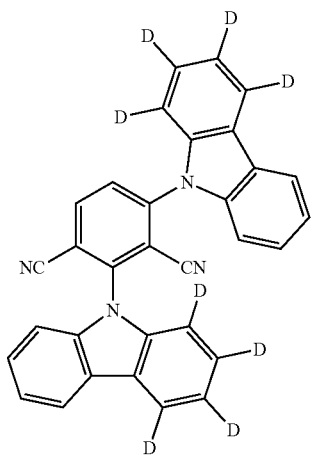
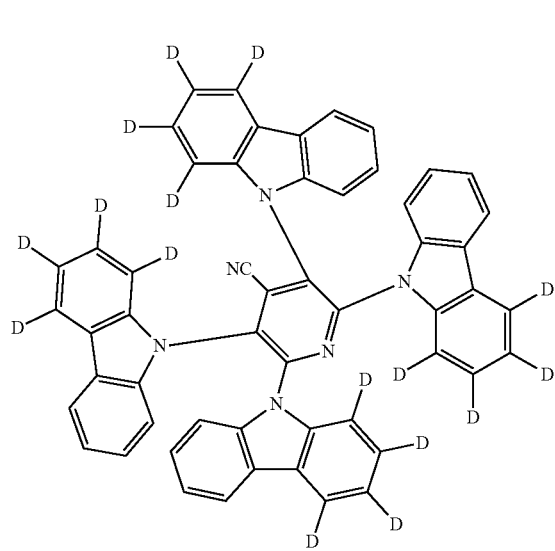
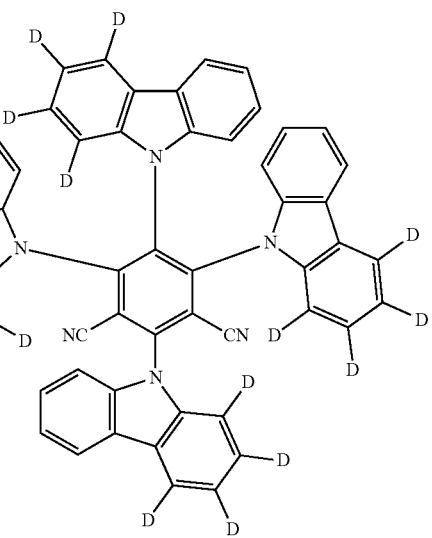

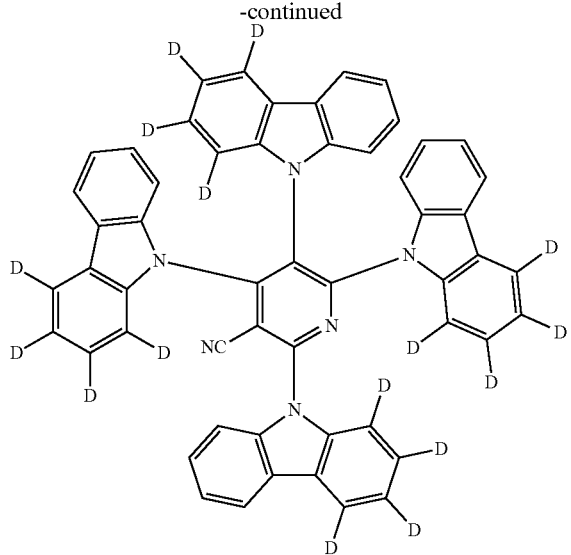
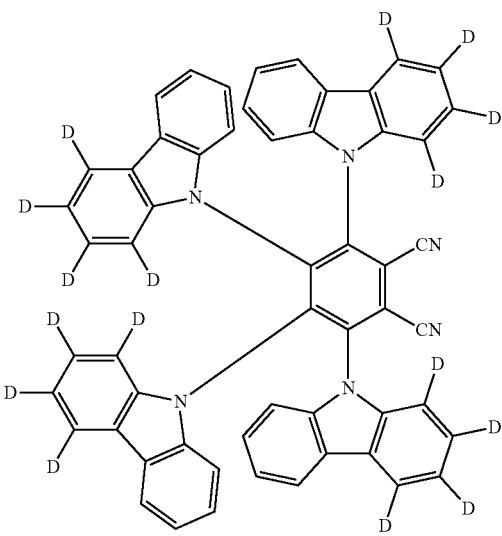
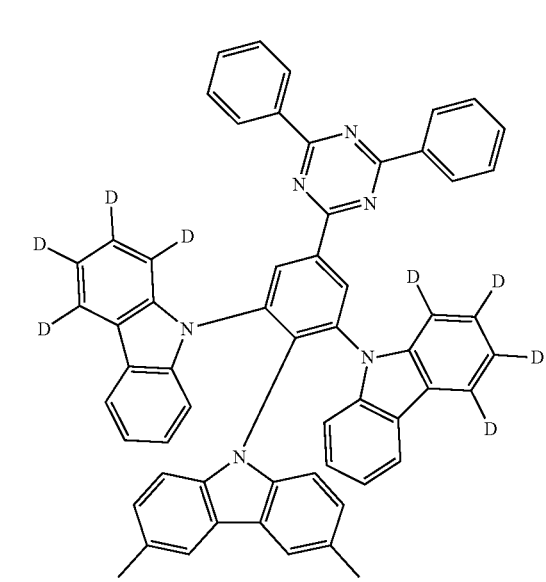
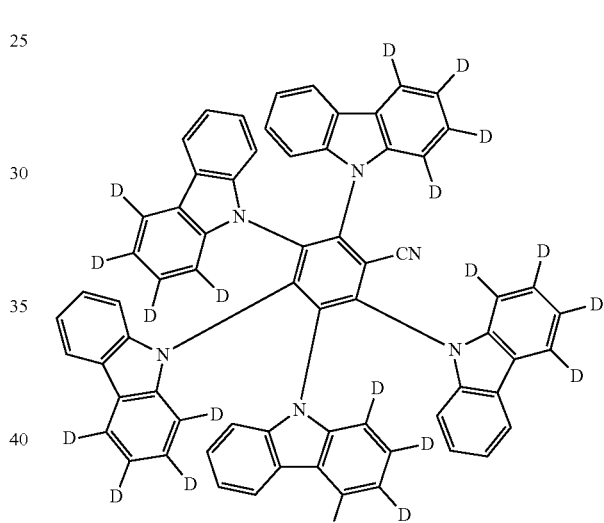
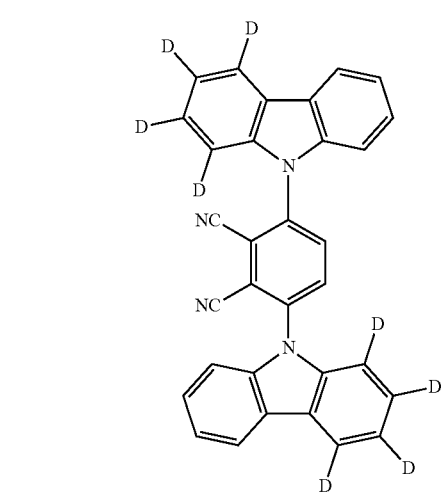
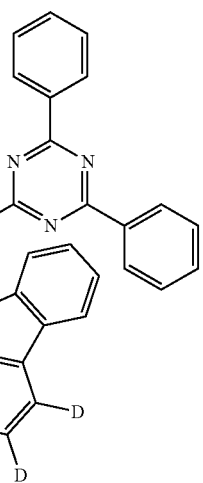

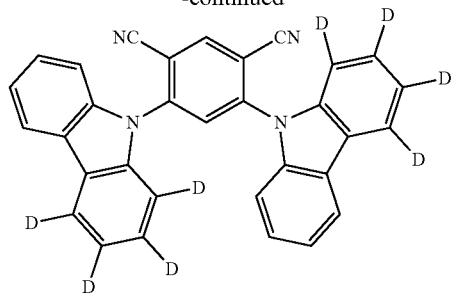
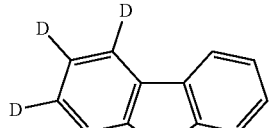
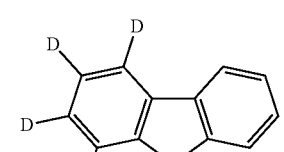
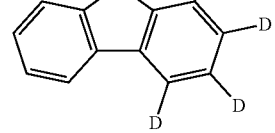
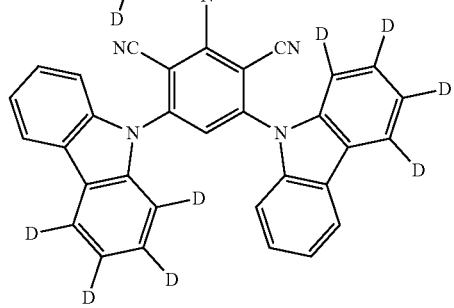
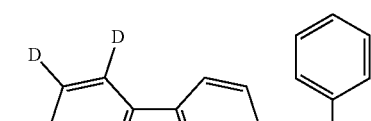
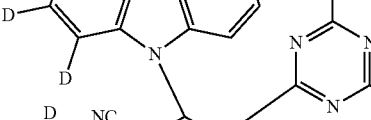
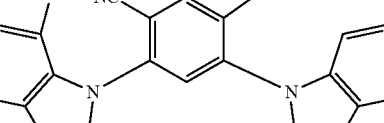
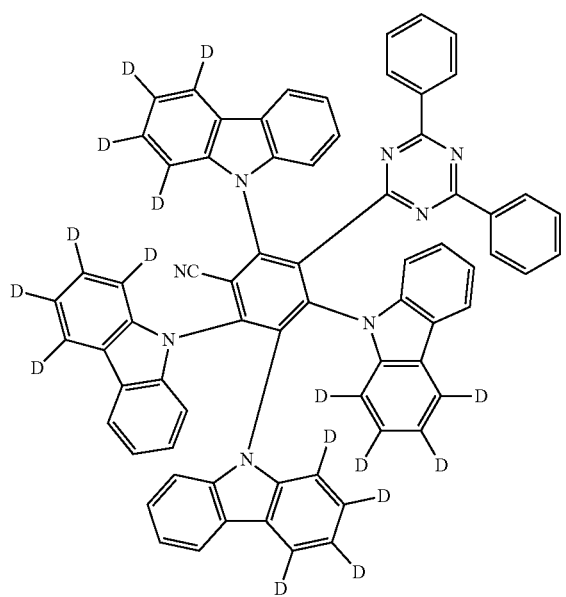
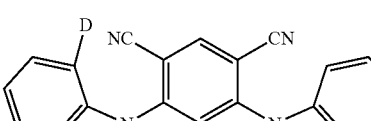
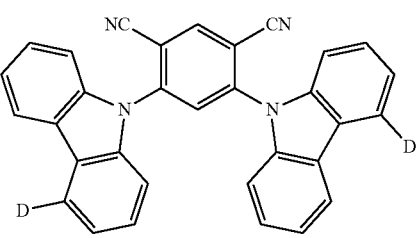
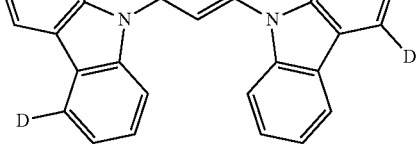

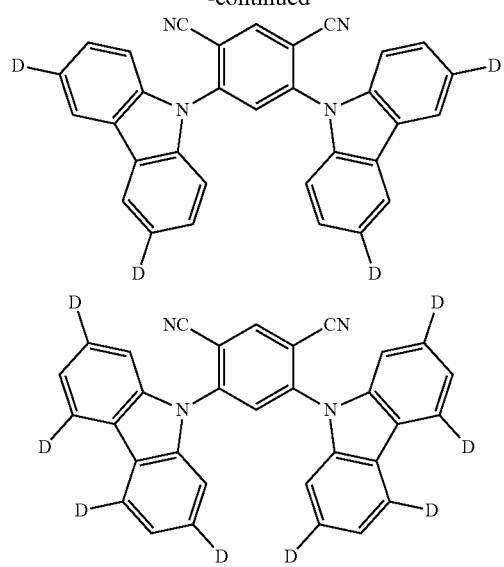
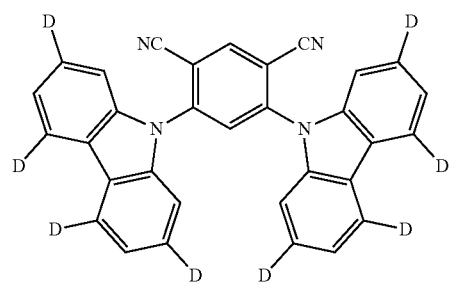
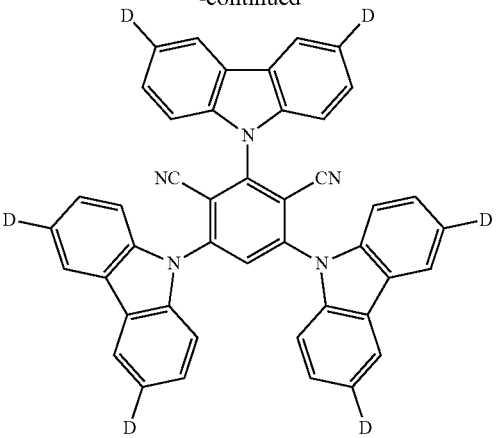
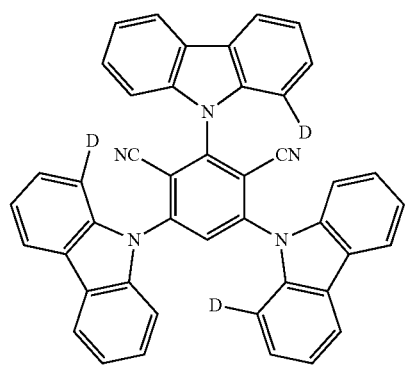
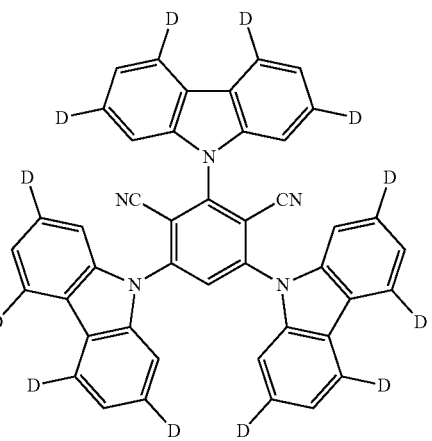
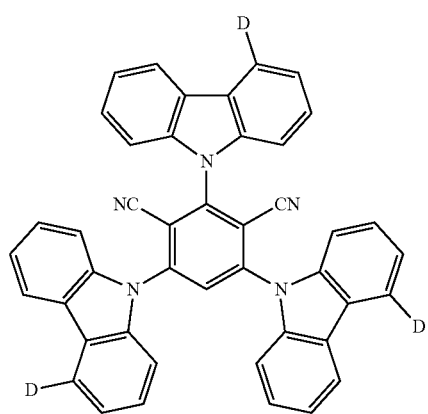
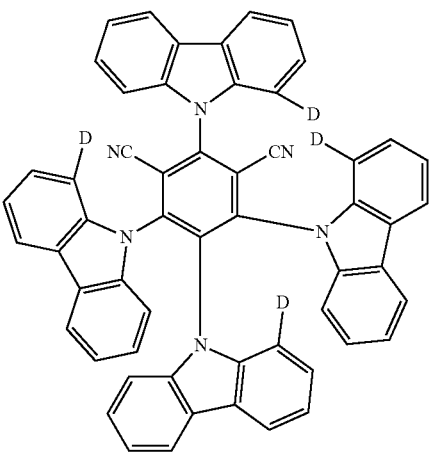

-continued
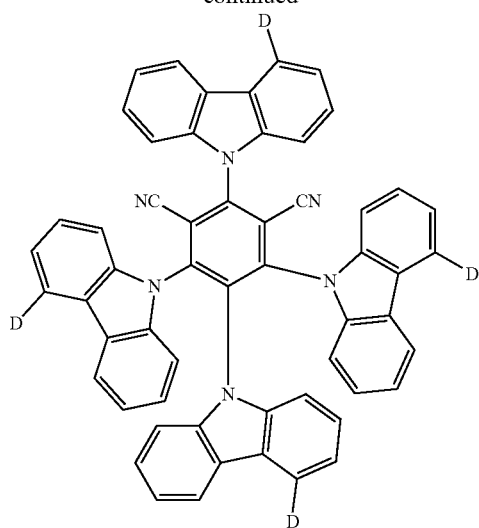
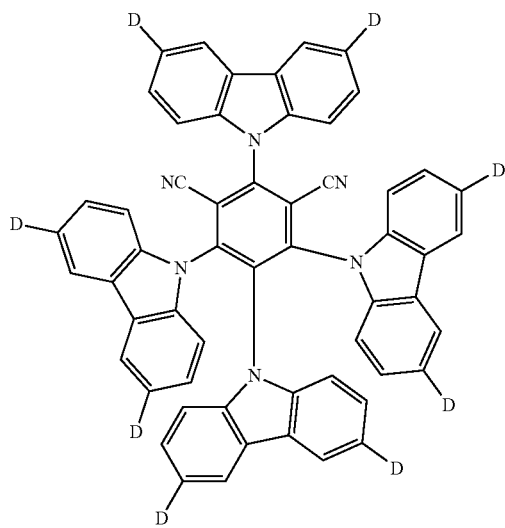
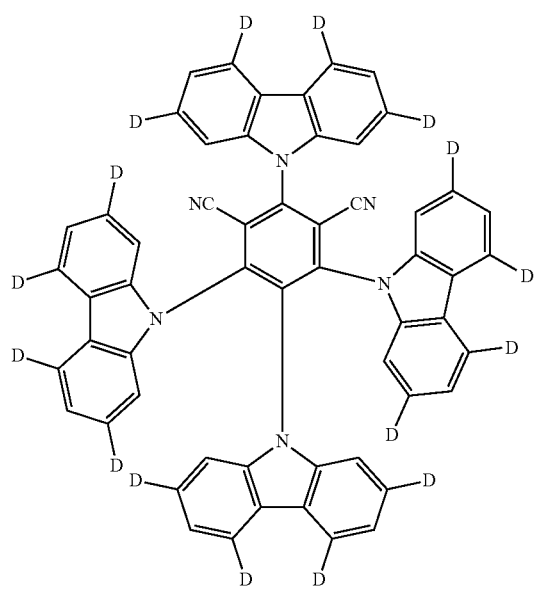
-continued
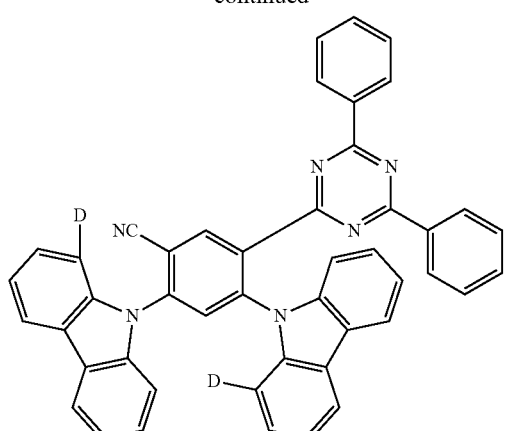
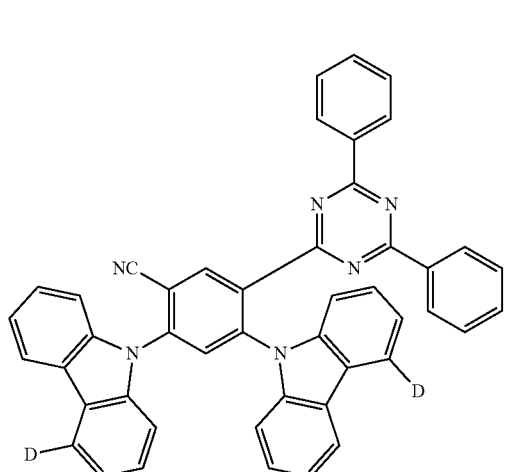
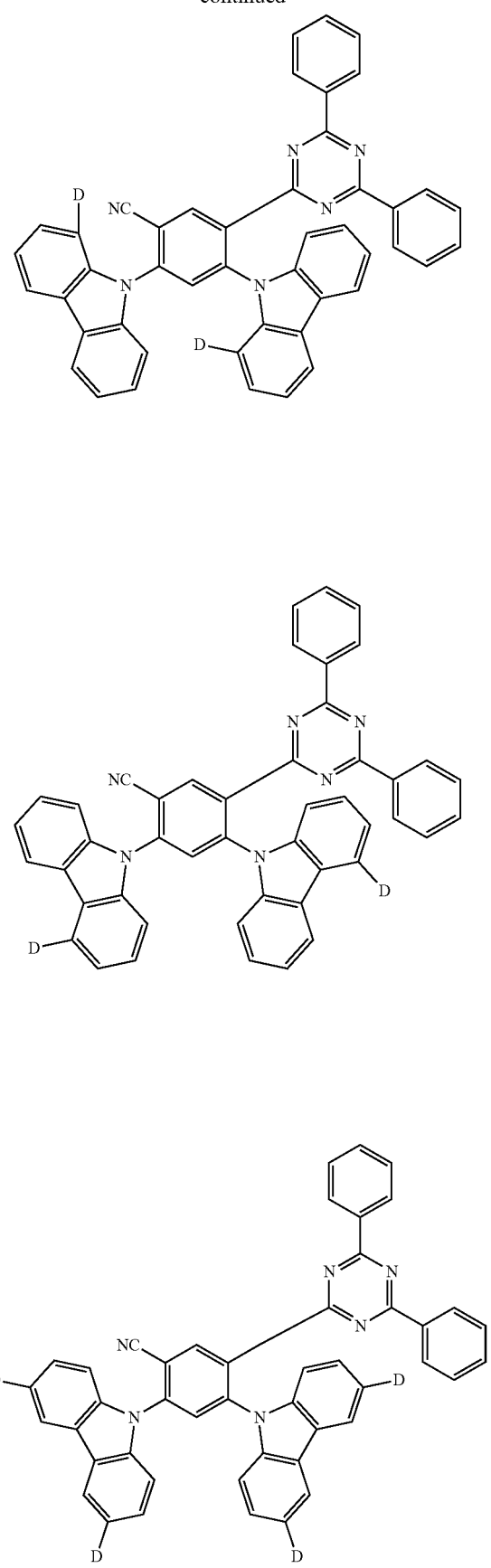

25
-continued
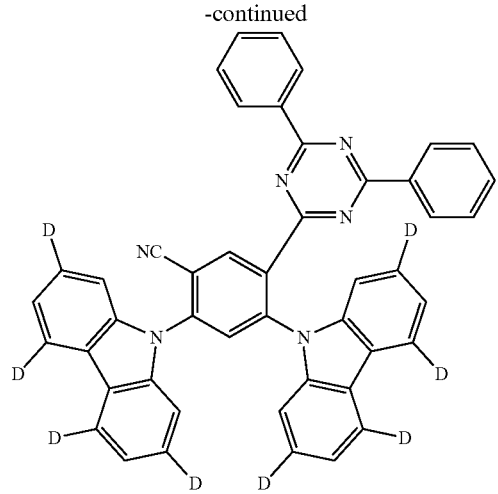
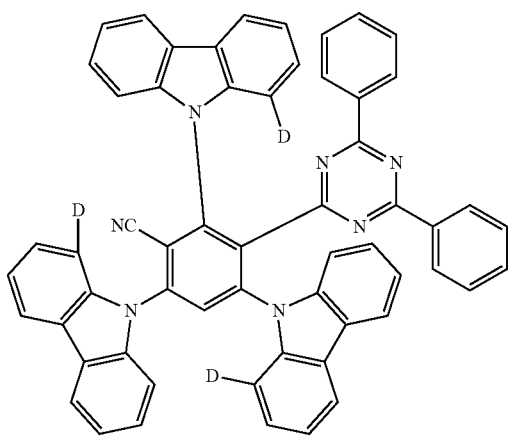
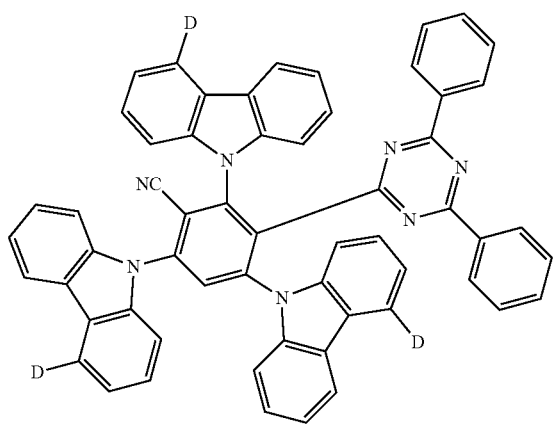
26
-continued
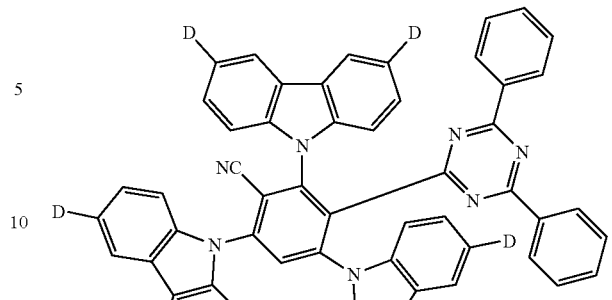
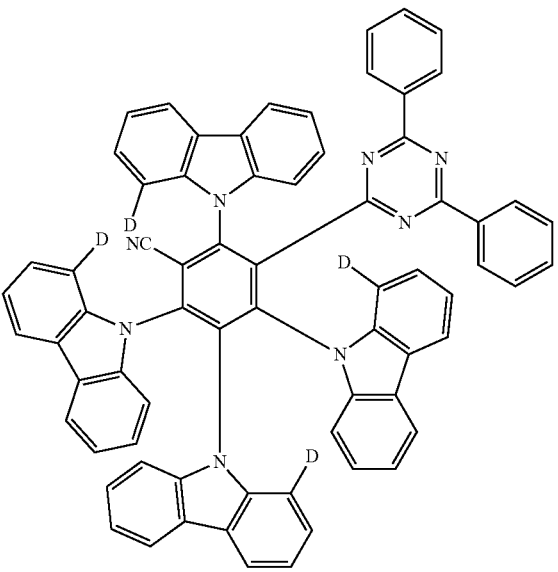

27
-continued
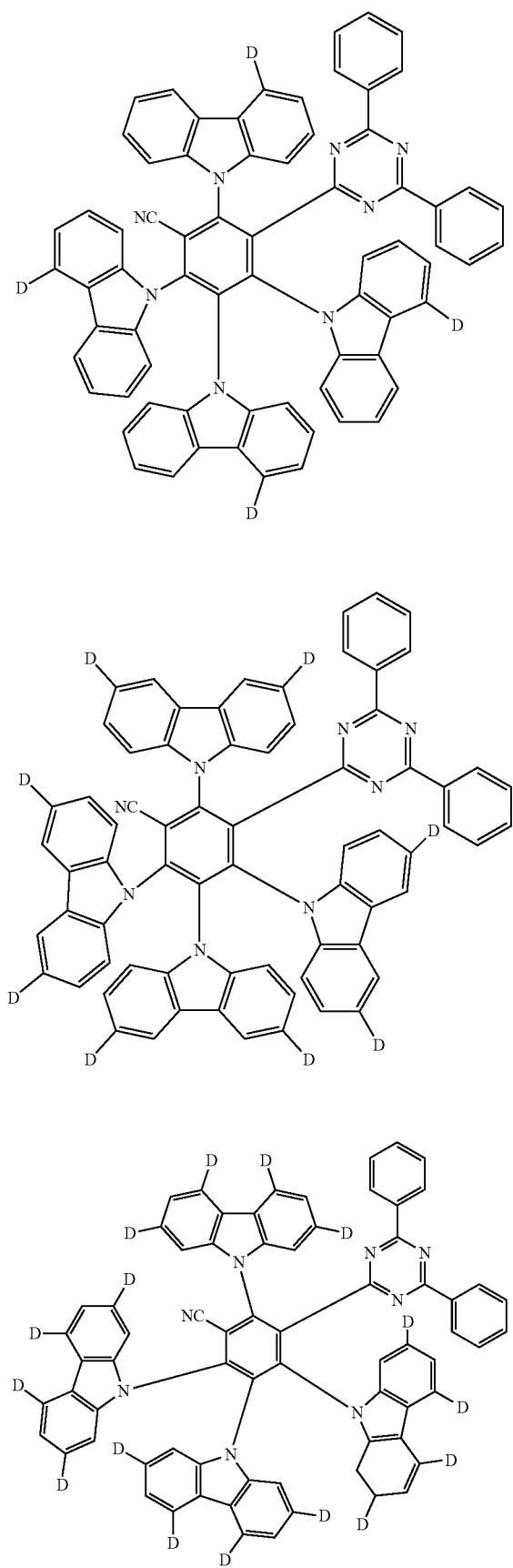
28
-continued
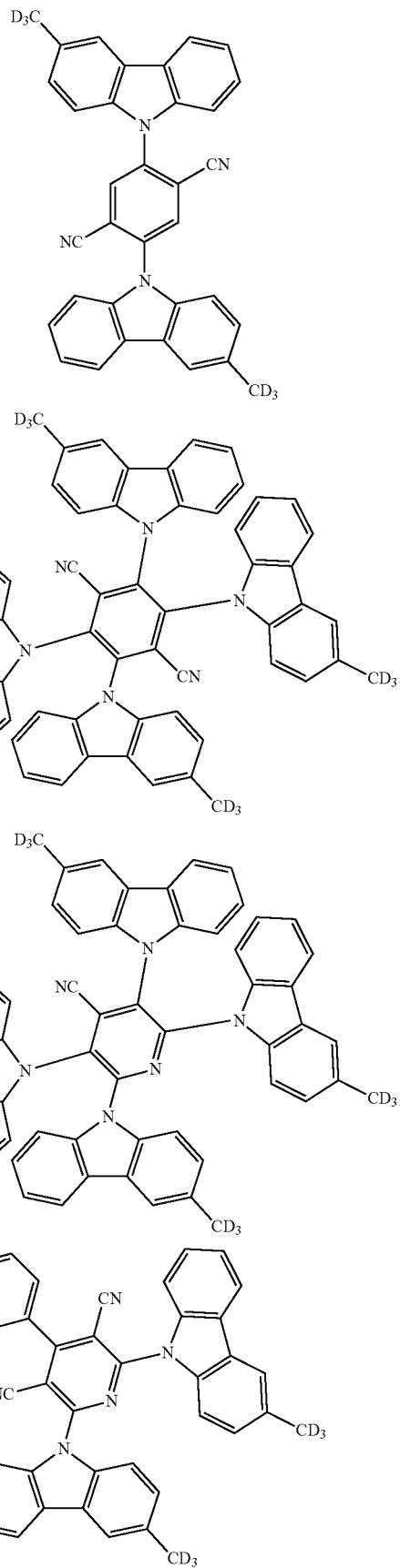

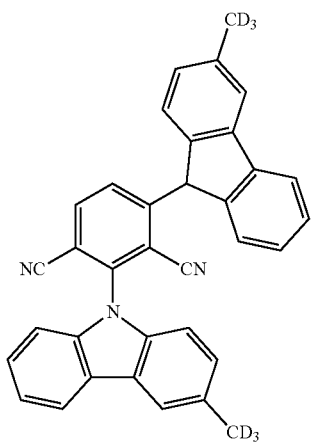
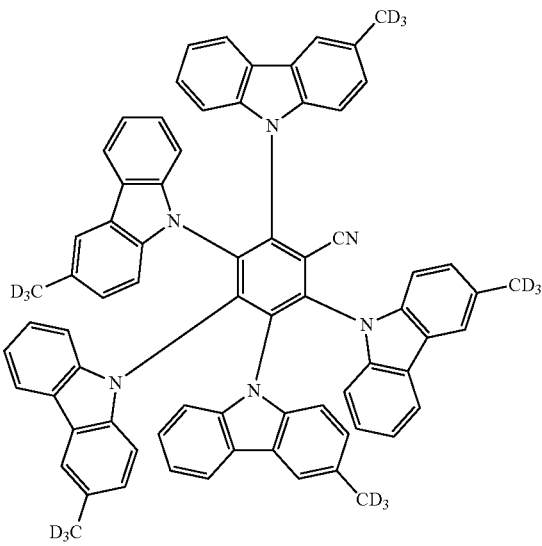
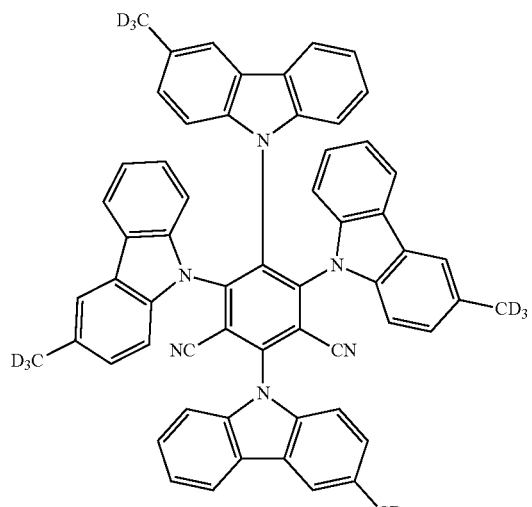
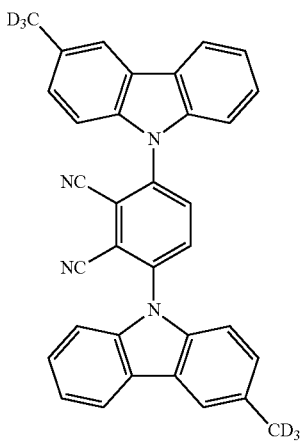
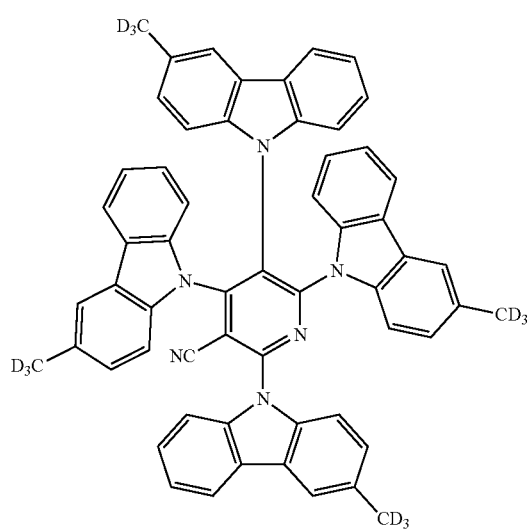
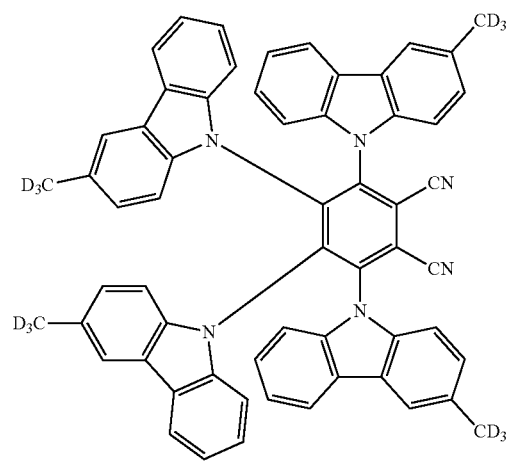

31
-continued
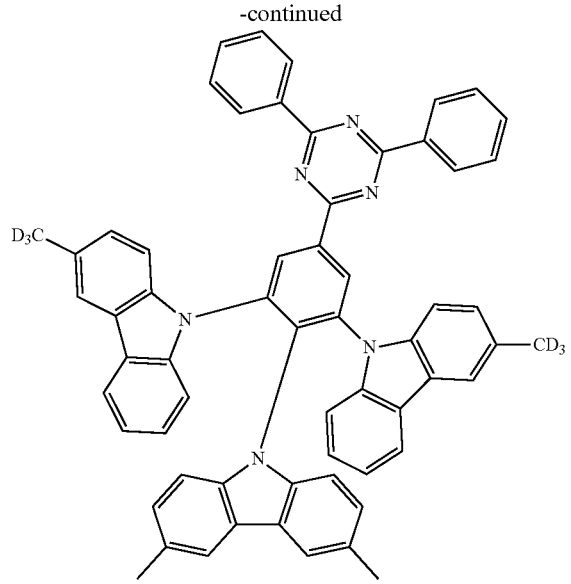
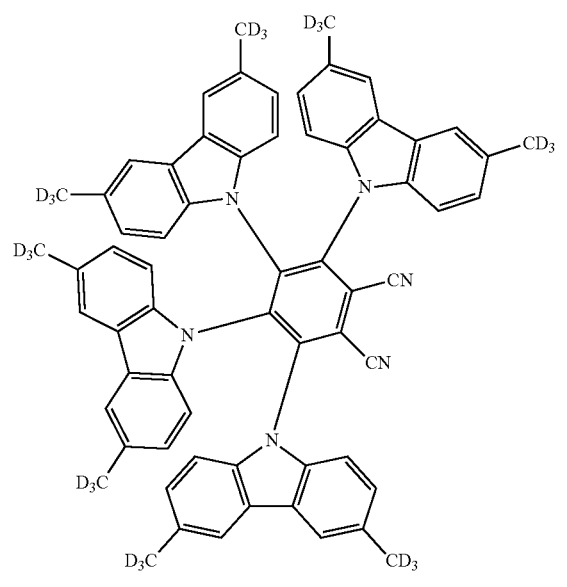
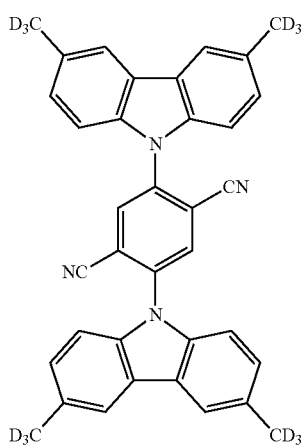
32
-continued
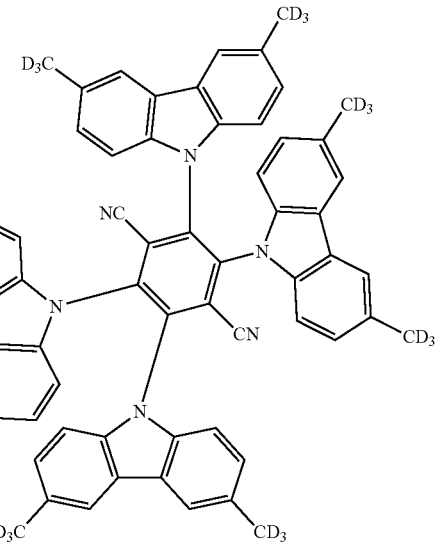
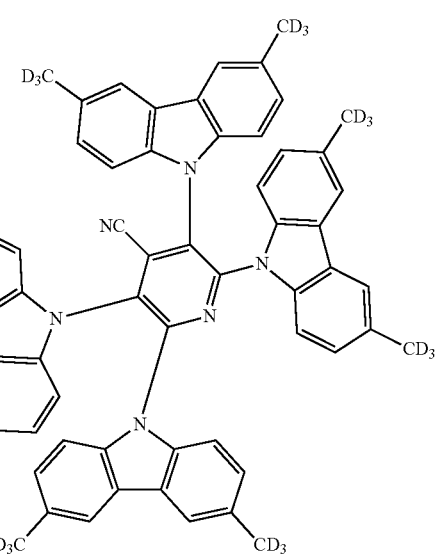
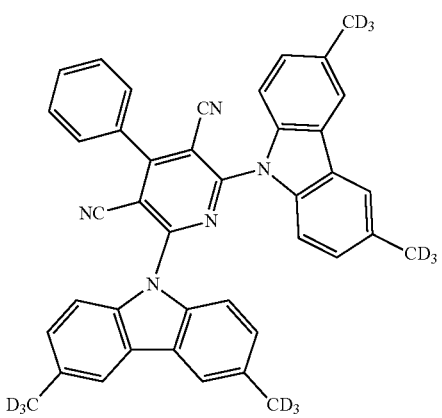

-continued
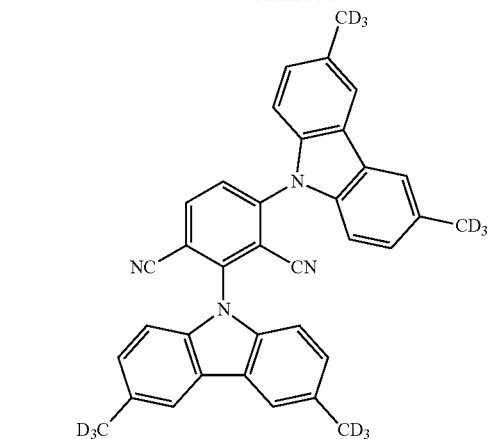
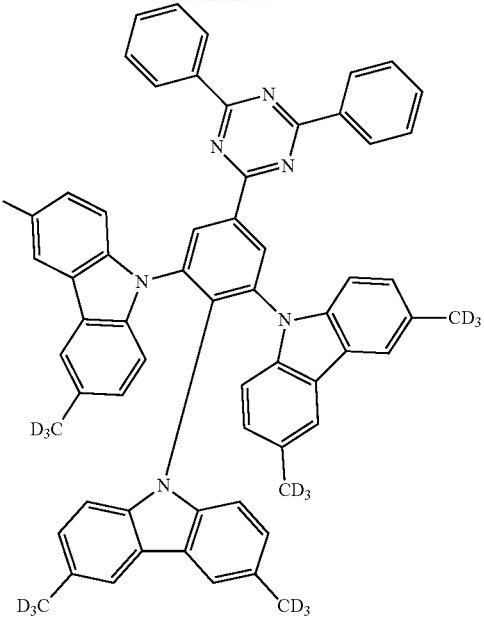
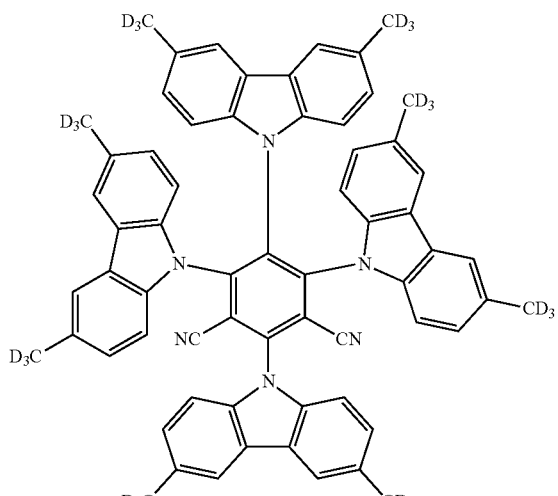
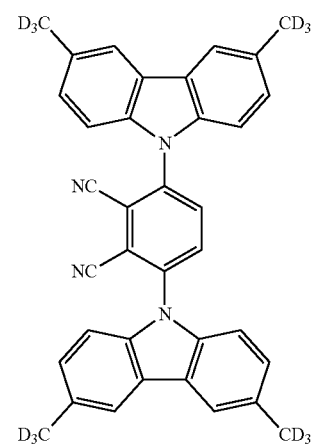
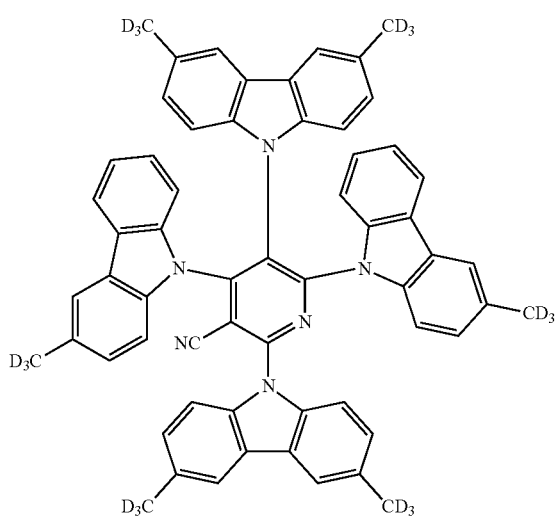
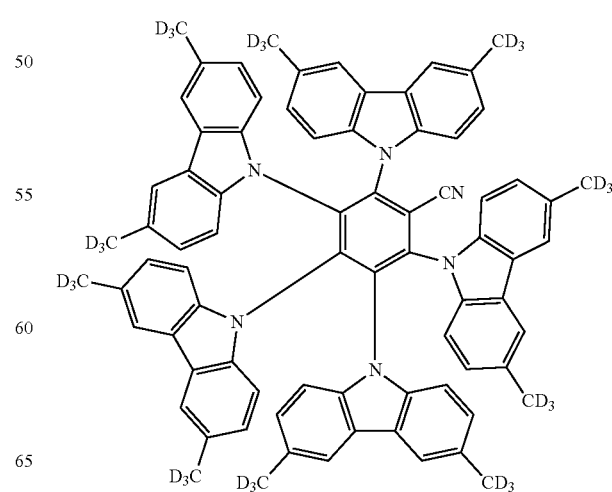

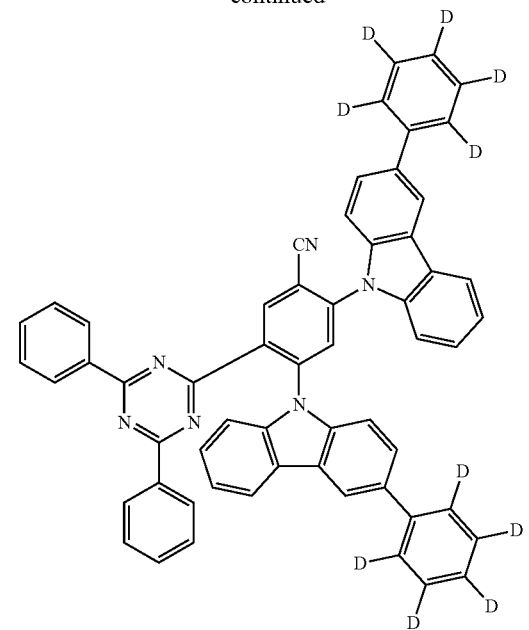
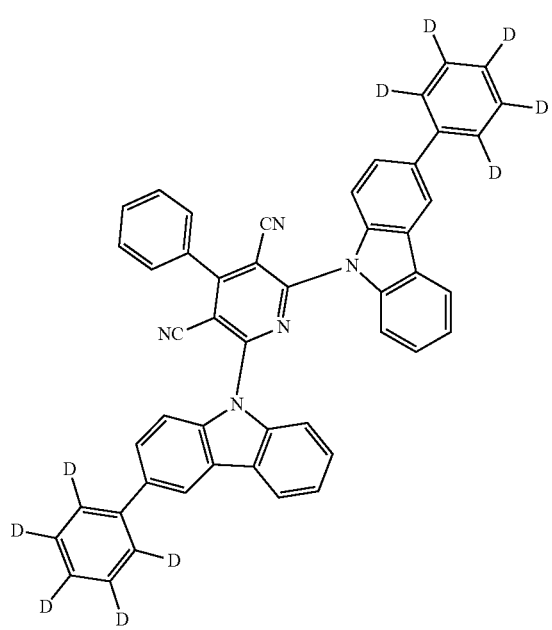
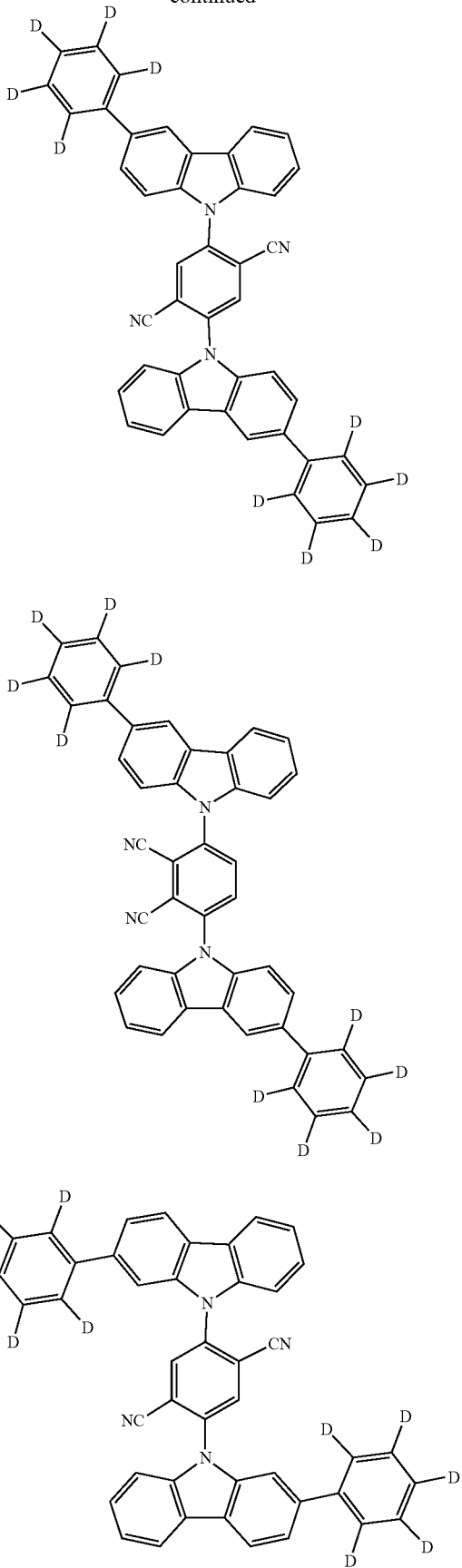

37
-continued
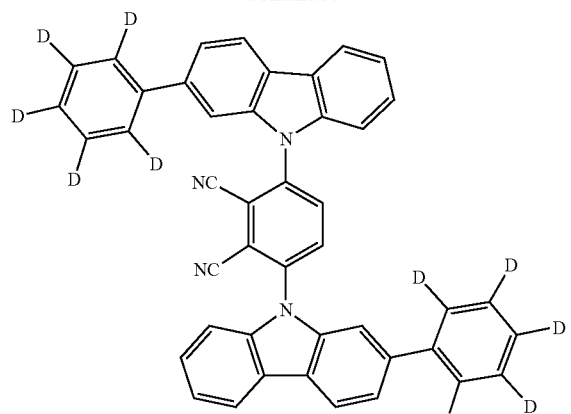
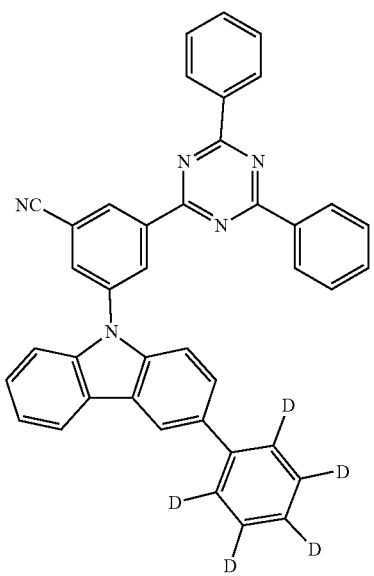
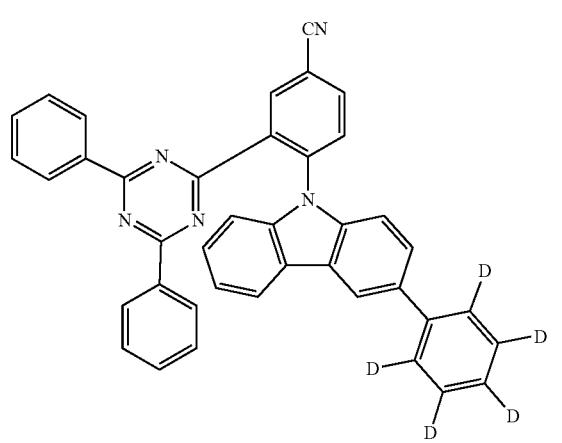
38
-continued
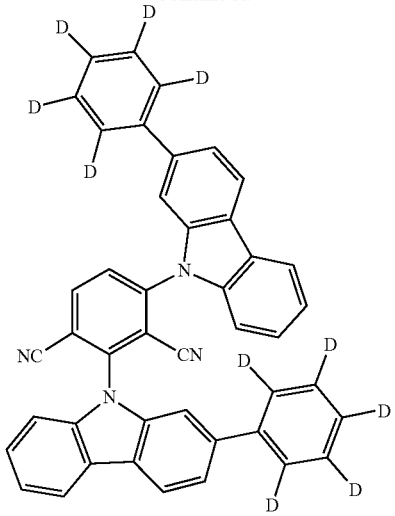
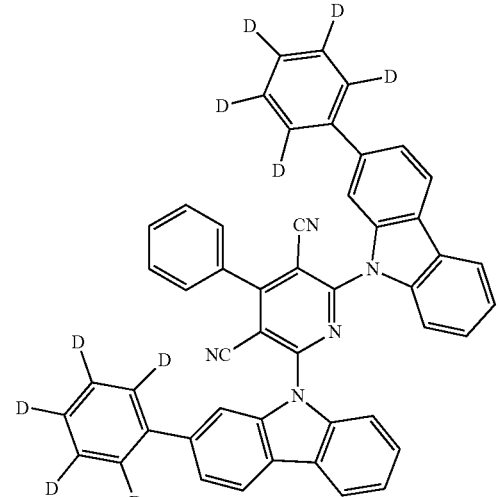
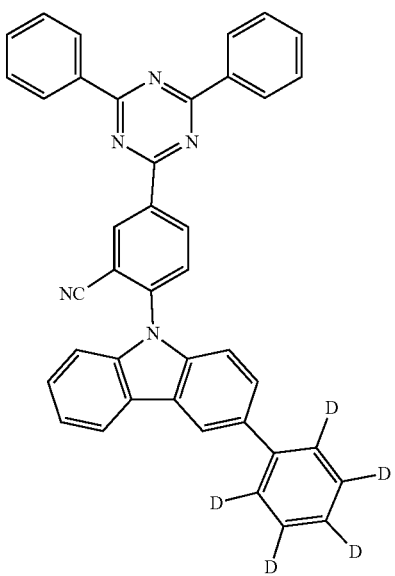

-continued
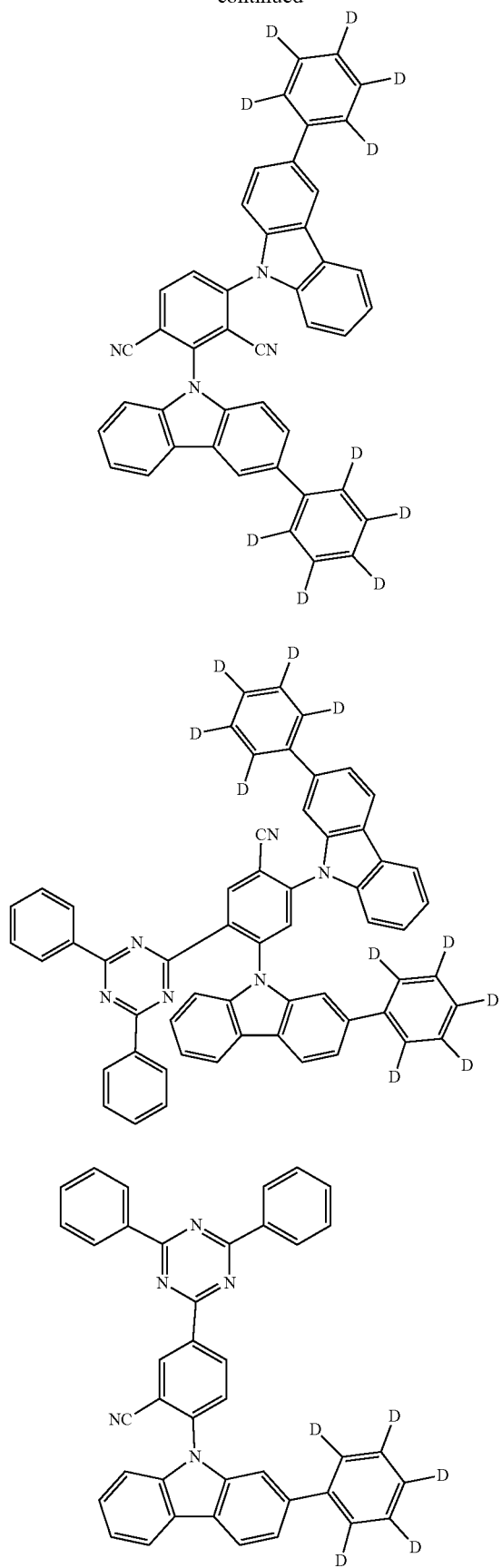
-continued
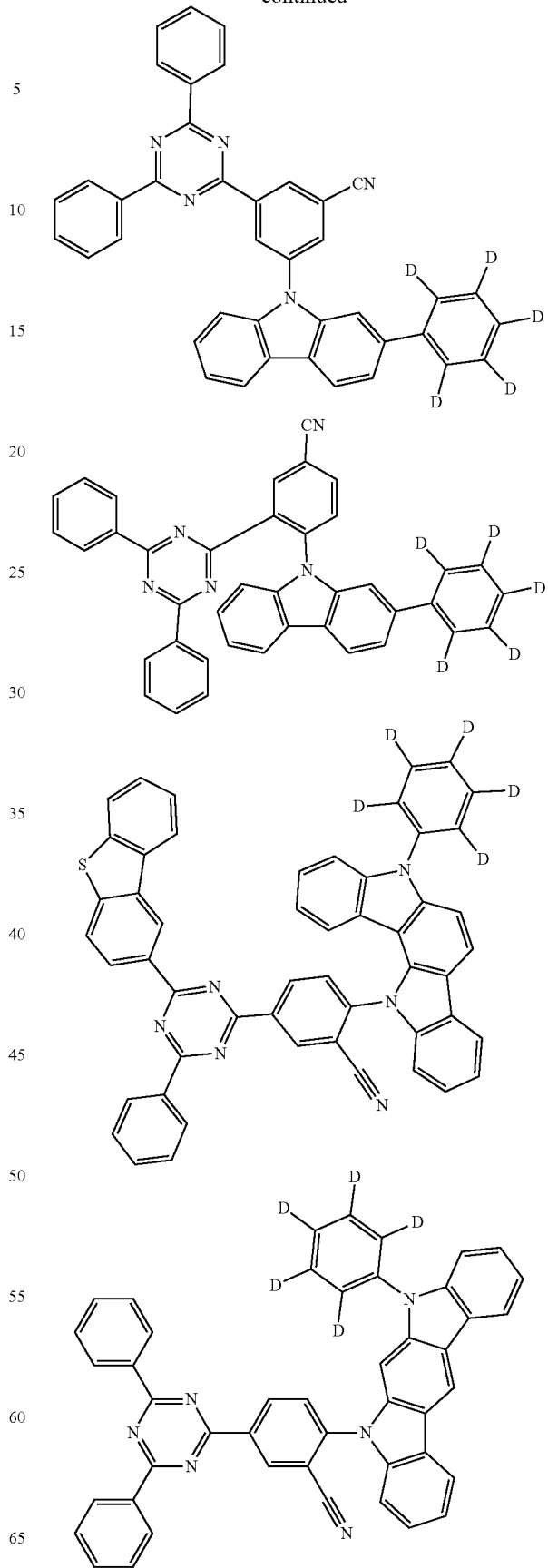

41
-continued
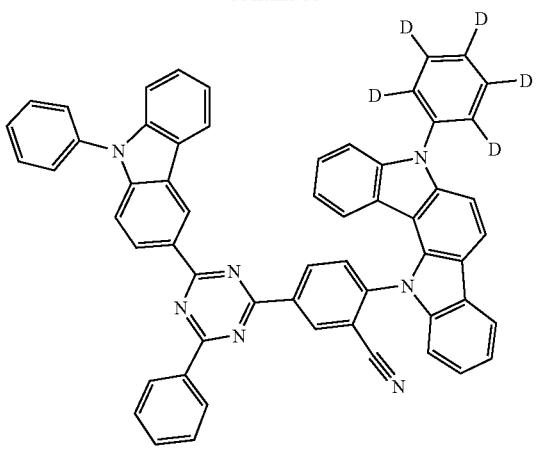
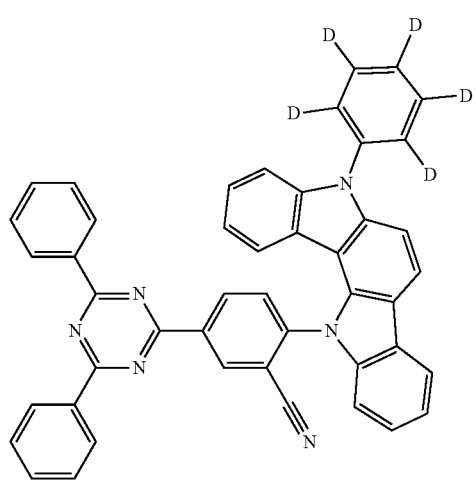
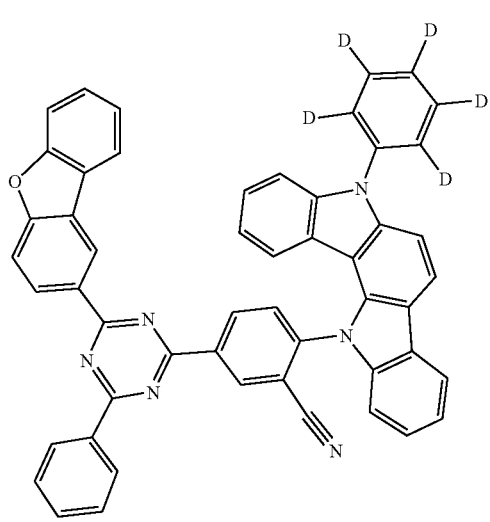
42
-continued
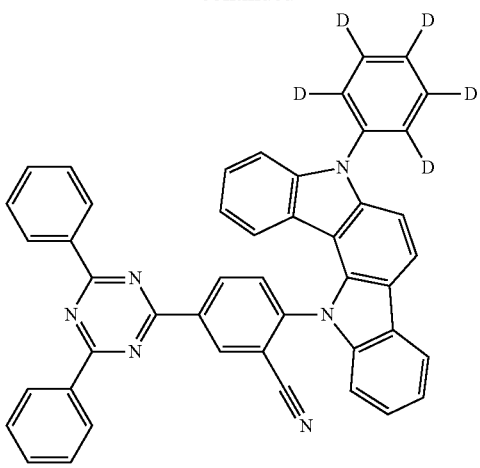
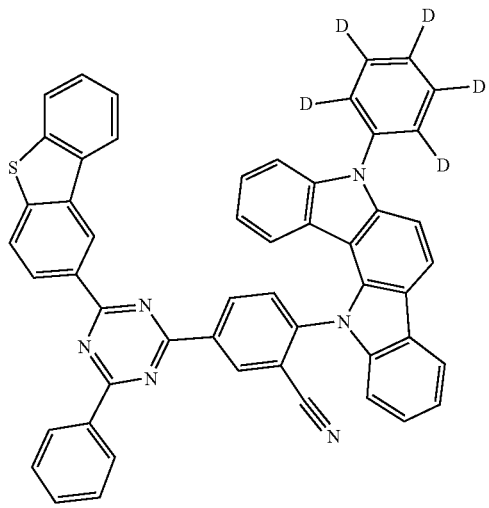
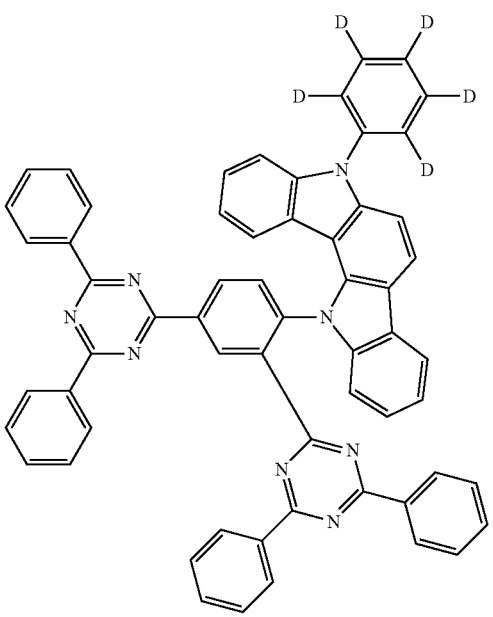

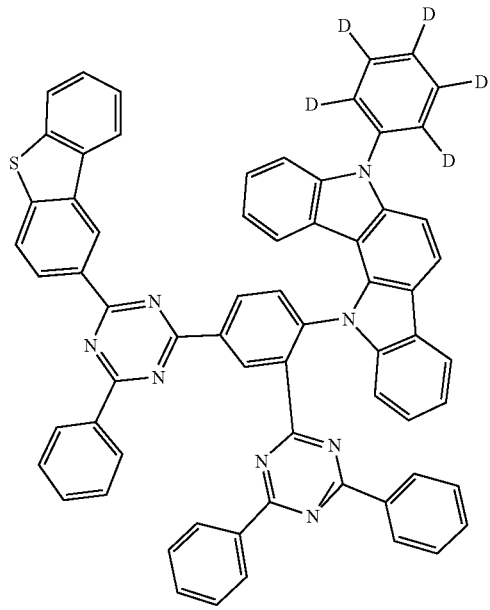
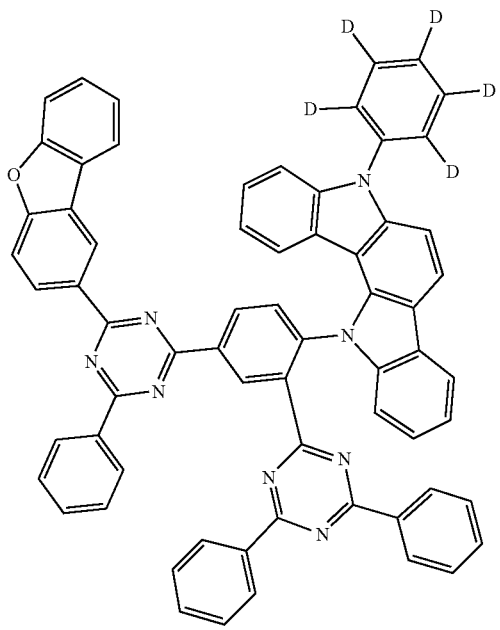
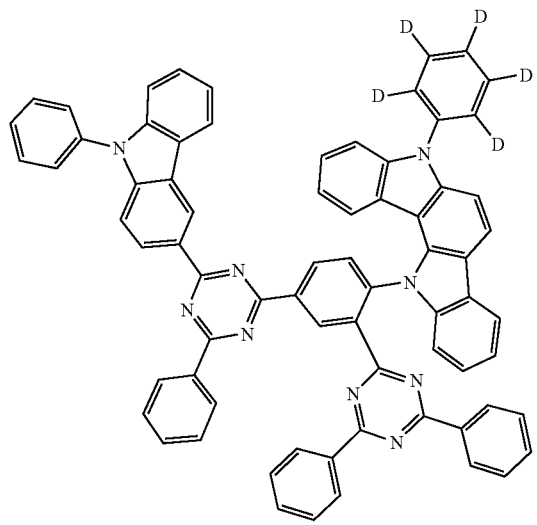
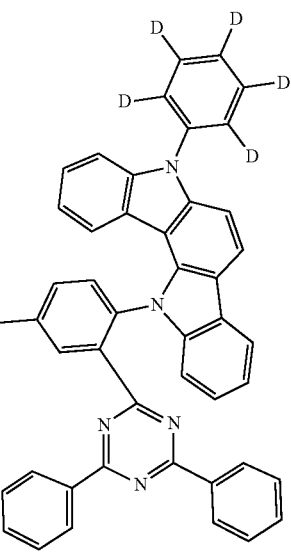

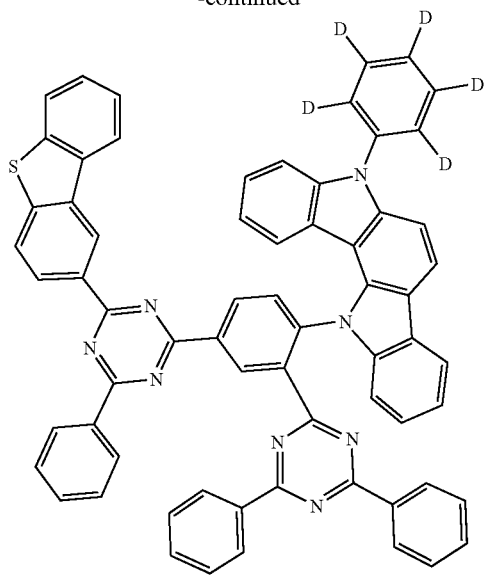
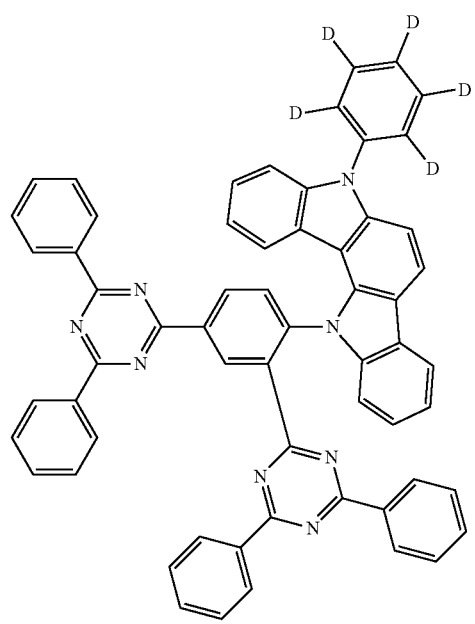
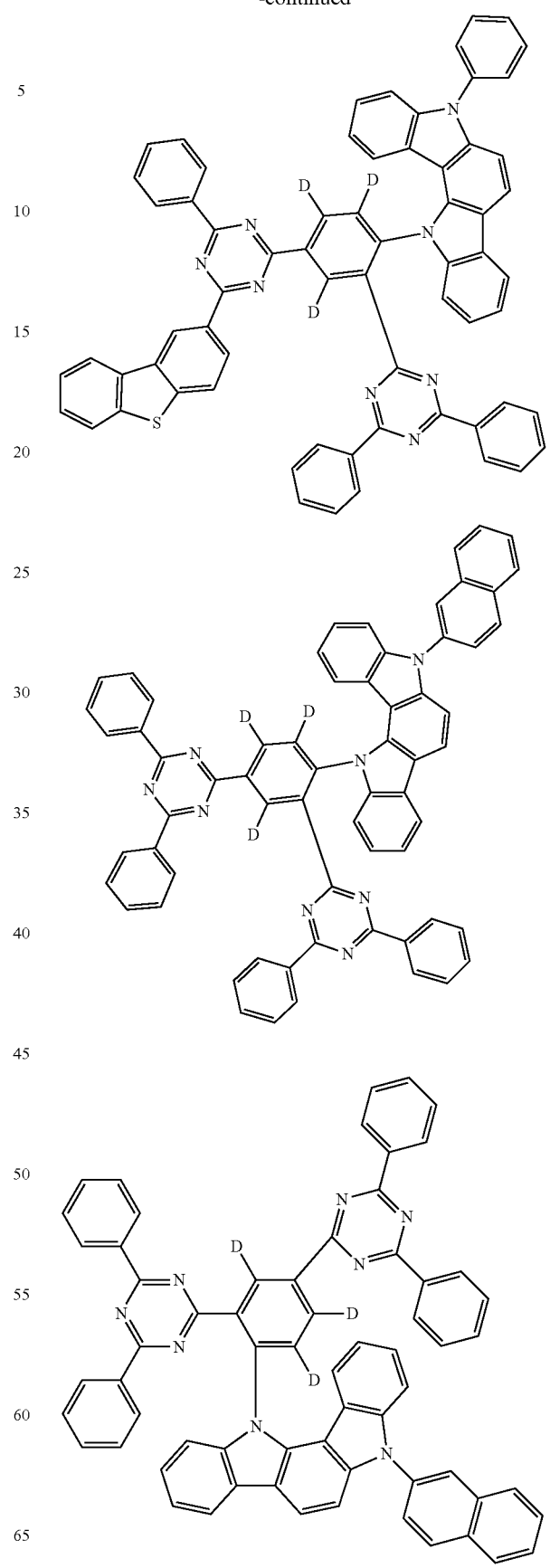

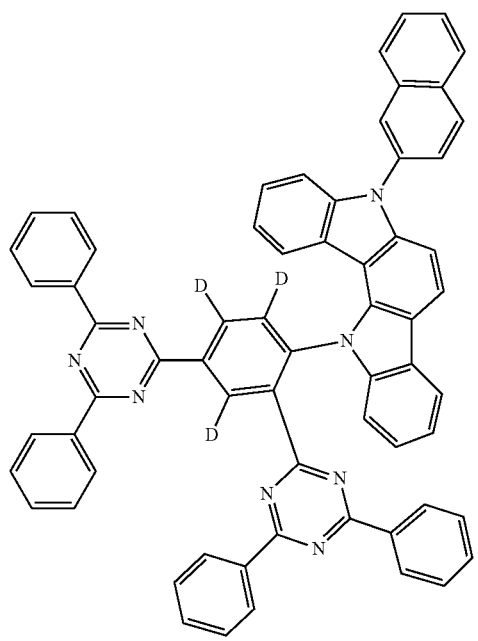
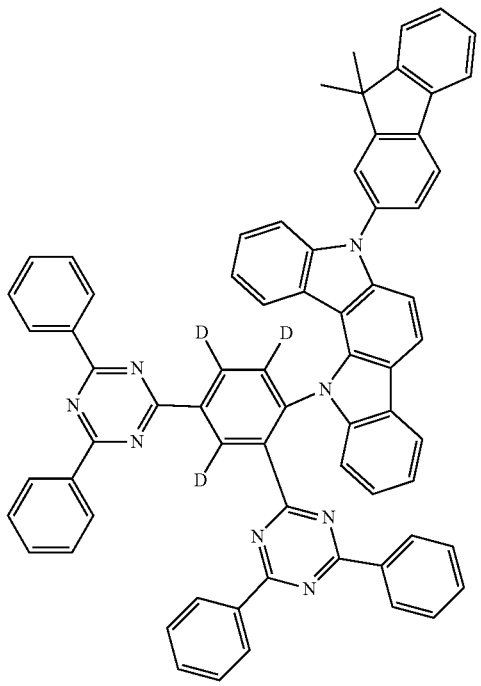
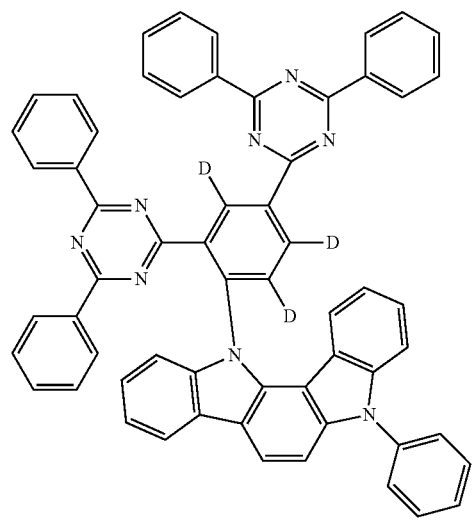
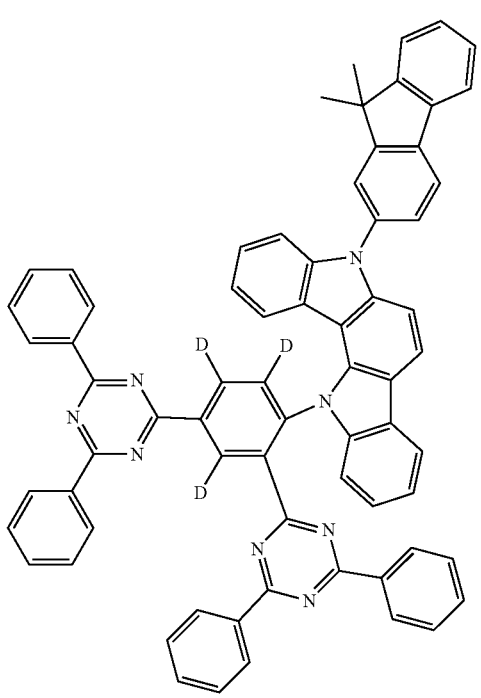

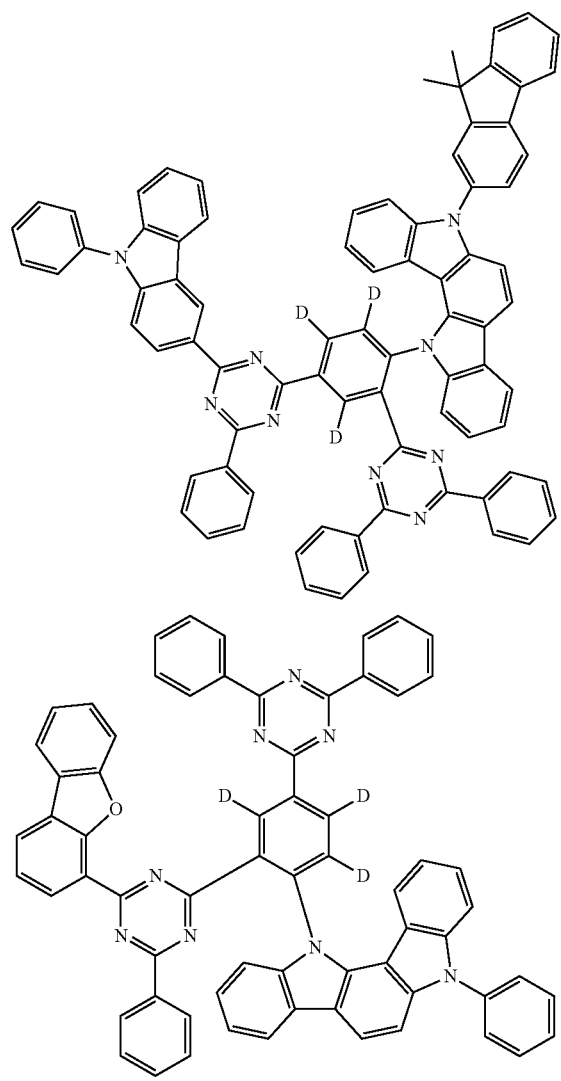
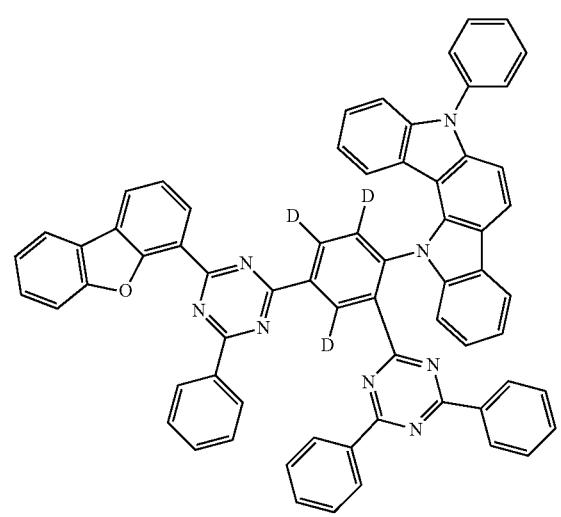
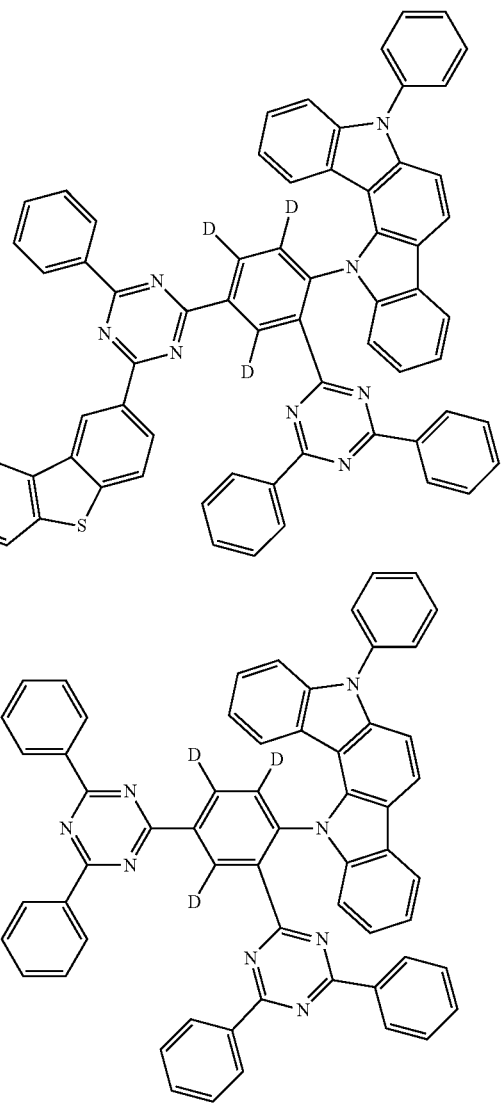
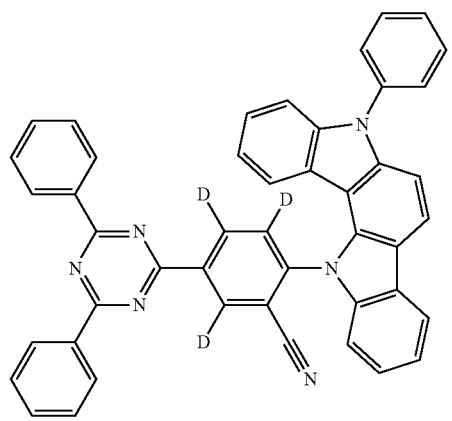

51
-continued
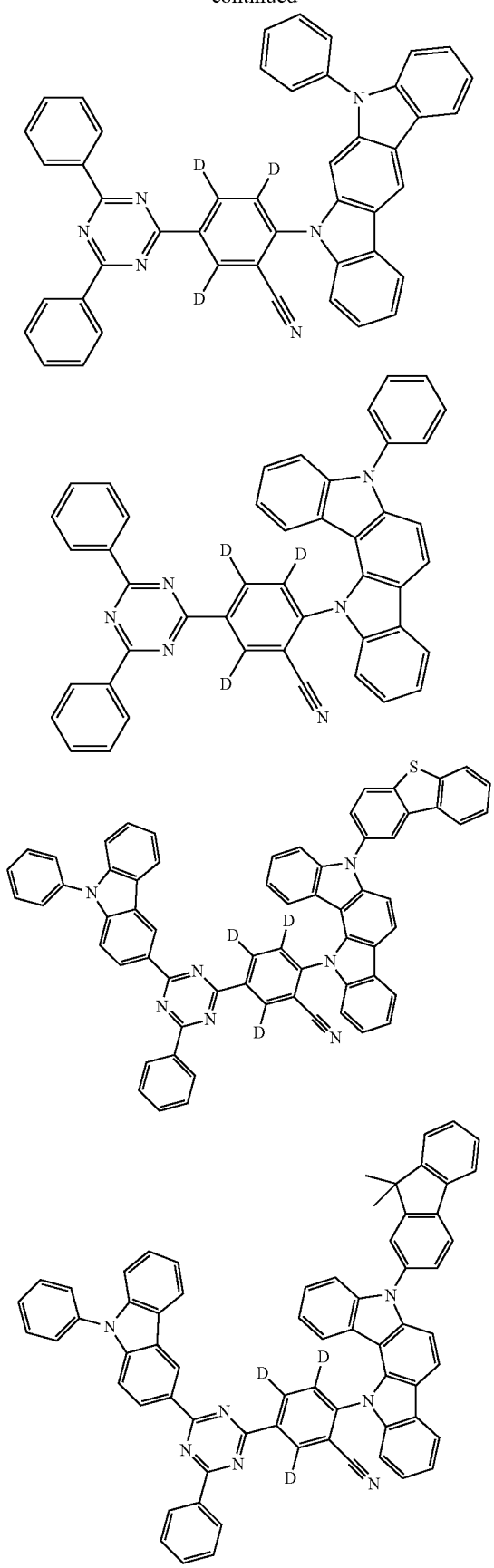
52
-continued
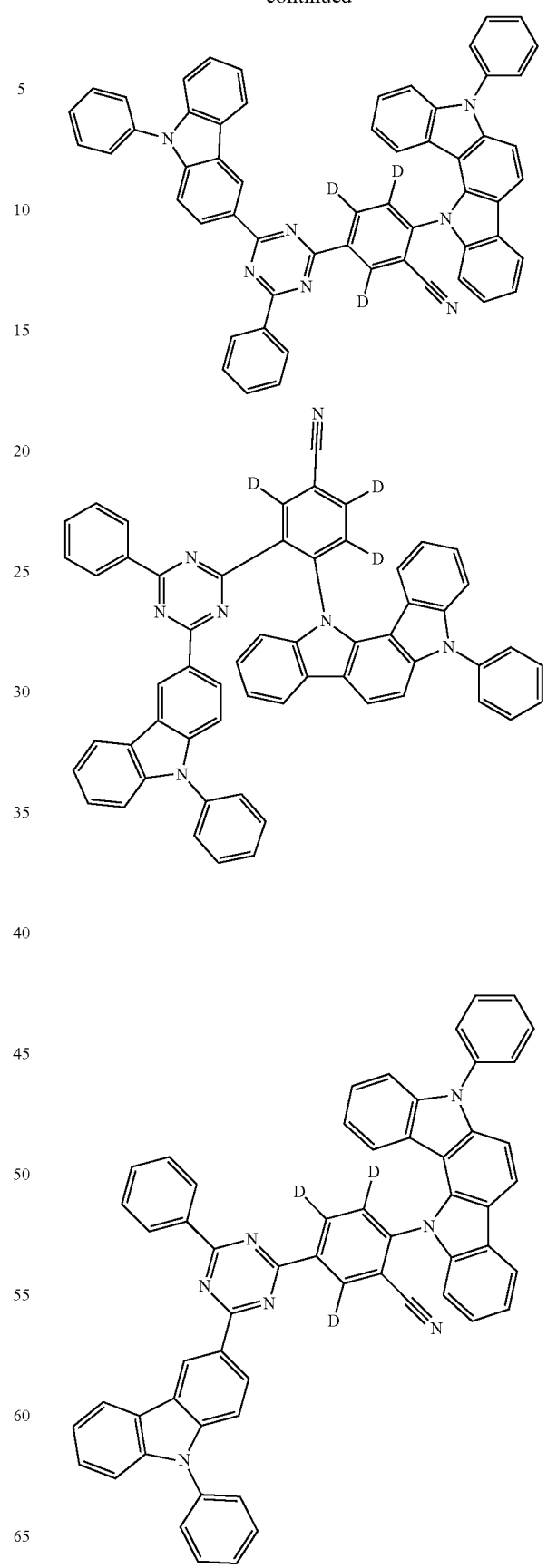

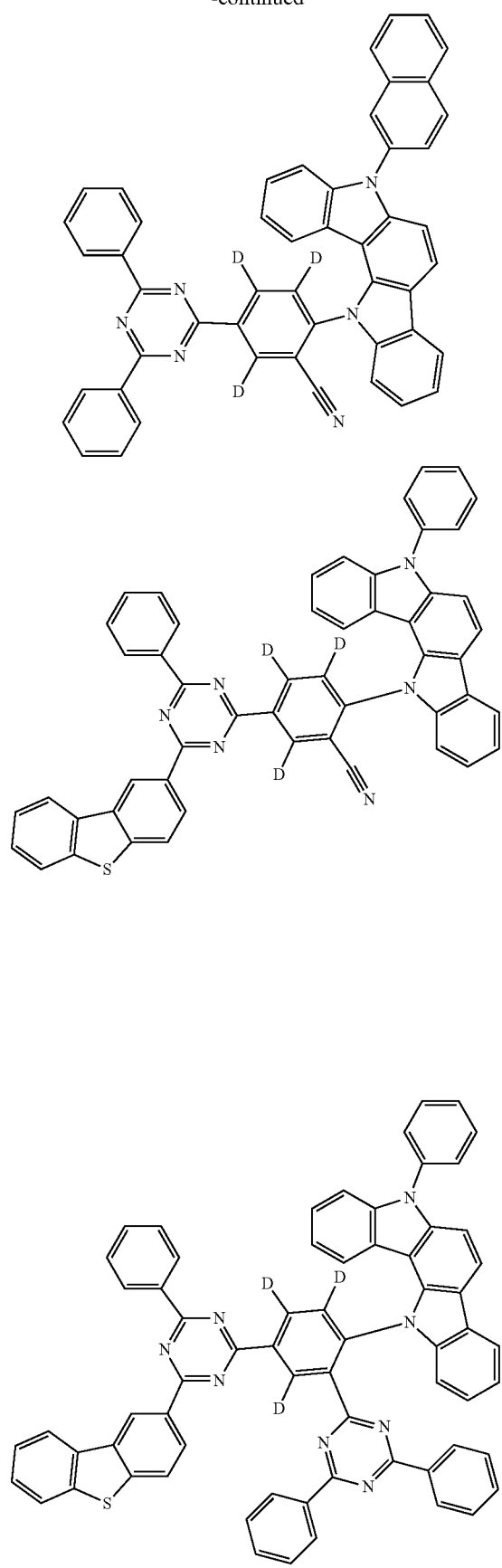
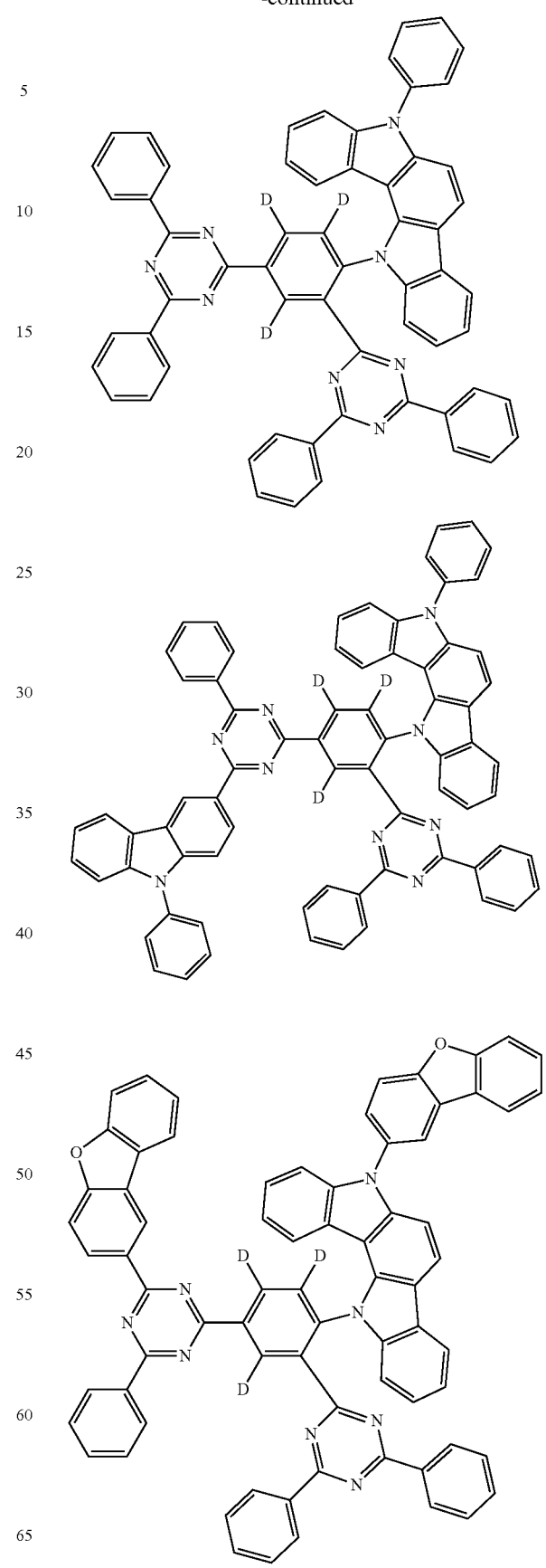

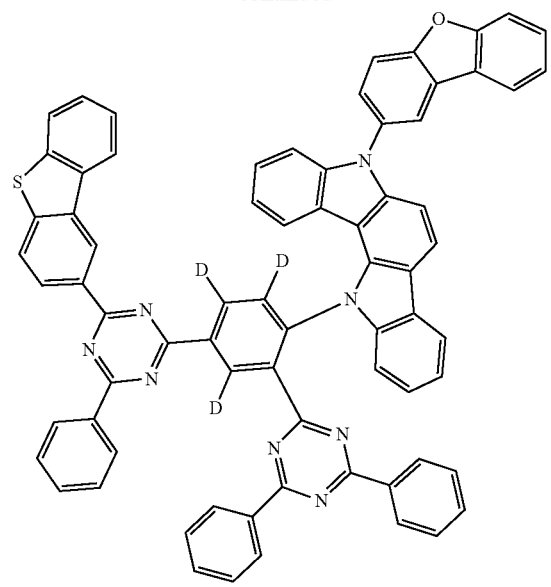
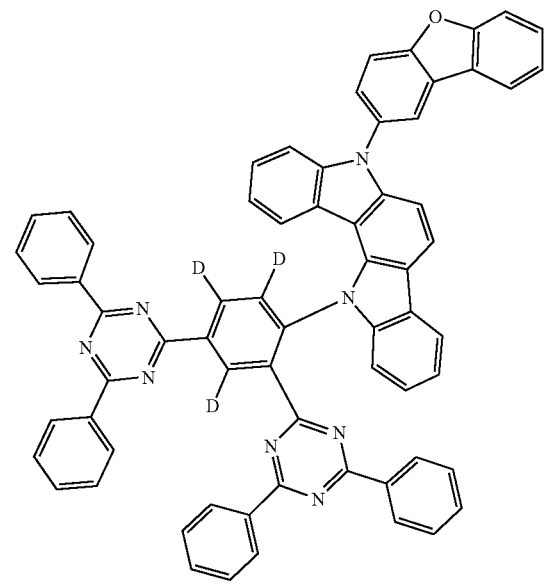
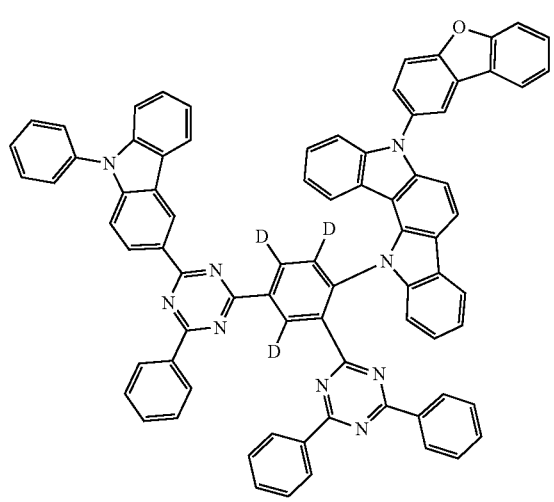
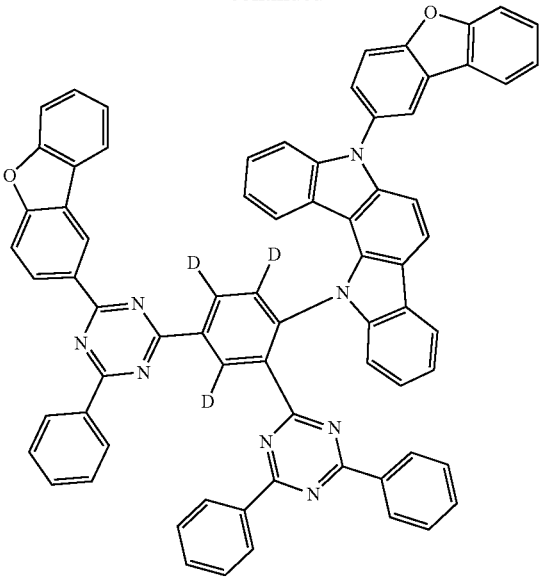
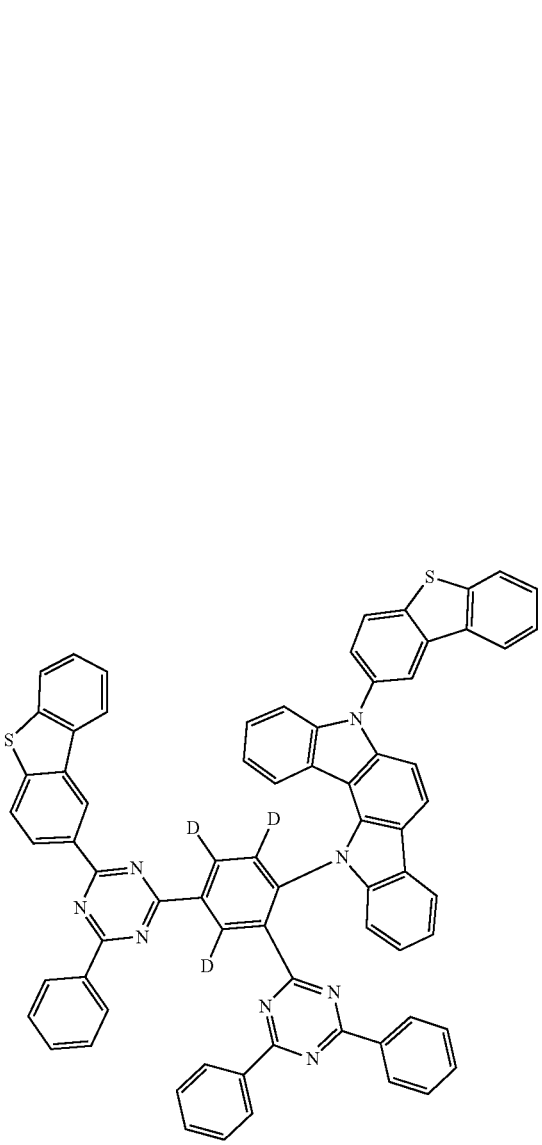

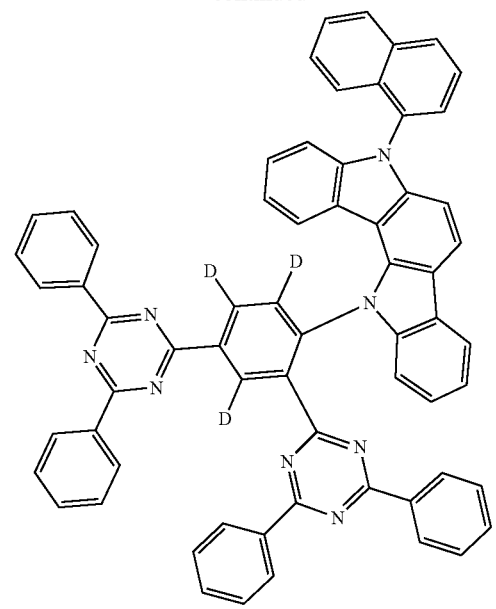
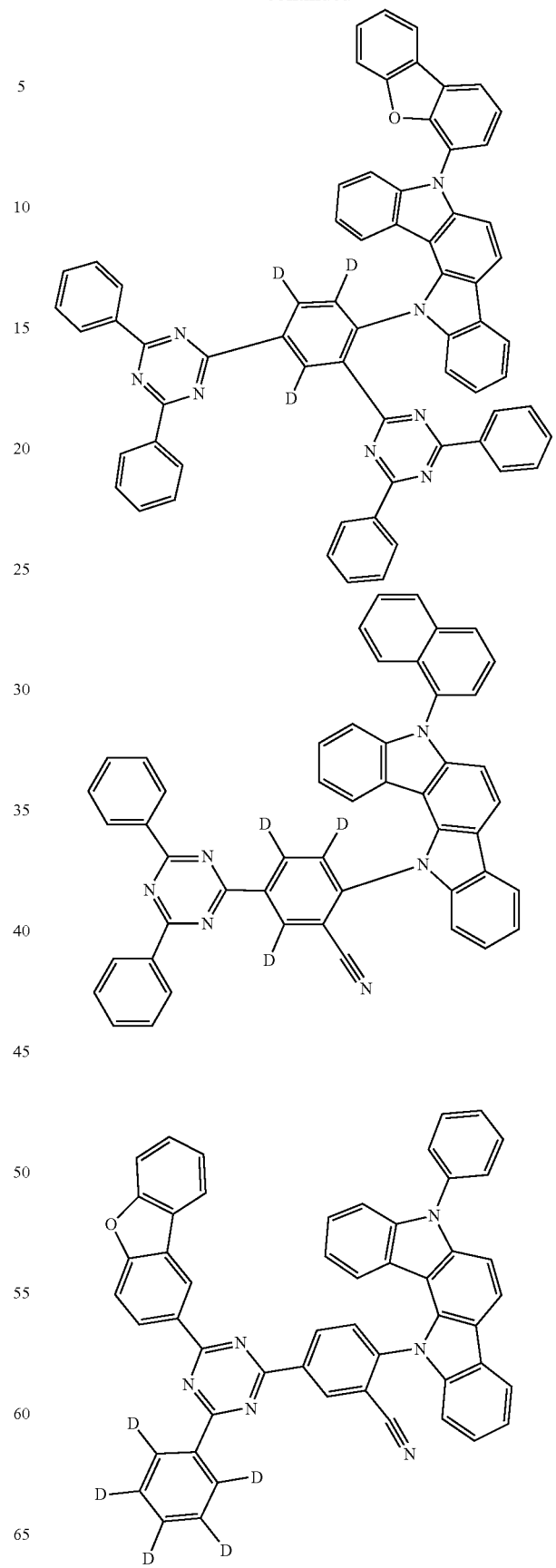

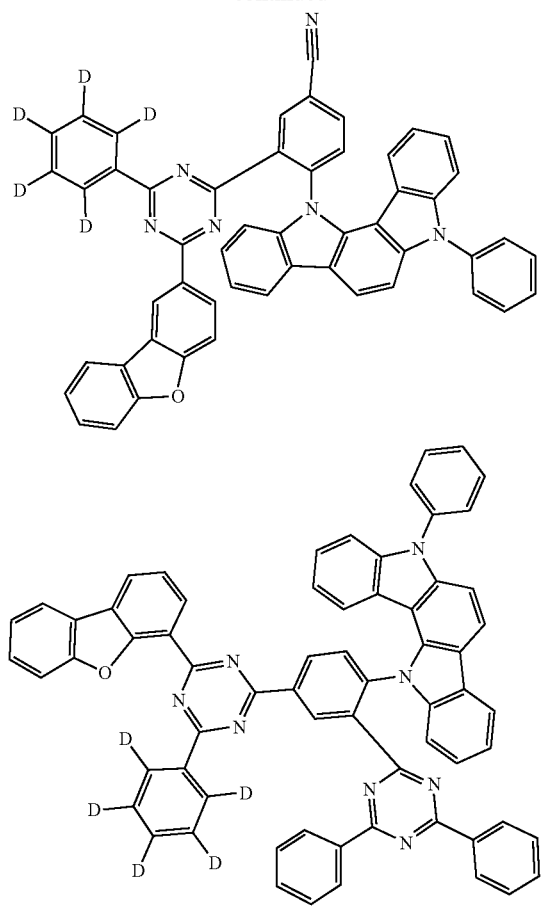
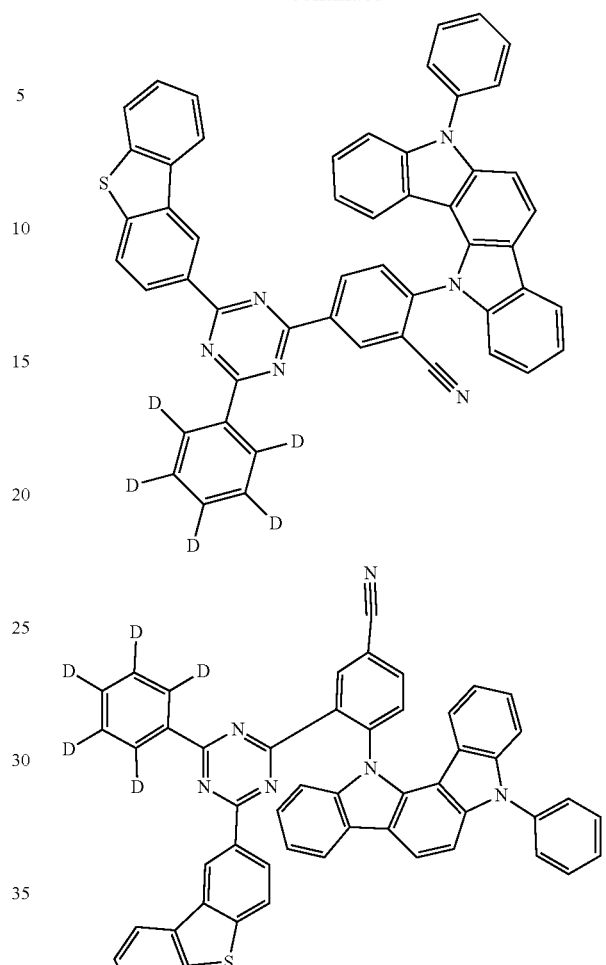
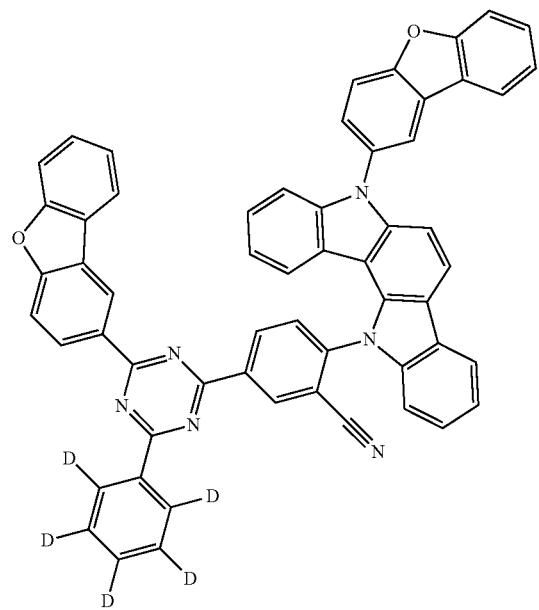

61
-continued
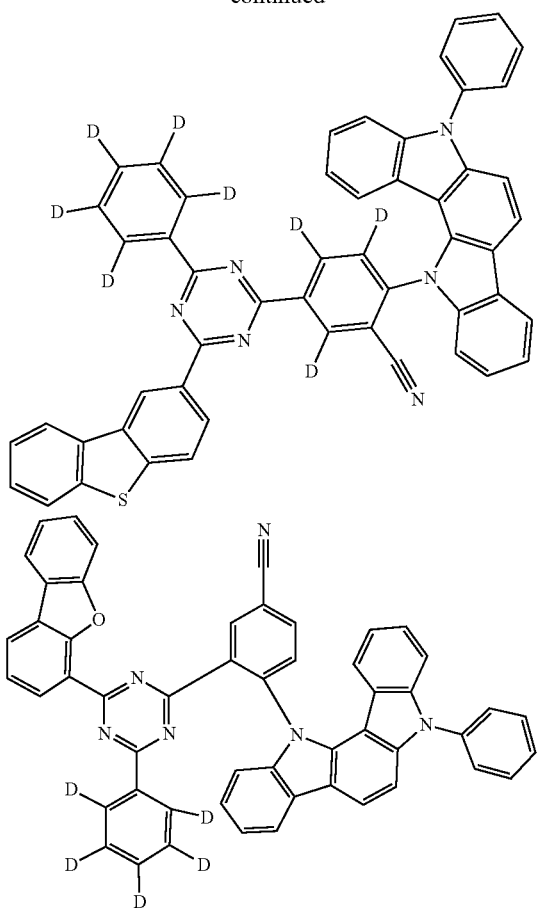
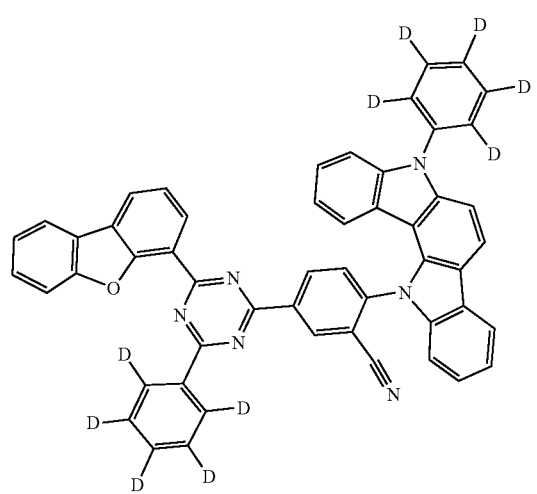
62
-continued
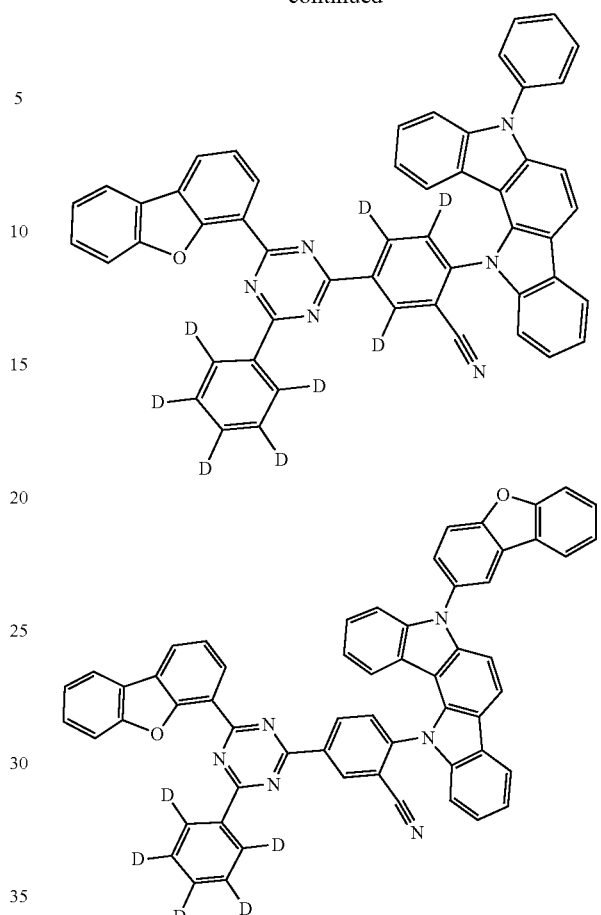
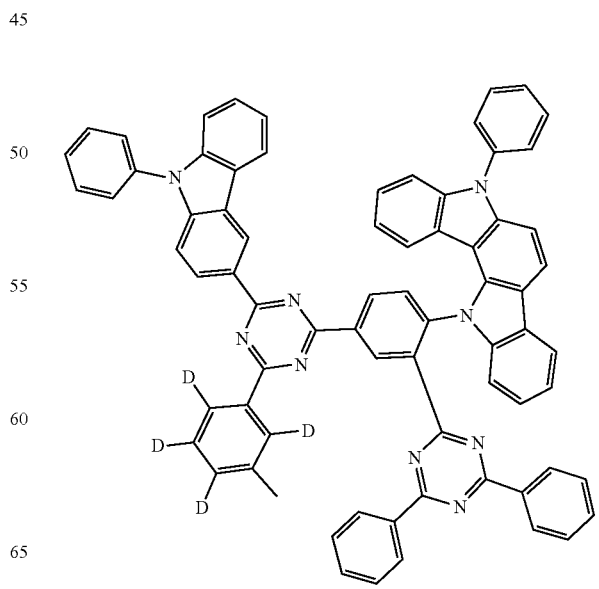

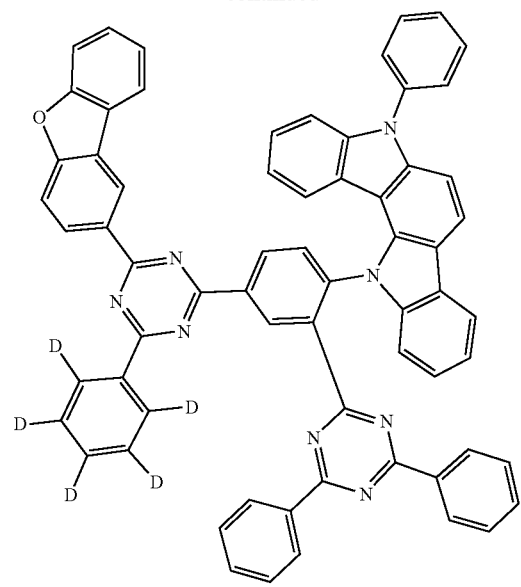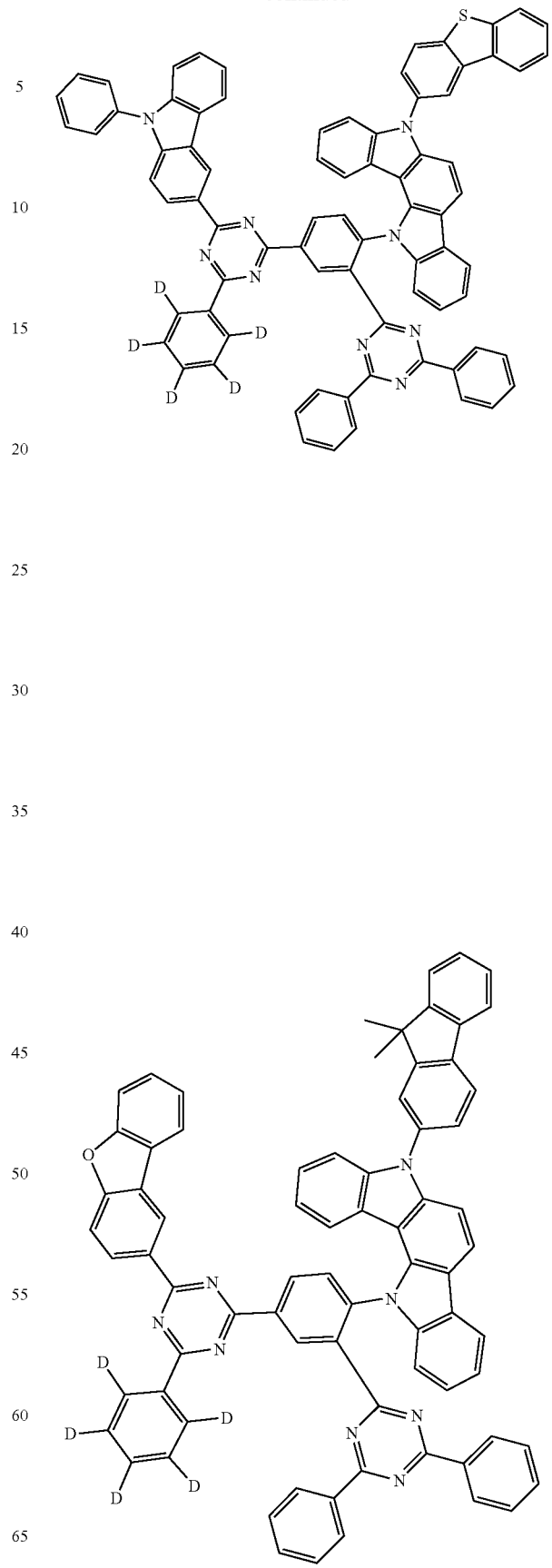

65
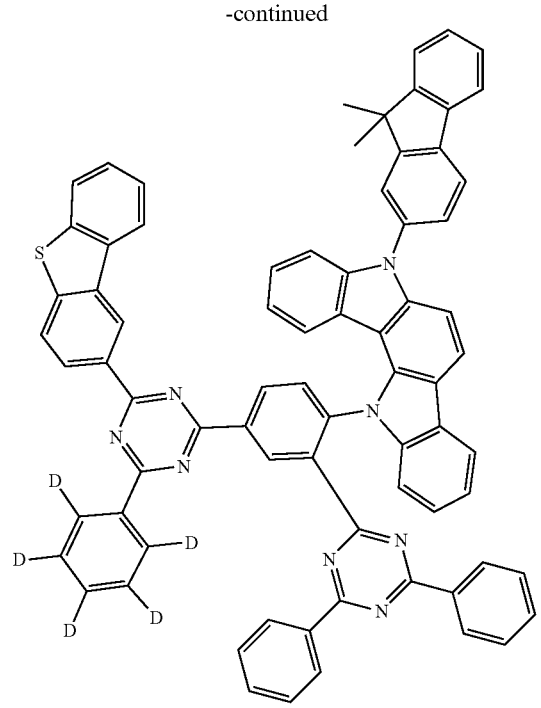
66
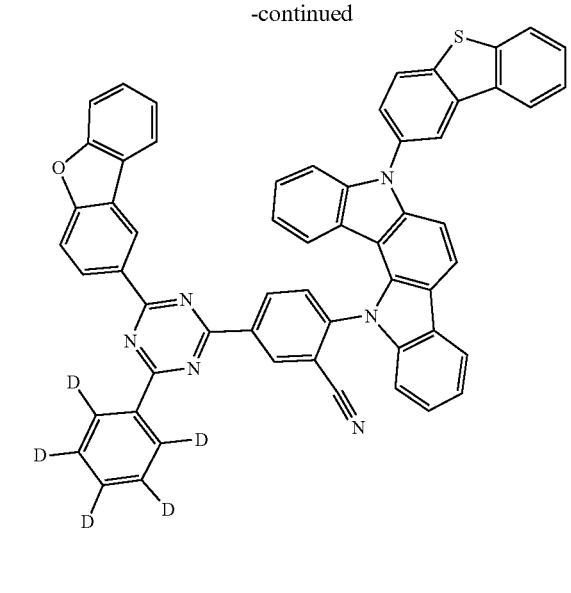

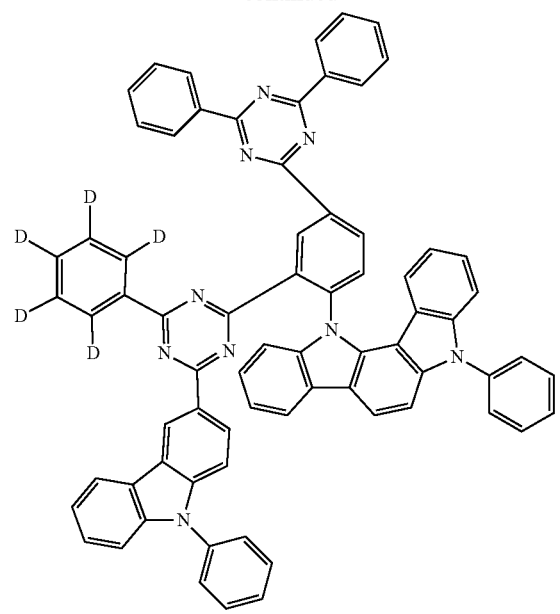
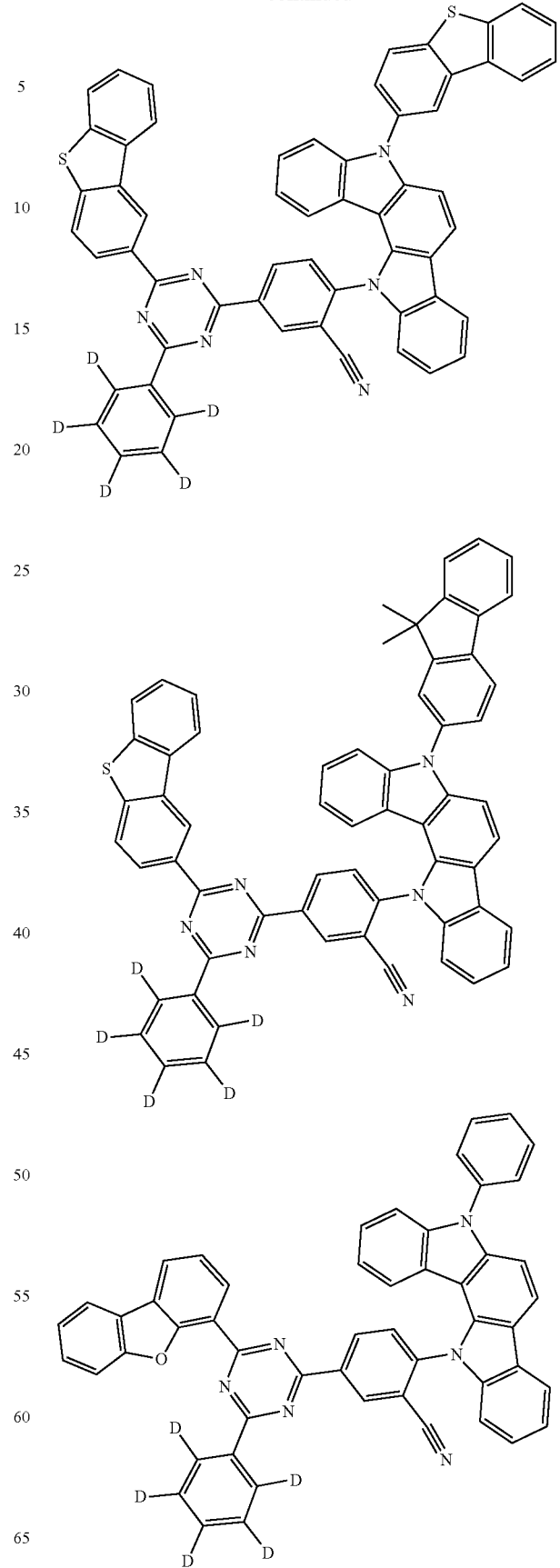

69
-continued
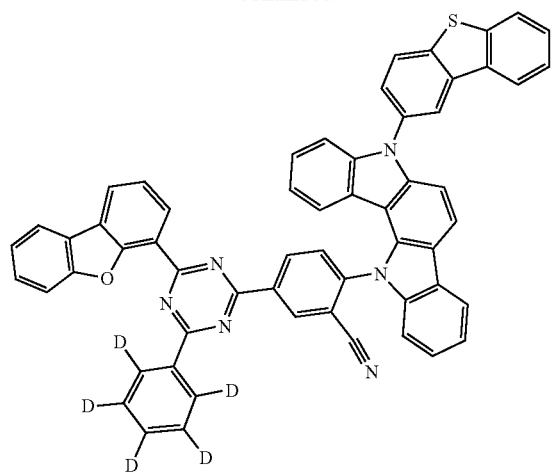
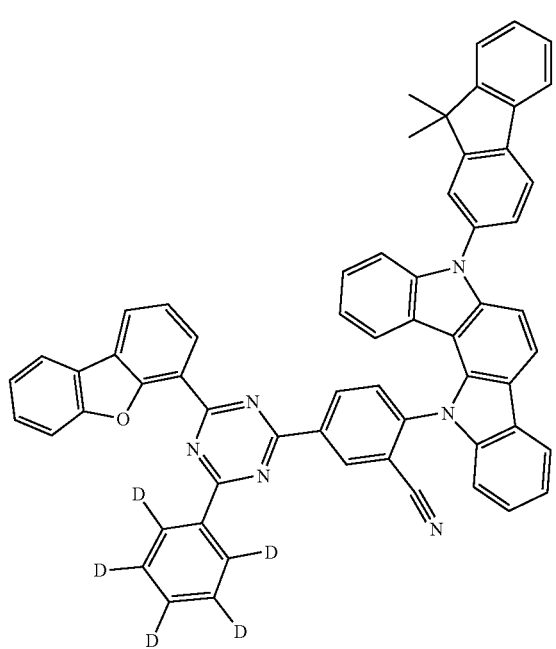
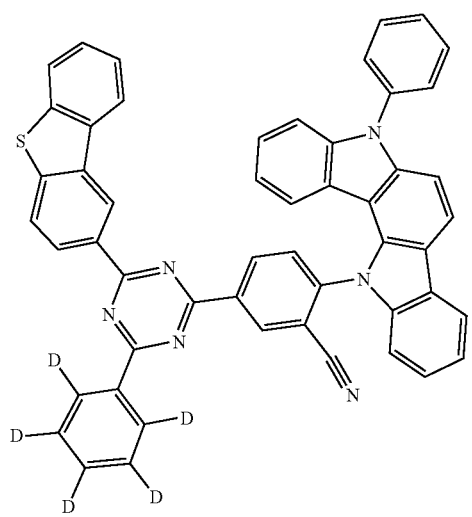
70
-continued
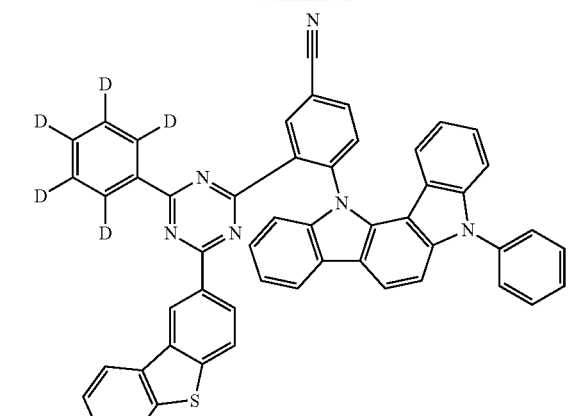
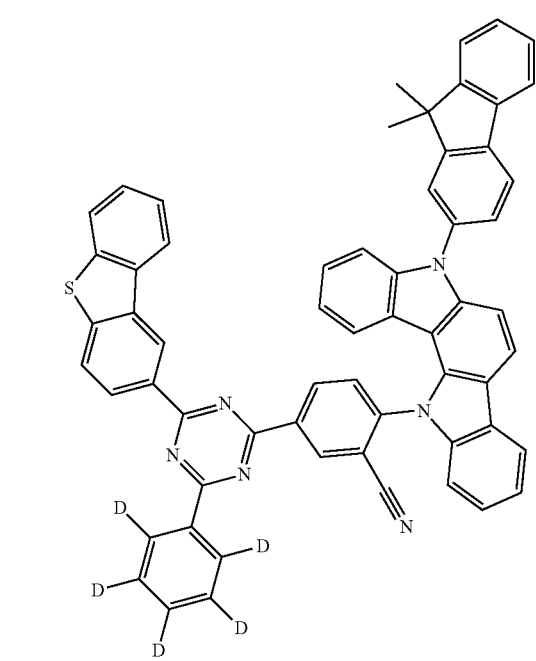
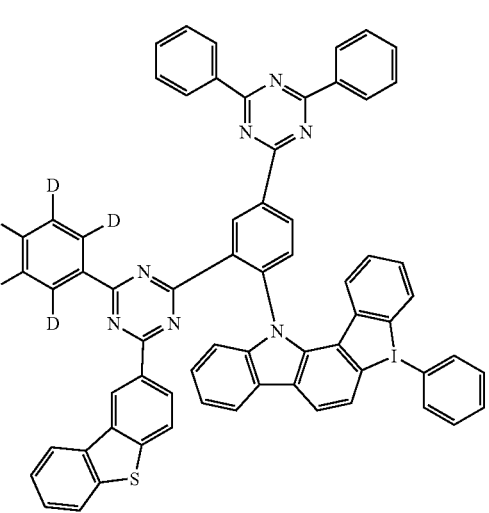

71
-continued
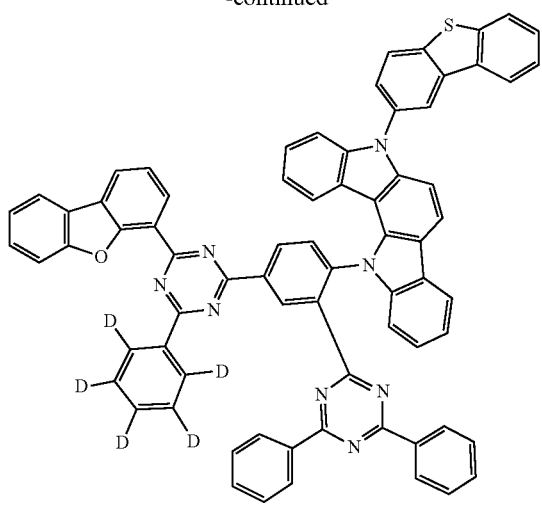
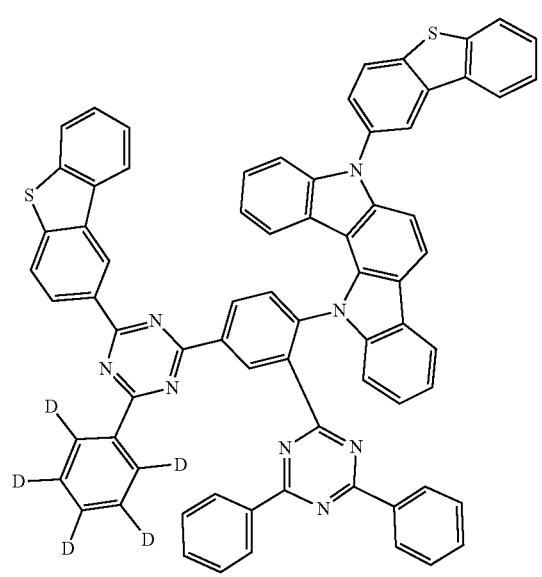
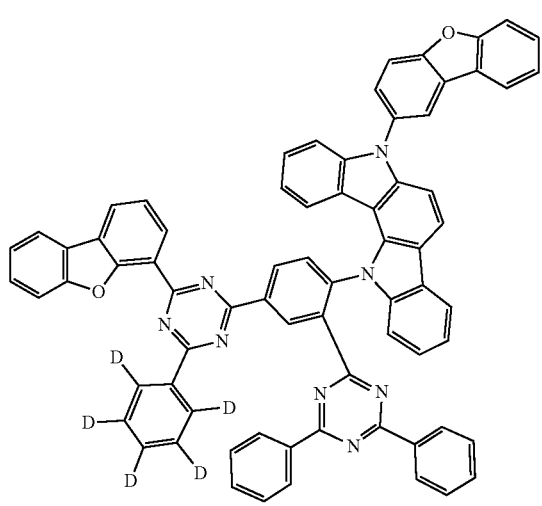
72
-continued
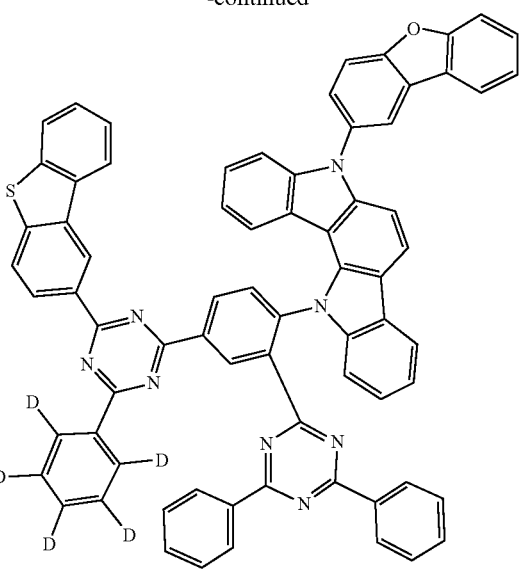
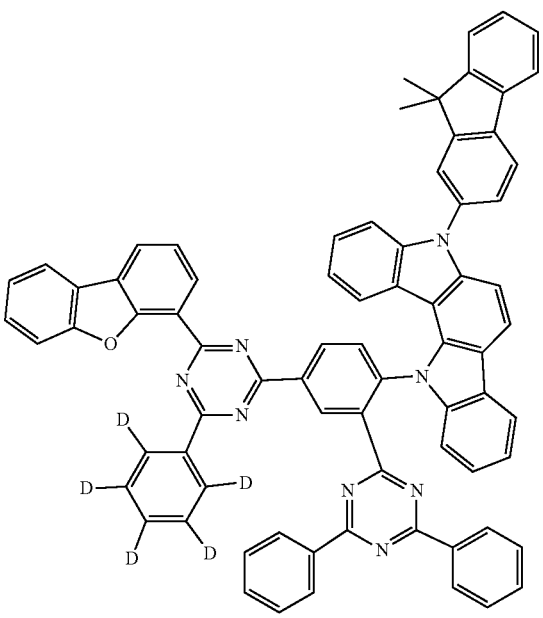

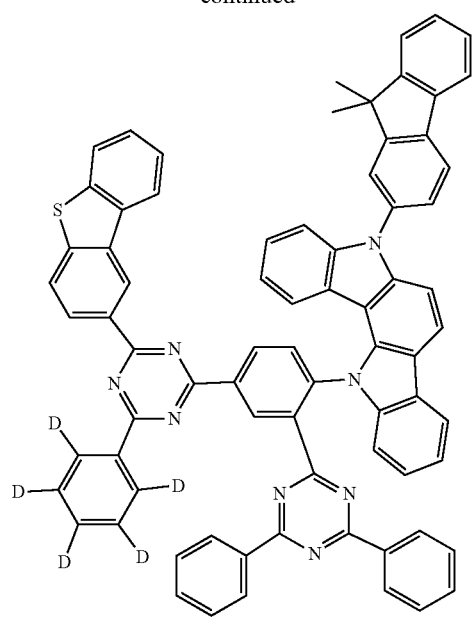
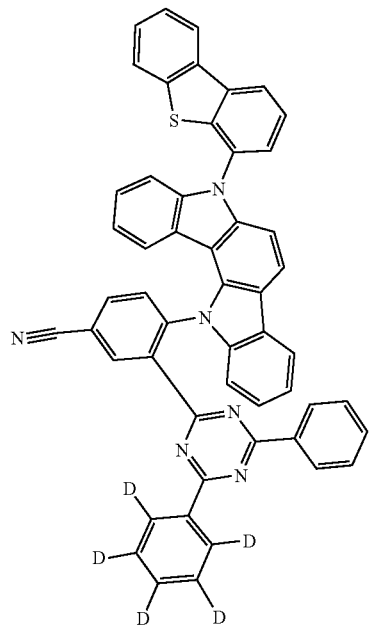
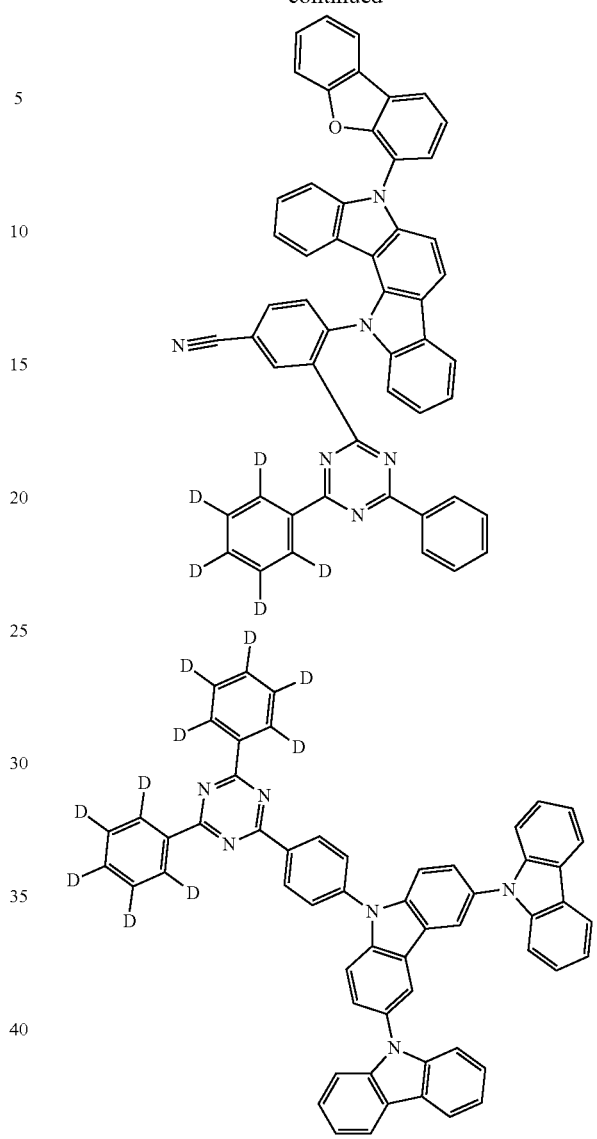

-continued
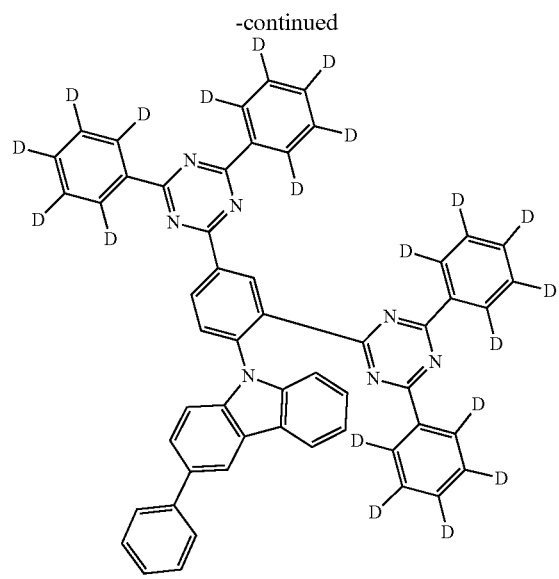
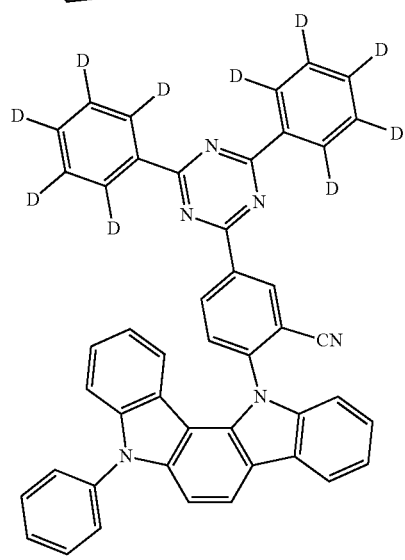
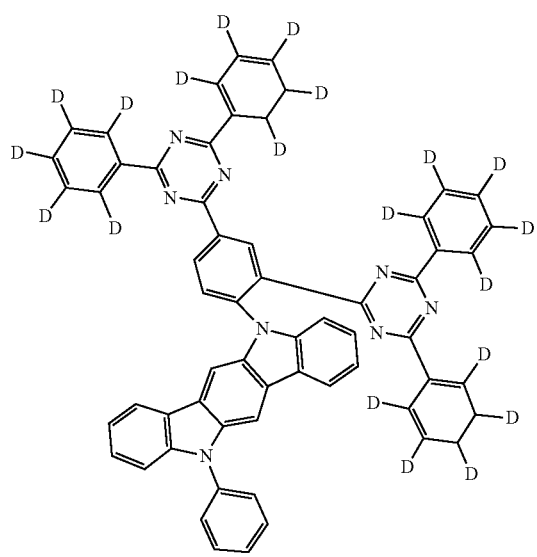
-continued
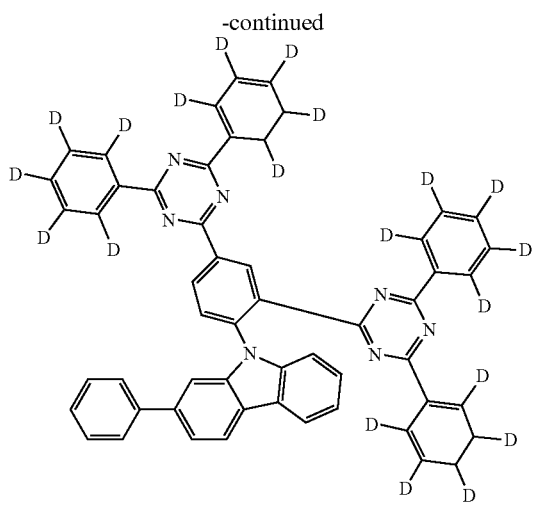
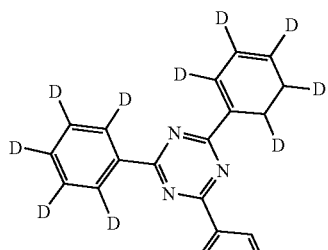
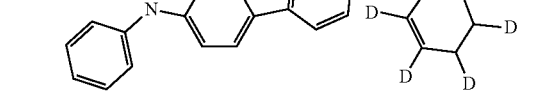
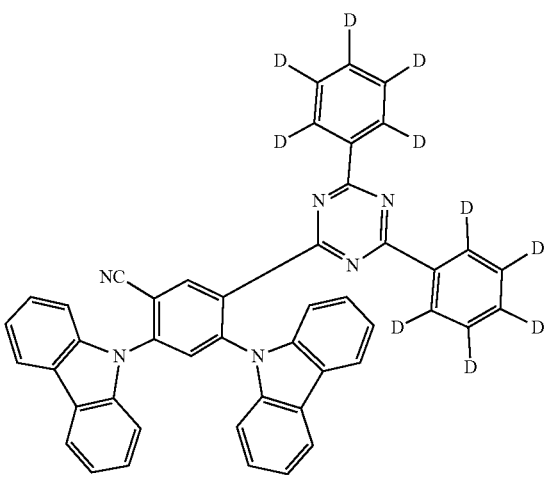

-continued
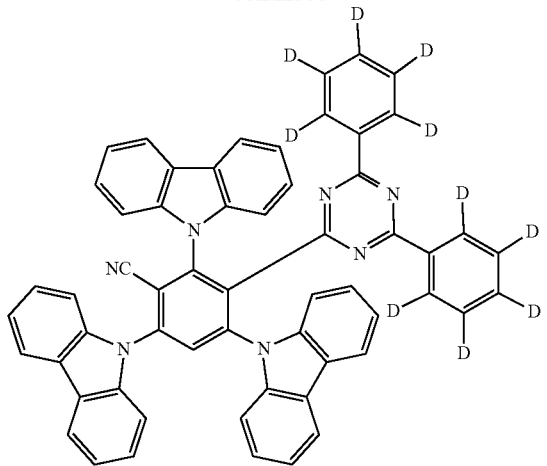
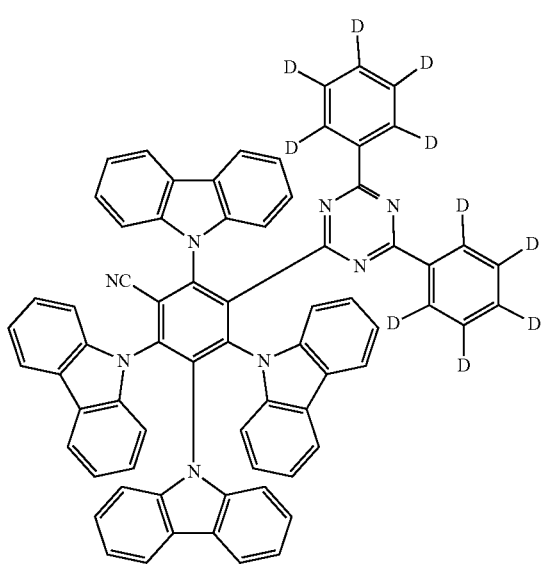
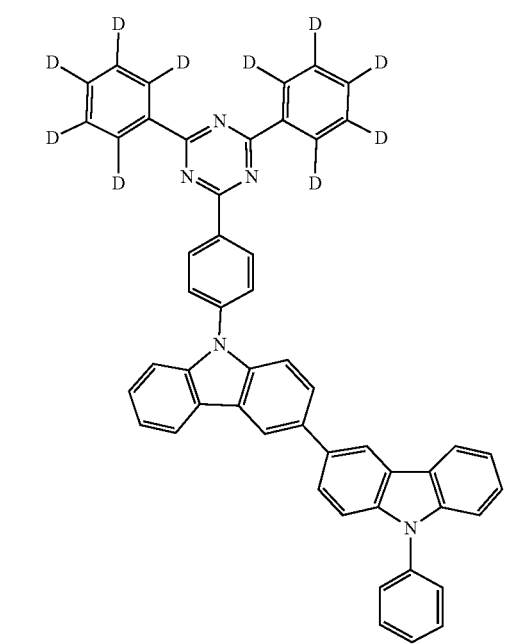
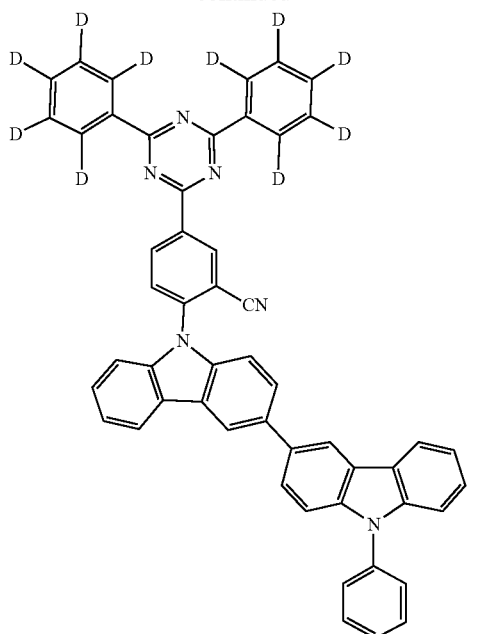
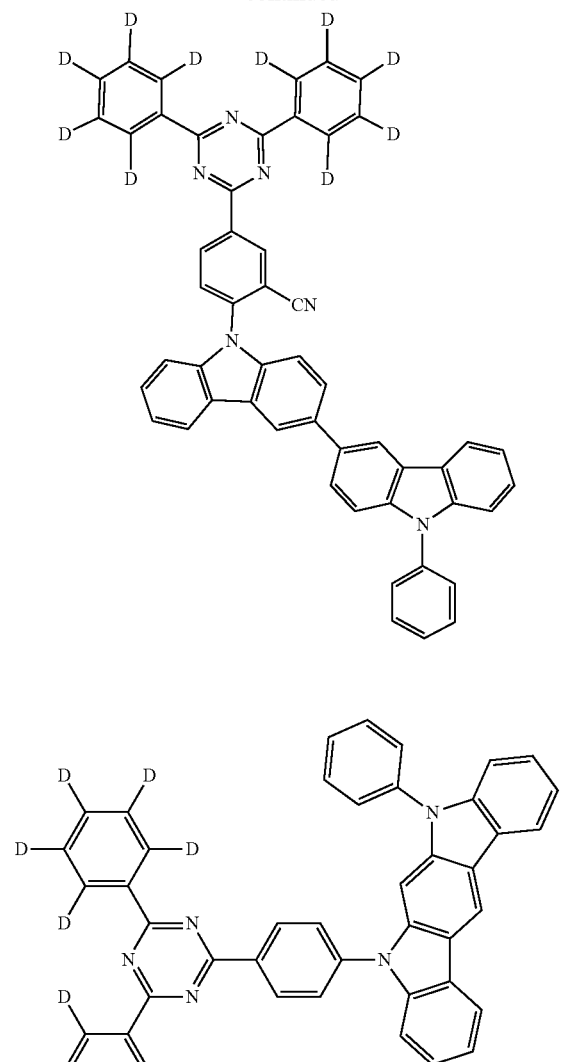
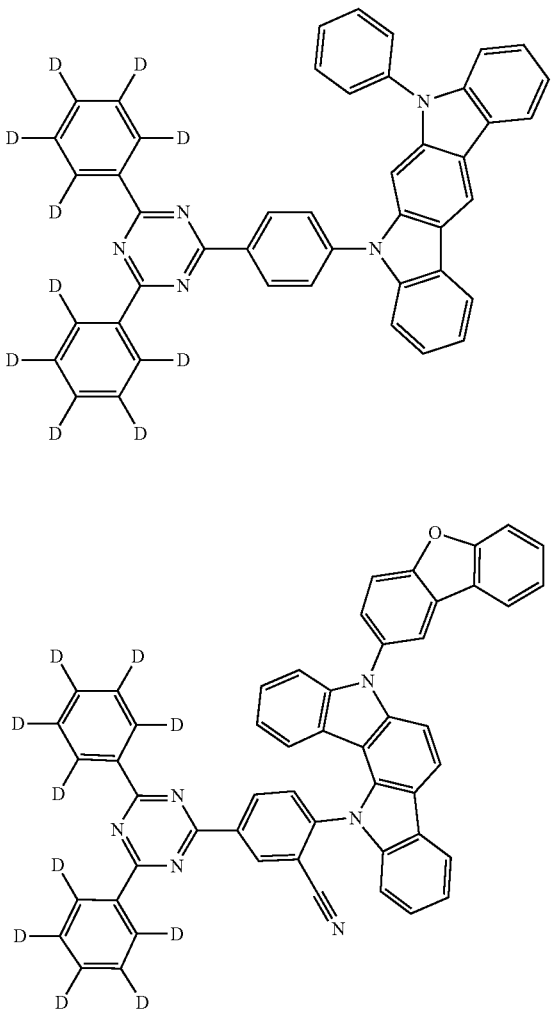

-continued
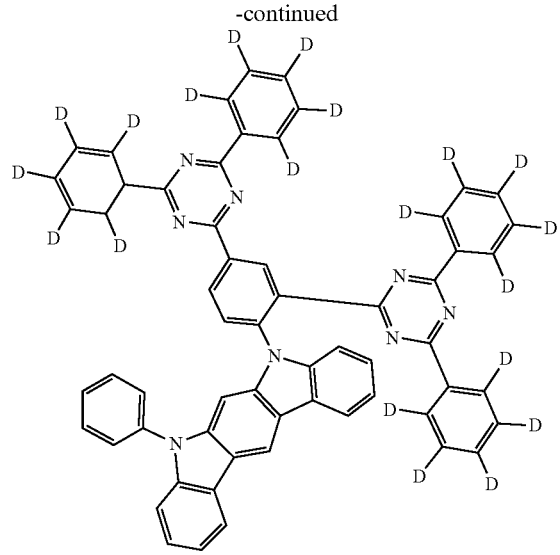
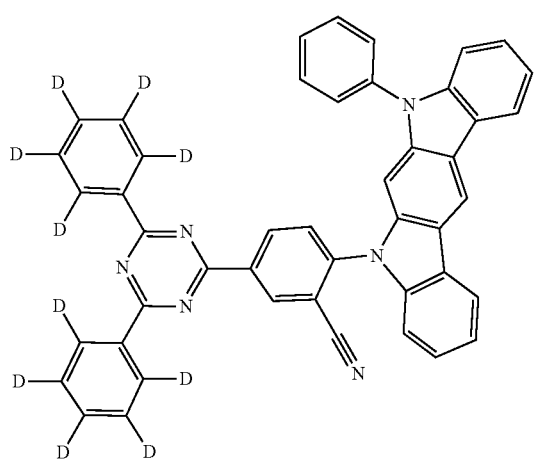
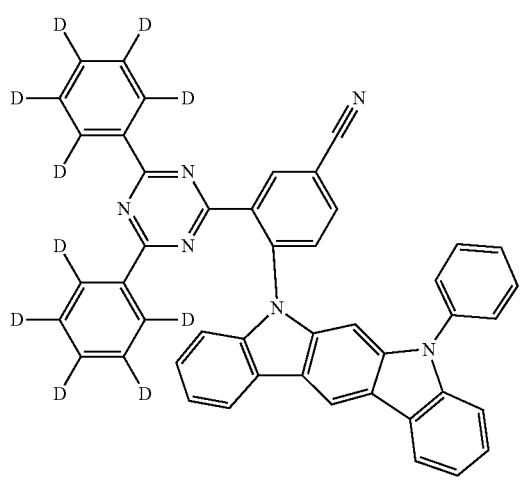
-continued
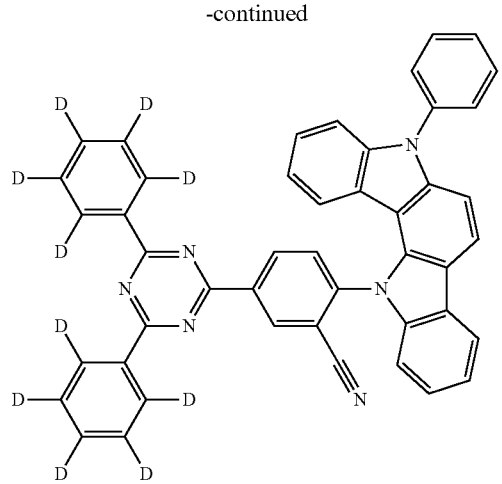
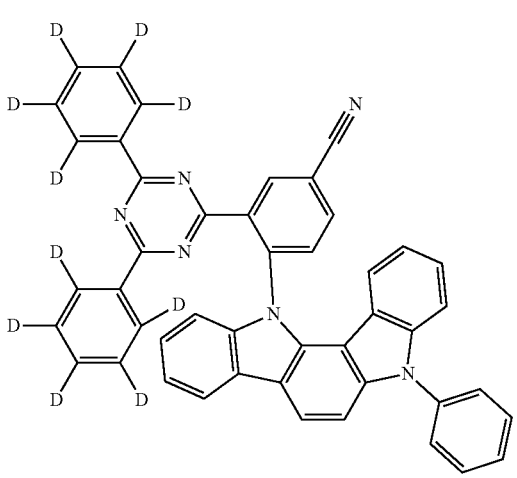
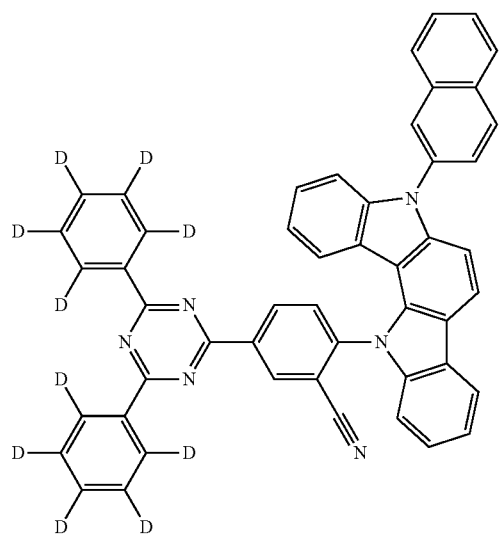

81
-continued
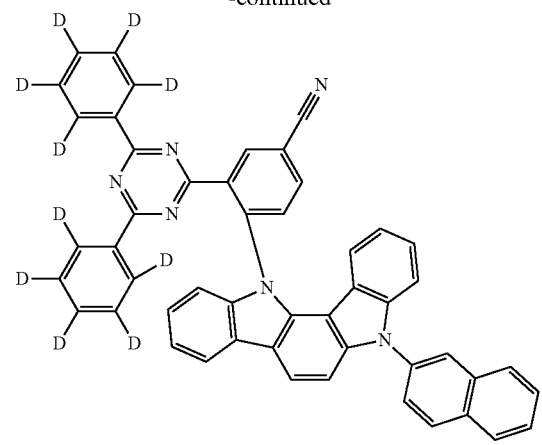
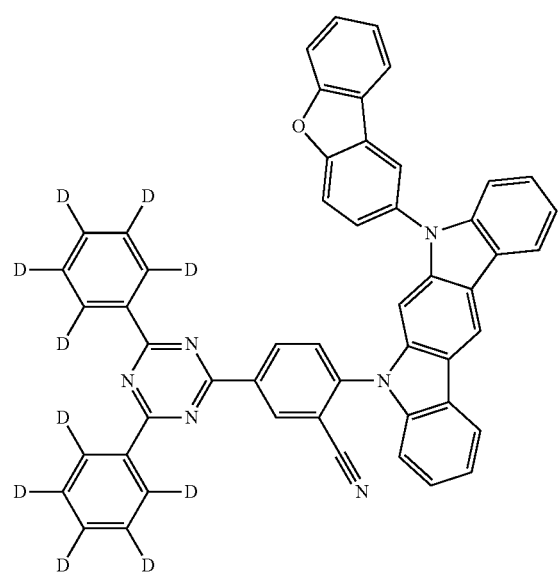
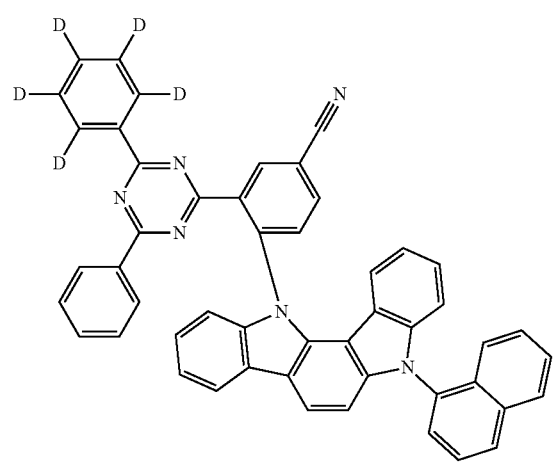
82
-continued
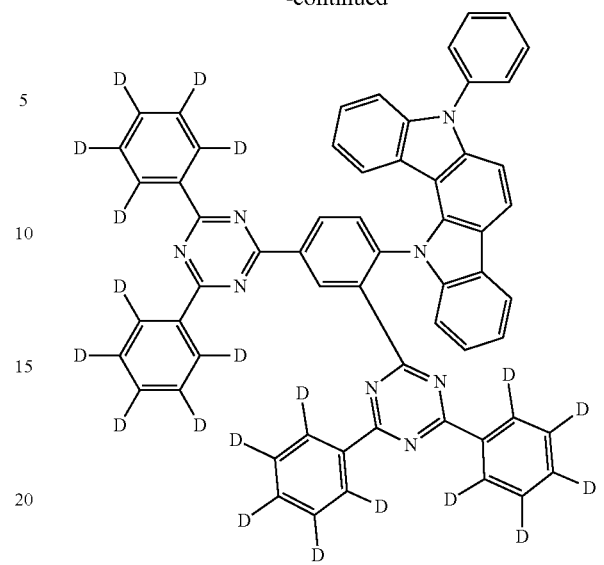
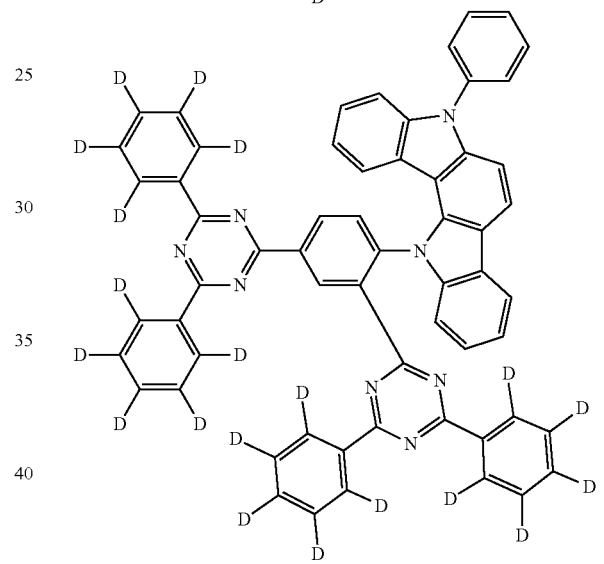
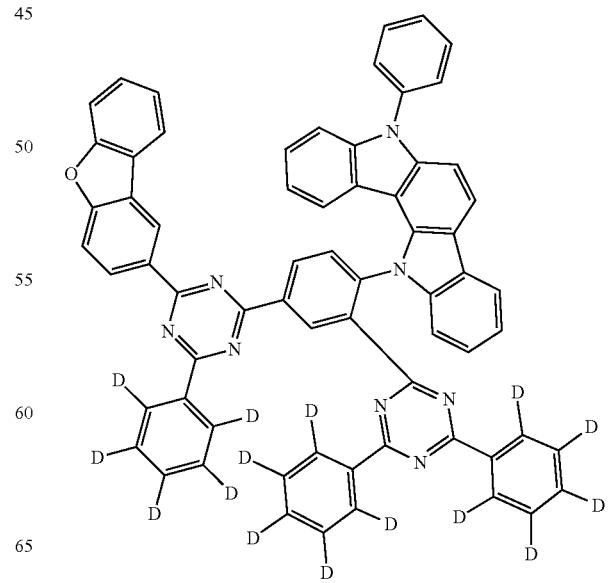

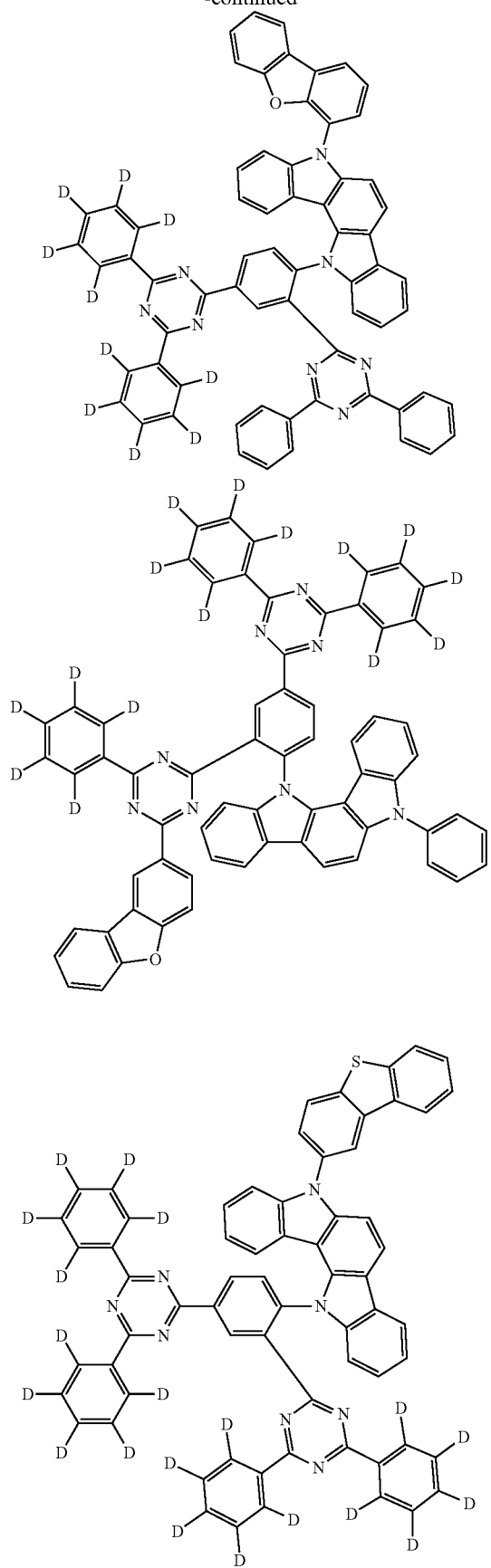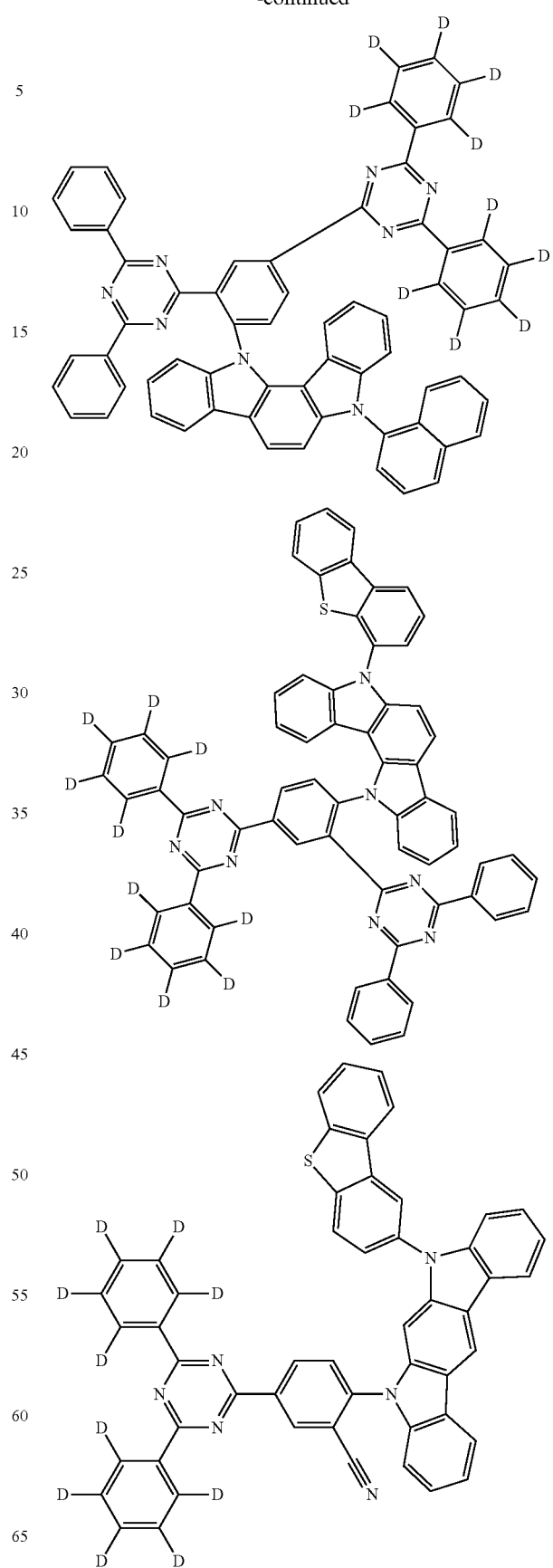

85
-continued
86
-continued
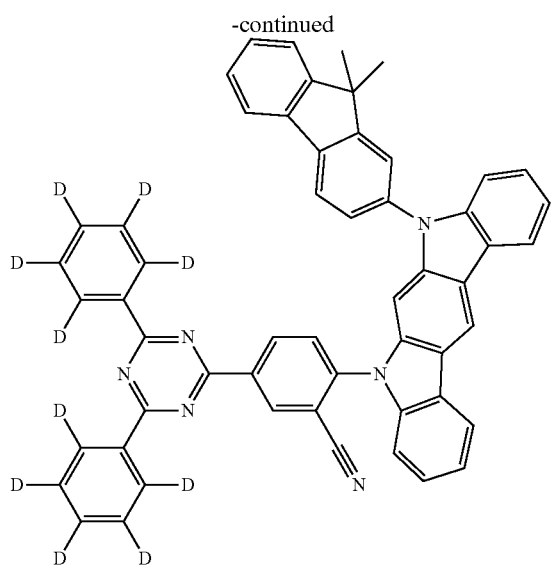
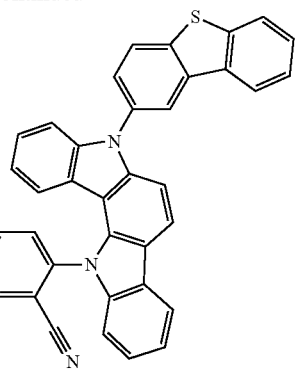
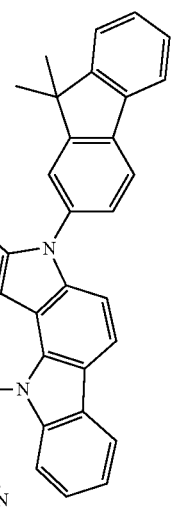
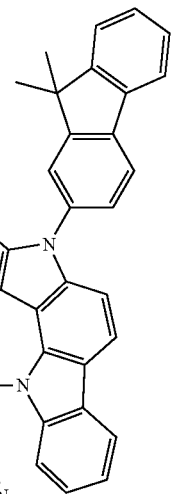

87
-continued
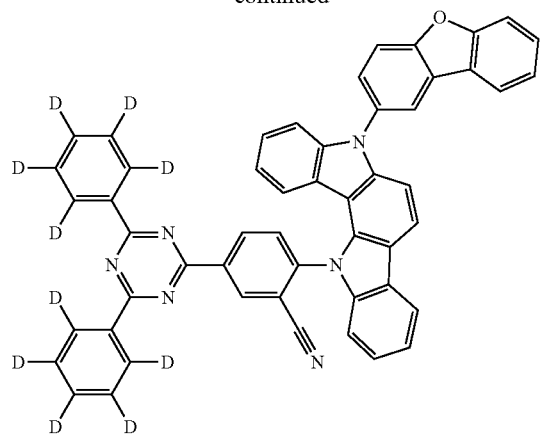
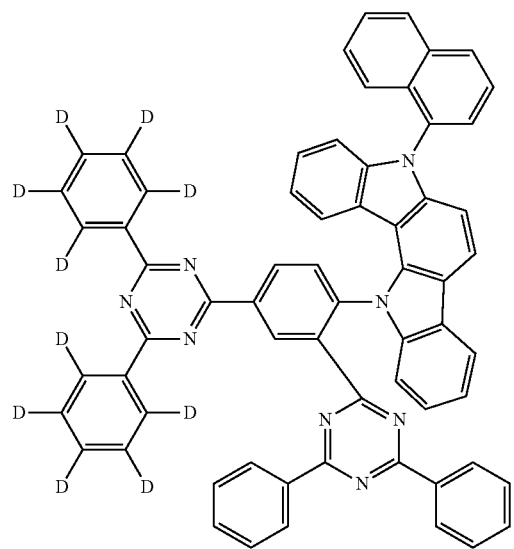
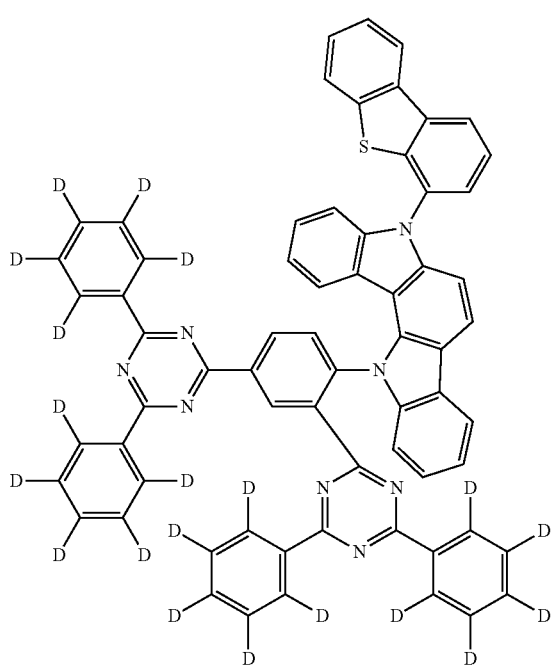
88
-continued
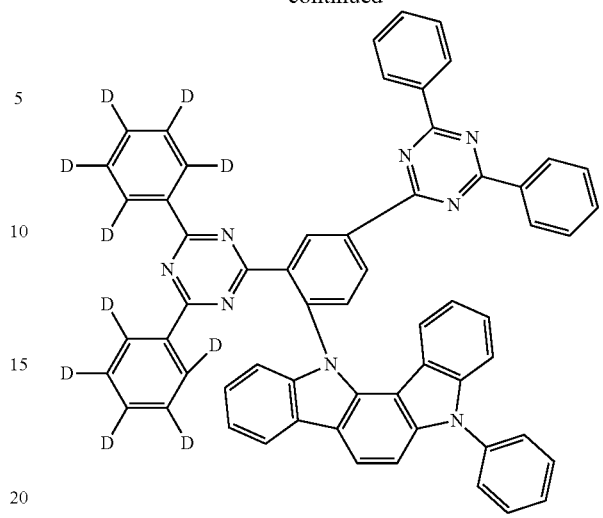
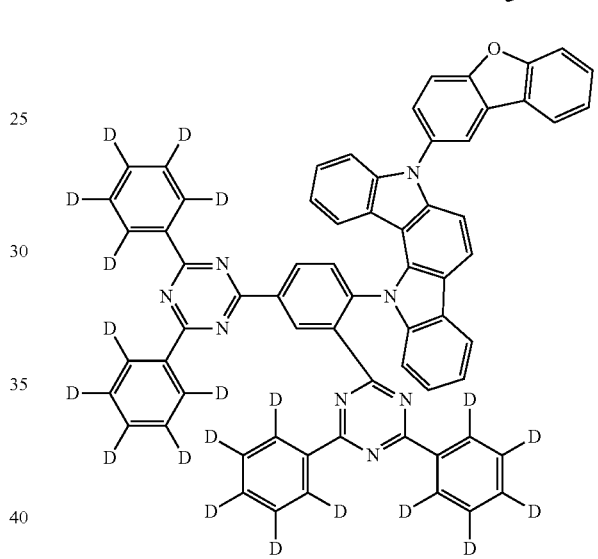
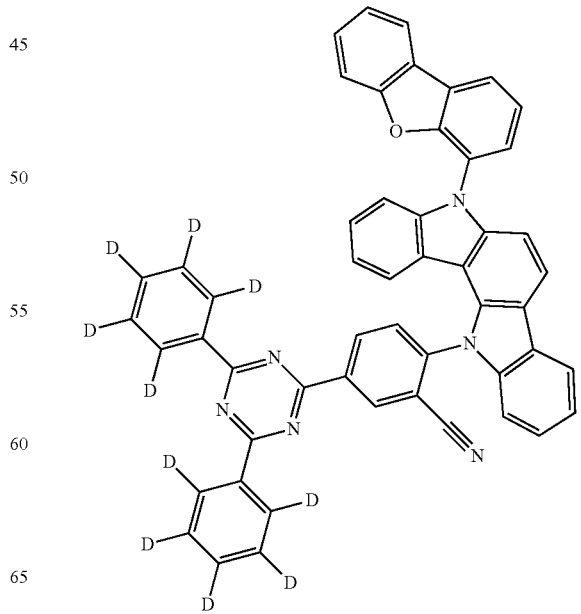

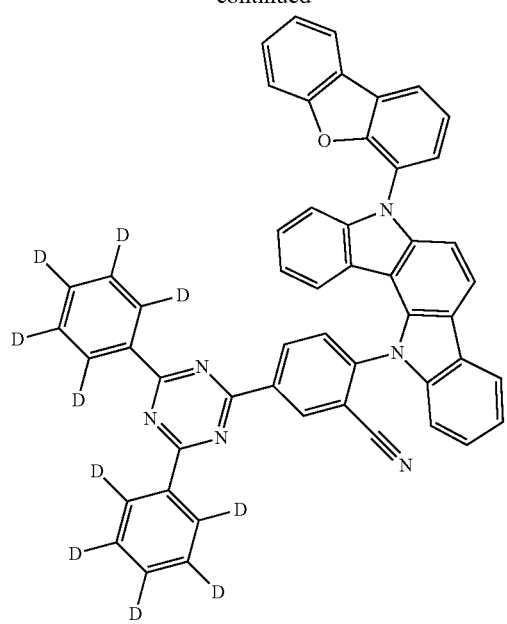
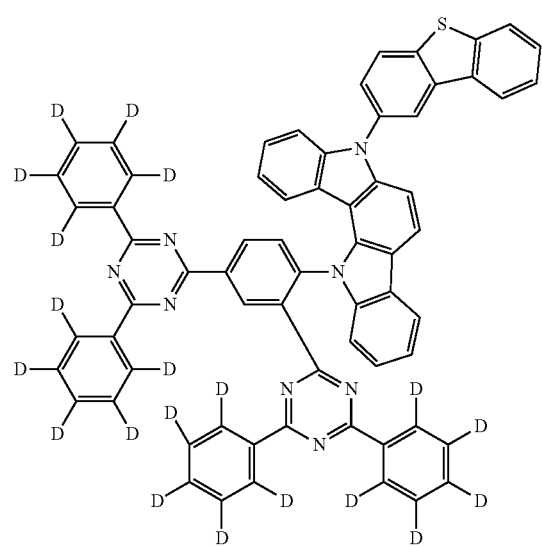
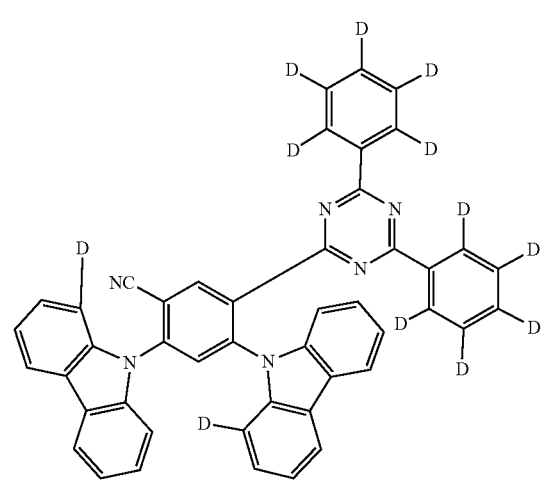
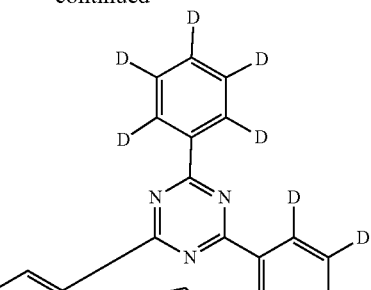
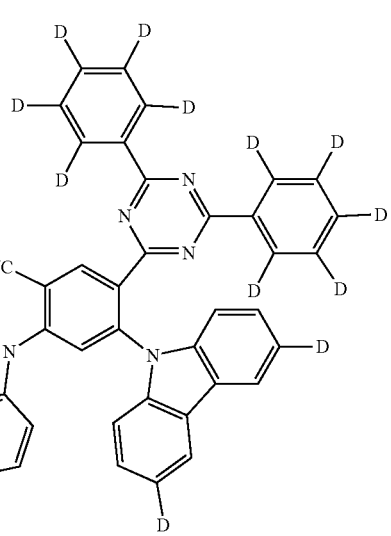
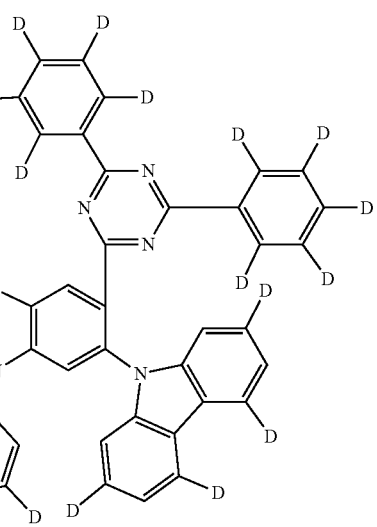

-continued
91
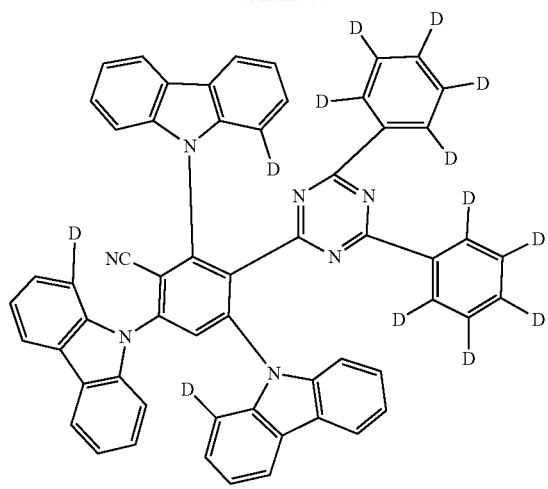
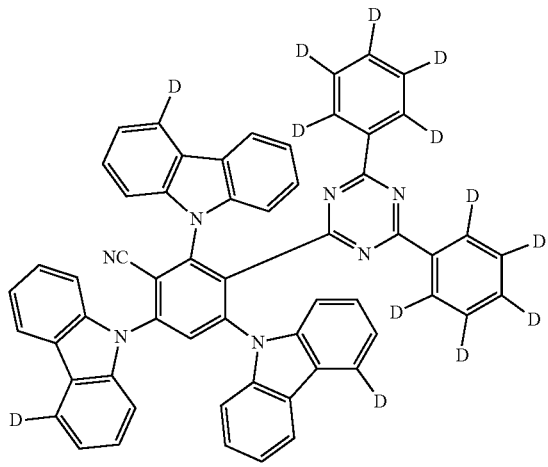
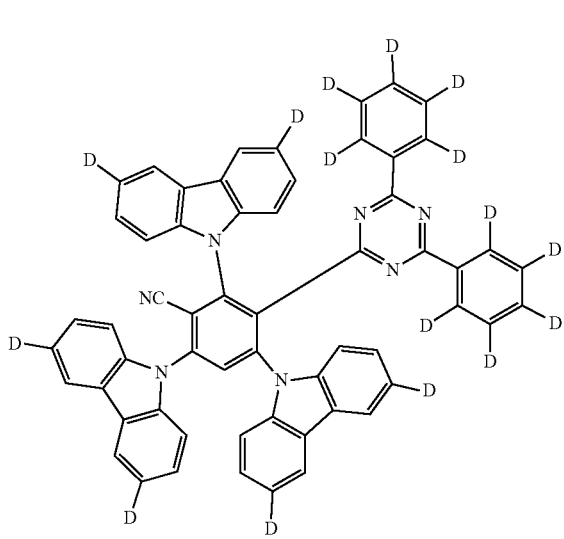
92
-continued
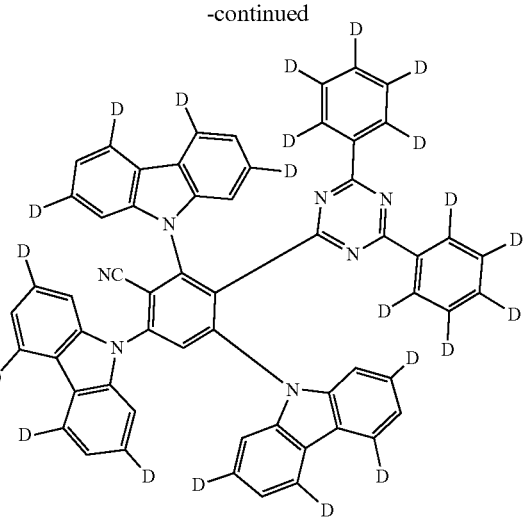
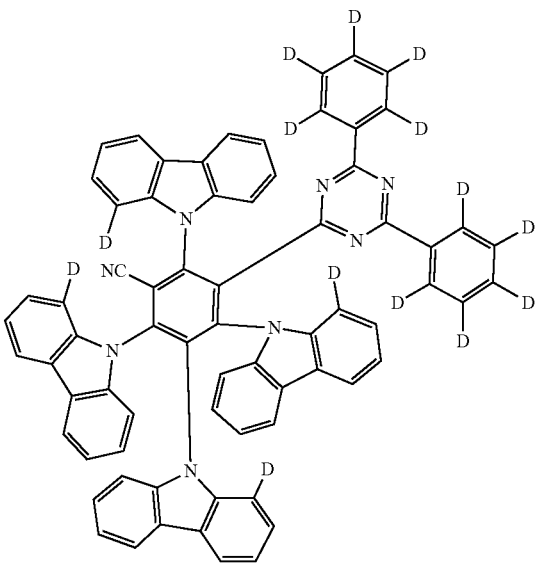
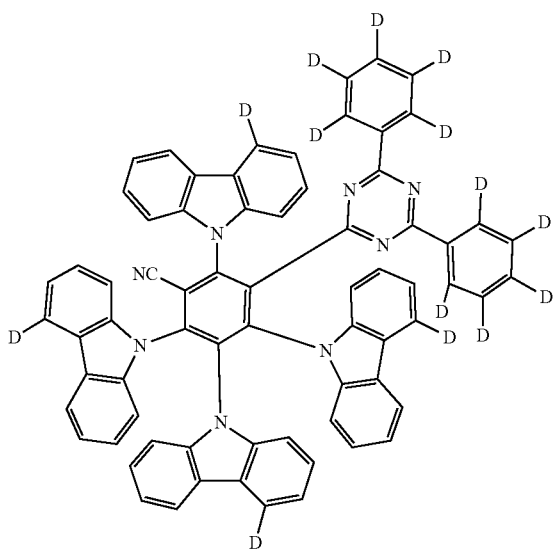

-continued
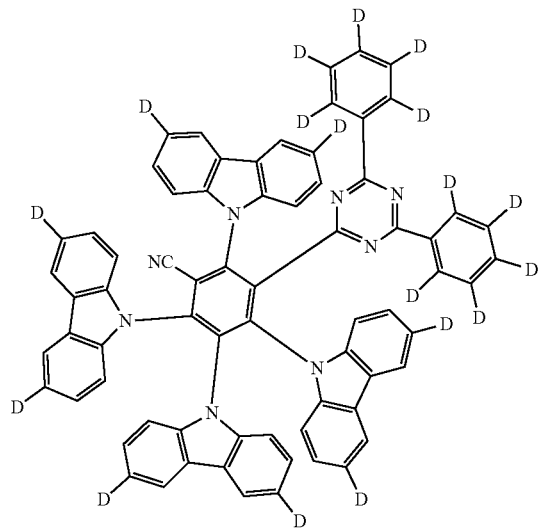
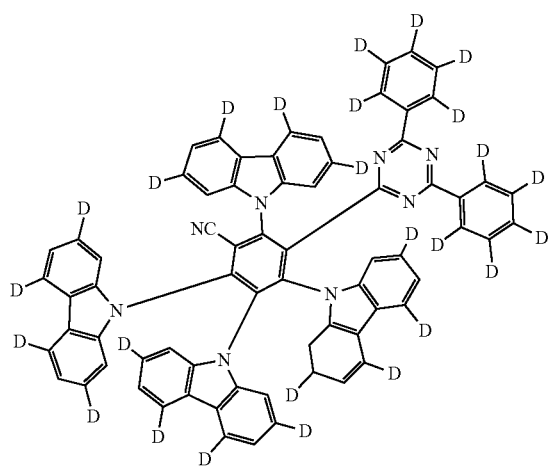
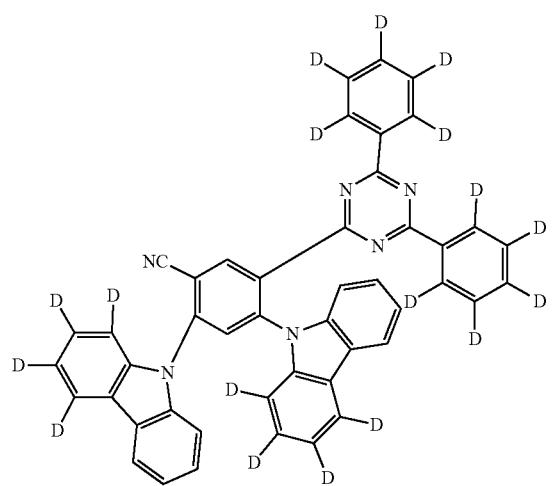
-continued
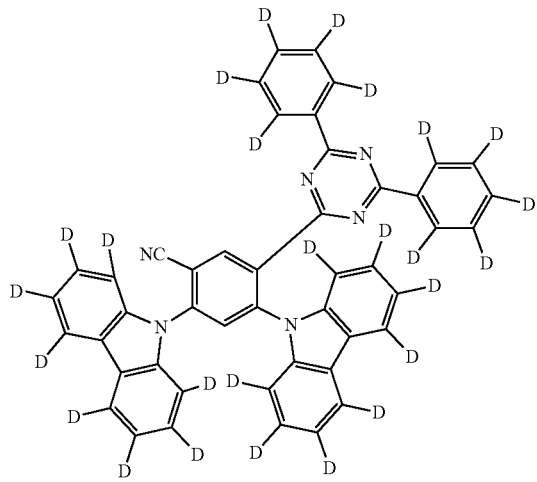
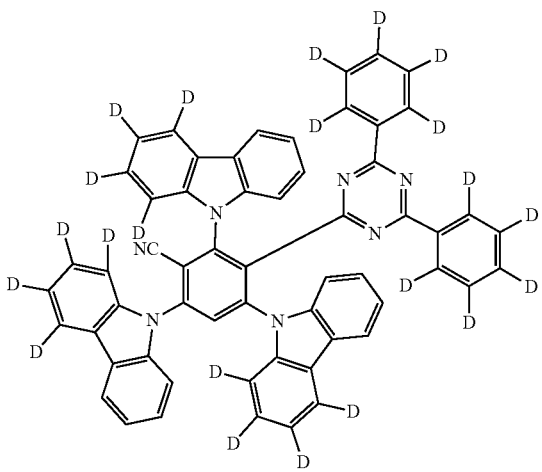
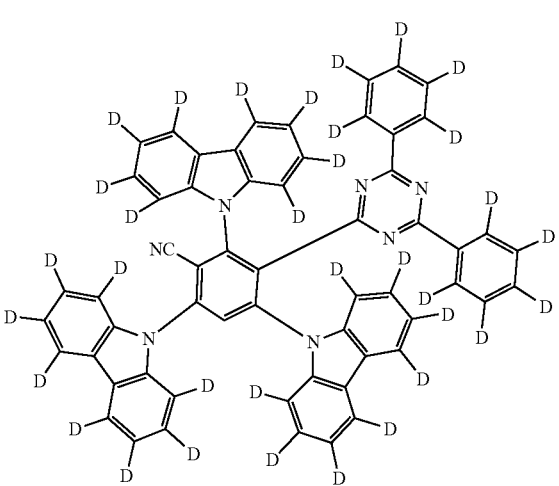

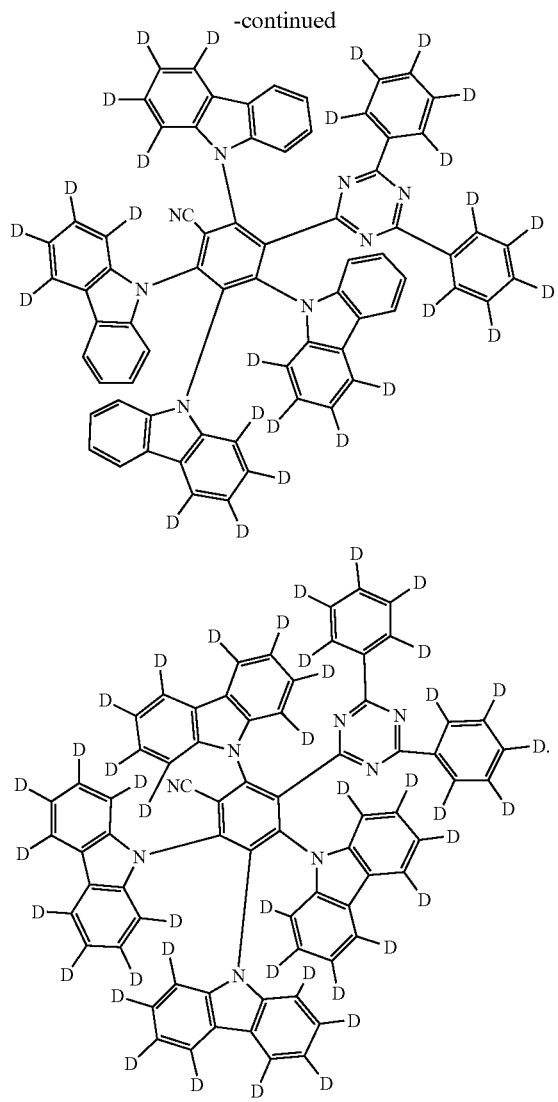

In an exemplary embodiment, the compound represented by Formula 1 is a fluorescent material.

In an exemplary embodiment, the compound represented by Formula 1 is a delayed fluorescent material.

In an exemplary embodiment, the compound represented by Formula 1 may be used as a green dopant of a light emitting layer.

An exemplary embodiment of the present specification provides an organic light emitting device including: a first electrode; a second electrode provided to face the first electrode; and a light emitting layer provided between the first electrode and the second electrode, in which the light emitting layer includes the above-described compound represented by Formula 1.

In an exemplary embodiment, the light emitting layer may also be composed of only the above-described compound represented by Formula 1, and may further include other materials in addition to the compound represented by Formula 1. In an exemplary embodiment, the compound represented by Formula 1 may also be used as a host, and may also be used with other host materials to serve as a dopant. In an exemplary embodiment, the compound represented by Formula 1 may also receive holes and electrons through the host to produce excitons, and may also directly receive holes and electrons from layers adjacent to a light emitting layer to produce excitons without passing through the host. How-ever, the role of the compound represented by Formula 1 in the light emitting layer is not limited thereto, and may contribute to improvement in characteristics of the device in various ways according to the combination of the compounds included in the light emitting layer.

An exemplary embodiment of the present specification includes: a first electrode; a second electrode provided to face the first electrode; and a light emitting layer provided between the first electrode and the second electrode, and the light emitting layer includes the compound represented by Formula 1 as a dopant, and further includes a host.

In an exemplary embodiment, the mechanism by which light emission may occur in the light emitting layer is not limited, and may vary depending on the compound used in the light emitting layer.

In an exemplary embodiment, holes and electrons move to the compound (dopant) represented by Formula 1 through a host, excitons are produced at a ratio of 3:1 for the triplet and the singlet in the dopant, and then excitons produced for the triplet of the dopant are transferred to the singlet of the dopant to emit light, and excitons produced for the singlet may emit light as it is at the singlet. In another exemplary embodiment, a host acting only as a matrix material is included in the light emitting layer, and holes; electrons; or holes and electrons are injected into the dopant without passing through the host, and thus, excitons may also be formed at the triplet and the singlet. However, this is merely an example of the light emission mechanism, and light emission may occur by other different light emission mechanisms.

In an exemplary embodiment, the light emitting layer includes the compound represented by Formula 1 as a dopant.

In an exemplary embodiment, the emission wavelength of the compound represented by Formula 1 is 500 nm to 565 nm.

In an exemplary embodiment, the difference ($\Delta ST_D$) between the singlet energy level ($S1_D$) and the triplet energy level ($T1_D$) of the compound represented by Formula 1 is 0 eV to 0.3 eV; preferably 0 eV to 0.2 eV.

In the present specification, the difference ($\Delta ST_D$) between the singlet energy level ($S1_D$) and the triplet energy level ($T1_D$) of the compound represented by Formula 1 means an absolute value of $T1_D-S1_D$.

When the difference ($\Delta ST_D$) between the singlet energy level ($S1_D$) and the triplet energy level ($T1_D$) of the compound represented by Formula 1 satisfies the above range, the ratio and speed at which the excitons produced at the triplet move to the singlet due to the reverse intersystem crossing (RISC) are increased, and thus the time for excitons to stay at the triplet is reduced, so that there is an advantage in that the efficiency and service life of the organic light emitting device are increased.

In an exemplary embodiment, the host has the triplet energy level ($T1_H$) of 2.4 eV or more.

In an exemplary embodiment, the host has the singlet energy level ($S1_H$) of 2.1 eV to 2.8 eV.

In an exemplary embodiment, the triplet energy level ($T1_H$) of the host is higher than the triplet energy level ($T1_D$) of the compound represented by Formula 1.

In an exemplary embodiment, the singlet energy level ($S1_H$) of the host is higher than the singlet energy level ($S1_D$) of the compound represented by Formula 1, and when the energy relationship is satisfied, it is possible to prevent excitons of the dopant from reversely moving back to the host.

In an exemplary embodiment, the host may be dibenzofuran; a dibenzofuran derivative; dibenzothiophene; or a dibenzothiophene derivative.

In an exemplary embodiment, the host is at least one selected from the structures.

97 98
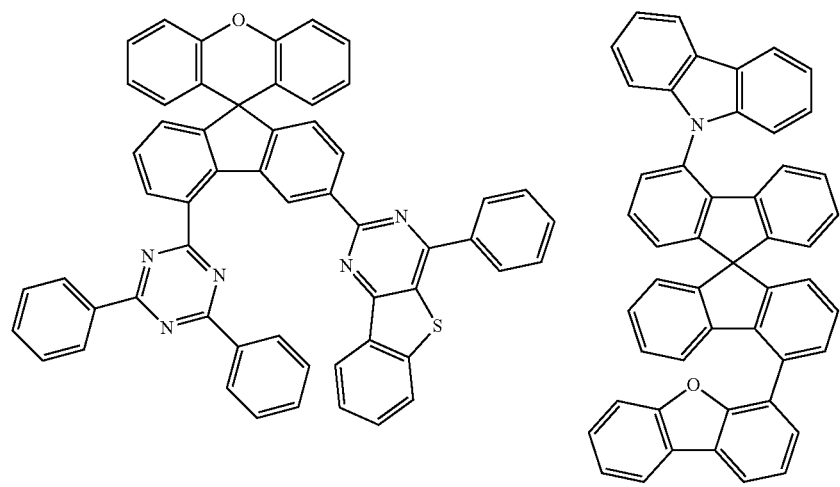
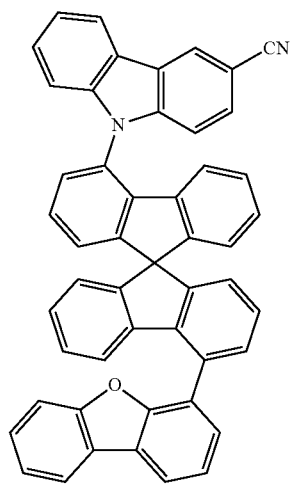
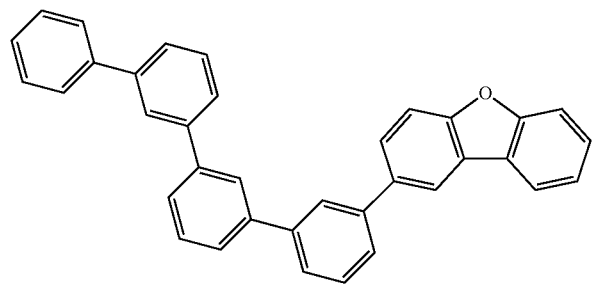
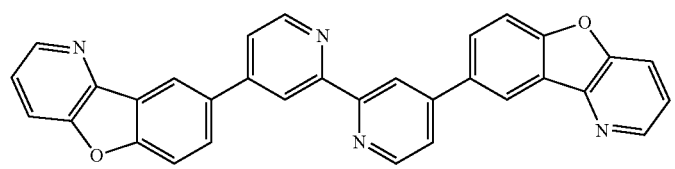
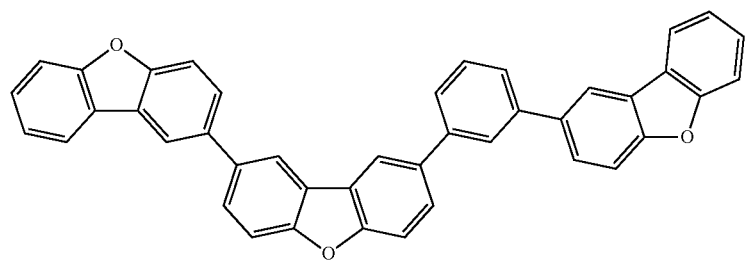
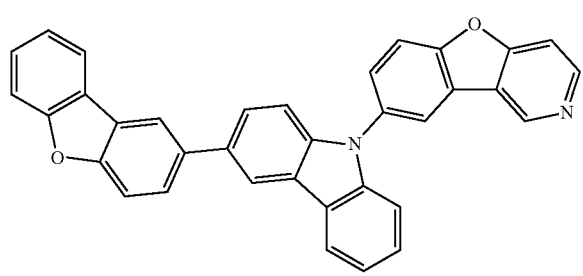
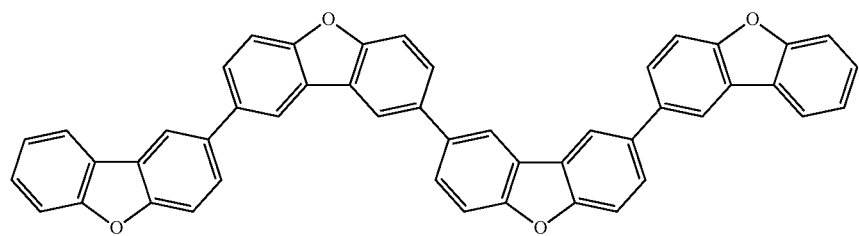

-continued
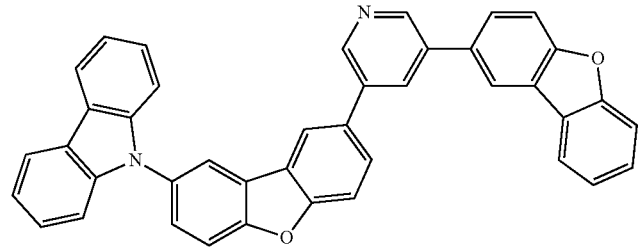
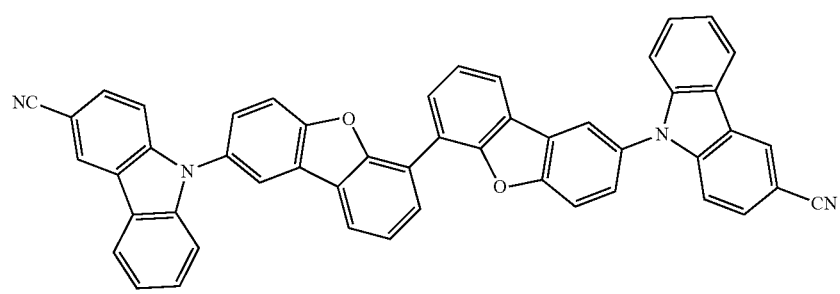
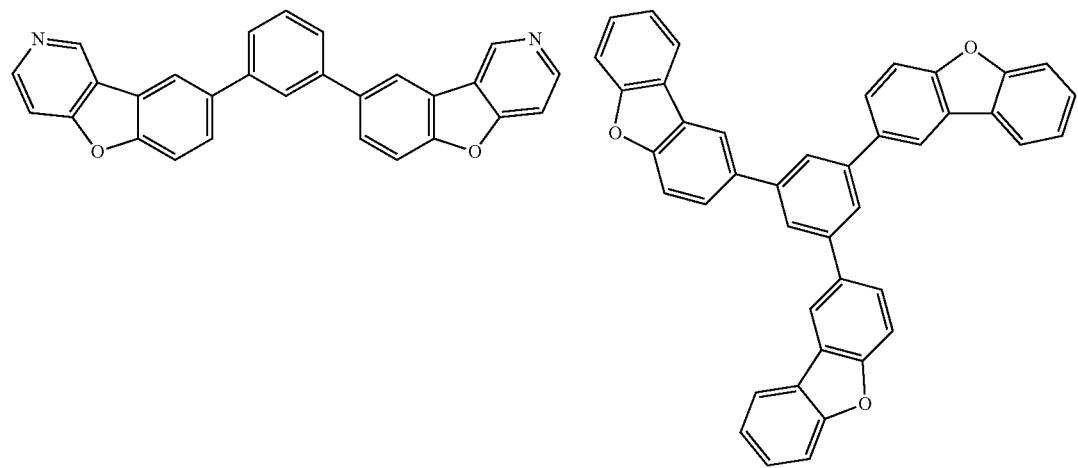
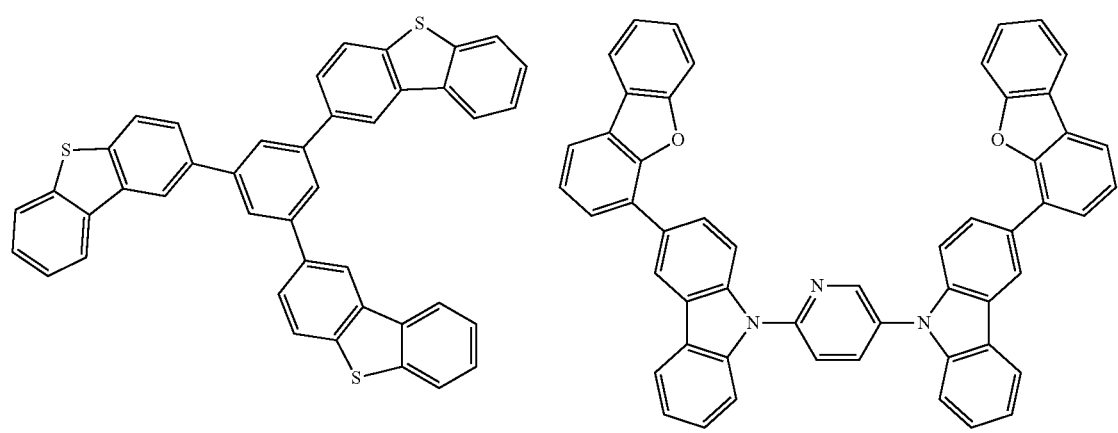

-continued
101
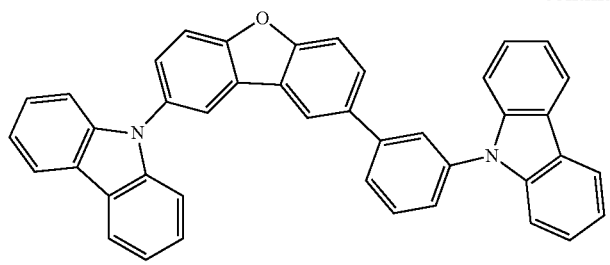
102
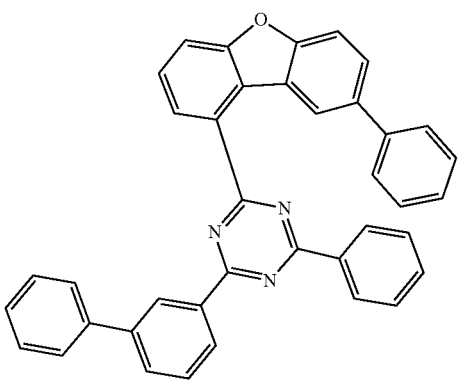
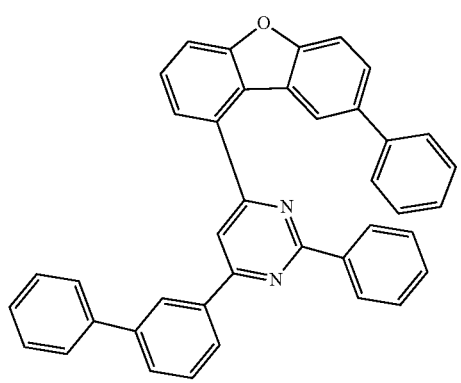
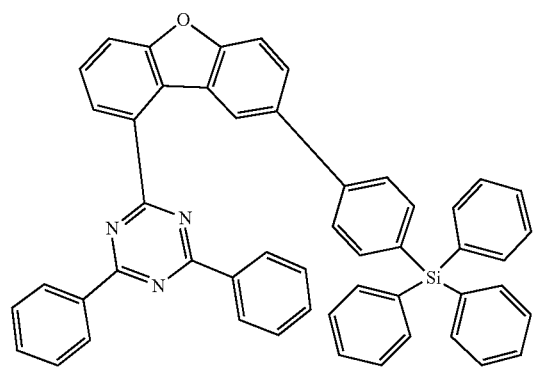
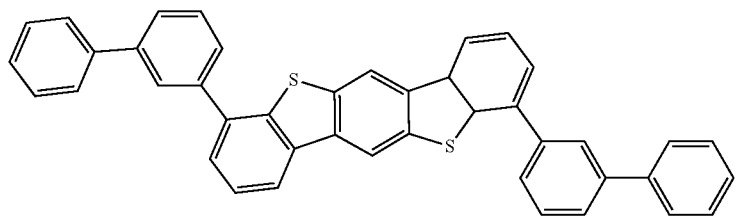
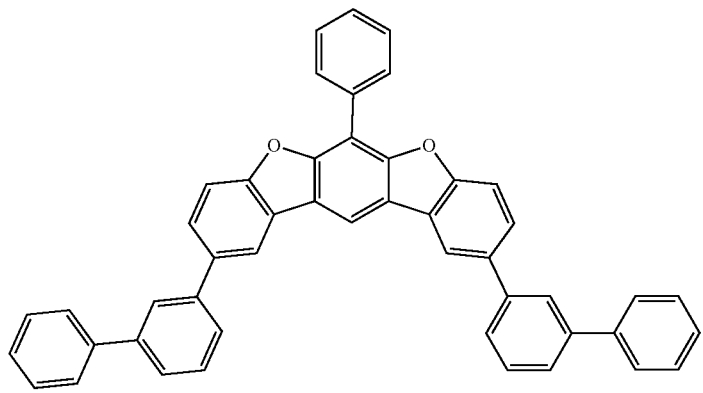

-continued
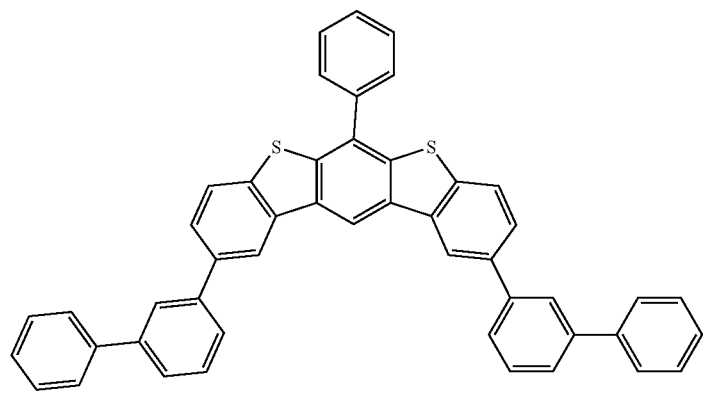
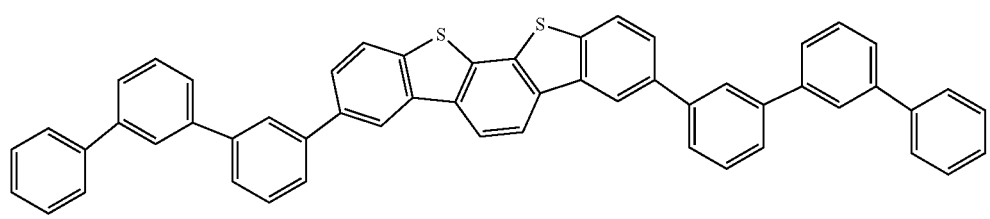
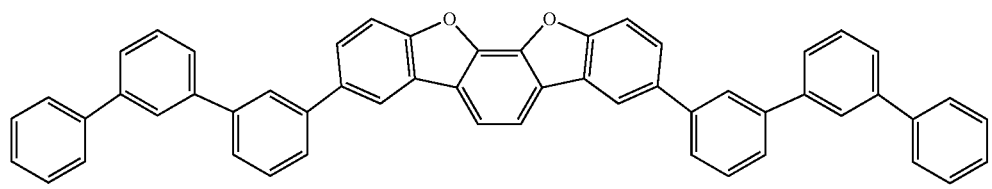
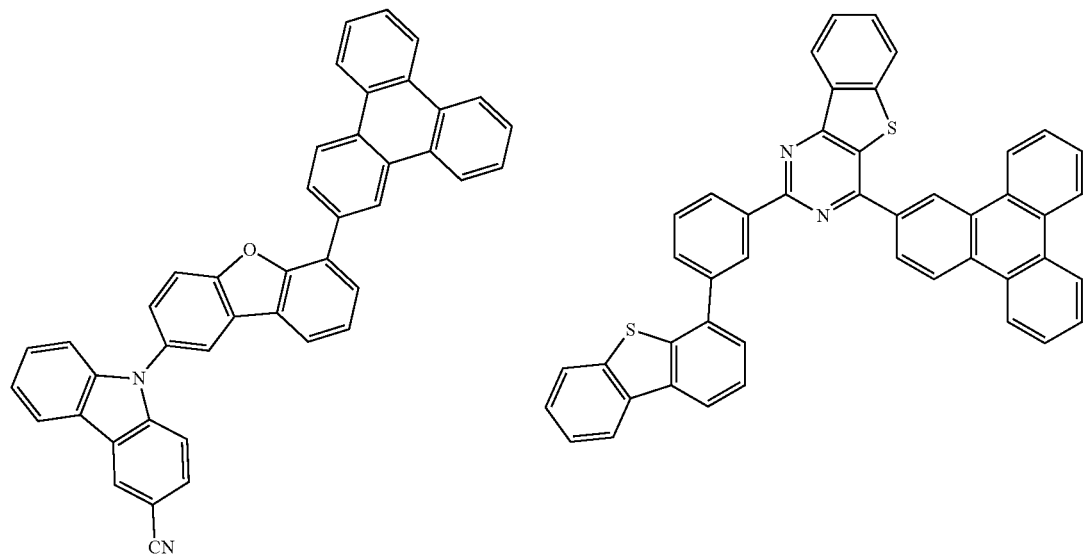

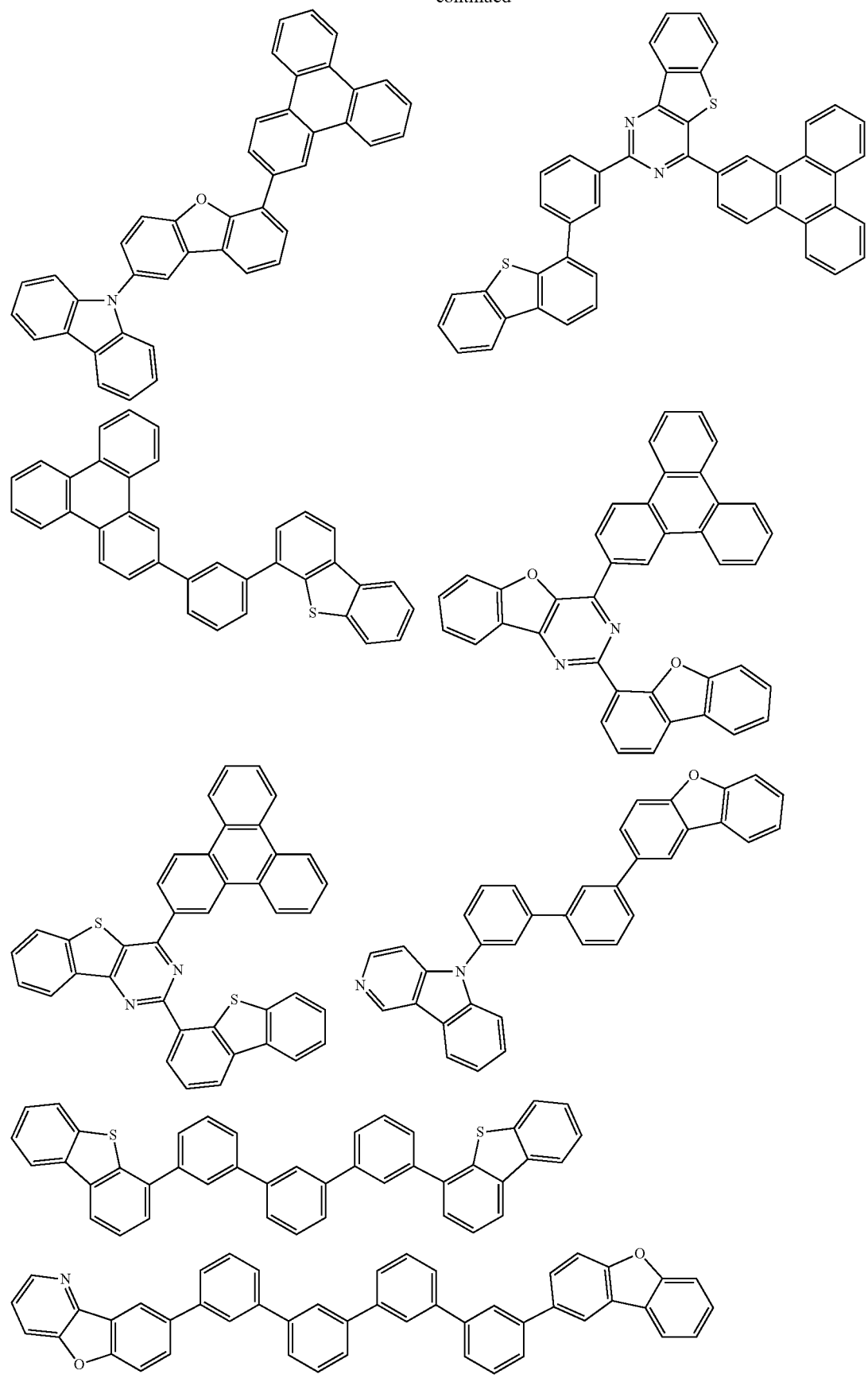

-continued
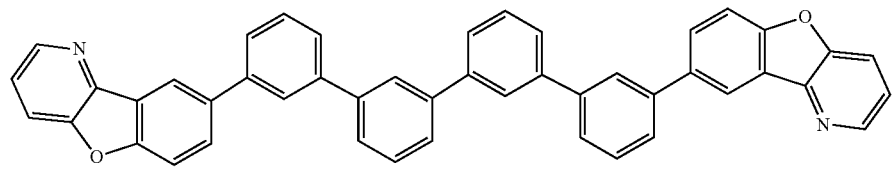
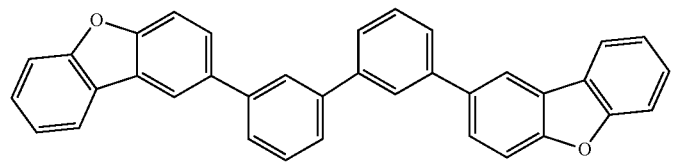
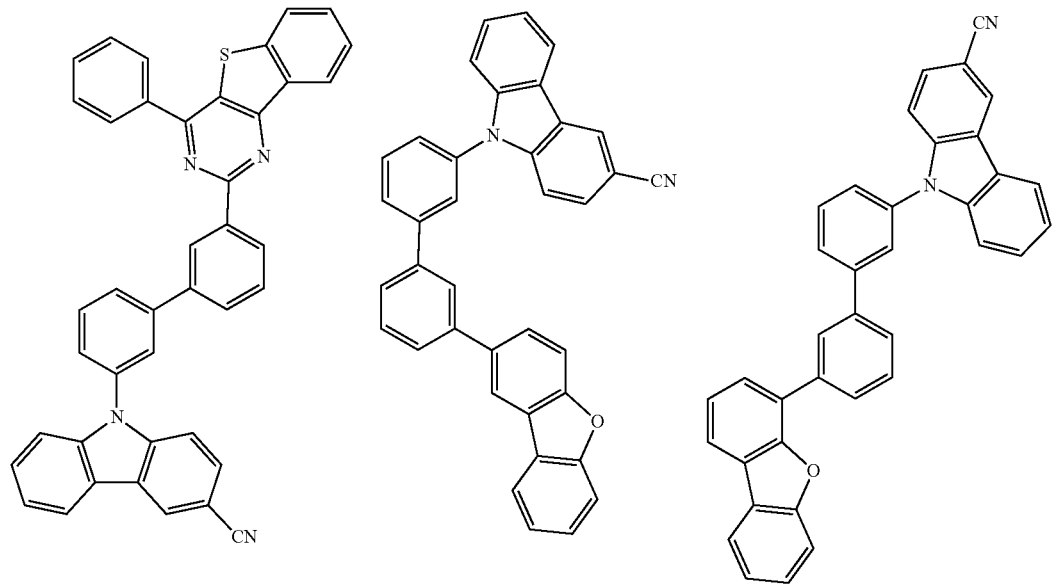
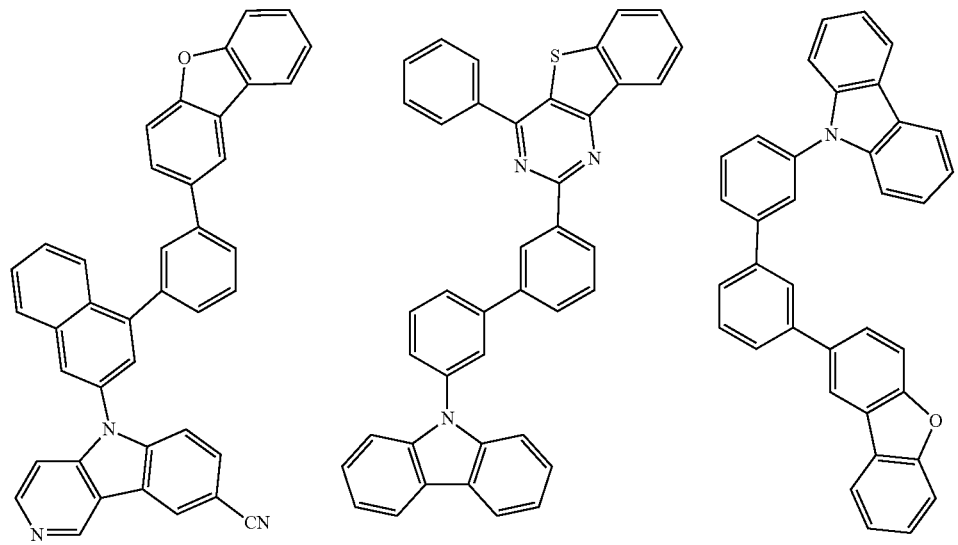

109 -continued 110
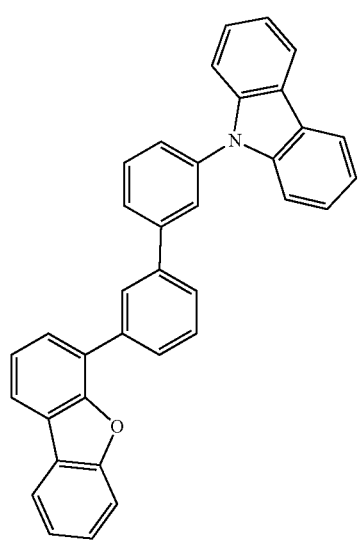
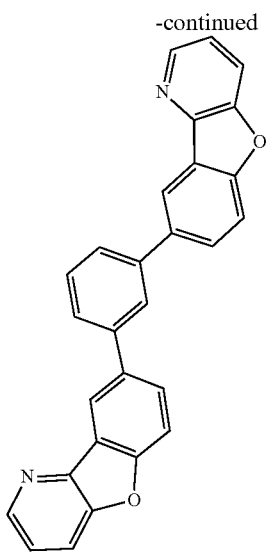
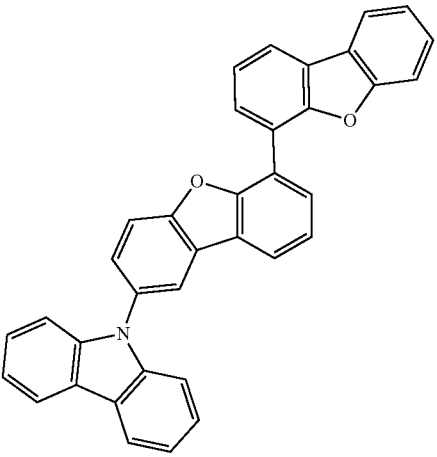
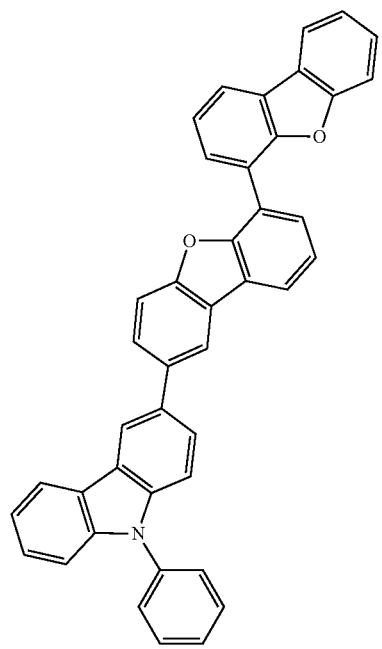
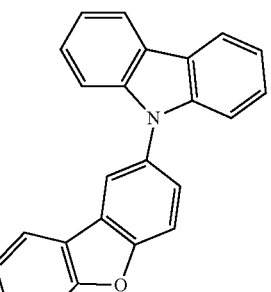
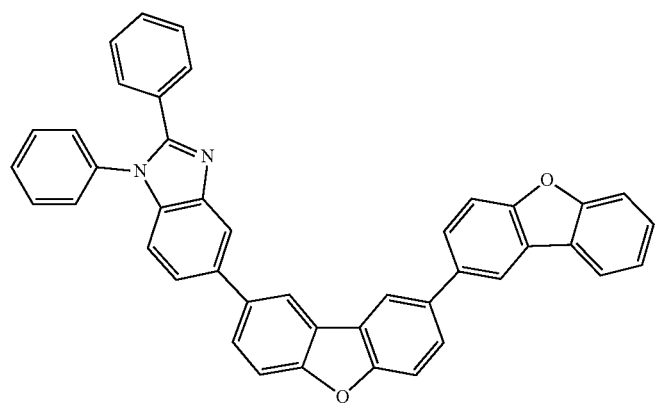

-continued
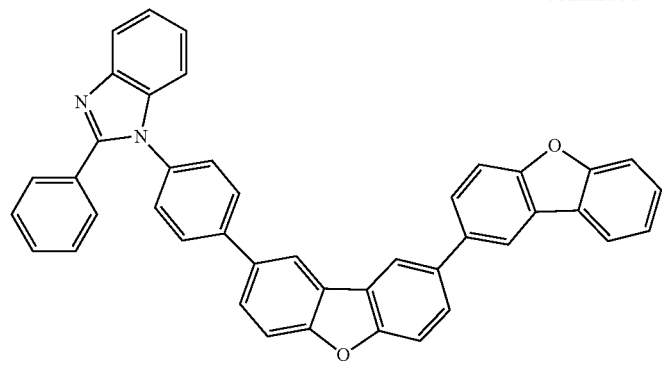
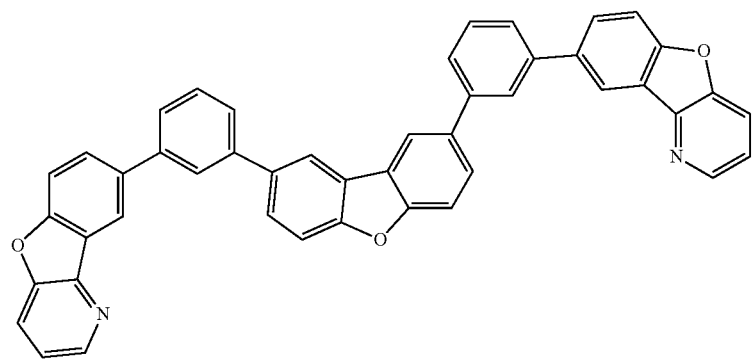
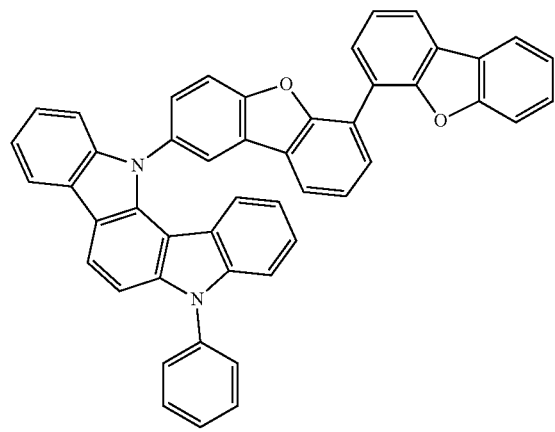
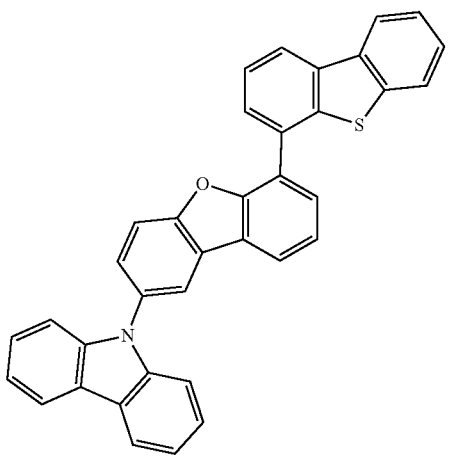
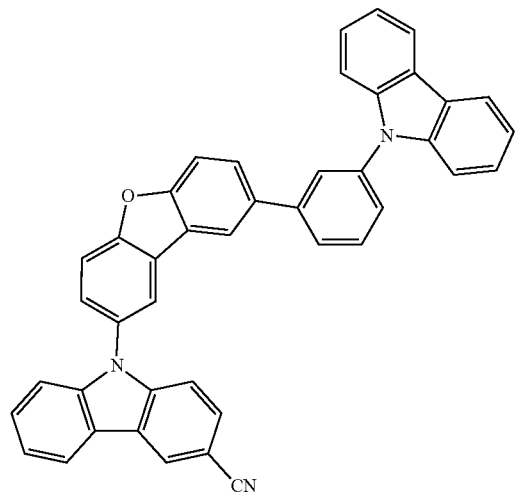
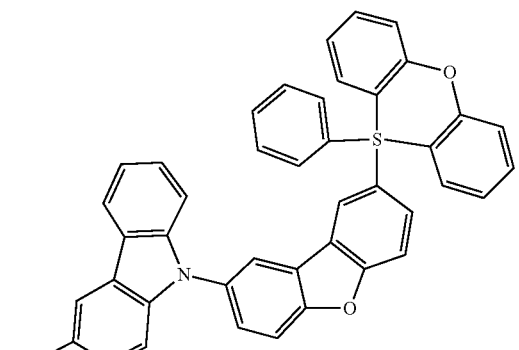

-continued
113
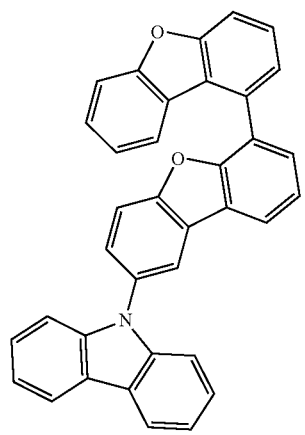
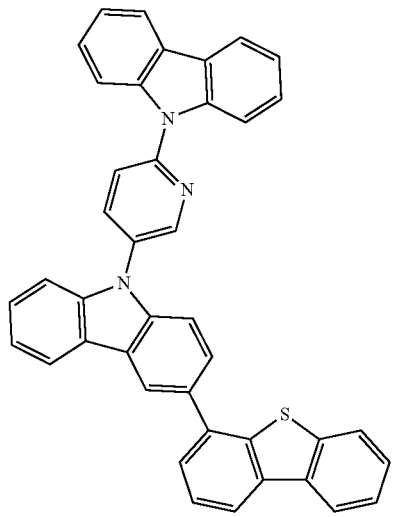
114
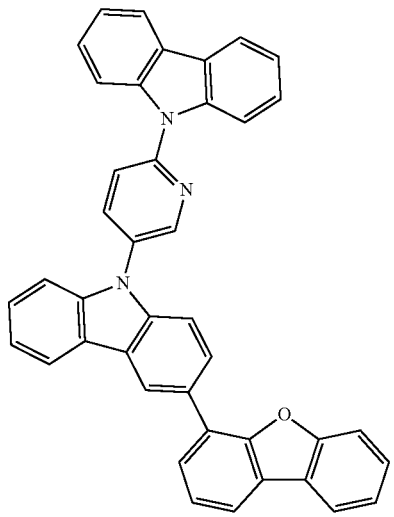
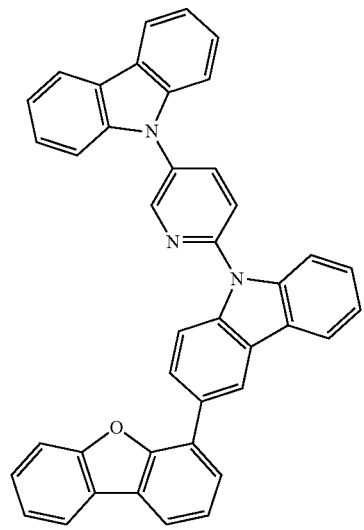
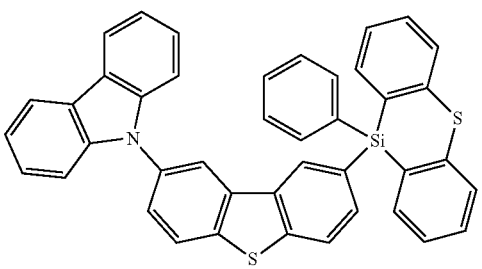
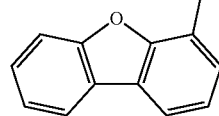
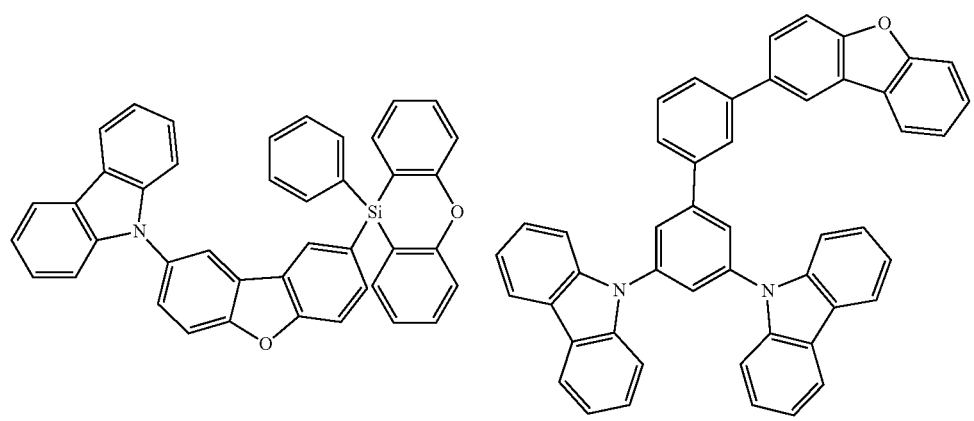

-continued
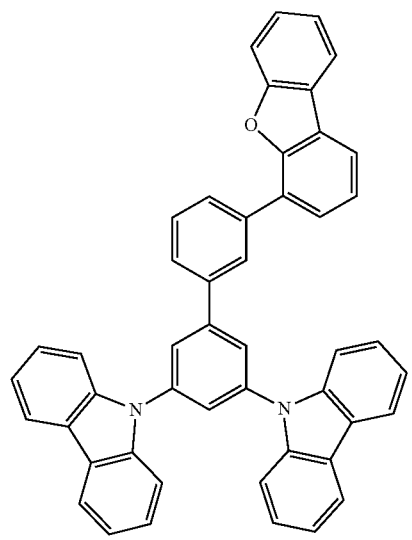
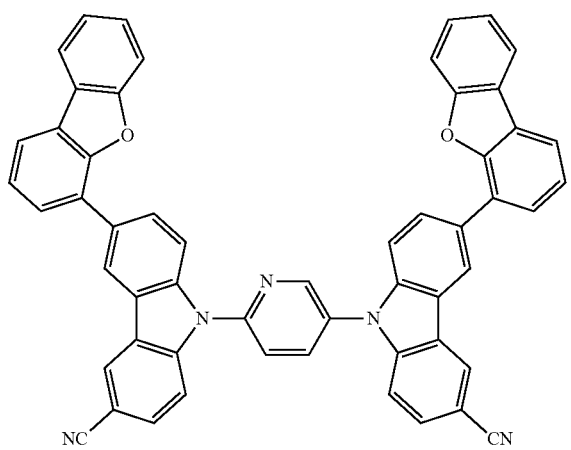
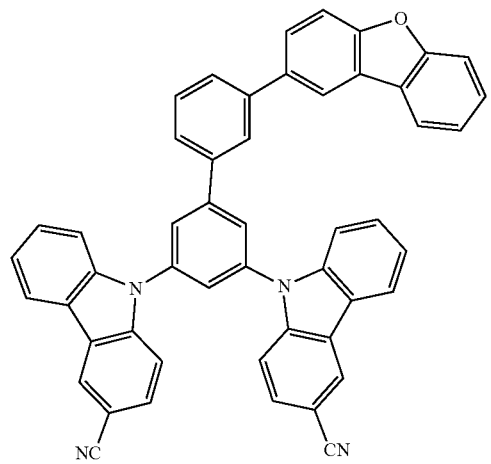
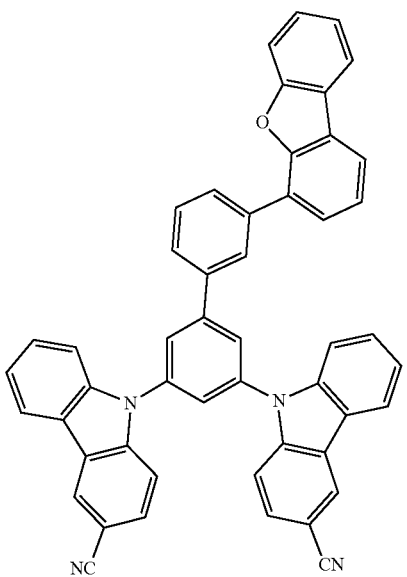
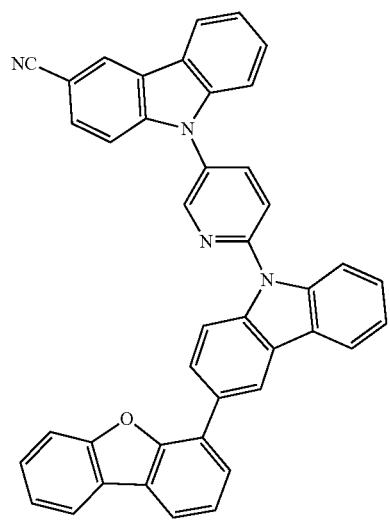
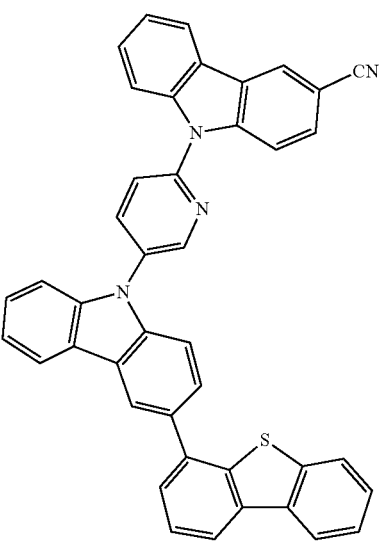

-continued
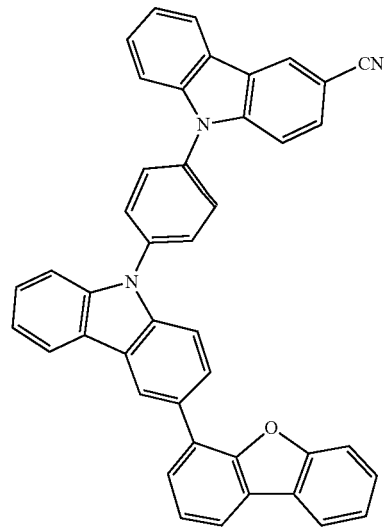
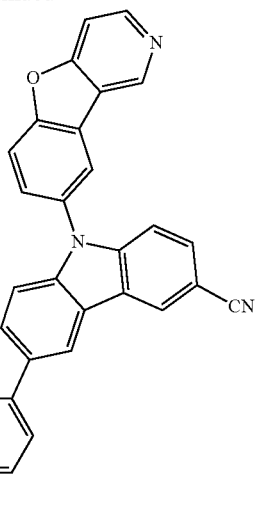
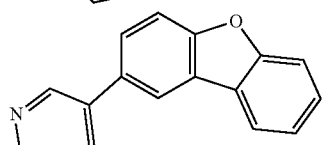
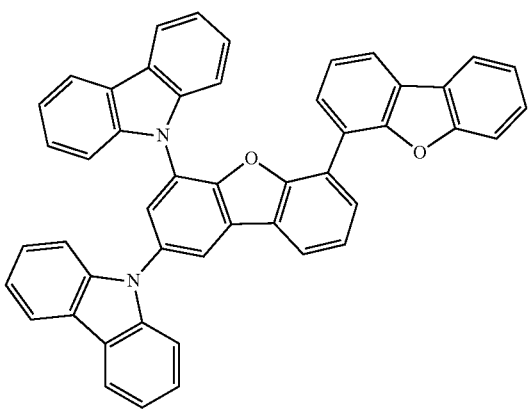
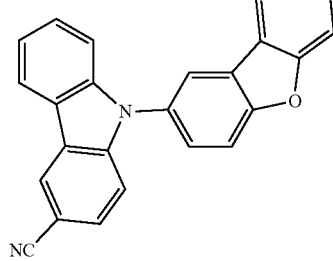
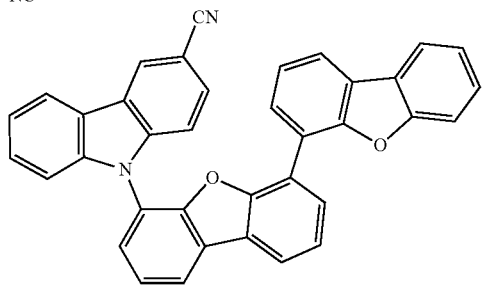
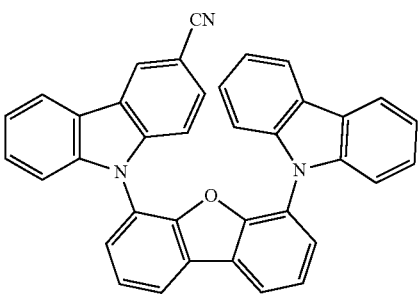
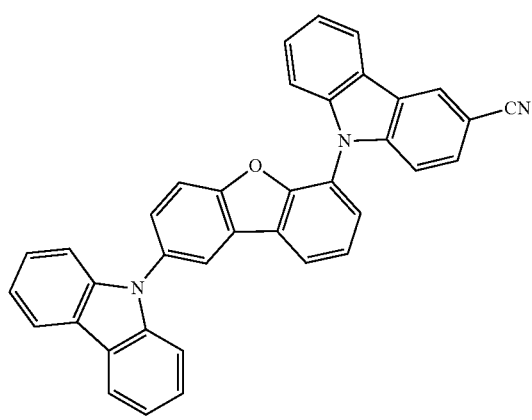
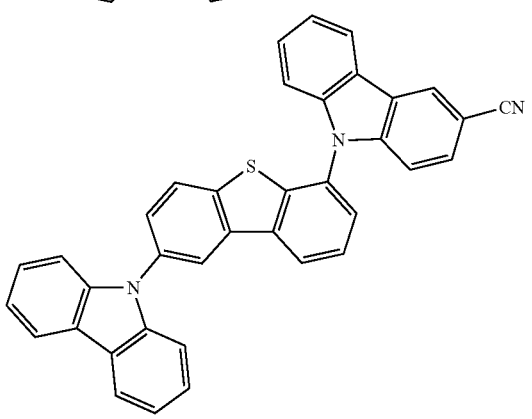

119
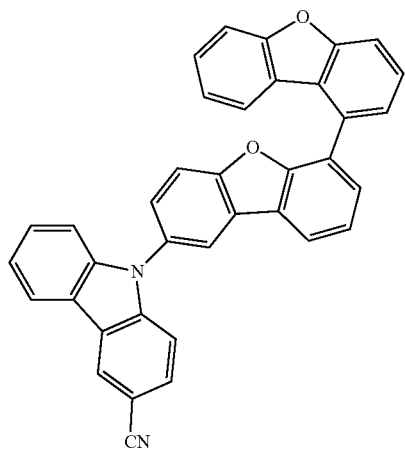
120
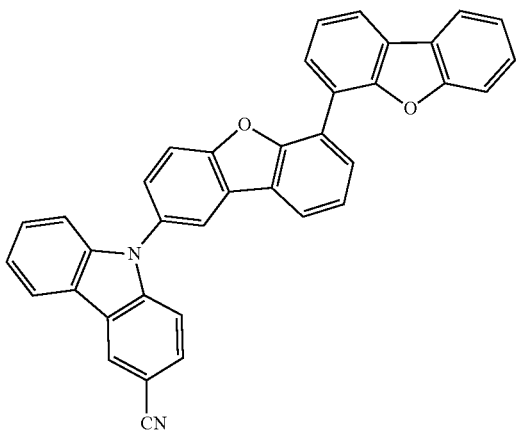
-continued
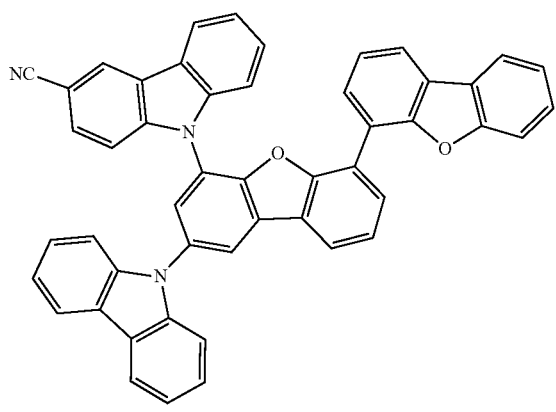
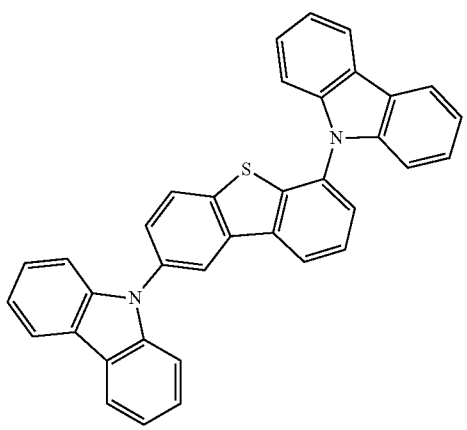
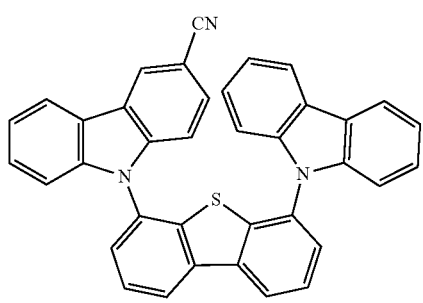
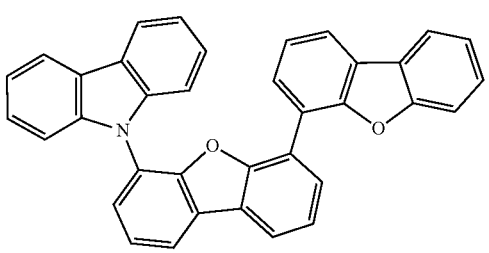
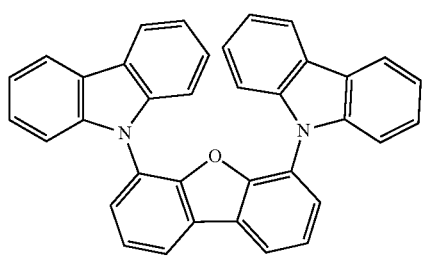
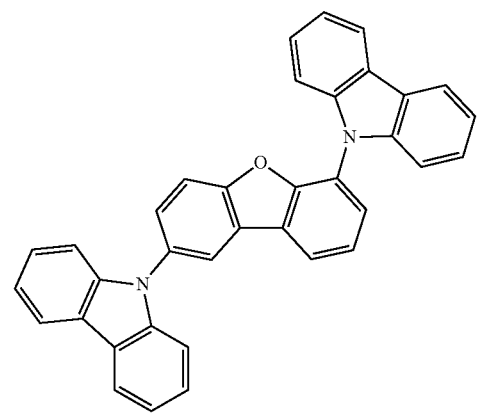

-continued

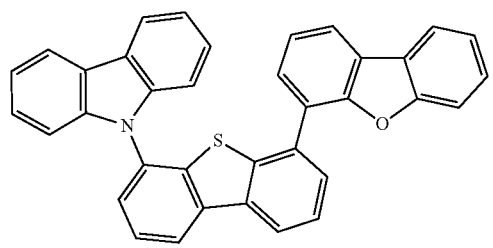
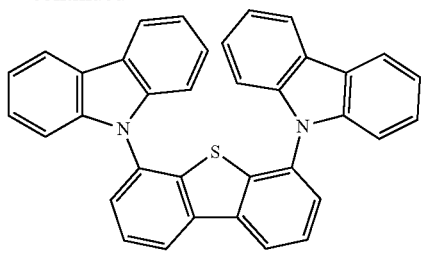
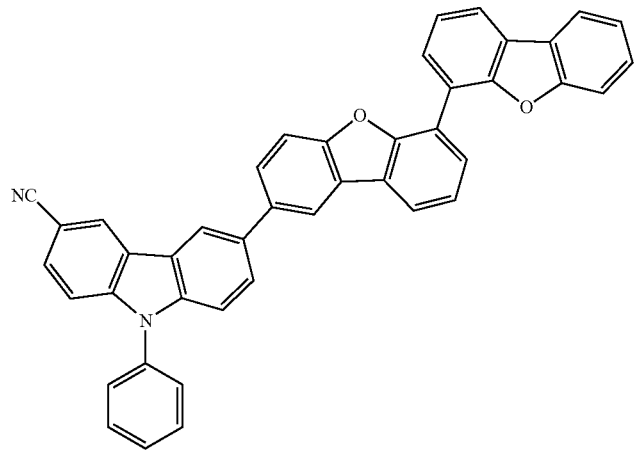
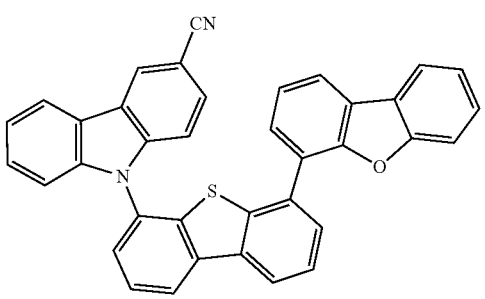
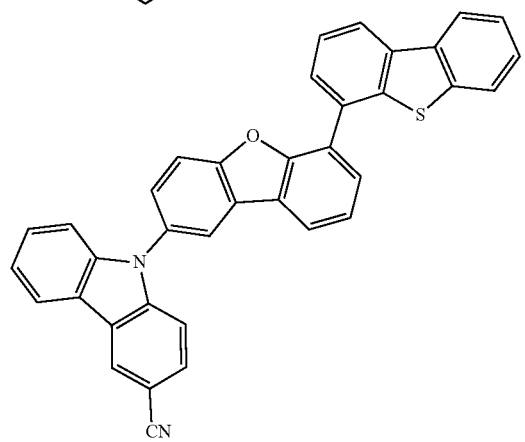
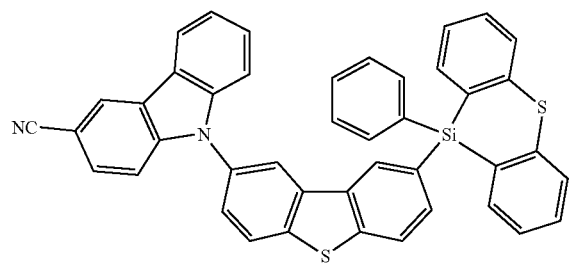

In an exemplary embodiment, a light emitting layer including the compound represented by Formula 1 may further include a fluorescent light emitting type material.

When the light emitting layer further includes a fluorescent light emitting material, excitons move from the compound represented by Formula 1 to the fluorescent light emitting material to finally emit light in the fluorescent light emitting type material, so that the color purity of the device may be increased by using a fluorescent light emitting type material having a narrow full width at half maximum, and the service life of the device may be increased by preventing exciton-polaron quenching of the compound represented by Formula 1.

In an exemplary embodiment, the light emitting layer may further include other fluorescent light emitting type materials.

In an exemplary embodiment, the fluorescent light emitting type material may be a fluorene derivative; a naphthalene derivative; an anthracene derivative; a tetracene derivative; a pyrene derivative; a chrysene derivative; a fluoranthene derivative; a perylene derivative; a quinolino[2,3-b]acridine-7,14(5H,12H)-dione derivative; a 4H-chromene derivative; a 1,2,3,5,6,7-hexahydropyrido[3,2,1-ij]quinoline derivative; a benzo-a-pyrone (=coumarine) derivative; a 4H-pyran derivative; a benzo[d]thiazole derivative; a pyrrole derivative; a quinazole derivative; a carbazole derivative; a 2,3,6,7-tetrahydro-1H-pyrano[2,3-f]pyrido[3,2,1-ij]quinolin-11(5H)-one derivative; a boron-based derivative, or the like, but is not limited thereto.

In an exemplary embodiment, the organic light emitting device further includes a phosphorescent light emitting type light emitting layer in addition to a light emitting layer including the compound represented by Formula 1.

In an exemplary embodiment, the organic light emitting device includes a plurality of light emitting layers, and the light emitting layers are formed to be adjacent to each other.

In the present specification, the case where any organic material layer includes any compound means that one or more compounds are included.

In an exemplary embodiment, when one or more compounds represented by Formula 1 are included in the light emitting layer, a part by weight of the compound represented by Formula 1 means the sum of parts by weight of the one or more compounds represented by Formula 1.

In an exemplary embodiment, the organic light emitting device further includes one or more organic material layers.

In an exemplary embodiment, the organic light emitting device further includes one or more organic material layers between the first electrode and the light emitting layer.

In an exemplary embodiment, the organic light emitting device further includes one or more organic material layers between the second electrode and the light emitting layer.

In an exemplary embodiment, the organic light emitting device of the present invention may have a structure including a hole injection layer, a hole transport layer, a layer which simultaneously transports and injects holes, an hole adjusting layer, a light emitting layer, an electron adjusting layer, an electron transport layer, an electron injection layer, a layer which simultaneously transports and injects electrons, and the like, as organic material layers.

In another exemplary embodiment, the organic light emitting device may be a normal type organic light emitting device in which a positive electrode, one or more organic material layers, and a negative electrode are sequentially stacked on a substrate.

In an exemplary embodiment, the organic light emitting device may be an inverted type organic light emitting device in which a negative electrode, one or more organic material layers, and a positive electrode are sequentially stacked on a substrate.

In an exemplary embodiment, the first electrode is a positive electrode, and the second electrode is a negative electrode.

In another exemplary embodiment, the first electrode is a negative electrode, and the second electrode is a positive electrode.

The structures of the organic light emitting device according to an exemplary embodiment of the present specification are exemplified in FIGS. 1 and 2.

The organic light emitting device according to an exemplary embodiment of the present invention may be composed of a substrate 1, a positive electrode 2, a light emitting layer 8, and a negative electrode 4, as illustrated in FIG. 1. In an exemplary embodiment, the compound represented by Formula 1 is included in the light emitting layer 8.

The organic light emitting device according to an exemplary embodiment of the present invention may be composed of a substrate 1, a positive electrode 2, a hole injection layer 5, a hole transport layer 6, a hole adjusting layer 7, a light emitting layer 8, an electron transport layer 9, an electron injection layer 10, and a negative electrode 4, as illustrated in FIG. 2. In an exemplary embodiment, the compound represented by Formula 1 is included in the light emitting layer 8.

However, the structure of the organic light emitting device according to an exemplary embodiment of the present specification is not limited to those of FIGS. 1 and 2, and may be any one of the following structures.

(1) Positive electrode/Hole transport layer/Light emitting layer/Negative electrode
(2) Positive electrode/Hole injection layer/Hole transport layer/Light emitting layer/Negative electrode
(3) Positive electrode/Hole transport layer/Light emitting layer/Electron transport layer/Negative electrode
(4) Positive electrode/Hole transport layer/Light emitting layer/Electron transport layer/Electron injection layer/Negative electrode
(5) Positive electrode/Hole injection layer/Hole transport layer/Light emitting layer/Electron transport layer/Negative electrode
(6) Positive electrode/Hole injection layer/Hole transport layer/Light emitting layer/Electron transport layer/Electron injection layer/Negative electrode
(7) Positive electrode/Hole transport layer/Hole adjusting layer/Light emitting layer/electron transport layer/Negative electrode
(8) Positive electrode/Hole transport layer/Hole adjusting layer/Light emitting layer/Electron transport layer/Electron injection layer/Negative electrode
(9) Positive electrode/Hole injection layer/Hole transport layer/Hole adjusting layer/Light emitting layer/Electron transport layer/Negative electrode
(10) Positive electrode/Hole transport layer/Light emitting layer/Electron adjusting layer/Electron transport layer/Negative electrode
(11) Positive electrode/Hole transport layer/Light emitting layer/Electron adjusting layer/Electron transport layer/Electron injection layer/Negative electrode
(12) Positive electrode/Hole injection layer/Hole transport layer/Light emitting layer/Electron adjusting layer/Electron transport layer/Negative electrode
(13) Positive electrode/Hole injection layer/Hole transport layer/Light emitting layer/Electron adjusting layer/Electron transport layer/Electron injection layer/Negative electrode When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation.

Further, the compound represented by Formula 1 may be formed as an organic material layer by not only a vacuum deposition method, but also a solution application method when an organic light emitting device is manufactured.

Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate. However, the manufacturing method is not limited thereto.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer which injects holes received from an electrode into the light emitting layer or an adjacent layer provided on the side of the light emitting layer. As the hole injection material, it is preferred to use a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is a value between the work function of the positive electrode material and the HOMO of a peripheral organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer. The hole transport material is suitably a material having high hole mobility which may receive holes from a positive electrode or a hole injection layer and transfer the holes to a light emitting layer. Specific examples of the hole transport material include arylamine-based organic materials, conductive polymers, block copolymers having both conjugated portions and non-conjugated portions, and the like, but are not limited thereto.

The hole adjusting layer is a layer that prevents the inflow of electrons from a light emitting layer to a positive electrode, and adjusts the performance of the entire device by adjusting the flow of holes to the light emitting layer. The hole adjusting material is preferably a compound having an ability to prevent the inflow of electrons from a light emitting layer to a positive electrode and to adjust the flow of holes to be injected into a light emitting layer or a light emitting material. In an exemplary embodiment, as the electron blocking layer, arylamine-based organic materials may be used, but the electron blocking layer is not limited thereto.

The light emitting material is a material which may receive holes and electrons from a hole transport layer and an electron transport layer, and combine the holes and the electrons to emit light in a visible ray region, and is preferably a material having high quantum efficiency for fluorescence or phosphorescence. In an exemplary embodiment of the present invention, the light emitting layer includes the compound represented by Formula 1.

In an exemplary embodiment, a light emitting layer including the compound represented by Formula 1 may further include other light emitting materials in the light emitting layer, or a light emitting layer which does not include the compound represented by Formula 1 may include other light emitting materials. Specific examples of the other light emitting materials include: 8-hydroxyquinoline aluminum complexes ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, rubrene, and the like, but are not limited thereto.

In an exemplary embodiment, the light emitting layer may include a host material and a dopant material. Examples of the host material include fused aromatic ring derivatives, or hetero ring-containing compounds, and the like. Specifically, examples of the fused aromatic ring derivative include anthracene derivatives, pyrene derivatives, naphthalene derivatives, pentacene derivatives, phenanthrene compounds, fluoranthene compounds, and the like, and examples of the hetero ring-containing compound include carbazole derivatives, dibenzofuran derivatives, ladder-type furan compounds, pyrimidine derivatives, and the like, but the examples thereof are not limited thereto. In an exemplary embodiment, the compound represented by Formula 1 may be used as a host material of a light emitting layer.

Examples of the dopant material of the light emitting layer include aromatic amine derivatives, styrylamine compounds, boron complexes, fluoranthene compounds, metal complexes, and the like. Specifically, the aromatic amine derivative is a fused aromatic ring derivative having a substituted or unsubstituted arylamine group, and may use pyrene, anthracene, chrysene, periflanthene, and the like having an arylamine group. As the styrylamine compound, it is possible to use a compound in which at least one arylvinyl group is substituted with a substituted or unsubstituted arylamine. Examples of the styrylamine compound include styrylamine, styryldiamine, styryltriamine, styryltetramine, and the like, but are not limited thereto. As the metal complex, it is possible to use iridium complexes, platinum complexes, and the like, but the metal complex is not limited thereto.

The electron adjust layer is a layer that blocks the inflow of holes from a light emitting layer to a negative electrode, and adjusts the performance of the entire device by adjusting the inflow of electrons to the light emitting layer. The electron adjusting material is preferably a compound having an ability to prevent the inflow of holes from a light emitting layer to a negative electrode and to adjust the flow of electrons to be injected into a light emitting layer or a light emitting material. As the electron adjusting material, it is possible to use an appropriate material according to the configuration of the organic material layer used in the device. The electron adjusting layer is located between a light emitting layer and a negative electrode, and is preferably provided to be brought into direct contact with the light emitting layer.

The electron transport layer is a layer which accepts electrons from an electron injection layer and transports the electrons to a light emitting layer. The electron transport material is suitably a material having high electron mobility which may proficiently receive electrons injected from a negative electrode and transfer the electrons to a light emitting layer. Examples of the electron transport material include: Al complexes of 8-hydroxyquinoline; complexes including $Alq_3$; organic radical compounds; hydroxyflavone-metal complexes, and the like, but are not limited thereto. The electron transport layer may be used with any desired negative electrode material, as used according to the related art. In an exemplary embodiment, as the negative electrode material, it is possible to use materials having a low work function; and an aluminum layer or a silver layer. Examples of the materials having low work function include cesium, barium, calcium, ytterbium, samarium, and the like, and after a layer is formed by using the material, an aluminum layer or a silver layer may be formed on the layer.

The electron injection layer is a layer which injects electrons received from an electrode into a light emitting layer. As the electron injection material, it is preferred to use a compound which has a capability of transporting electrons, an effect of injecting electrons from a negative electrode, and an excellent effect of injecting electrons into a light emitting layer or a light emitting material, prevents excitons produced from a light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the materials to be used.

Hereinafter, the present specification will be described in detail with reference to Examples for specifically describing the present specification. However, the Examples according to the present specification may be modified in various forms, and it is not interpreted that the scope of the present application is limited to the Examples described in detail below. The Examples of the present application are provided to more completely explain the present specification to a person with ordinary skill in the art.

PREPARATION EXAMPLES

The compound represented by Formula 1 may be formed by introducing various types of substituents with which deuterium is substituted as described below. Various compounds in specific examples were synthesized by the following preparation method.

Preparation Example 1-1: Synthesis of Compound 1

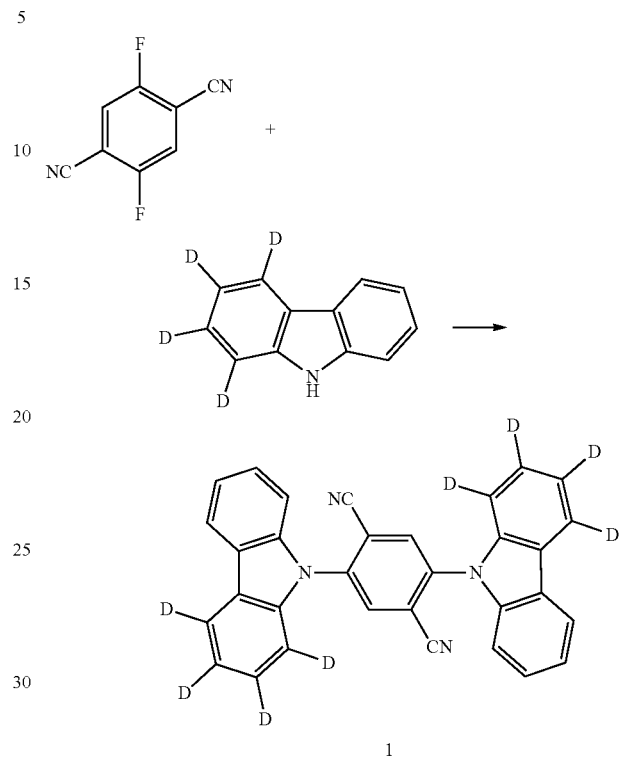

1

10 g (60.9 mmol) of 2,5-difluoroterephthalonitrile, 122 mmol of 9H-carbazole-1,2,3,4-d4, 100 mL of dimethylformamide (DMF), and 244 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 1 (25.6 g) (yield 90%).

MS[M+H]+=467

Preparation Example 1-2: Synthesis of Compound 2

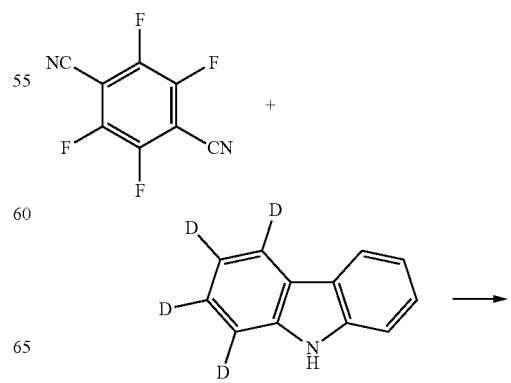

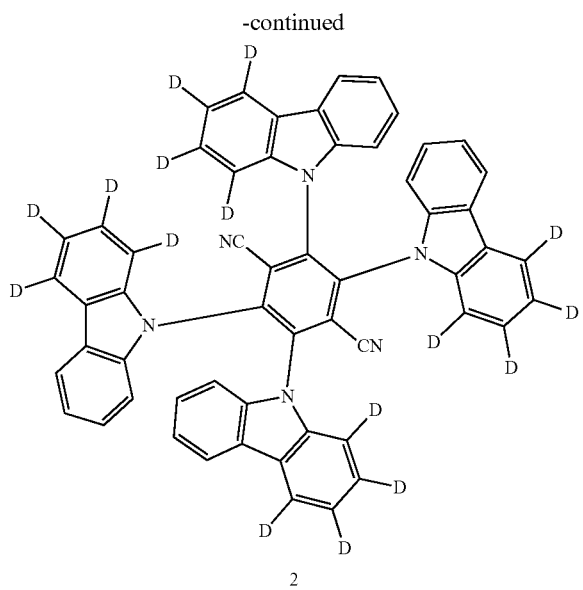

2

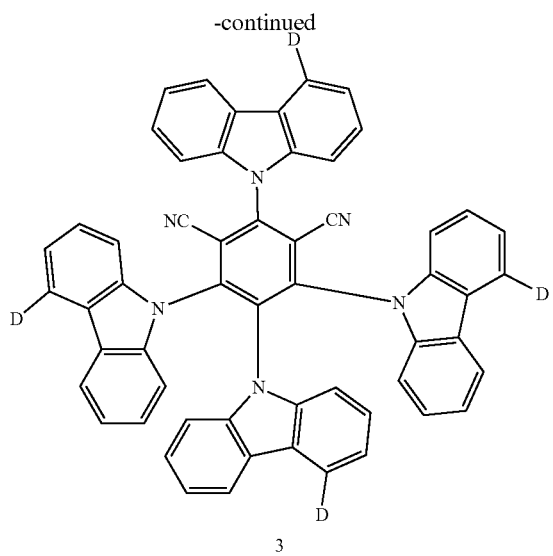

3

12.2 g (60.9 mmol) of 2,3,5,6-tetrafluoroterephthalonitrile, 243.6 mmol of 9H-carbazole-1,2,3,4-d4, 120 mL of DMF, and 487 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 2 (39.7 g) (yield 81%).

MS[M+H]+=805

Preparation Example 1-3: Synthesis of Compound 3

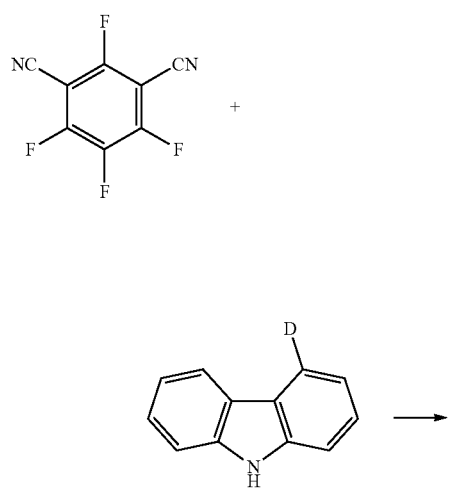

12.2 g (60.9 mmol) of 2,4,5,6-tetrafluoroisophthalonitrile, 43.6 mmol of 9H-carbazole-4-d, 120 mL of DMF, and 487 mmol of potassium carbonate were mixed, and the resulting mixture was heated to 100° C. and stirred for 3 hours. After reaction, a solid was obtained by filtering a reaction solution cooled to room temperature, and then the solid was recrystallized twice with tetrahydrofuran and ethanol to obtain Compound 3 (40.1 g) (yield 83%).

MS[M+H]+=793

Preparation Example 1-4: Synthesis of Compound 4

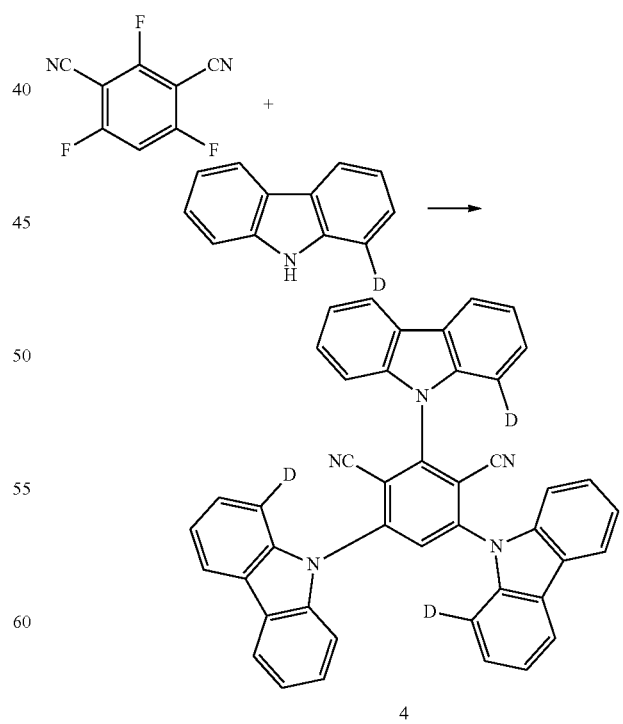

4

11.1 g (60.9 mmol) of 2,4,6-trifluoroisophthalonitrile, 182.7 mmol of 9H-carbazole-1-d, 110 mL of DMF, and 365.4 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 4 (30.5 g) (yield 80%).

MS[M+H]+=627

Preparation Example 1-5: Synthesis of Compound 5

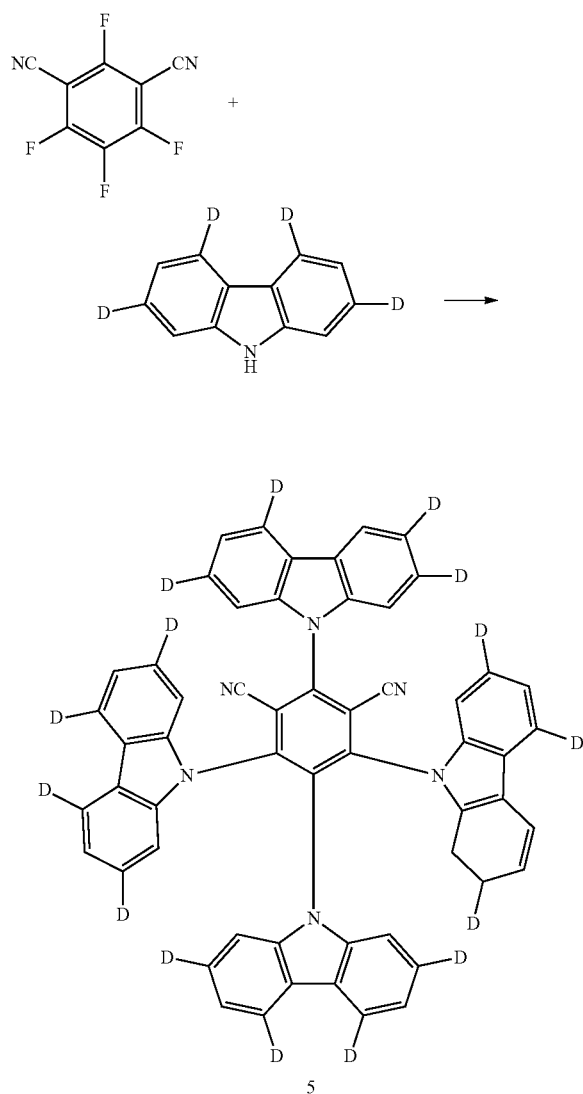

5

12.2 g (60.9 mmol) of 2,4,5,6-tetrafluoroisophthalonitrile, 243.6 mmol of 9H-carbazole-2,4,5,7-d4, 120 mL of DMF, and 487 mmol of potassium carbonate were mixed, and the resulting mixture was heated to 100° C. and stirred for 3 hours. After reaction, a solid was obtained by filtering a reaction solution cooled to room temperature, and then the solid was recrystallized twice with tetrahydrofuran and ethanol to obtain Compound 5 (37.8 g) (yield 77%).

MS[M+H]+=807

Preparation Example 1-6: Synthesis of Compound 6

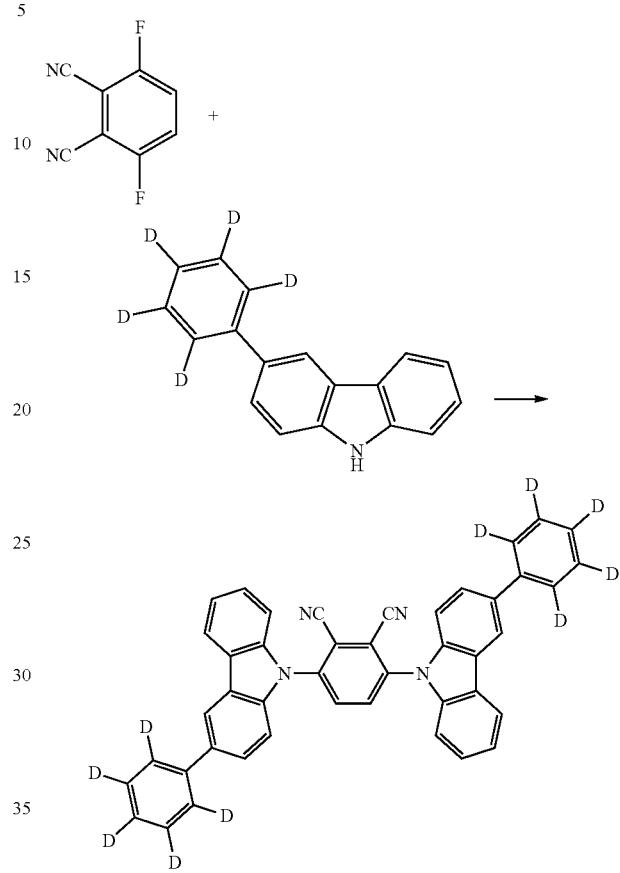

6

10 g (60.9 mmol) of 3,6-difluorophthalonitrile, 121.8 mmol of 3-(phenyl-d5)-9H-carbazole, 100 mL of DMF, and 243.6 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 6 (31.7 g) (yield 84%).

MS[M+H]+=621

Preparation Example 1-7: Synthesis of Compound 7

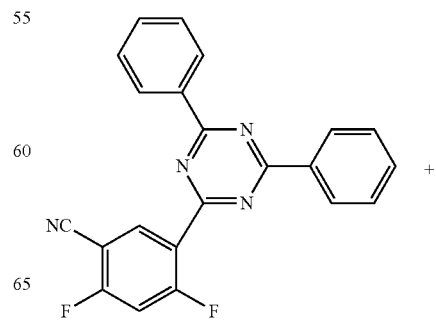

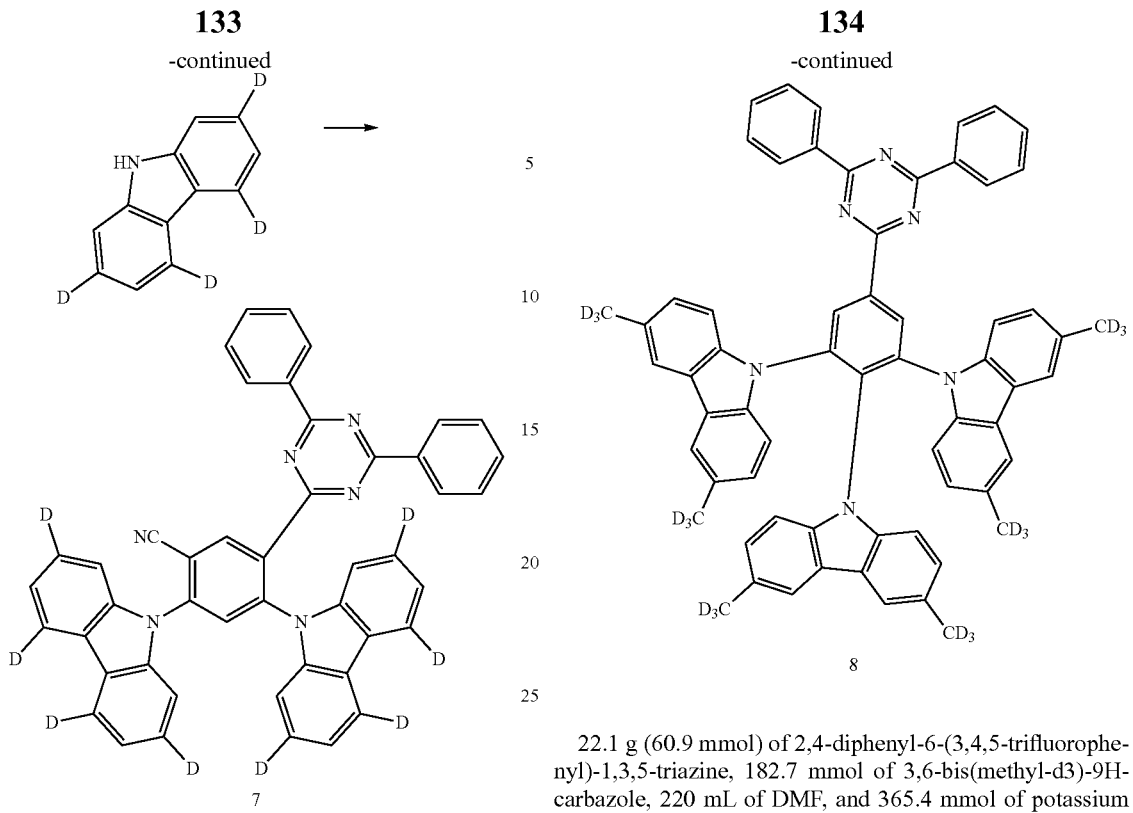

7

22.6 g (60.9 mmol) of 5-(4,6-diphenyl-1,3,5-triazin-2-yl)-2,4-difluorobenzonitrile, 121.8 mmol of 9H-carbazole-2,4,5,7-d4, 200 mL of DMF, and 243.6 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 7 (33.2 g) (yield 81%).

MS[M+H]+=673

Preparation Example 1-8: Synthesis of Compound 8

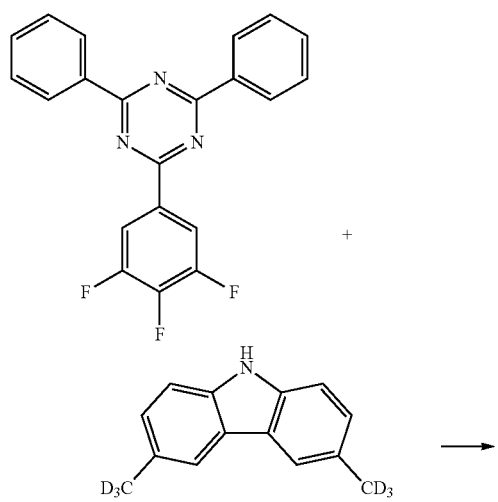

8

22.1 g (60.9 mmol) of 2,4-diphenyl-6-(3,4,5-trifluorophenyl)-1,3,5-triazine, 182.7 mmol of 3,6-bis(methyl-d3)-9H-carbazole, 220 mL of DMF, and 365.4 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 8 (44.1 g) (yield 83%).

MS[M+H]+=873

Preparation Example 1-9: Synthesis of Compound 9

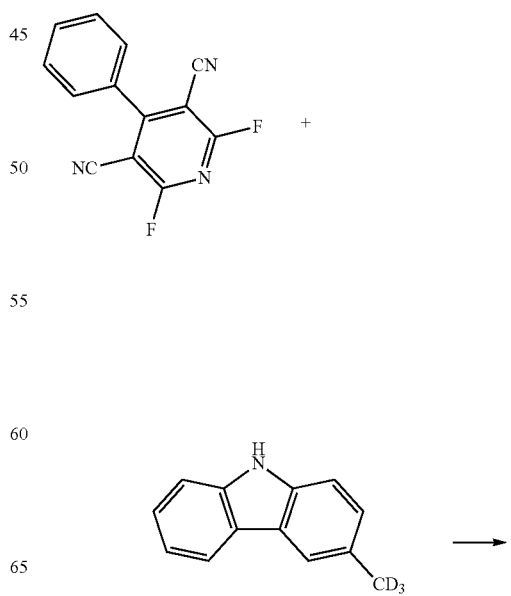

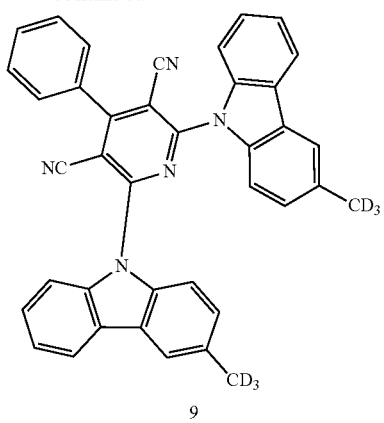

9

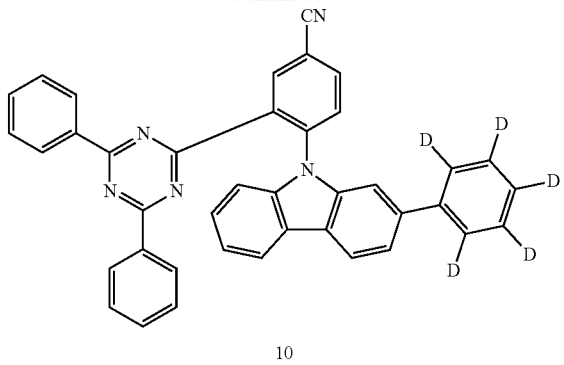

10

14.7 g (60.9 mmol) of 2,6-difluoro-4-phenylpyridine-3,5-dicarbonitrile, 121.8 mmol of 3-(methyl-d3)-9H-carbazole, 150 mL of DMF, and 243.6 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 9 (25.3 g) (yield 73%).

MS[M+H]+=570

Preparation Example 1-10: Synthesis of Compound 10

21.5 g (60.9 mmol) of 3-(4,6-diphenyl-1,3,5-triazin-2-yl)-4-fluorobenzonitrile, 60.9 mmol of 2-(phenyl-d5)-9H-carbazole, 220 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 10 (25.1 g) (yield 71%).

MS[M+H]+=581

Preparation Example 1-11: Synthesis of Compound 11

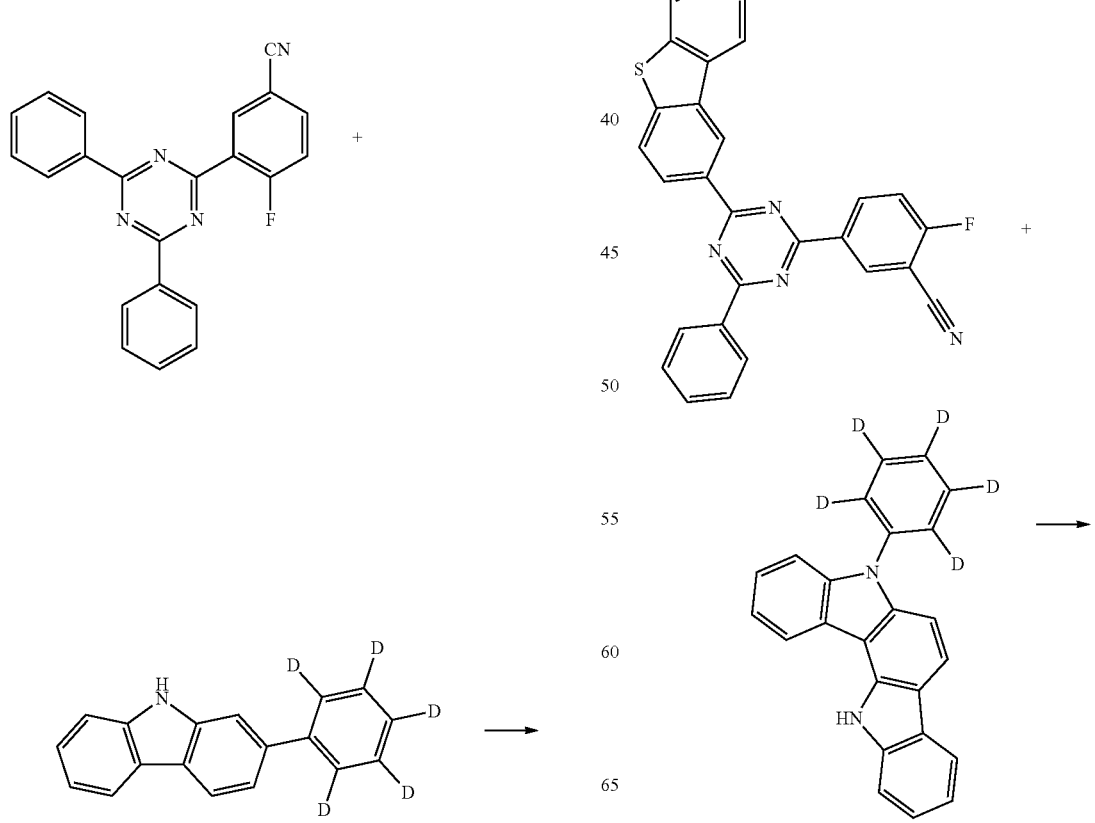

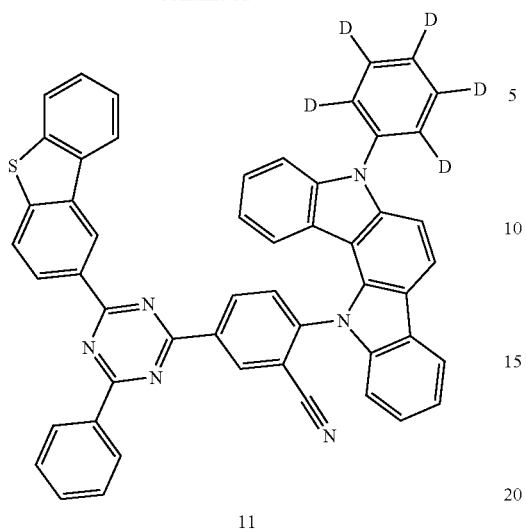

11

27.9 g (60.9 mmol) of 5-(4-(dibenzo[b,d]thiophen-2-yl)-6-phenyl-1,3,5-triazin-2-yl)-2-fluorobenzonitrile, 60.9 mmol of 5-(phenyl-d5)-5,12-dihydroindolo[3,2-a]carbazole, 280 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 11 (38.3 g) (yield 81%).

MS[M+H]+=776

Preparation Example 1-12: Synthesis of Compound 12

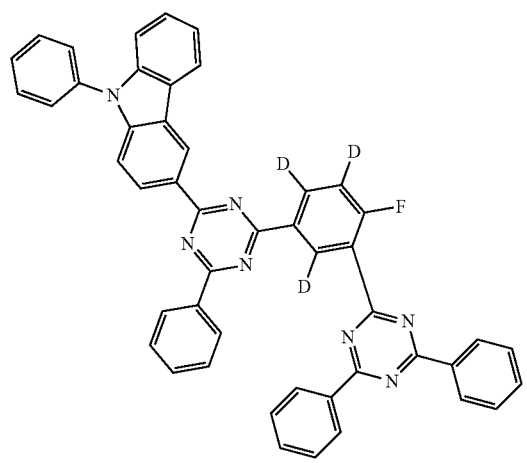

+

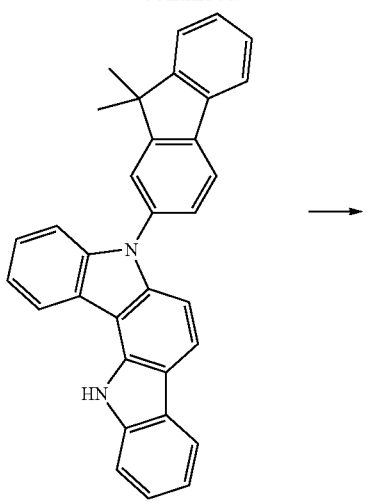

→

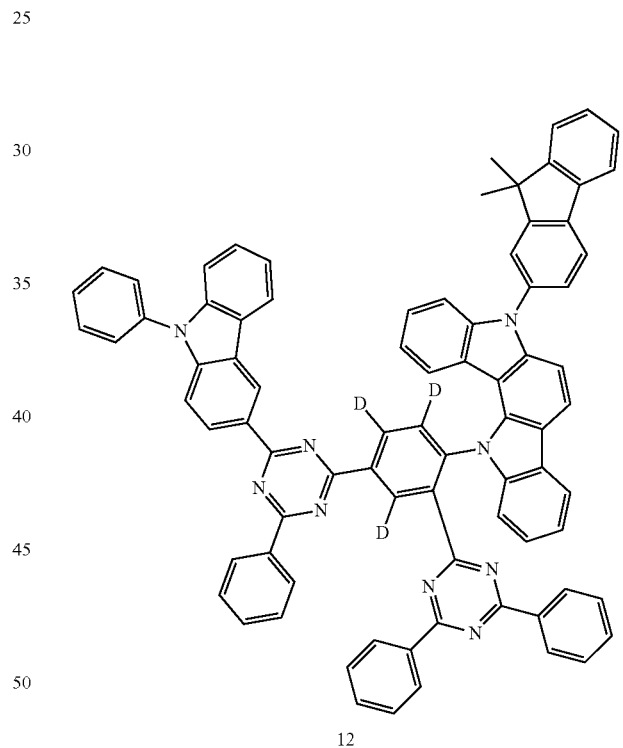

12

44.3 g (60.9 mmol) of 3-(4-(3-(4,6-diphenyl-1,3,5-triazin-2-yl)-4-fluorophenyl-2,5,6-d3)-6-phenyl-1,3,5-triazin-2-yl)-9-phenyl-9H-carbazole, 60.9 mmol of 5-(9,9-dimethyl-9H-fluoren-2-yl)-5,12-dihydroindolo[3,2-a]carbazole, 400 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 12 (49.2 g) (yield 70%).

MS[M+H]+=1155

Preparation Example 1-13: Synthesis of Compound 13

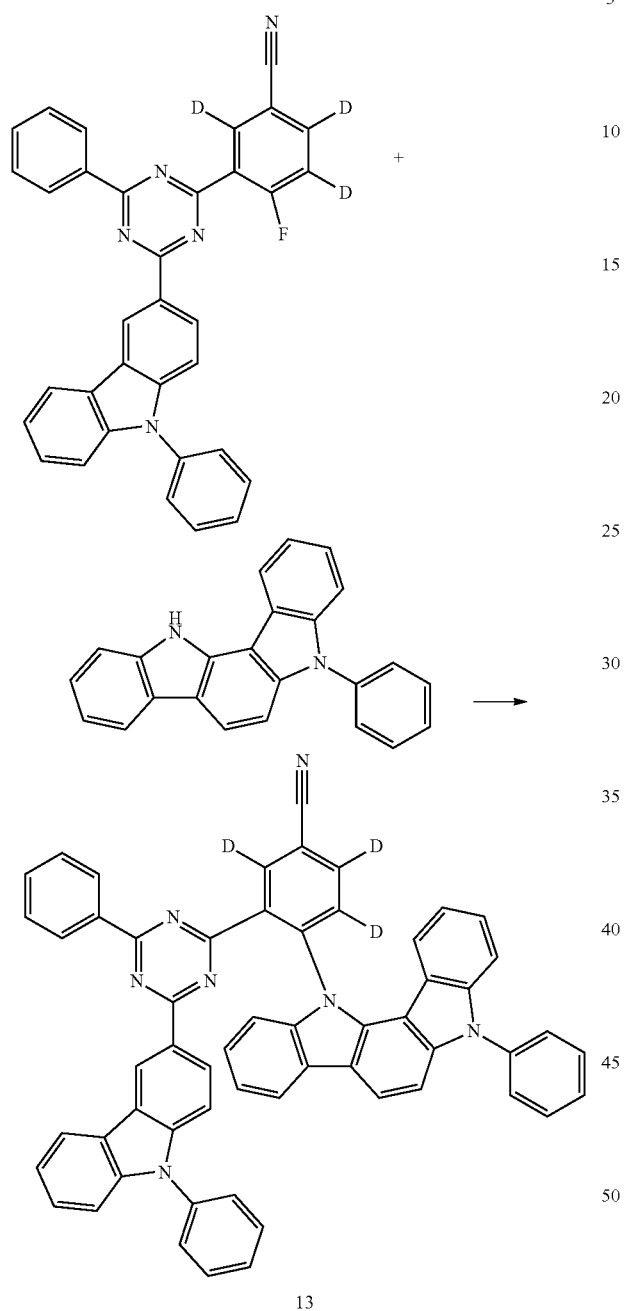

31.7 g (60.9 mmol) of 4-fluoro-3-(4-phenyl-6-(9-phenyl-9H-carbazol-3-yl)-1,3,5-triazin-2-yl)benzonitrile-2,5,6-d3, 60.9 mmol of 5-phenyl-5,12-dihydroindolo[3,2-a]carbazole, 300 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 13 (34.5 g) (yield 68%).

MS[M+H]+=833

Preparation Example 1-14: Synthesis of Compound 14

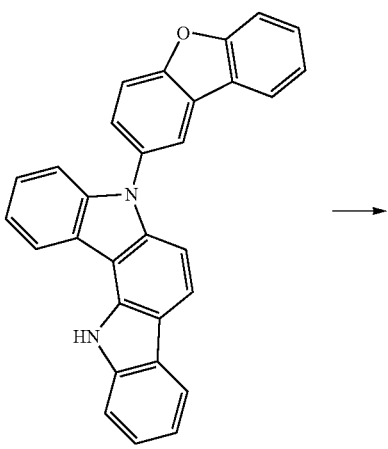

-continued

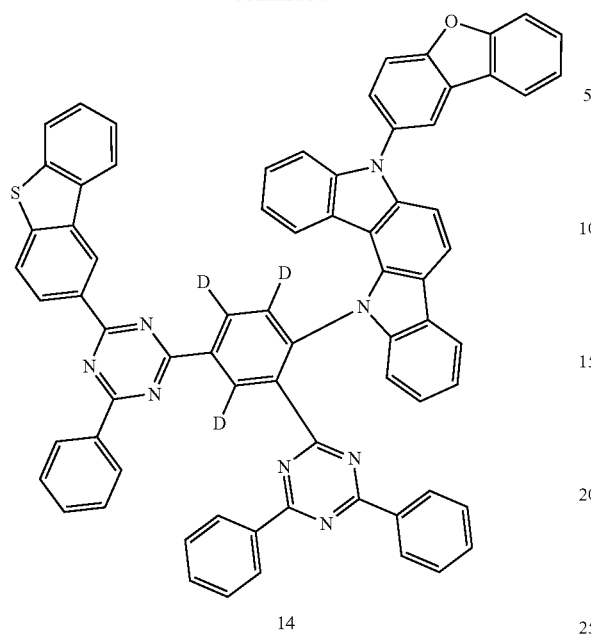

14

40.7 g (60.9 mmol) of 2-(dibenzo[b,d]thiophen-2-yl)-4-(3-(4,6-diphenyl-1,3,5-triazin-2-yl)-4-fluorophenyl-2,5,6-d3)-6-phenyl-1,3,5-triazine, 60.9 mmol of 5-(dibenzo[b,d]furan-2-yl)-5,12-dihydroindolo[3,2-a]carbazole, 350 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 14 (46.9 g) (yield 72%).

MS[M+H]+=1070

Preparation Example 1-15: Synthesis of Compound 15

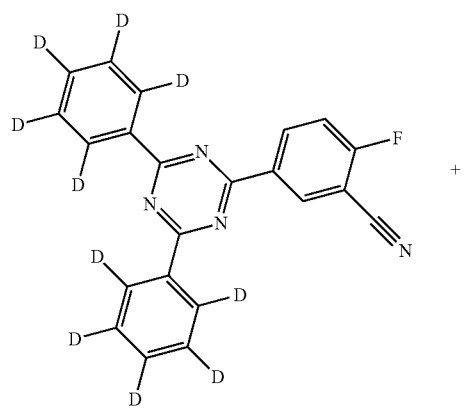

-continued

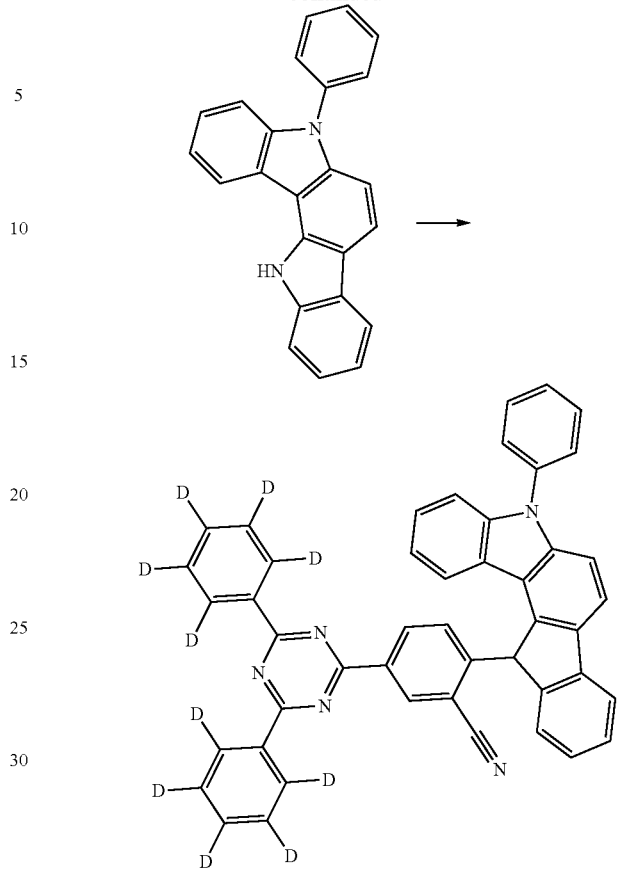

15

22.1 g (60.9 mmol) of 5-(4,6-bis(phenyl-d5)-1,3,5-triazin-2-yl)-2-fluorobenzonitrile, 60.9 mmol of 5-phenyl-5,12-dihydroindolo[3,2-a]carbazole, 220 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 15 (35.7 g) (yield 87%).

MS[M+H]+=675

Preparation Example 1-16: Synthesis of Compound 16

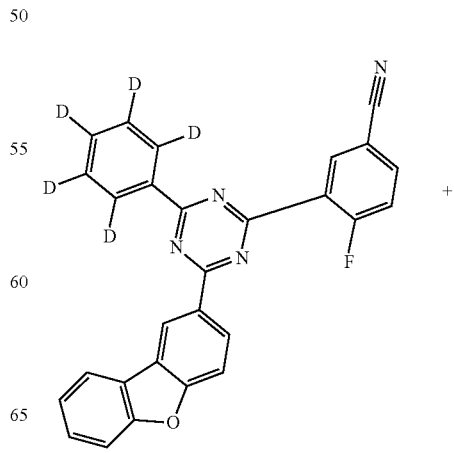

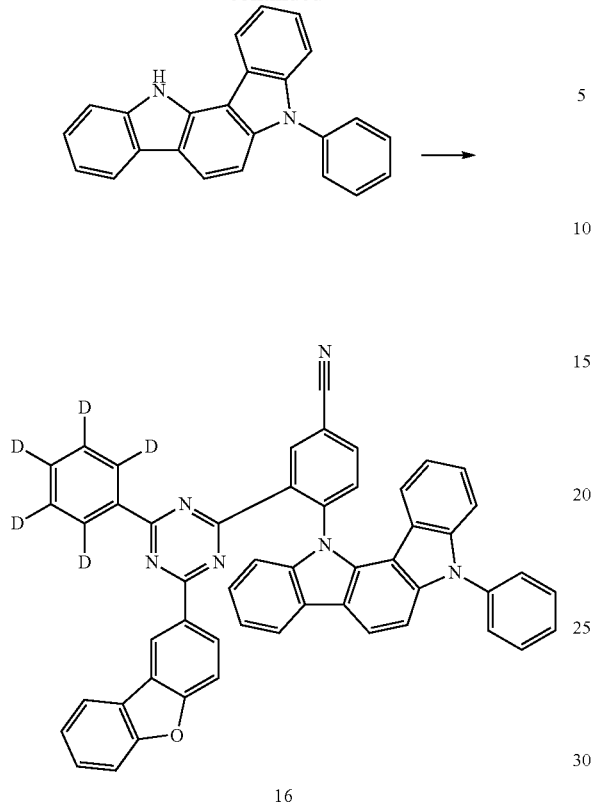

16

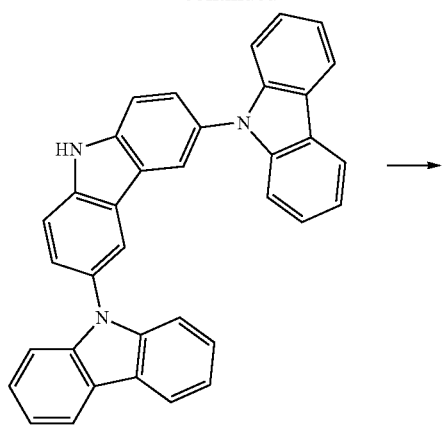

27.2 g (60.9 mmol) of 3-(4-(dibenzo[b,d]furan-2-yl)-6-(phenyl-d5)-1,3,5-triazin-2-yl)-4-fluorobenzonitrile, 60.9 mmol of 5-phenyl-5,12-dihydroindolo[3,2-a]carbazole, 250 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 16 (35.2 g) (yield 76%).

MS[M+H]+=760

Preparation Example 1-17: Synthesis of Compound 17

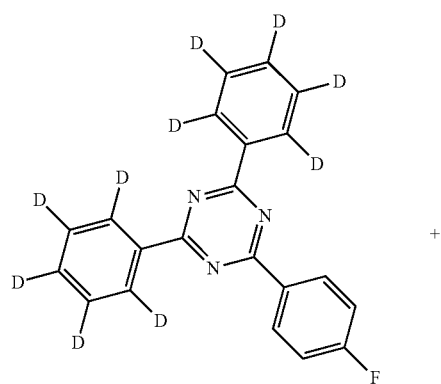

+

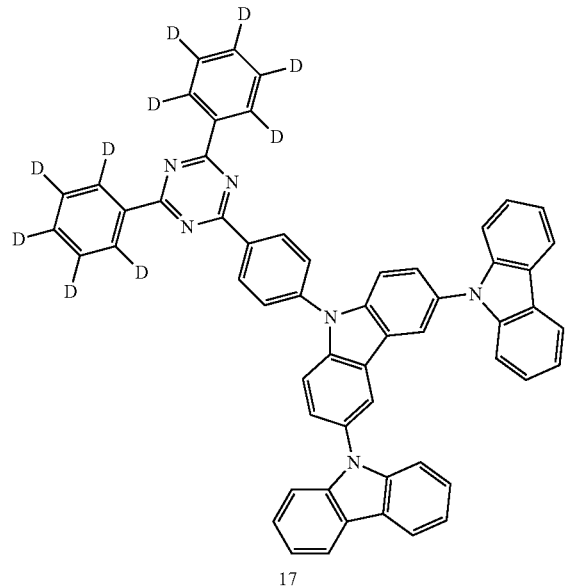

17

20.5 g (60.9 mmol) of 2-(4-fluorophenyl)-4,6-bis(phenyl-d5)-1,3,5-triazine, 60.9 mmol of 9'H-9,3':6',9''-tercarbazole, 200 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 17 (36.2 g) (yield 73%).

MS[M+H]+=815

Preparation Example 1-18: Synthesis of Compound 18

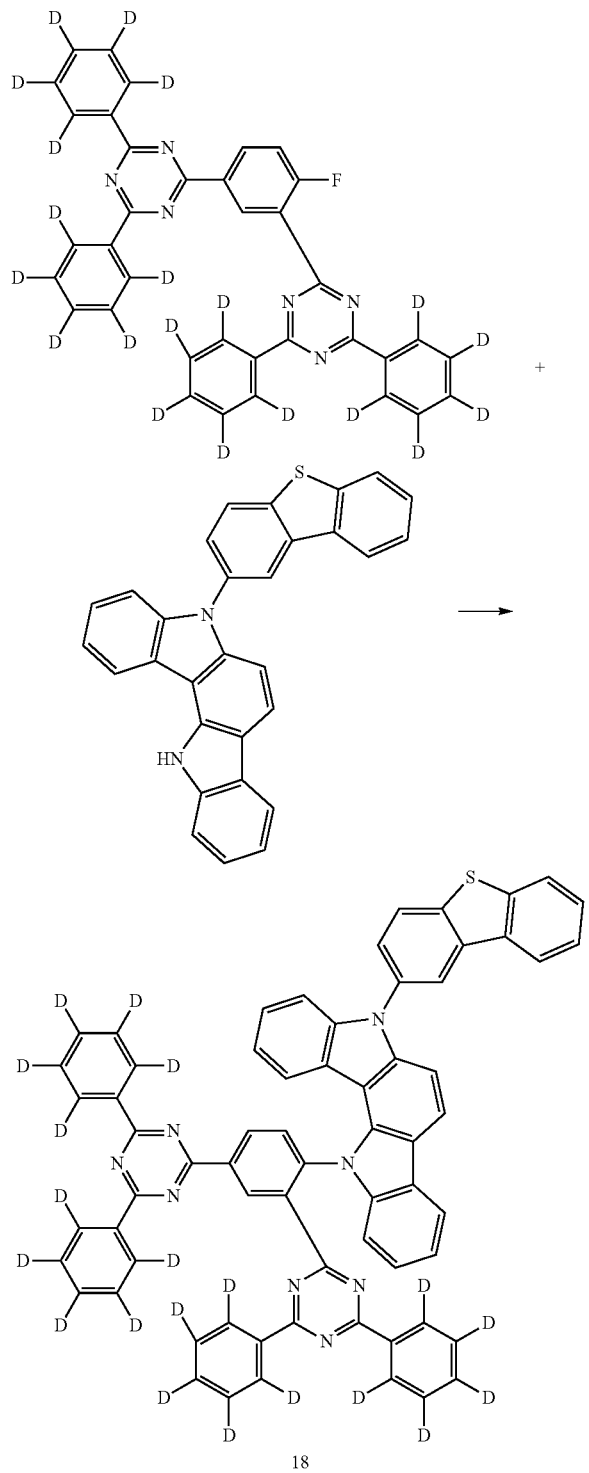

35.2 g (60.9 mmol) of 6,6'-(4-fluoro-1,3-phenylene)bis(2,4-bis(phenyl-d5)-1,3,5-triazine), 60.9 mmol of 5-(dibenzo[b,d]thiophen-2-yl)-5,12-dihydroindolo[3,2-a]carbazole, 300 mL of DMF, and 121.8 mmol of potassium carbonate were mixed, and the resulting mixture was heated to 100° C. and stirred for 3 hours. After reaction, a solid was obtained by filtering the reaction solution cooled to room temperature, and then the solid was recrystallized twice with tetrahydrofuran and ethanol to obtain Compound 18 (45.5 g) (yield 75%).

MS[M+H]+=997

Comparative Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After cleaning with distilled water was completed, the substrate was ultrasonically cleaned with a solvent of isopropyl alcohol, acetone and methanol, dried, and then transported to a plasma cleaner. Furthermore, the substrate was cleaned by using an oxygen plasma for 5 minutes, and then was transported to a vacuum deposition machine. Each thin film was stacked on the thus prepared ITO transparent electrode at a degree of vacuum of $5.0 \times 10^{-4}$ Pa by a vacuum deposition method. First, hexaazatriphenylene-hexanitrile (HAT-CN) was thermally vacuum-deposited to have a thickness of 500 Å on the ITO, thereby forming a hole injection layer.

The following compound NPB was vacuum-deposited on the hole injection layer, thereby forming a hole transport layer (300 Å).

The following compound EB1 was vacuum-deposited to have a film thickness of 100 Å on the hole transport layer, thereby forming an electron blocking layer (100 Å).

Subsequently, the following m-CBP and 4CzIPN were vacuum-deposited at a weight ratio of 70:30 to have a film thickness of 300 Å on the electron blocking layer, thereby forming a light emitting layer.

The above compound HB1 was vacuum deposited to have a film thickness of 100 Å on the light emitting layer, thereby forming a hole blocking layer.

The following compound ET1 and Compound lithium quinolate (LiQ) were vacuum-deposited at a weight ratio of 1:1 on the hole blocking layer, thereby forming an electron injection and transport layer having a thickness of 300 Å. Lithium fluoride (LiF) and aluminum were sequentially deposited on the electron injection and transport layer to have a thickness of 12 Å and 2,000 Å, respectively, thereby forming a negative electrode.

In the aforementioned procedure, the deposition rates of the organic materials were maintained at 0.4 Å/sec to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ torr to $5 \times 10^{-6}$ torr, thereby manufacturing an organic light emitting device.

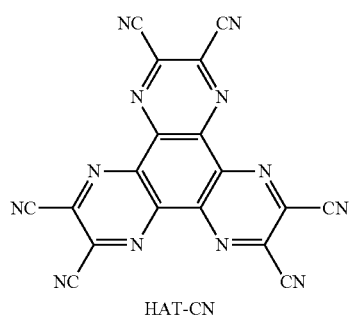
HAT-CN
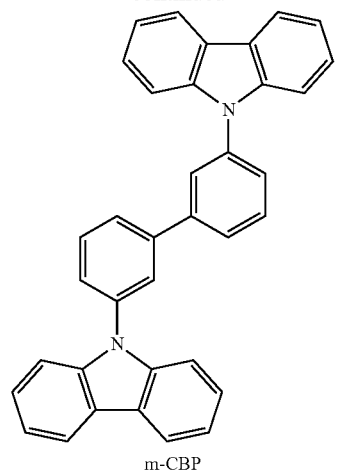
m-CBP
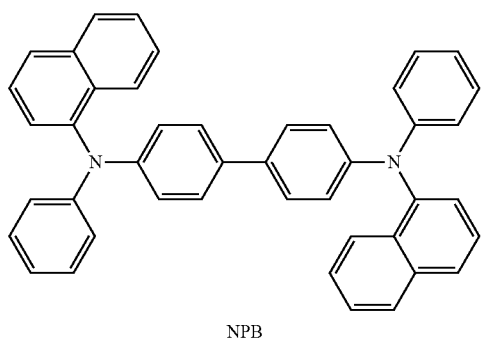
NPB
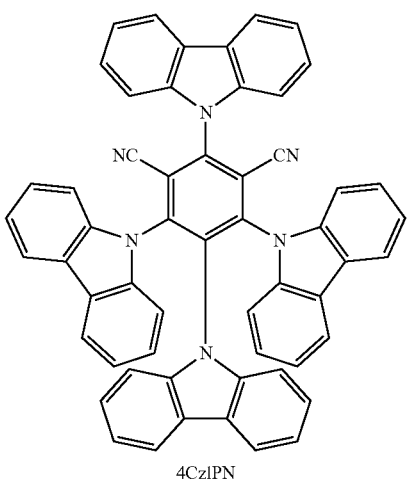
4CzIPN
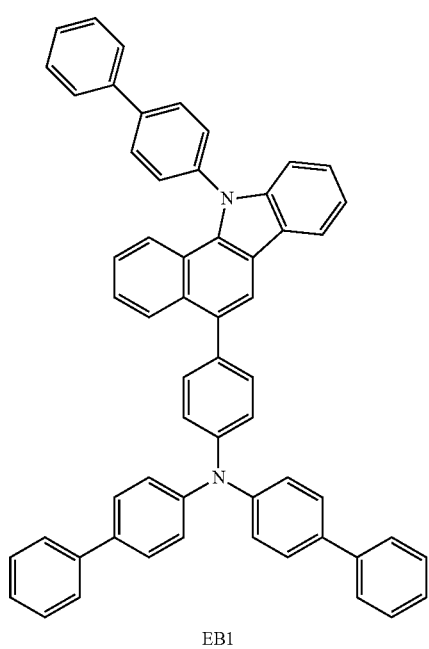
EB1
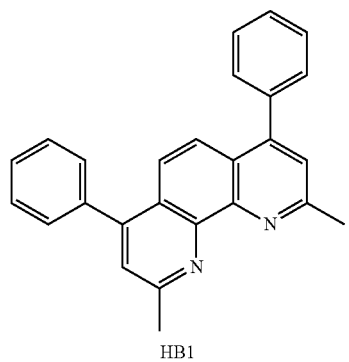
HB1

149
-continued

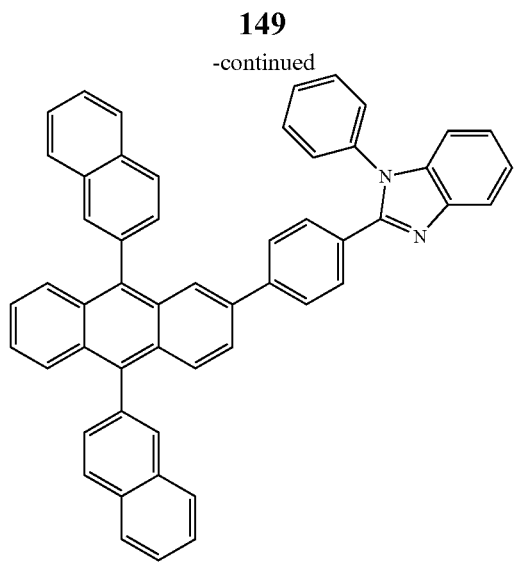

ET1

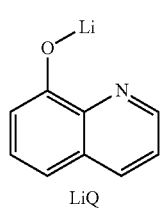

LiQ

Experimental Examples 1-1 to 1-18

Organic light emitting devices were manufactured in the same manner as in Comparative Example 1-1, except that the compounds of the following Table 1 were used instead of Compound 4CzIPN in Comparative Example 1-1.

Comparative Examples 1-2 to 1-7

Organic light emitting devices were manufactured in the same manner as in Comparative Example 1-1, except that the compounds of the following T1 to T6 were used instead of Compound 4CzIPN in Comparative Example 1-1.

T1

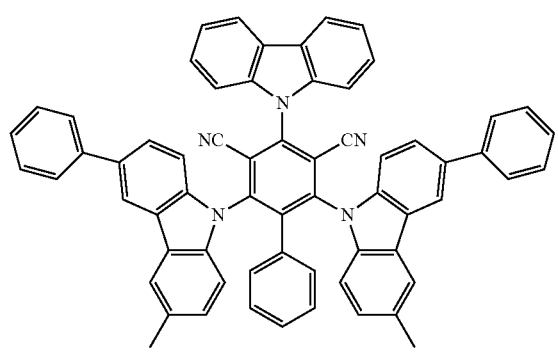

150
-continued

T2

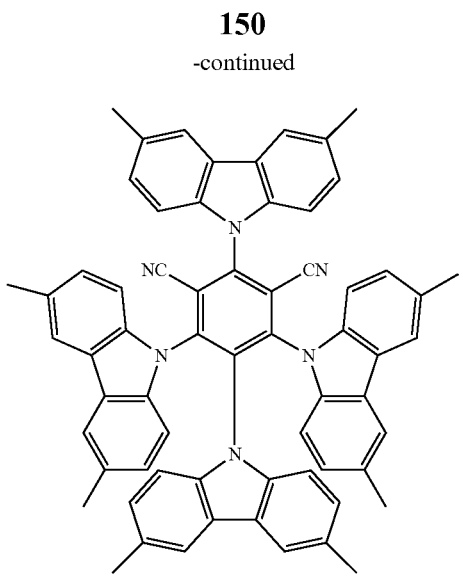

T3

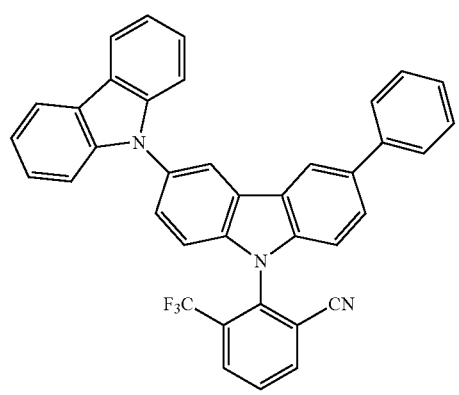

T4

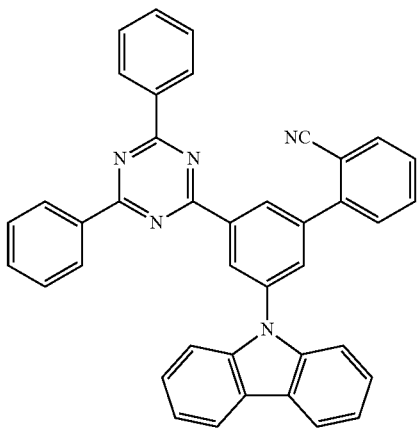

-continued

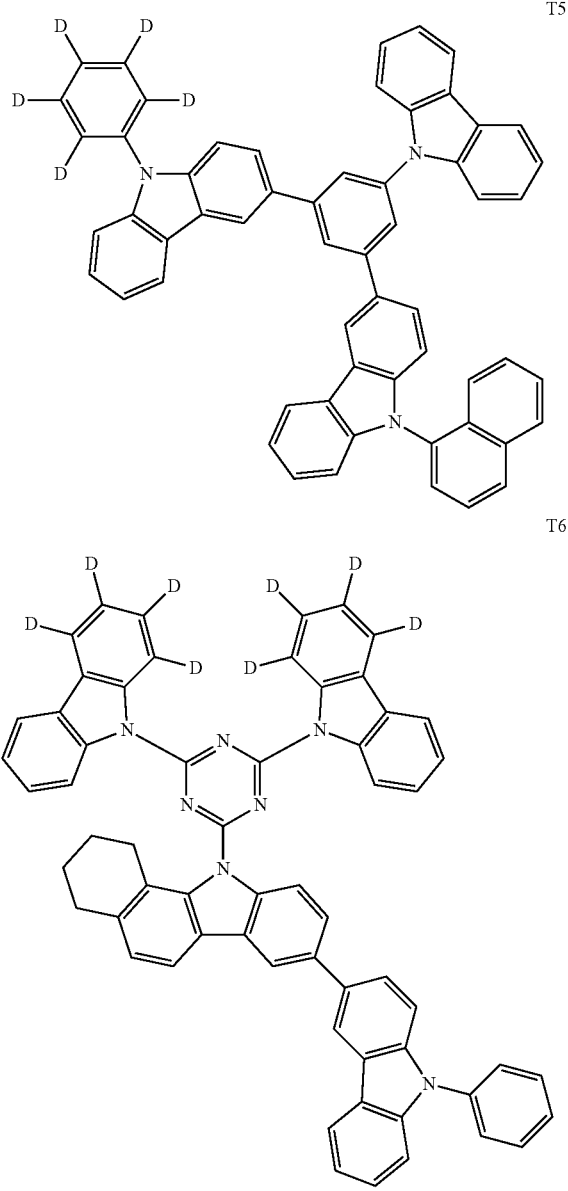 [SMILES: [2H]c1c([2H])c([2H])c(-n2c3ccccc3c3cc(-c4cc(-c5ccc6c(c5)c5ccccc5n6-c5cccc6ccccc56)cc(-n5c6ccccc6c6ccccc65)c4)ccc32)c([2H])c1[2H] ; [2H]c1c([2H])c([2H])c2c(c1[2H])c1ccccc1n2-c1nc(-n2c3ccc(-c4ccc5c(c4)c4ccccc4n5-c4ccccc4)cc3c3ccc4c(c32)CCCC4)nc(-n2c3ccccc3c3c([2H])c([2H])c([2H])c([2H])c32)n1]

T5

T6

For each of the organic light emitting devices in Experimental Examples 1-1 to 1-18 and Comparative Examples 1-1 to 1-7, the driving voltage (V) and current efficiency (cd/A) were measured at a current density of 10 mA/cm², the CIE color coordinate was measured at a luminance of 3000 cd/m², and the time (T95) taken for the brightness to be reduced to 95% at 3000 cd/m² was measured, and the results thereof are shown in the following Table 1.

TABLE 1

| Classification | Compound (Light emitting layer) | Voltage (V) | Efficiency (cd/A) | CIE color coordinate (x, y) | T95 (hr) |
|---|---|---|---|---|---|
| Experimental Example 1-1 | 1 | 4.1 | 21 | (0.23, 0.62) | 99 |
| Experimental Example 1-2 | 2 | 4.2 | 20 | (0.23, 0.63) | 95 |
| Experimental Example 1-3 | 3 | 4.0 | 20 | (0.22, 0.64) | 97 |
| Experimental Example 1-4 | 4 | 4.1 | 22 | (0.23, 0.63) | 98 |
| Experimental Example 1-5 | 5 | 4.1 | 21 | (0.22, 0.64) | 95 |
| Experimental Example 1-6 | 6 | 4.0 | 21 | (0.22, 0.63) | 92 |
| Experimental Example 1-7 | 7 | 4.2 | 20 | (0.22, 0.63) | 92 |
| Experimental Example 1-8 | 8 | 4.1 | 20 | (0.23, 0.63) | 97 |
| Experimental Example 1-9 | 9 | 4.2 | 21 | (0.22, 0.64) | 99 |
| Experimental Example 1-10 | 10 | 4.1 | 22 | (0.23, 0.63) | 95 |
| Experimental Example 1-11 | 11 | 4.0 | 21 | (0.22, 0.64) | 94 |
| Experimental Example 1-12 | 12 | 4.1 | 20 | (0.23, 0.64) | 92 |
| Experimental Example 1-13 | 13 | 4.2 | 21 | (0.22, 0.62) | 90 |
| Experimental Example 1-14 | 14 | 4.1 | 20 | (0.22, 0.63) | 96 |
| Experimental Example 1-15 | 15 | 4.1 | 22 | (0.23, 0.62) | 94 |
| Experimental Example 1-16 | 16 | 4.0 | 21 | (0.22, 0.63) | 96 |
| Experimental Example 1-17 | 17 | 4.0 | 20 | (0.23, 0.63) | 99 |
| Experimental Example 1-18 | 18 | 4.0 | 23 | (0.23, 0.64) | 100 |
| Comparative Example 1-1 | 4CzIPN | 4.7 | 15 | (0.21, 0.61) | 53 |
| Comparative Example 1-2 | T1 | 4.7 | 14 | (0.22, 0.60) | 51 |
| Comparative Example 1-3 | T2 | 4.8 | 15 | (0.21, 0.61) | 54 |
| Comparative Example 1-4 | T3 | 4.8 | 3 | (0.12, 0.24) | 10 |
| Comparative Example 1-5 | T4 | 4.9 | 4 | (0.18, 0.31) | 9 |
| Comparative Example 1-6 | T5 | 4.8 | 1 | (0.16, 0.23) | 2 |
| Comparative Example 1-7 | T6 | 4.7 | 5 | (0.17, 0.33) | 3 |

As shown in Table 1, the devices of Experimental Examples 1-1 to 1-18 in which the compound of Formula 1 was used had lower voltage and more improved efficiency than the device of Comparative Example 1-1 in which the material of Compound 4CzIPN was used.

Further, it could be seen that the characteristics of the devices in which the compound of Formula 1 was used were all improved in terms of voltage, efficiency, and color purity as compared to the devices of Comparative Examples 1-2 to 1-7.

Therefore, it could be confirmed that the compound according to the present invention is excellent in the ability to emit light and has high color purity, and thus can be applied to a delayed fluorescence organic light emitting device.

Comparative Example 2-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After cleaning with distilled water was completed, the substrate was ultrasonically cleaned with a solvent of isopropyl alcohol, acetone and methanol, dried, and then transported to a plasma cleaner. Furthermore, the substrate was cleaned by using oxygen plasma for 5 minutes, and then was transported to a vacuum deposition machine. Each thin film was stacked on the thus prepared ITO transparent electrode at a degree of vacuum of $5.0 \times 10^{-4}$ Pa by a vacuum deposition method. First, hexaazatriphenylene-hexanitrile (HAT-CN) was thermally vacuum deposited to have a thickness of 500 Å on the ITO, thereby forming a hole injection layer.

The following compound NPB was vacuum-deposited on the hole injection layer, thereby forming a hole transport layer (300 Å).

The following compound EB1 was vacuum-deposited to have a film thickness of 100 Å on the hole transport layer, thereby forming an electron blocking layer (100 Å).

Subsequently, the following compounds m-CBP, 4CzIPN, and GD1 were vacuum-deposited at a weight ratio of 68:30:2 to have a film thickness of 300 Å on the electron blocking layer, thereby forming a light emitting layer.

The following compound HB1 was vacuum-deposited to have a film thickness of 100 Å on the light emitting layer, thereby forming a hole blocking layer.

The following compound ET1 and Compound lithium quinolate (LiQ) were vacuum-deposited at a weight ratio of 1:1 on the hole blocking layer, thereby forming an electron injection and transport layer having a thickness of 300 Å. Lithium fluoride (LiF) and aluminum were sequentially deposited on the electron injection and transport layer to have a thickness of 12 Å and 2,000 Å, respectively, thereby forming a negative electrode.

In the aforementioned procedure, the deposition rates of the organic materials were maintained at 0.4 Å/sec to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ torr to $5 \times 10^{-6}$ torr, thereby manufacturing an organic light emitting device.

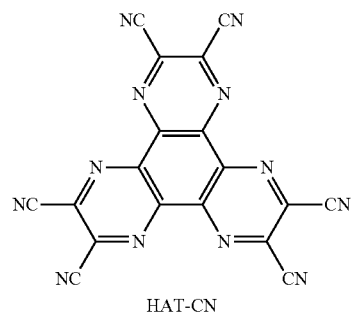

HAT-CN

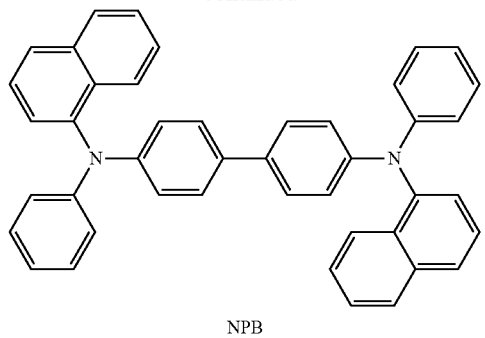

NPB

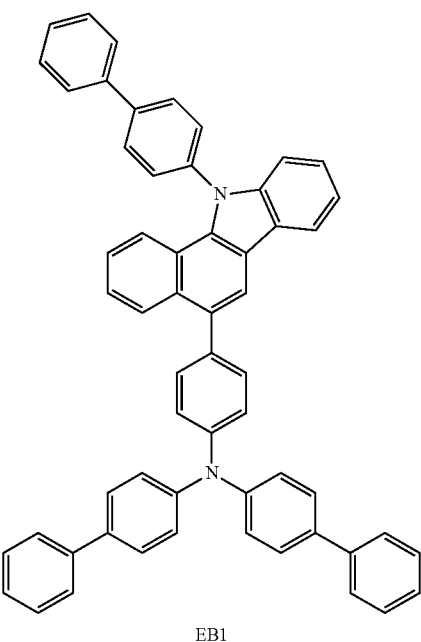

EB1

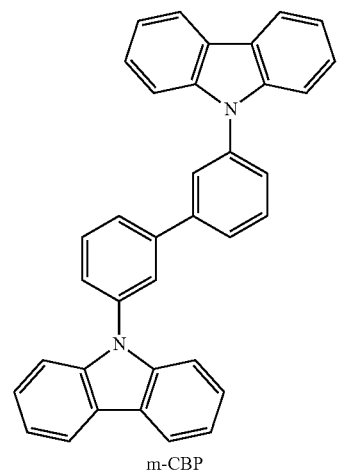

m-CBP

-continued

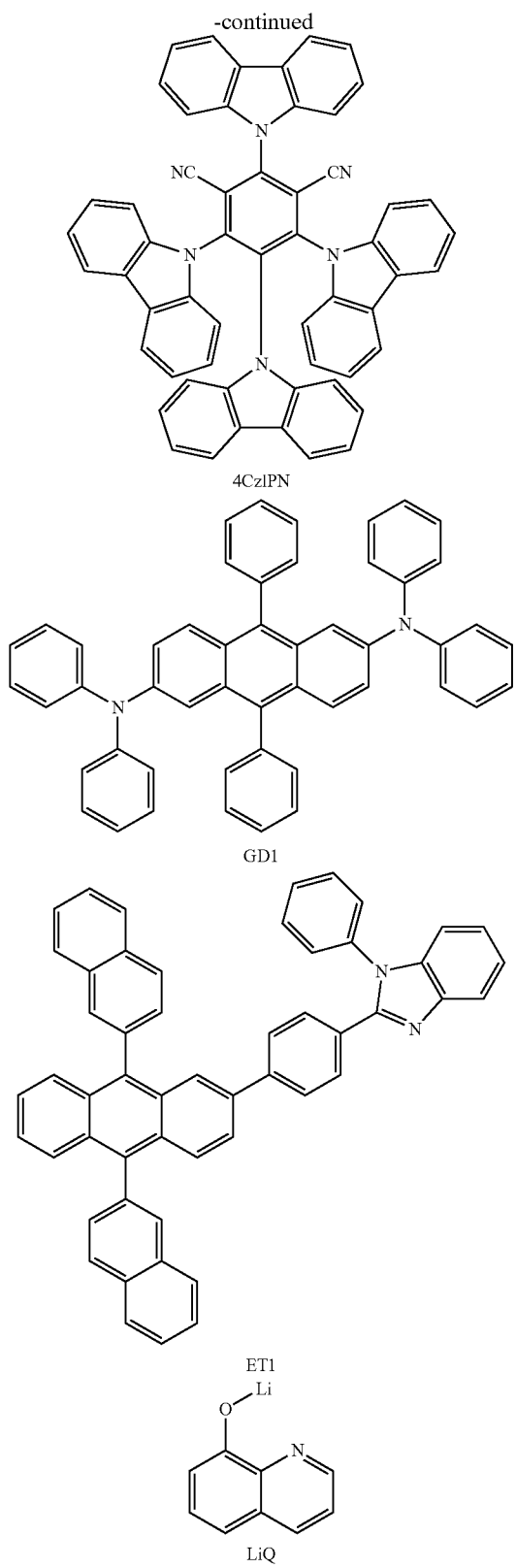

4CzIPN

GD1

ET1

LiQ

Experimental Examples 2-1 to 2-18

Organic light emitting devices were manufactured in the same manner as in Comparative Example 2-1, except that the compounds in the following Table 2 were used instead of Compound 4CzIPN in Comparative Example 2-1.

Comparative Examples 2-2 to 2-7

Organic light emitting devices were manufactured in the same manner as in Comparative Example 2-1, except that the compounds in the following Table 2 were used instead of Compound 4CzIPN in Comparative Example 2-1.

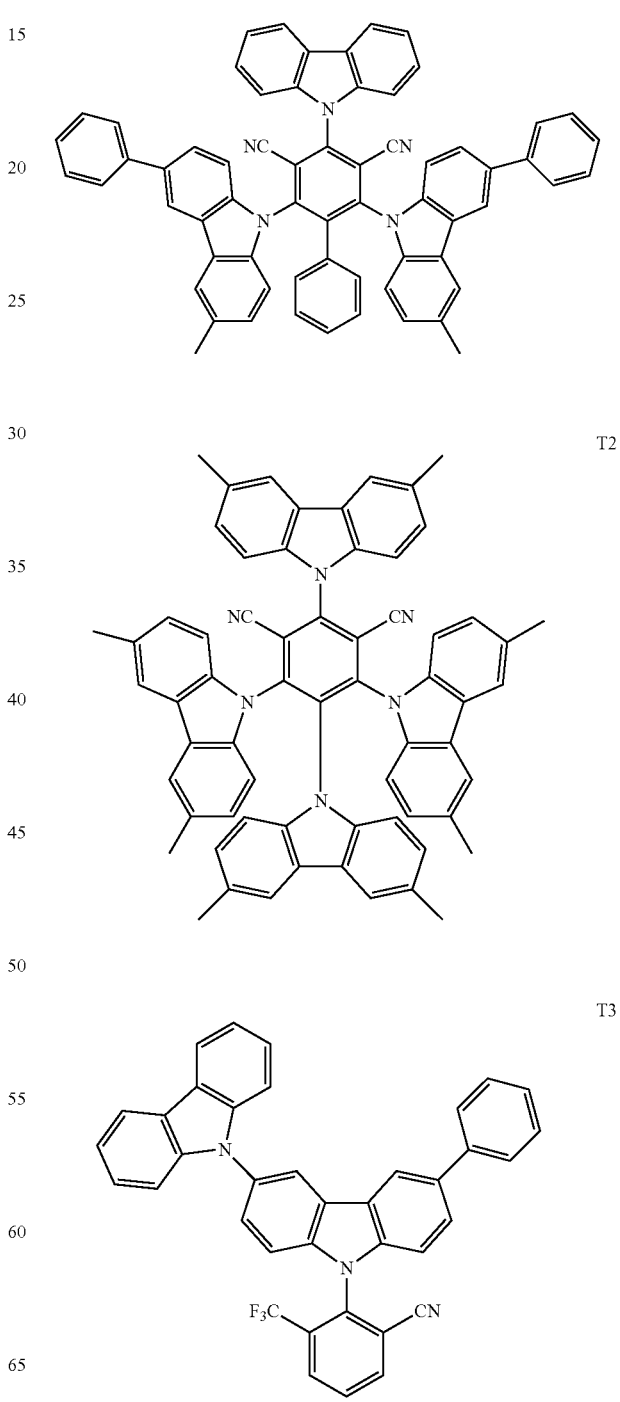

T1

T2

T3

-continued

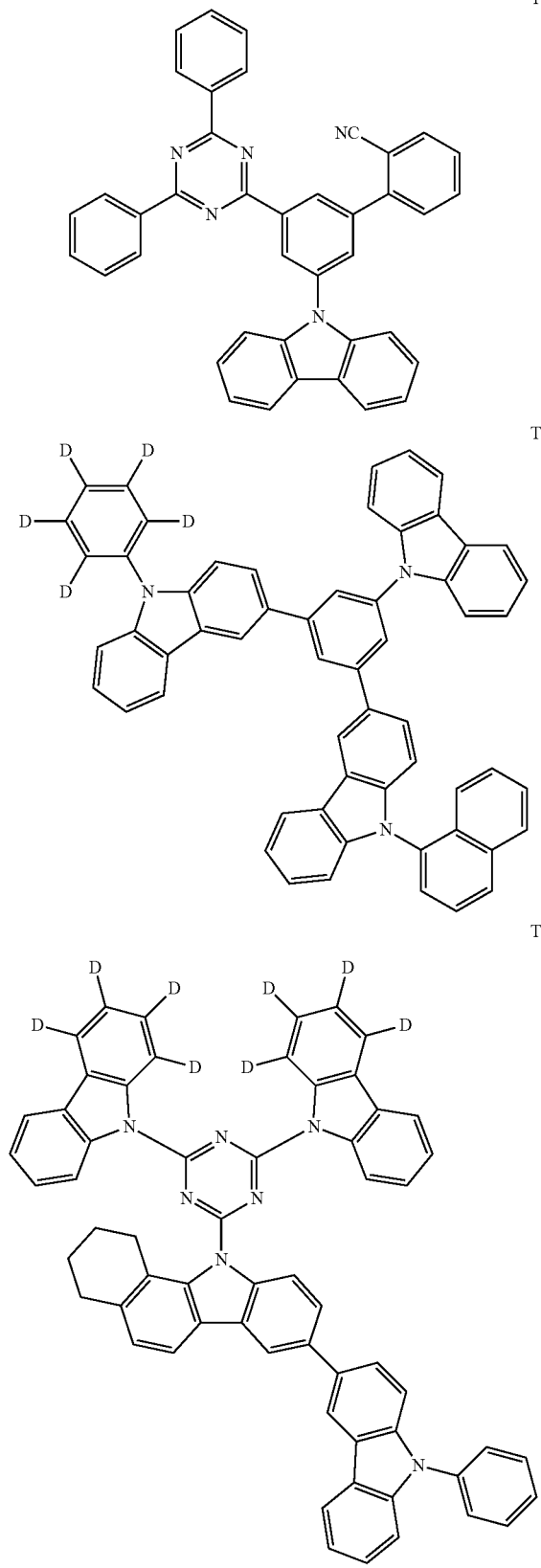

For each of the organic light emitting devices in Experimental Examples 2-1 to 2-18 and Comparative Examples 2-1 to 2-7, the driving voltage (V) and current efficiency (cd/A) were measured at a current density of 10 mA/cm² and the CIE color coordinate was measured at a luminance of 3000 cd/m², and the results thereof are shown in the following Table 2.

TABLE 2

| Classification | Compound (Light emitting layer) | Voltage (V) | Efficiency (cd/A) | CIE color coordinate (x, y) |
|---|---|---|---|---|
| Experimental Example 2-1 | 1 | 4.1 | 21 | (0.19, 0.68) |
| Experimental Example 2-2 | 2 | 4.0 | 22 | (0.19, 0.69) |
| Experimental Example 2-3 | 3 | 4.1 | 21 | (0.18, 0.68) |
| Experimental Example 2-4 | 4 | 4.2 | 21 | (0.19, 0.68) |
| Experimental Example 2-5 | 5 | 4.1 | 22 | (0.18, 0.68) |
| Experimental Example 2-6 | 6 | 4.1 | 22 | (0.19, 0.69) |
| Experimental Example 2-7 | 7 | 4.2 | 20 | (0.19, 0.69) |
| Experimental Example 2-8 | 8 | 4.0 | 21 | (0.18, 0.69) |
| Experimental Example 2-9 | 9 | 4.1 | 22 | (0.19, 0.69) |
| Experimental Example 2-10 | 10 | 4.1 | 21 | (0.19, 0.68) |
| Experimental Example 2-11 | 11 | 4.2 | 21 | (0.18, 0.68) |
| Experimental Example 2-12 | 12 | 4.0 | 20 | (0.18, 0.68) |
| Experimental Example 2-13 | 13 | 4.2 | 20 | (0.18, 0.69) |
| Experimental Example 2-14 | 14 | 4.1 | 21 | (0.18, 0.68) |
| Experimental Example 2-15 | 15 | 4.1 | 21 | (0.19, 0.68) |
| Experimental Example 2-16 | 16 | 4.2 | 20 | (0.19, 0.69) |
| Experimental Example 2-17 | 17 | 4.1 | 21 | (0.19, 0.68) |
| Experimental Example 2-18 | 18 | 4.0 | 22 | (0.19, 0.69) |
| Comparative Example 2-1 | 4CzIPN | 4.6 | 16 | (0.16, 0.67) |
| Comparative Example 2-2 | T1 | 4.7 | 13 | (0.16, 0.66) |
| Comparative Example 2-3 | T2 | 4.6 | 16 | (0.17, 0.68) |
| Comparative Example 2-4 | T3 | 4.8 | 4 | (0.15, 0.31) |
| Comparative Example 2-5 | T4 | 4.8 | 4 | (0.18, 0.37) |
| Comparative Example 2-6 | T5 | 4.7 | 3 | (0.16, 0.25) |
| Comparative Example 2-7 | T6 | 4.8 | 4 | (0.16, 0.27) |

As shown in Table 2, the devices of Experimental Examples 2-1 to 2-18 in which the compound of Formula 1 was used had lower voltage and more improved efficiency than the device of Comparative Example 2-1 in which the material of Compound 4CzIPN was used.

Further, it could be seen that the characteristics of the devices in which the compound of Formula 1 was used were all improved in terms of voltage and efficiency as compared to the devices of Comparative Examples 2-1 to 2-7.

Therefore, it could be confirmed that the compound according to the present invention is excellent in the ability to emit light, can tune the emission wavelength, and thus can realize an organic light emitting device with high color purity.

The invention claimed is:

1. A compound represented by the following Formula 1:

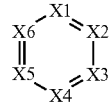

[Formula 1]

wherein in Formula 1,

X1 to X6 are the same as or different from each other, and are each independently N, C(A1), C(A2), C(A3), C(A4), C—H, C-D, or C—R', and R' is an aryl group, wherein three of X1 to X6 are C-D, one thereof is C(A2), one thereof is C(A4), and one thereof is N, C(A2), C(A4), C—H, C-D, or C—R'; or at least one of X1 to X6 is C(A1) or C(A2), at least one thereof is C(A3) or C(A4), and at least one of X1 to X6 is C(A1) or C(A3), A1 is any one of the following a-2 to a-4, and A1's are the same as or different from each other provided that there are two or more A1's,

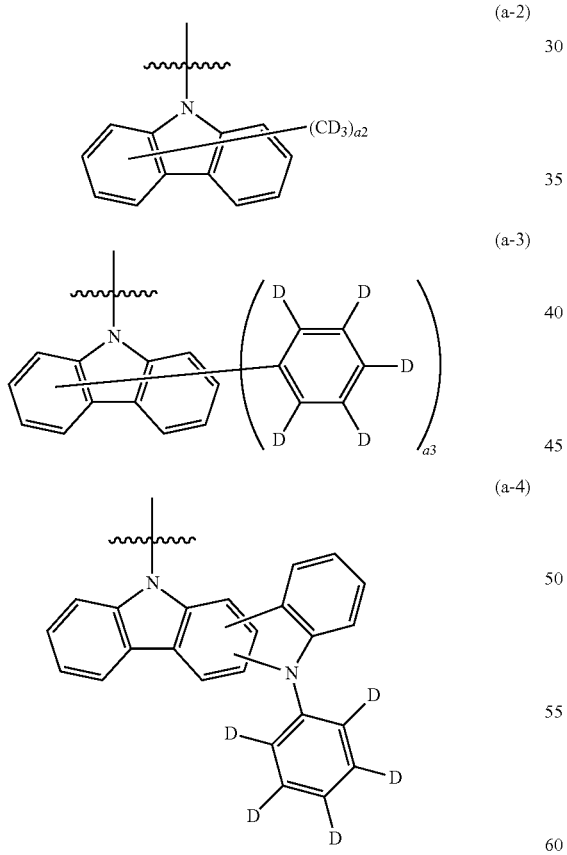

wherein in a-2 to a-3, a2 is an integer from 1 to 8, and a3 is an integer from 1 to 8, A2 is the following b-1 or b-2, and A2's are the same as or different from each other provided that there are two or more A2's,

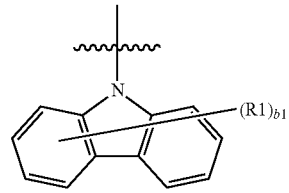

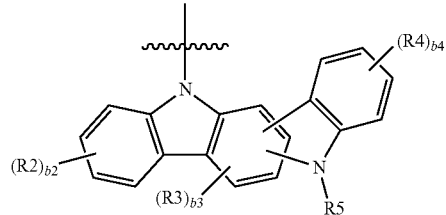

A3 is the following c-1 or c-2, and A3's are the same as or different from each other provided that there are two or more A3's,

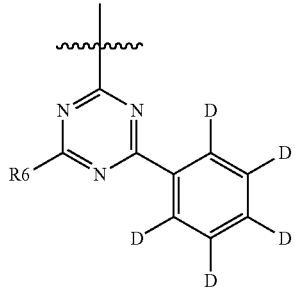

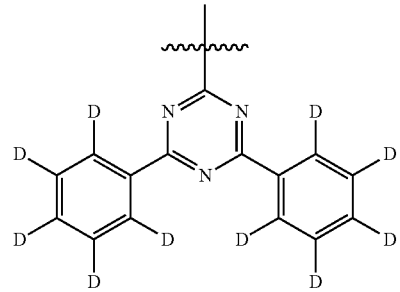

A4 is the following d-1 or d-2, and A4's are the same as or different from each other provided that there are two or more A4's,

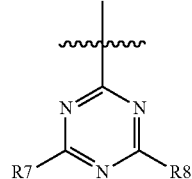

-continued

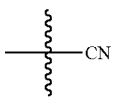
(d-2)

wherein in b-1, b-2, c-1, and d-1,

R1 to R8 are the same as or different from each other, and are each independently any one selected from the group consisting of hydrogen; an alkyl group; an aryl group; and a heteroaryl group, or a group to which two or more groups selected from the group are linked to each other, b1 is an integer from 0 to 8, and R1's are the same as or different from each other provided that b1 is 2 or more, b2 is an integer from 0 to 4, and R2's are the same as or different from each other provided that b2 is 2 or higher, b3 is an integer from 0 to 2, and R3's are the same as or different from each other provided that b3 is 2, and b4 is an integer from 0 to 4, and R4's are the same as or different from each other provided that b4 is 2 or higher.

2. The compound of claim 1, wherein Formula 1 is represented by the following Formula 1-1 or 1-2:

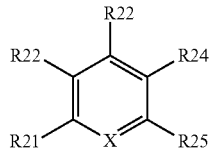
[Formula 1-1]

wherein in Formula 1-1,

X is N or CR26, and R26 is A1, A2, A3, A4, H, D, or an aryl group,

R21 to R25 are the same as or different from each other, and are each independently A1, A2, A3, A4, H, D, or an aryl group, wherein at least one of R21 to R25 is A1 or A2, at least one thereof is A3 or A4, and at least one of R21 to R25 is A1 or A3,

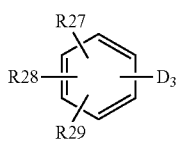
[Formula 1-2]

wherein in Formula 1-2,

R27 is A2, R28 is A4, and R29 is A2, A4, H, D, or an aryl group, and wherein in Formulae 1-1 and 1-2, the definitions of A1, A2, A3, and A4 are the same as those defined in Formula 1.

3. The compound of claim 2, wherein Formula 1-2 is represented by the following Formula 2:

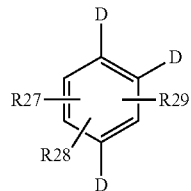
[Formula 2]

wherein in Formula 2, the definitions of R27 to R29 are the same as those defined in Formula 1-2.

4. The compound of claim 1, wherein a-2 is the following a-21 or a-22:

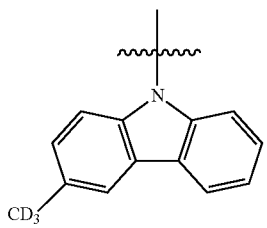
(a-21)

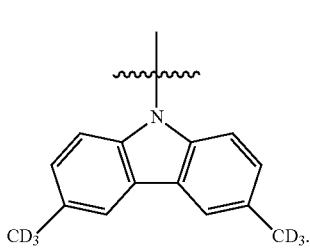
(a-22)

5. The compound of claim 1, wherein a-3 is any one of the following a-31 to a-33:

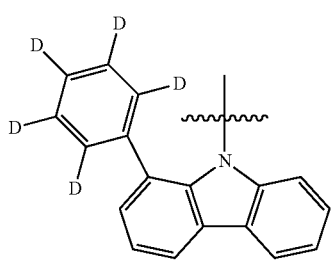
(a-31)

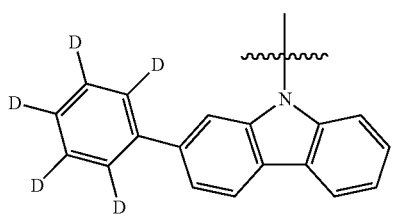
(a-32)

(a-33)
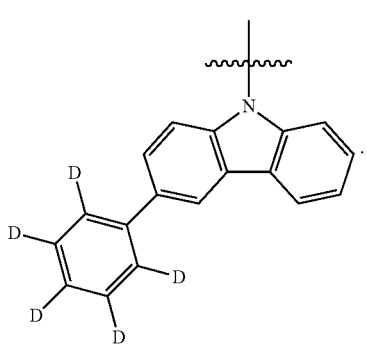
6. The compound of claim 1, wherein the compound represented by Formula 1 is any one selected from the following compounds:
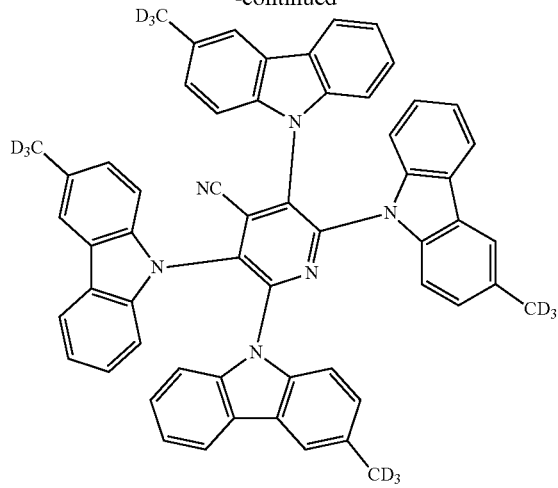
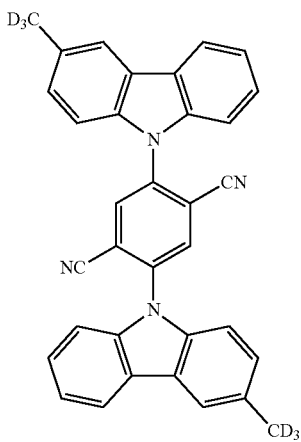
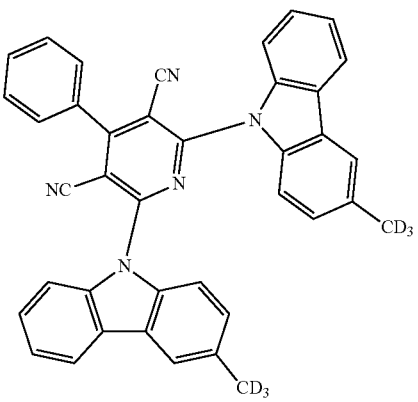
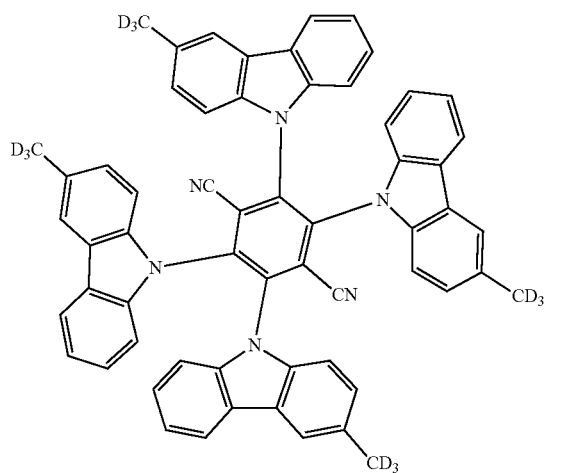
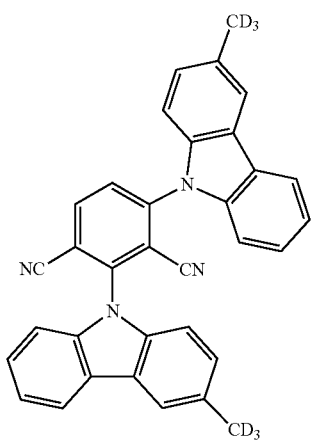

165
-continued
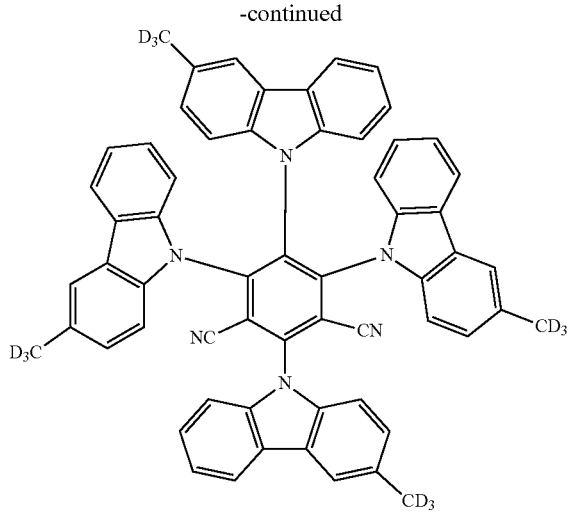
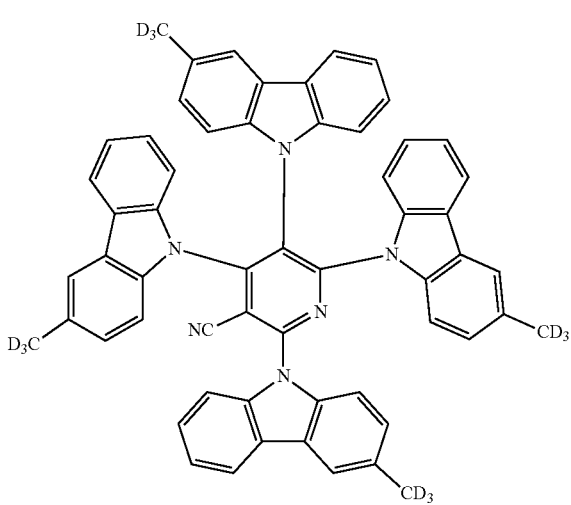
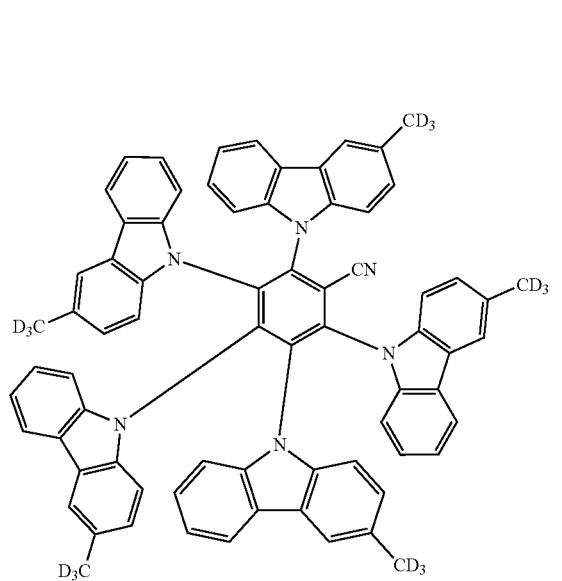
166
-continued
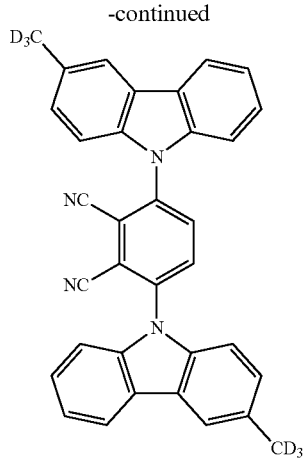
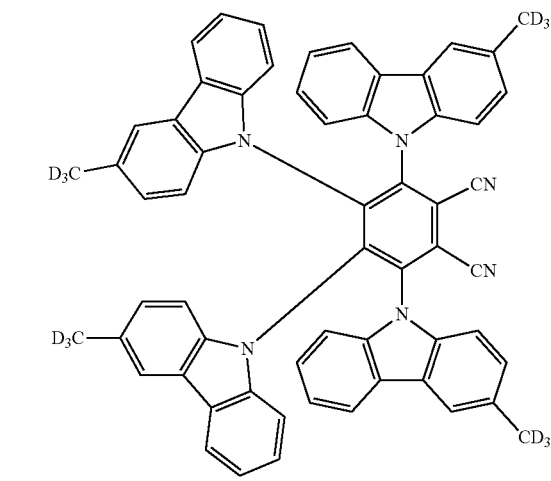
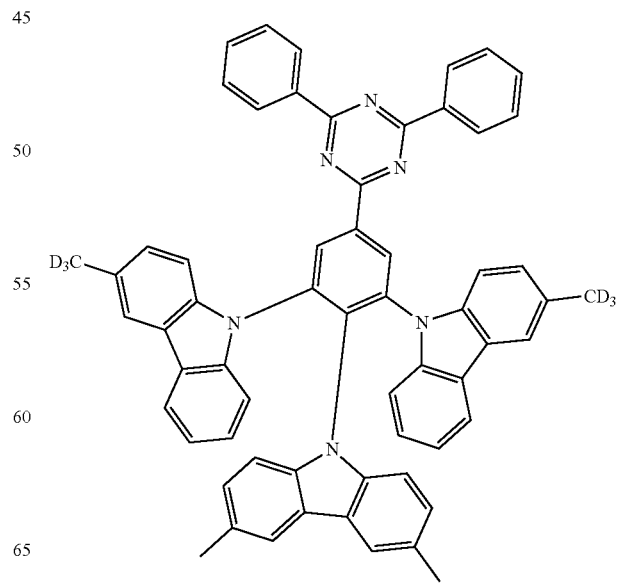

167
-continued
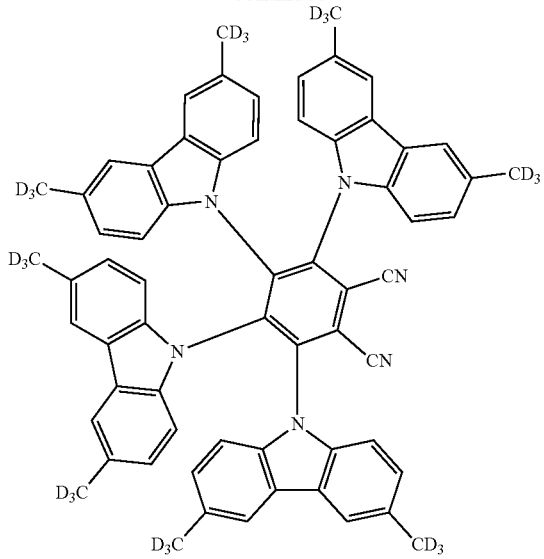
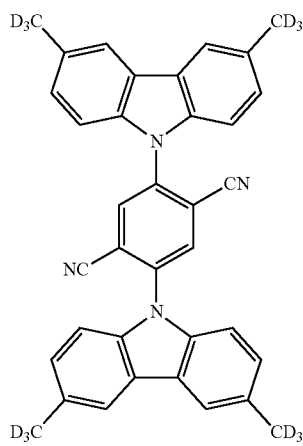
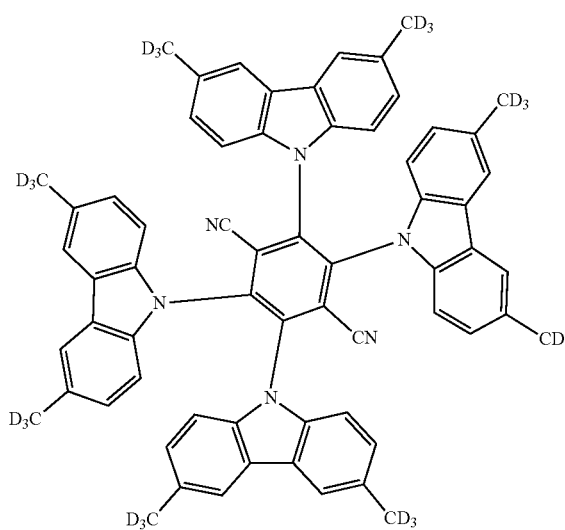
168
-continued
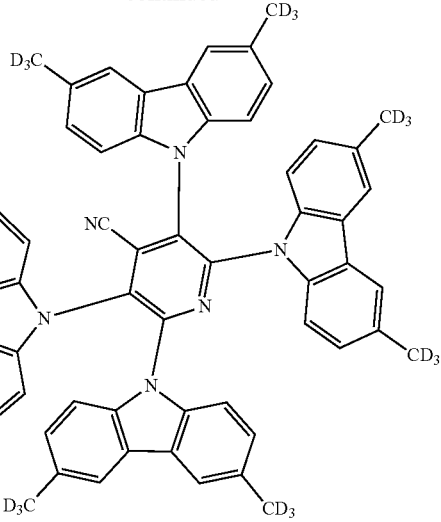
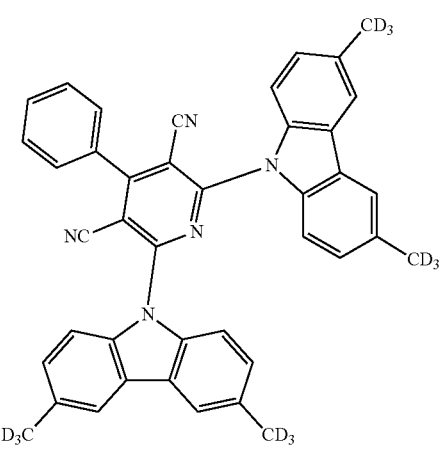
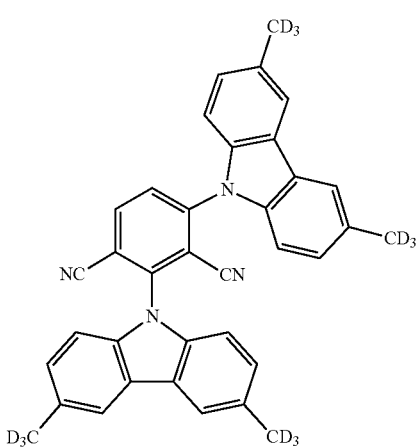

169
-continued
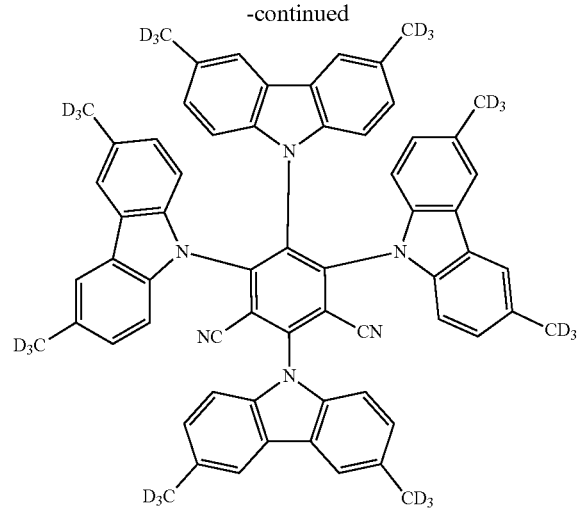
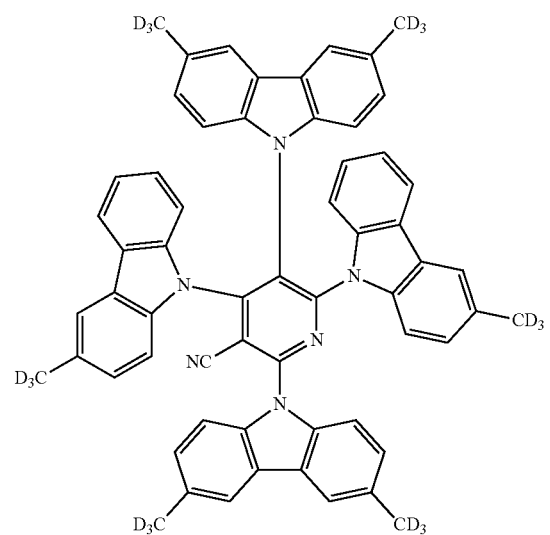
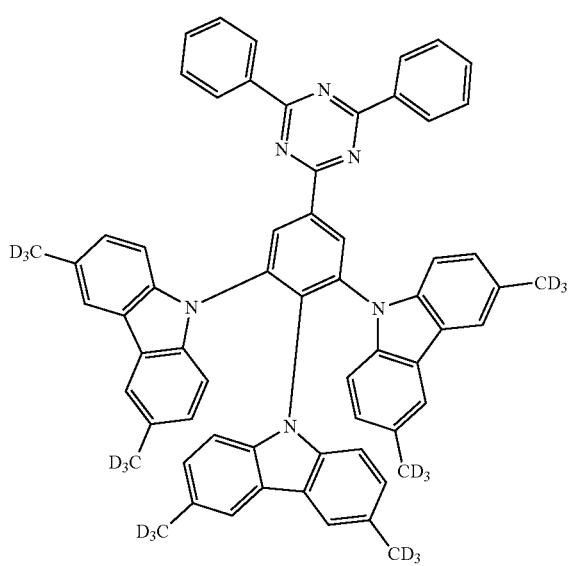
170
-continued
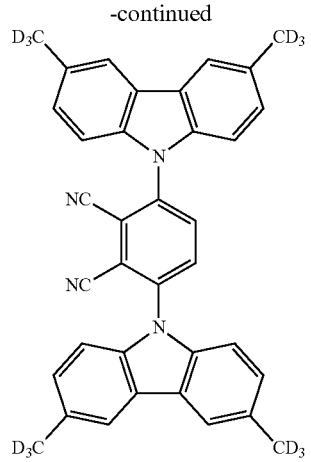
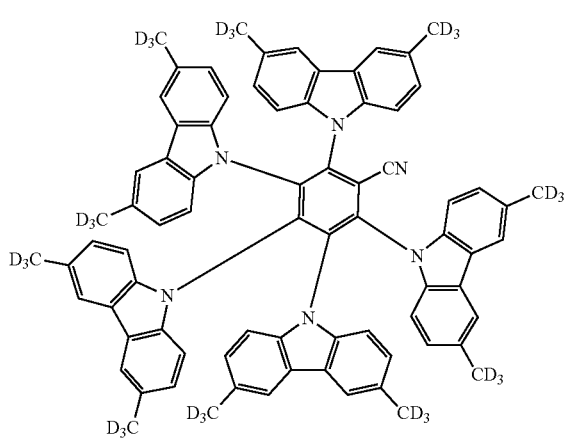
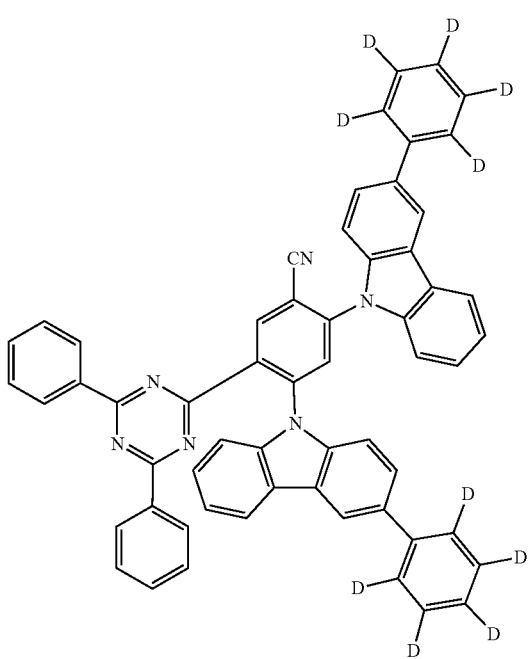

171
-continued
172
-continued
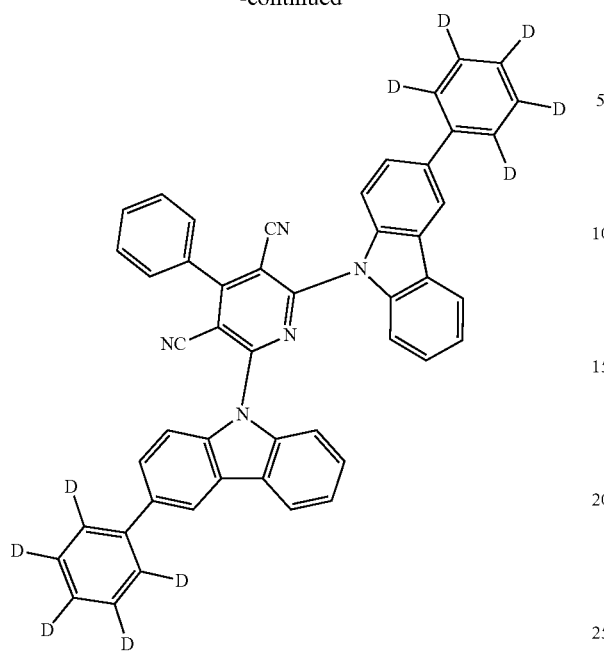
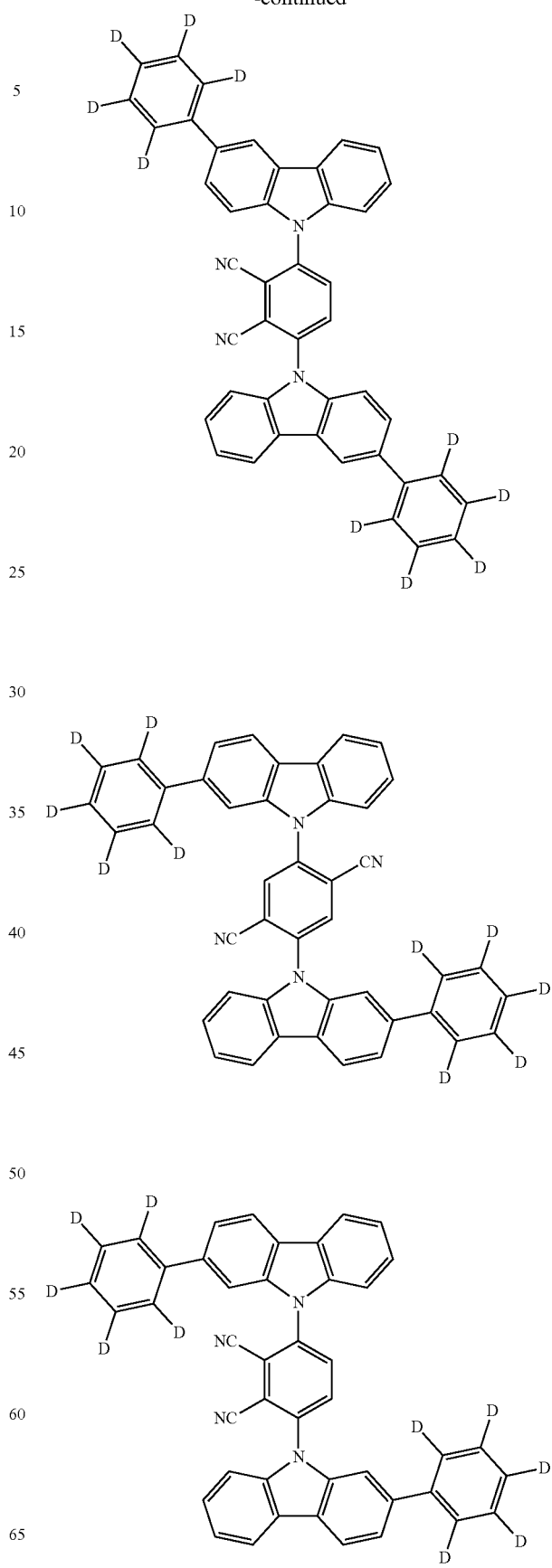

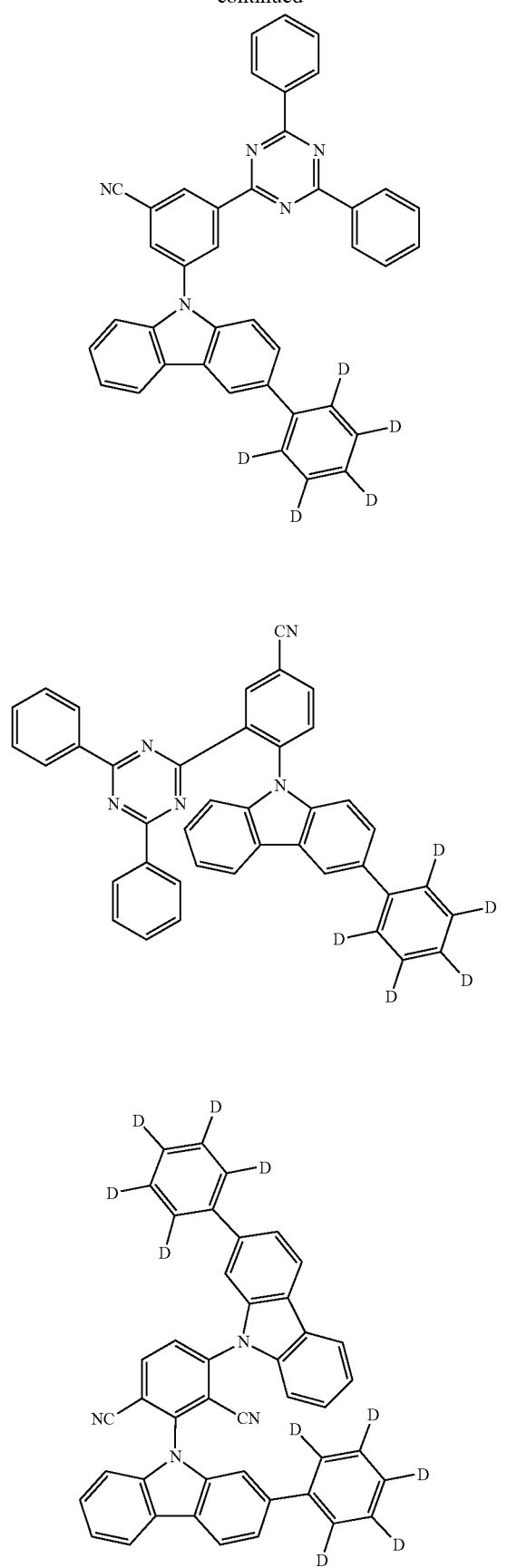
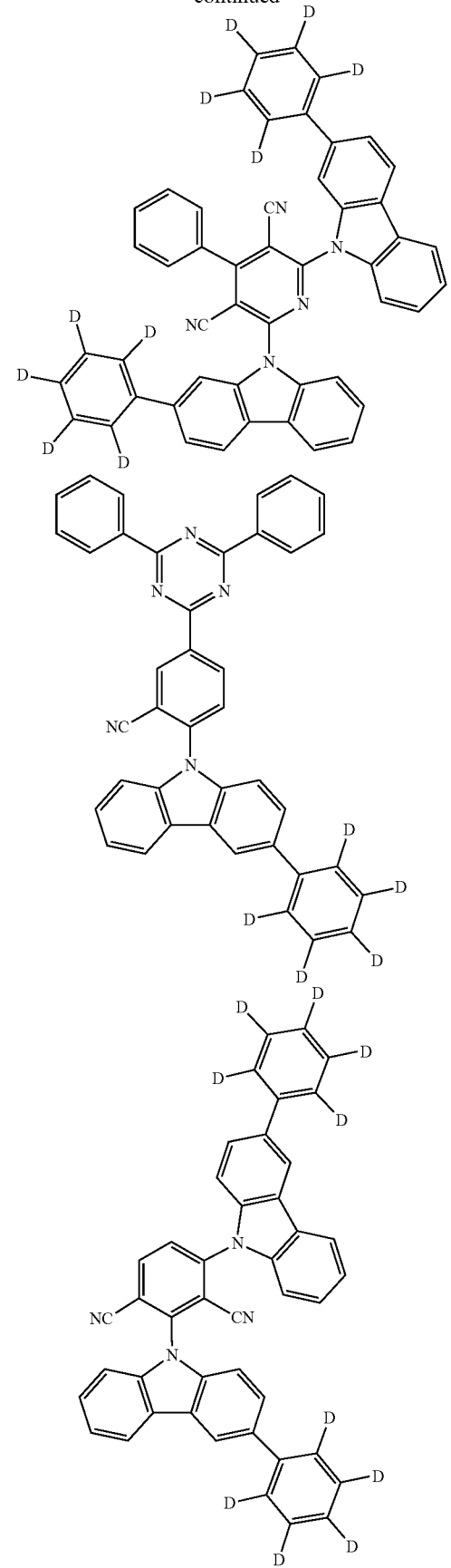

175
-continued
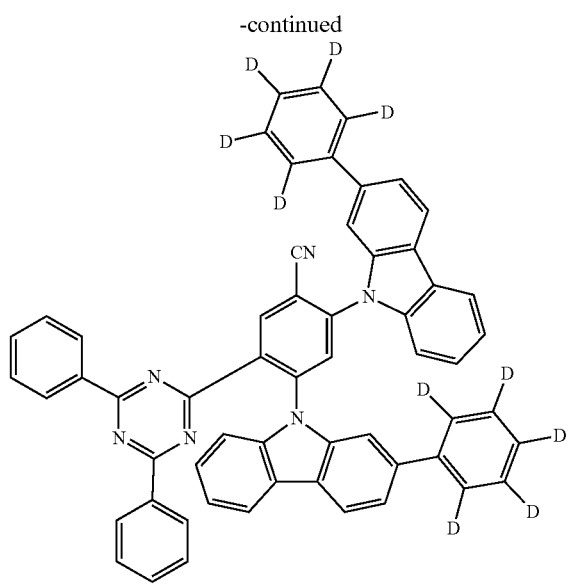
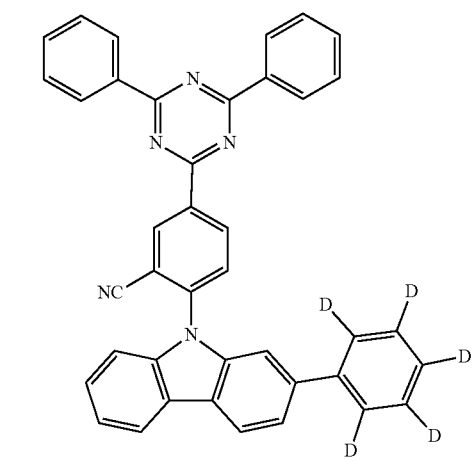
176
-continued
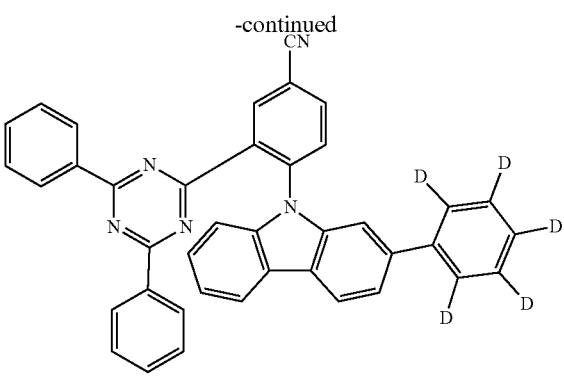
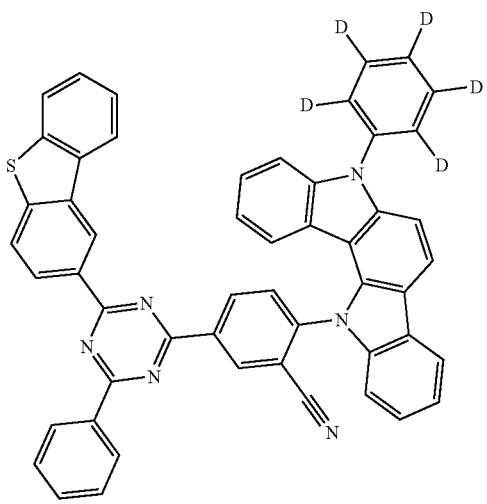
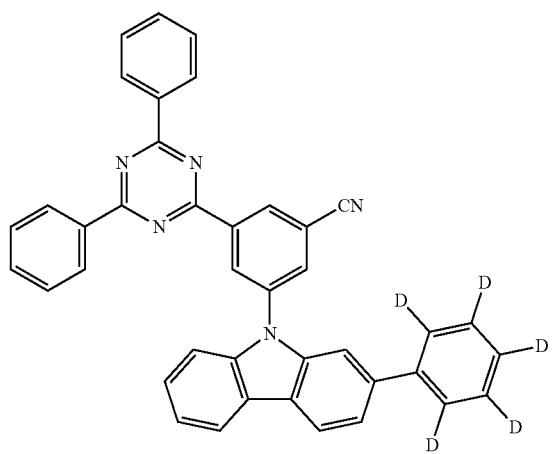
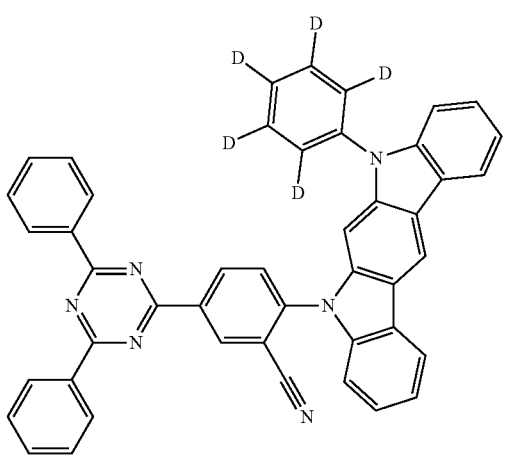

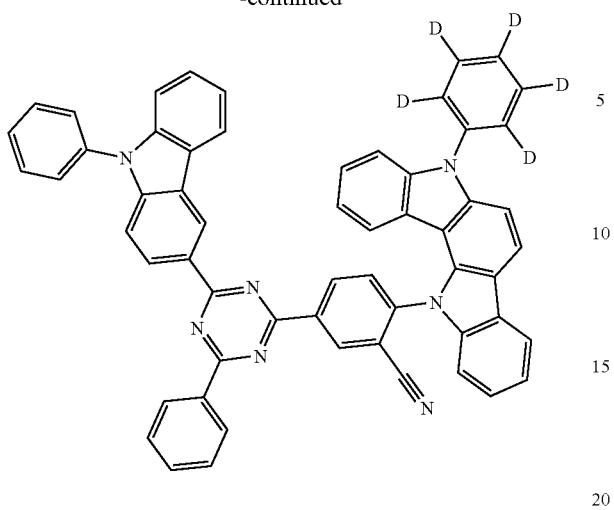
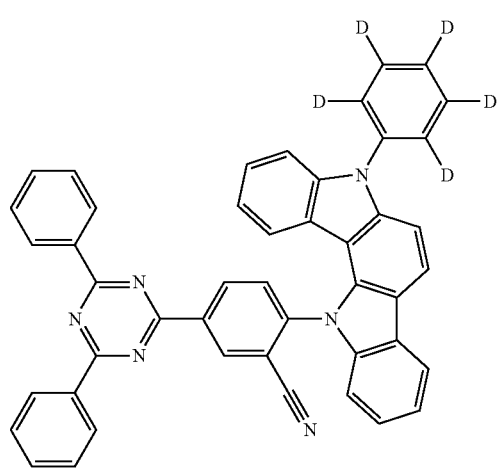
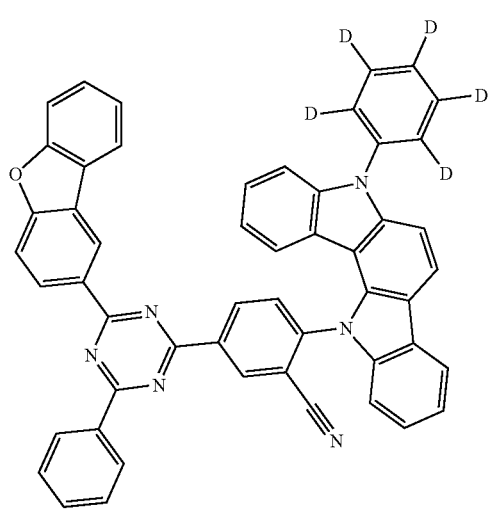
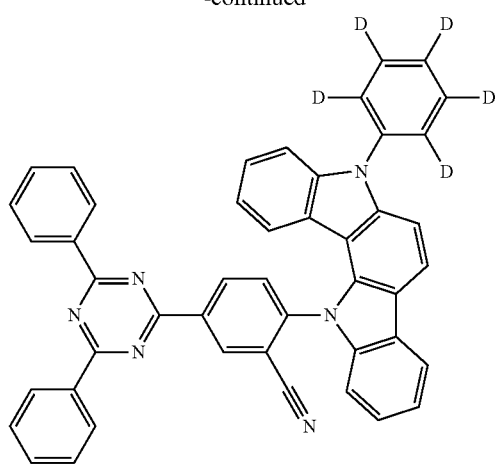
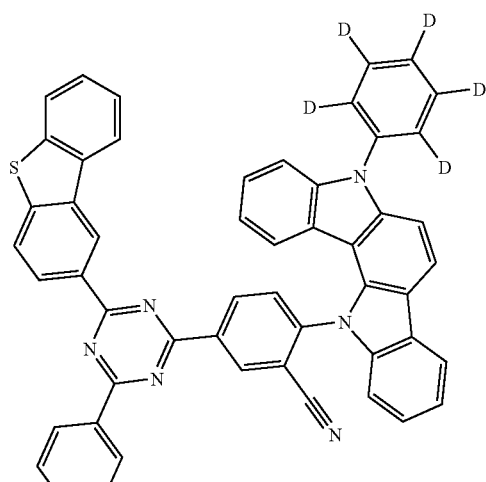
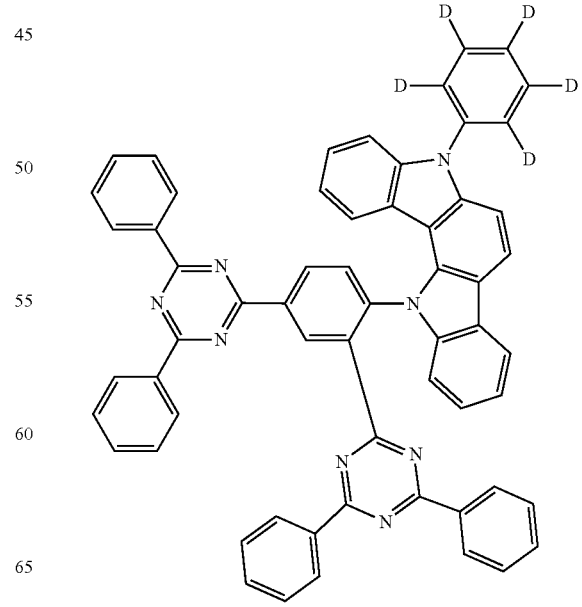

179
-continued
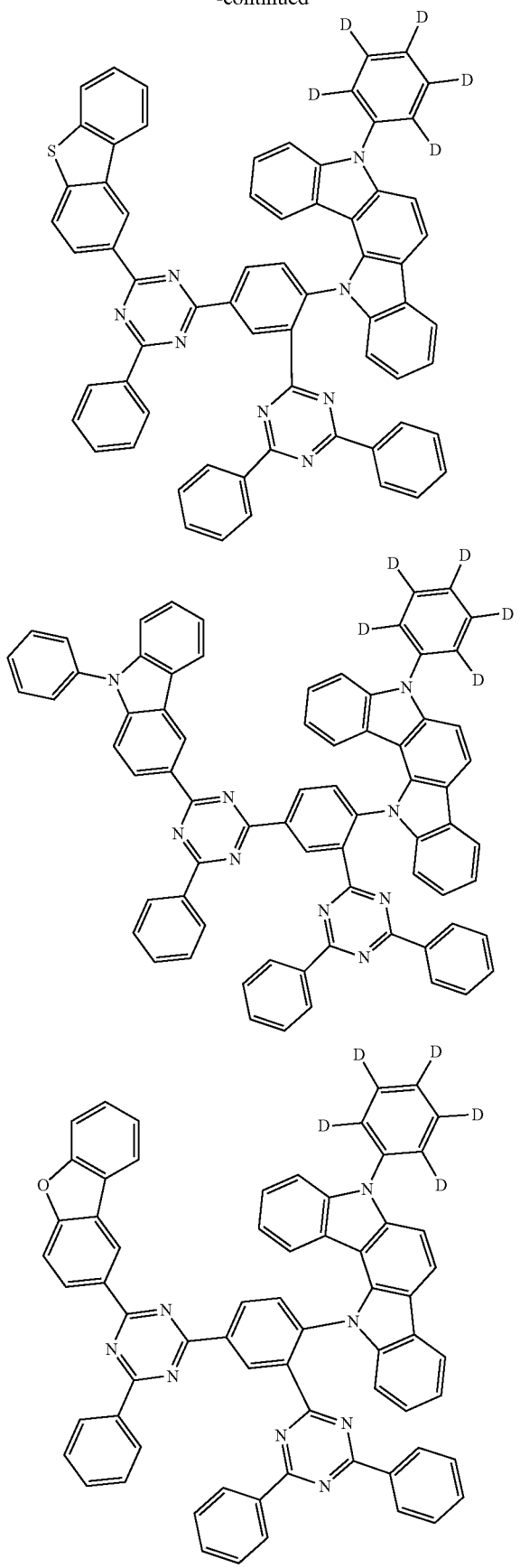
180
-continued
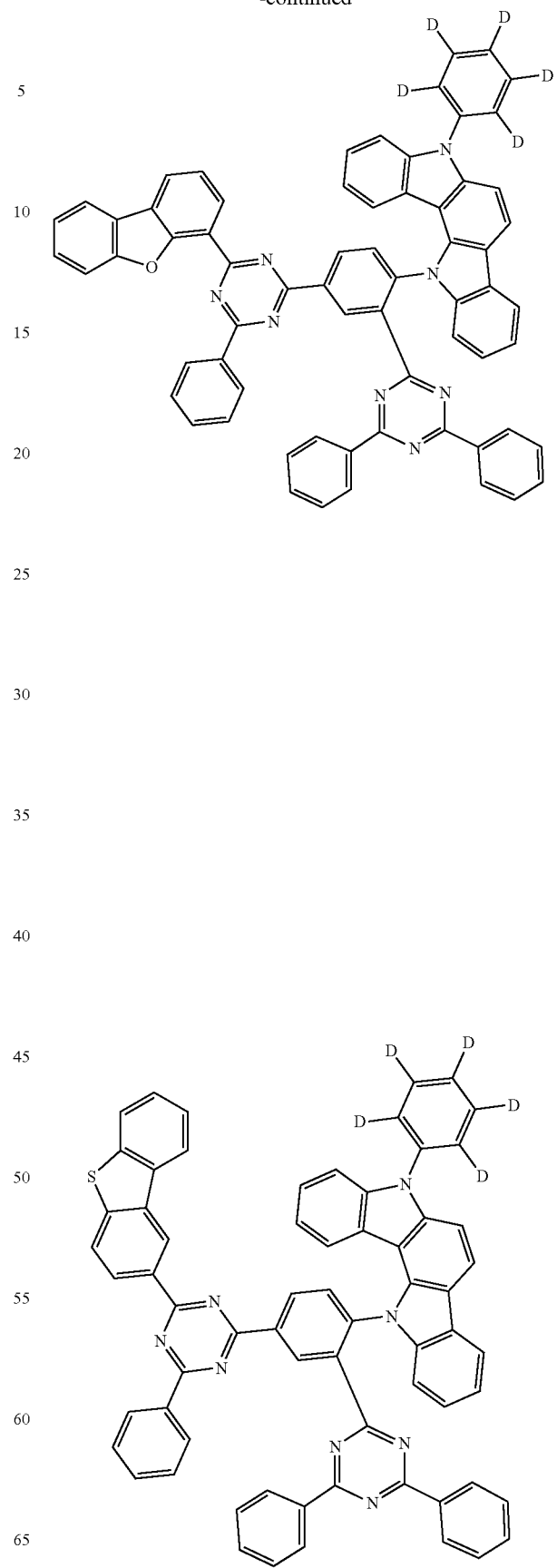

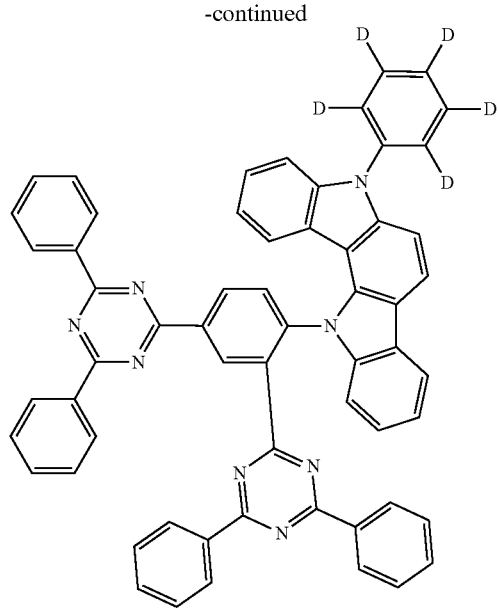
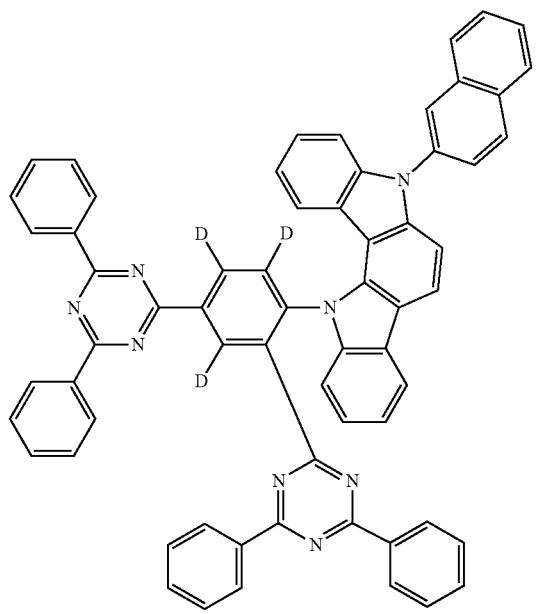
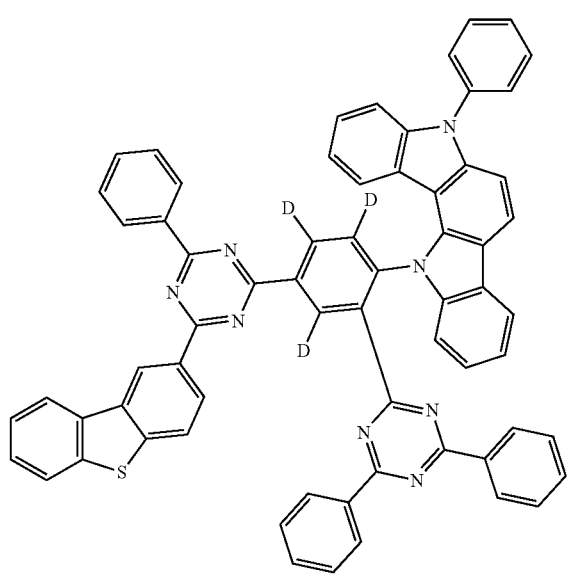
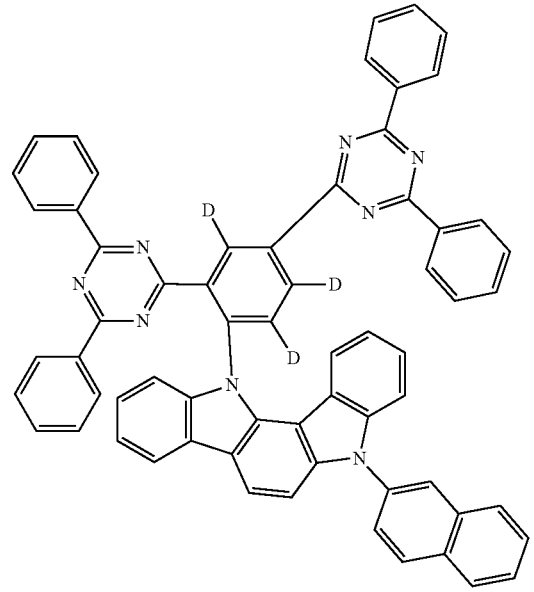

183
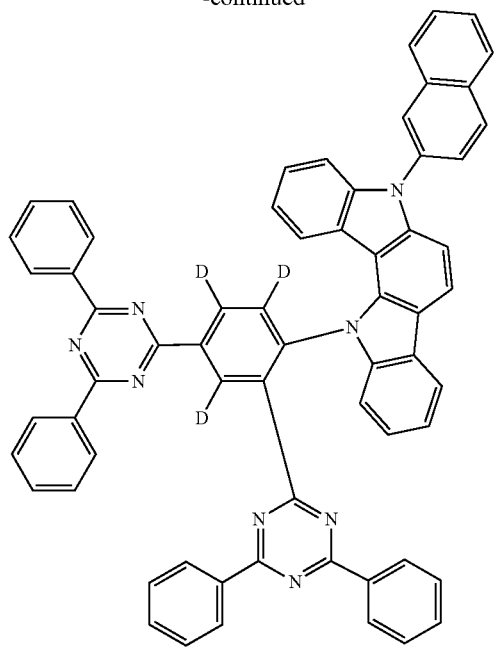
184
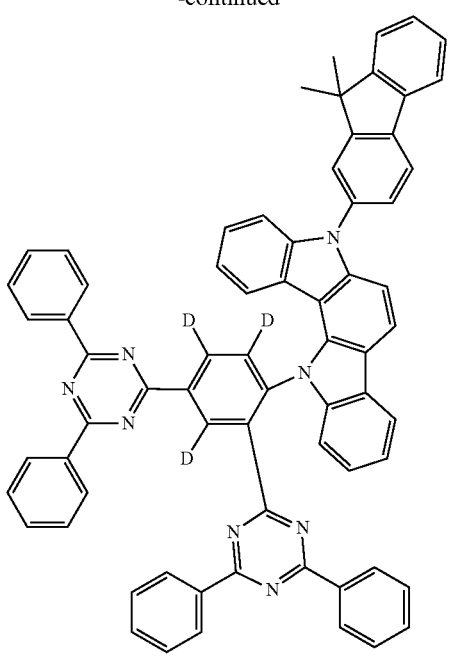
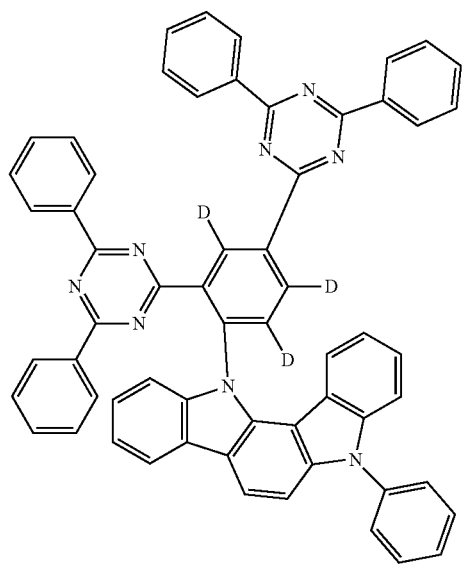
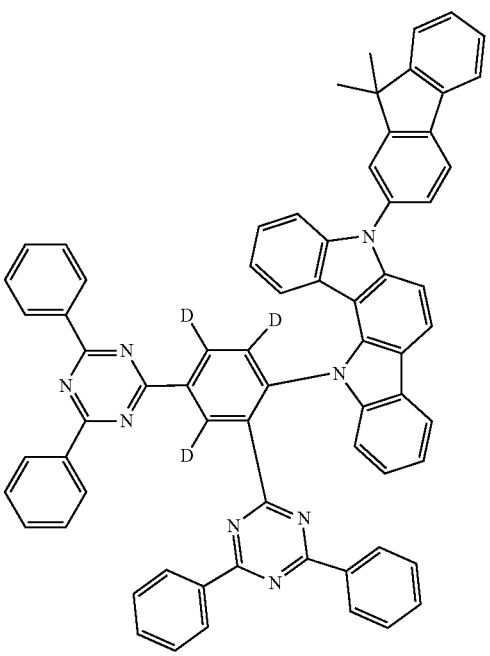

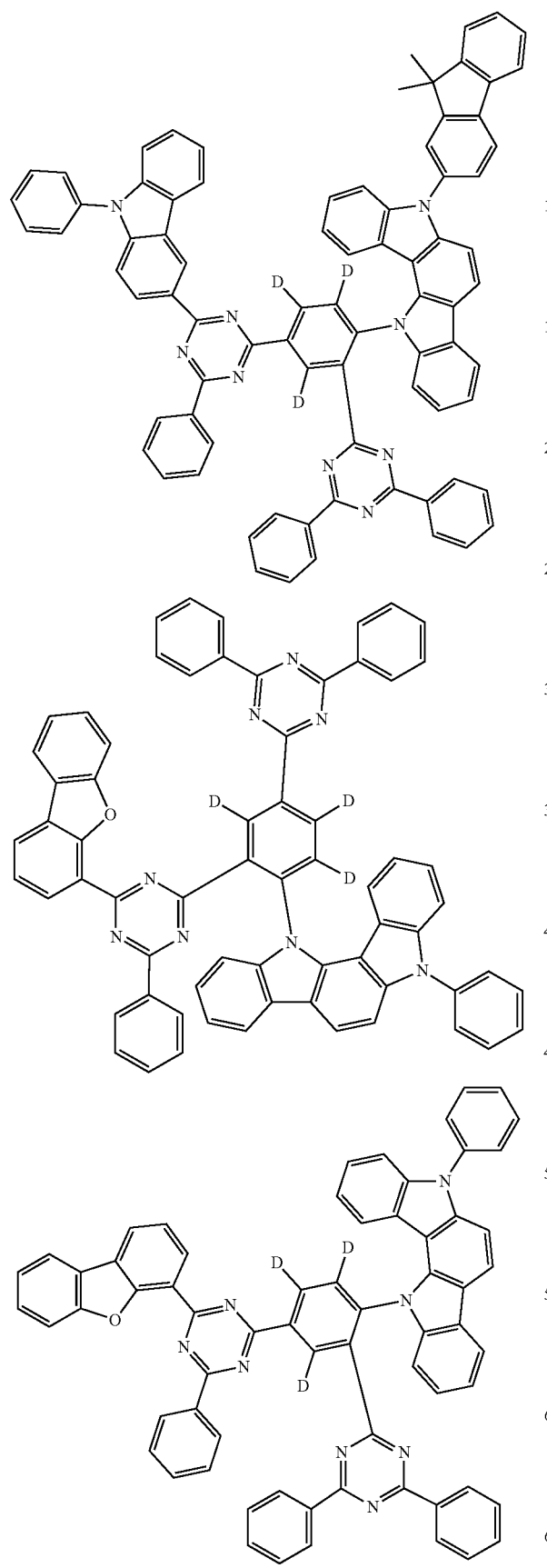
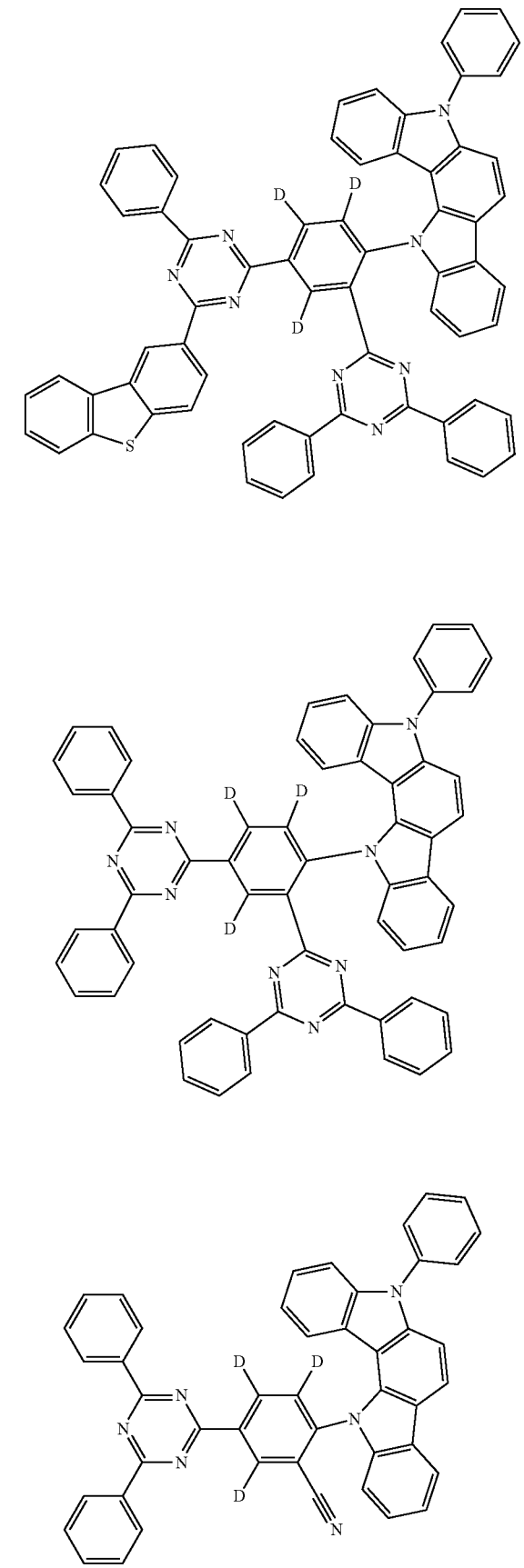

187
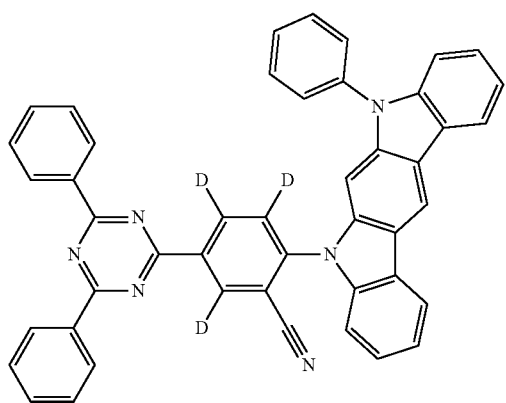
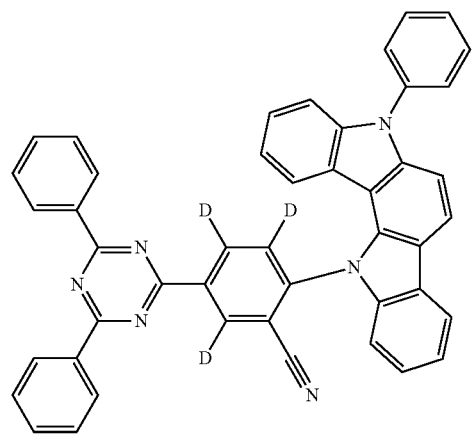
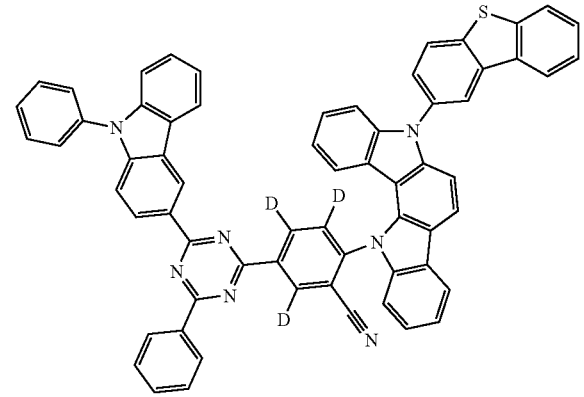
188
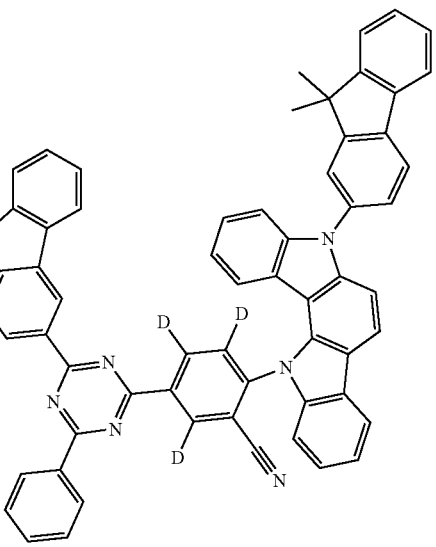
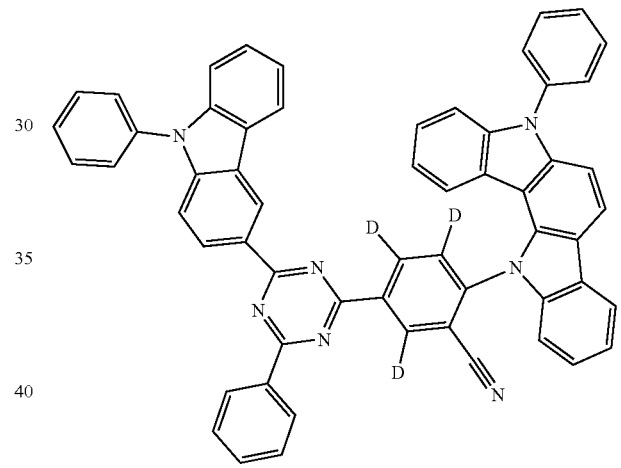
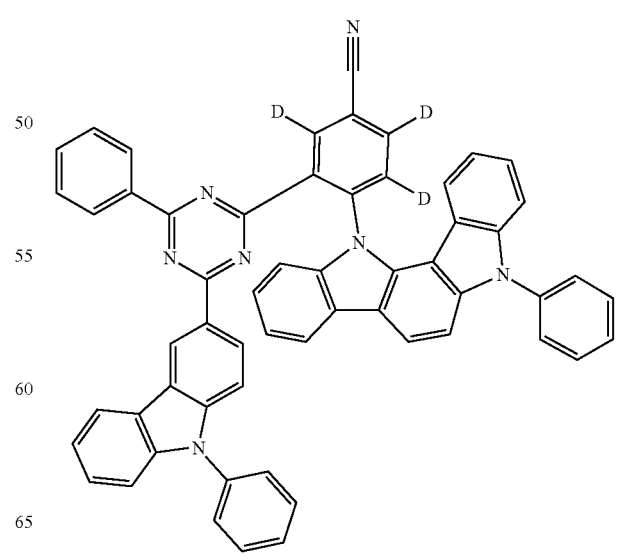

189
-continued
190
-continued
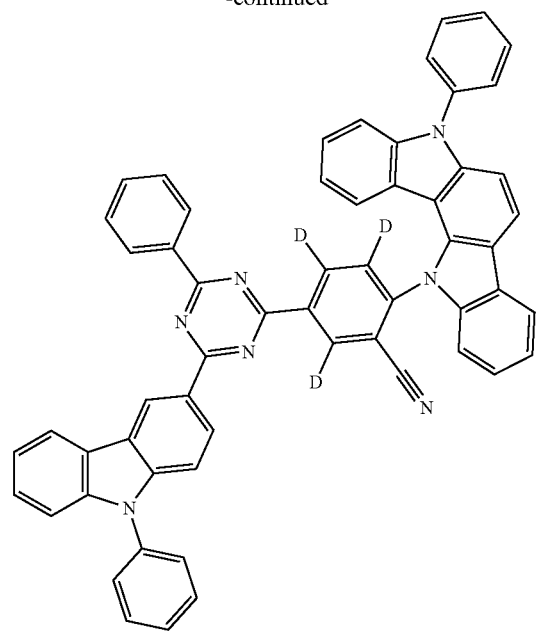
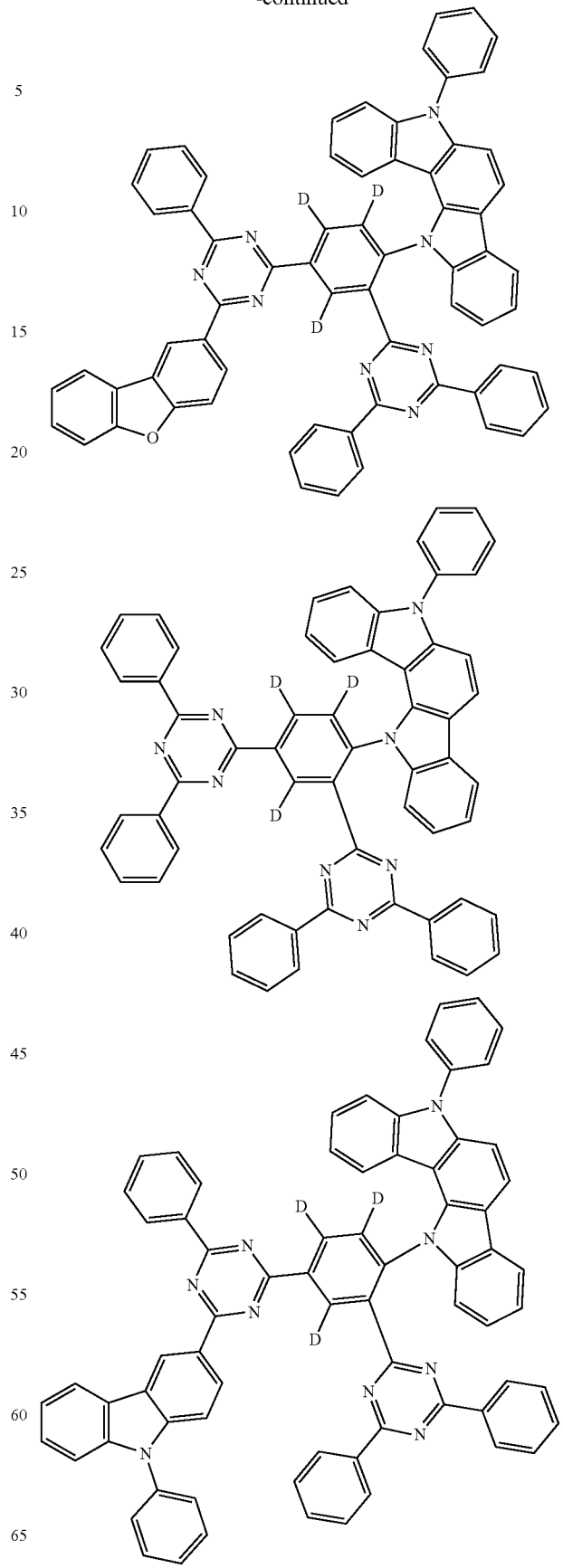

191
-continued
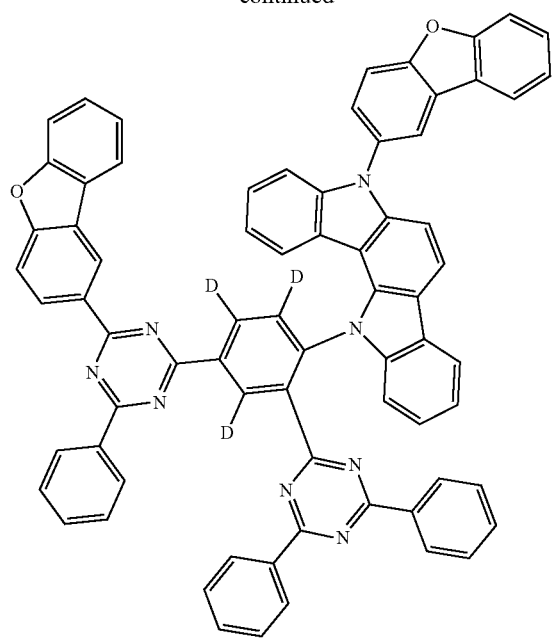
192
-continued
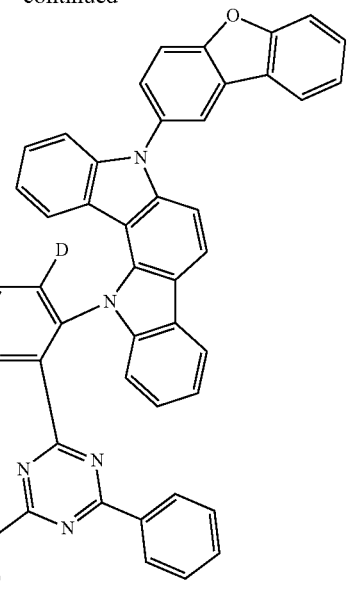
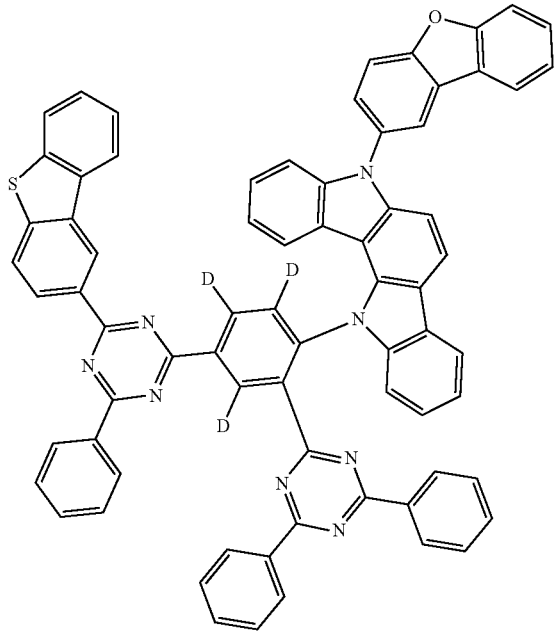
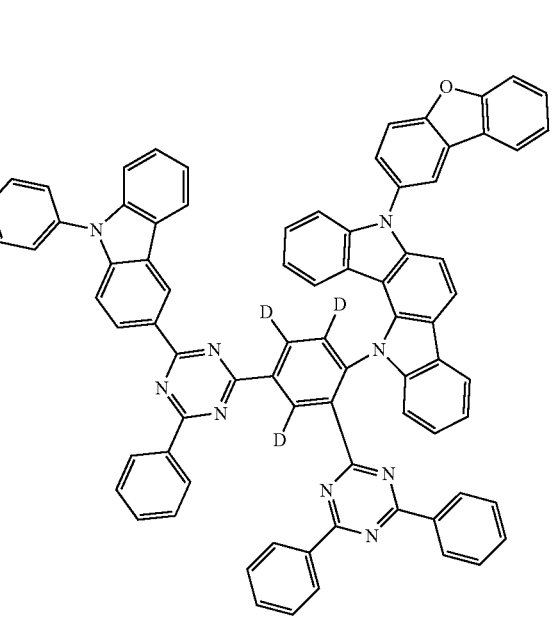

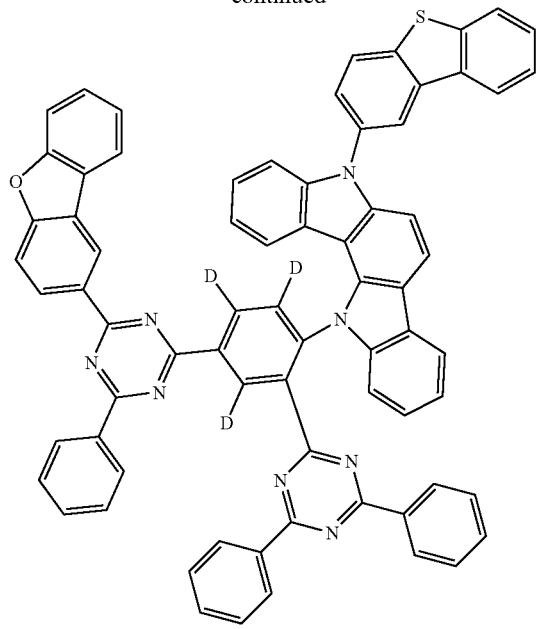
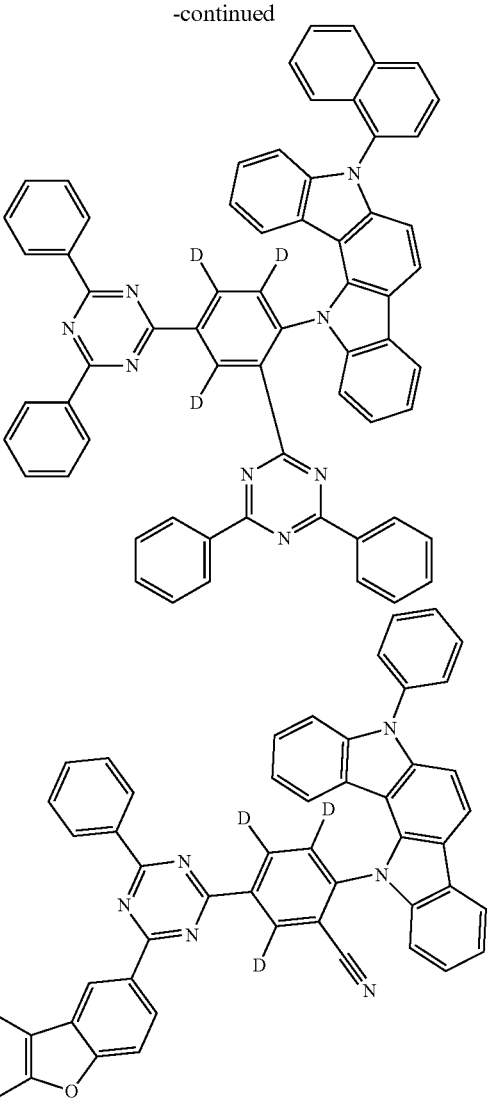
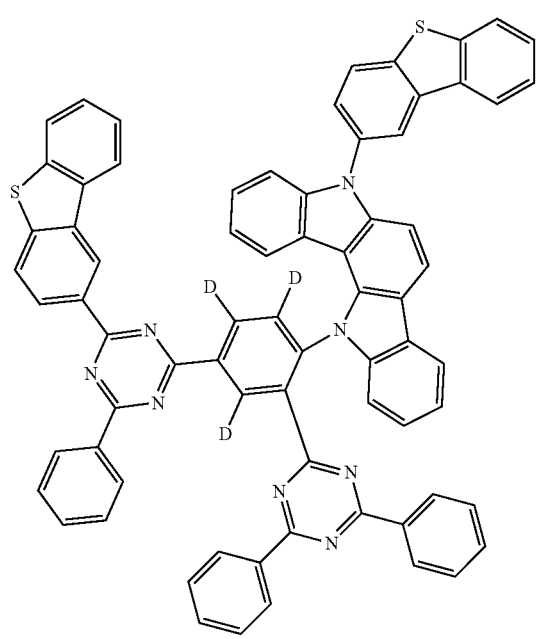

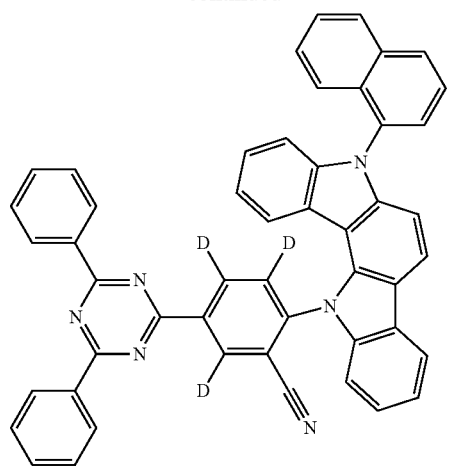
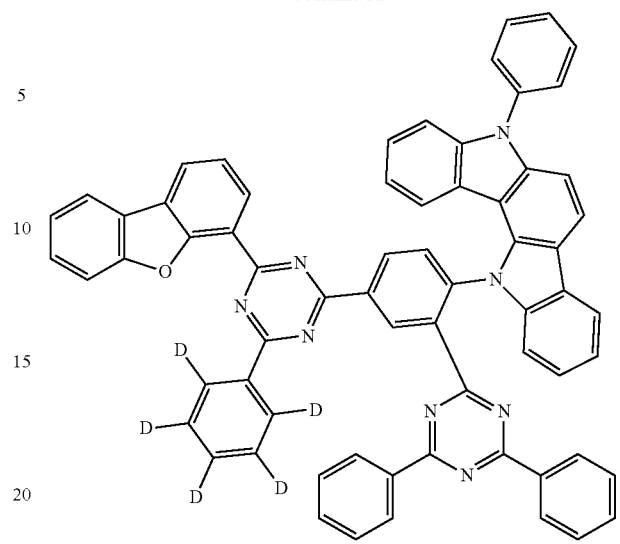
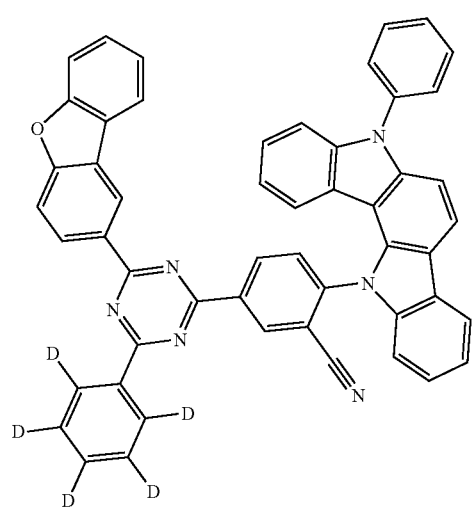
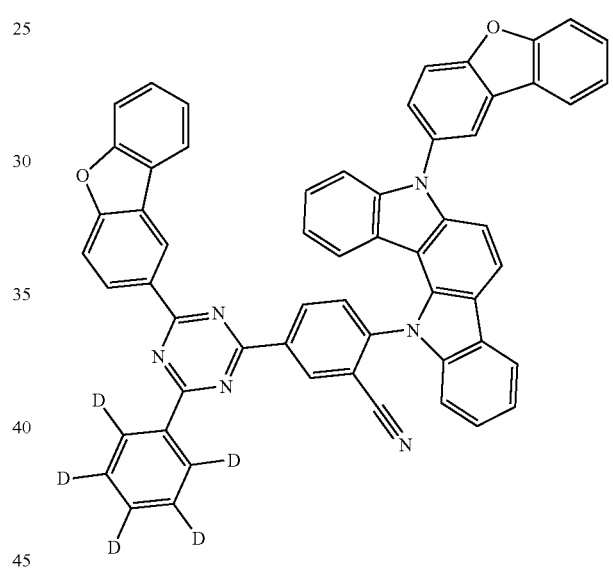
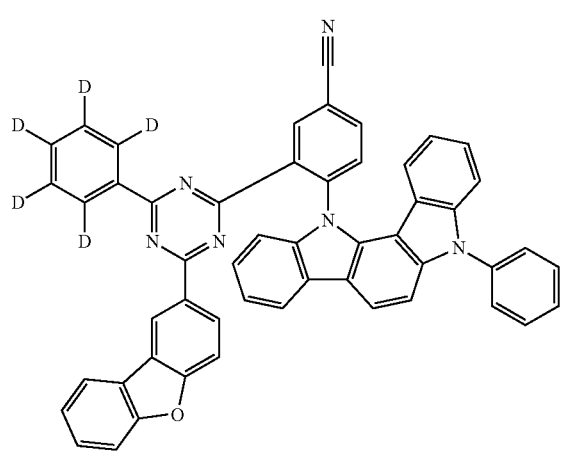
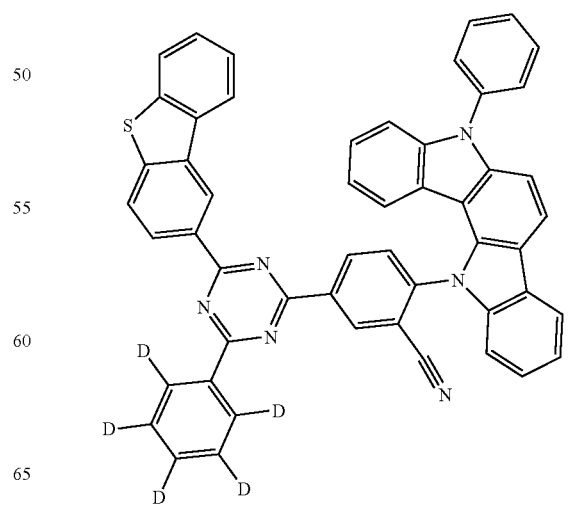

197
-continued
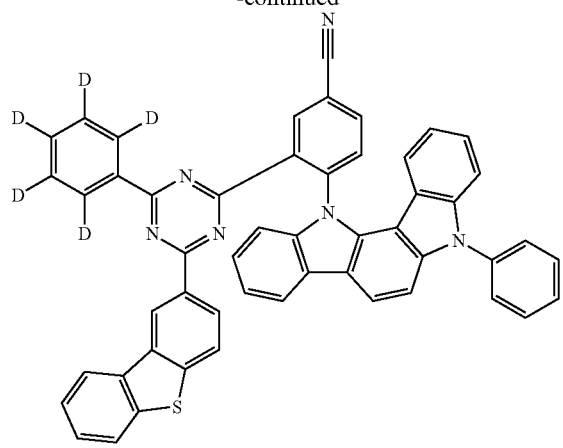
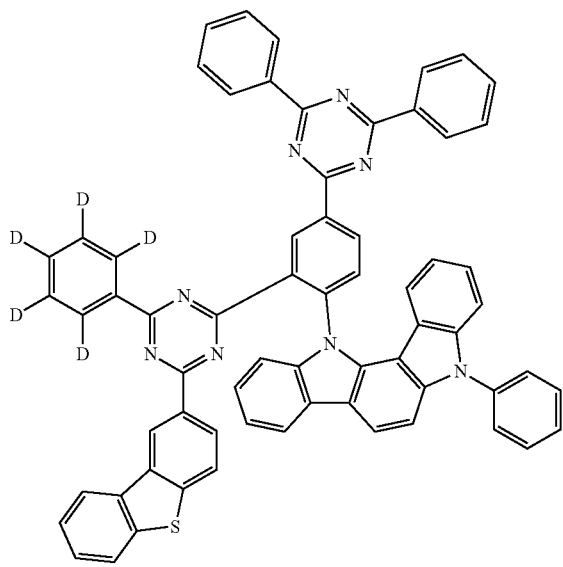
198
-continued
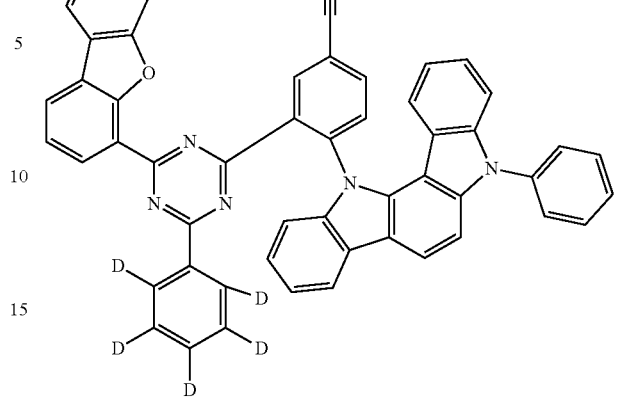
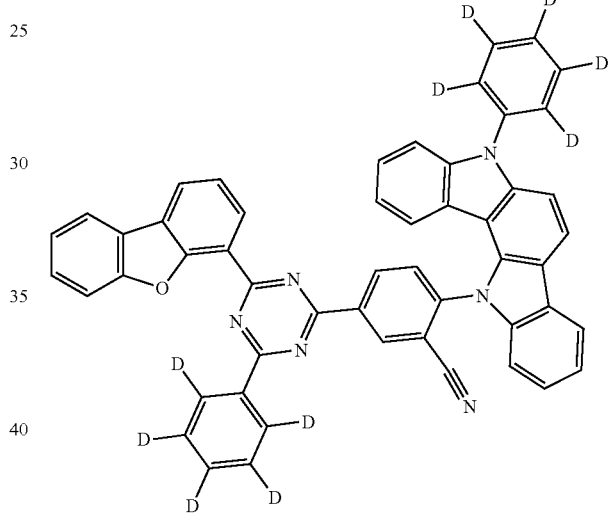
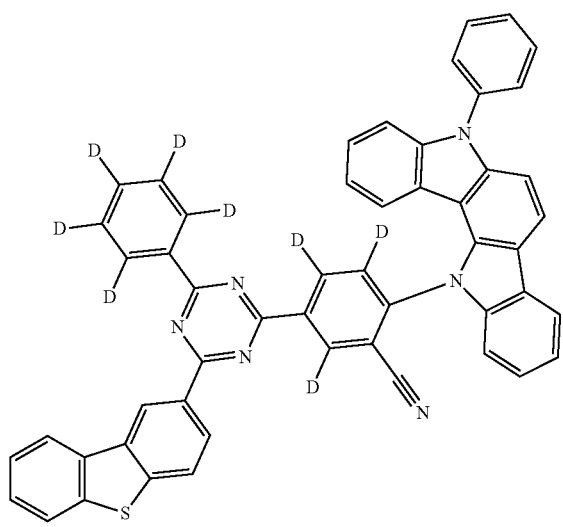
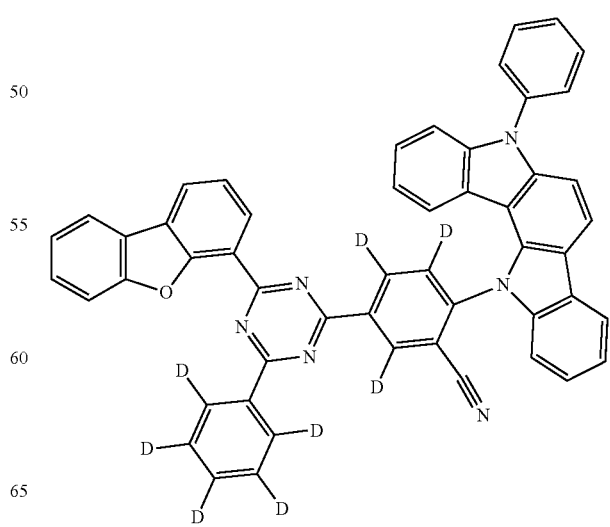

199
-continued
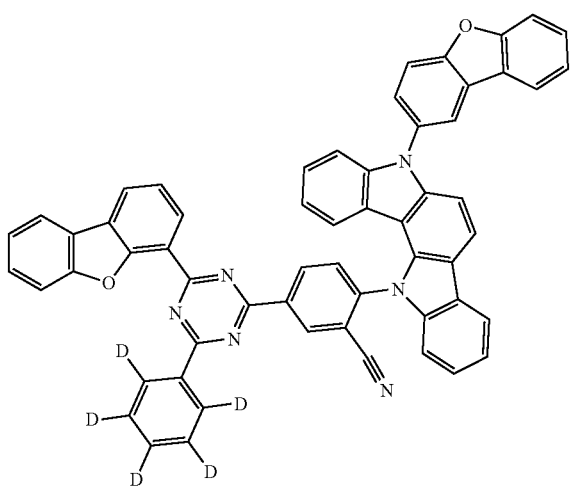
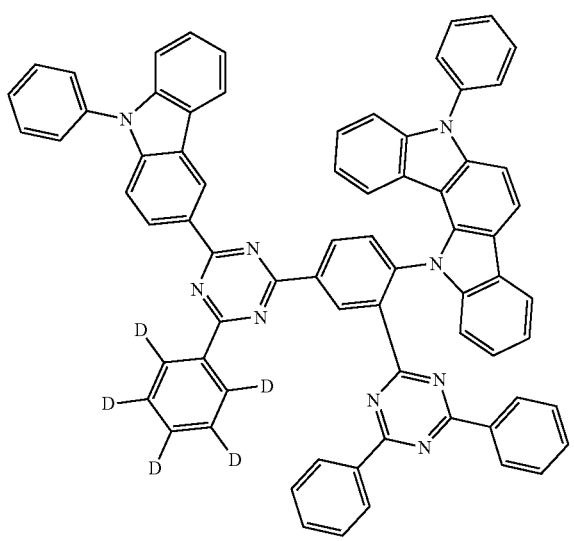
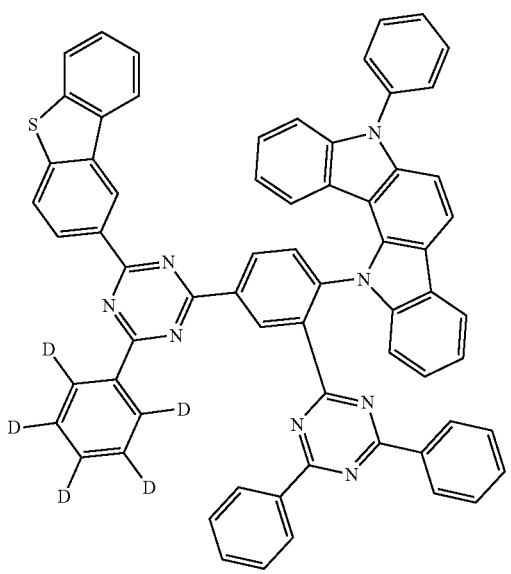
200
-continued
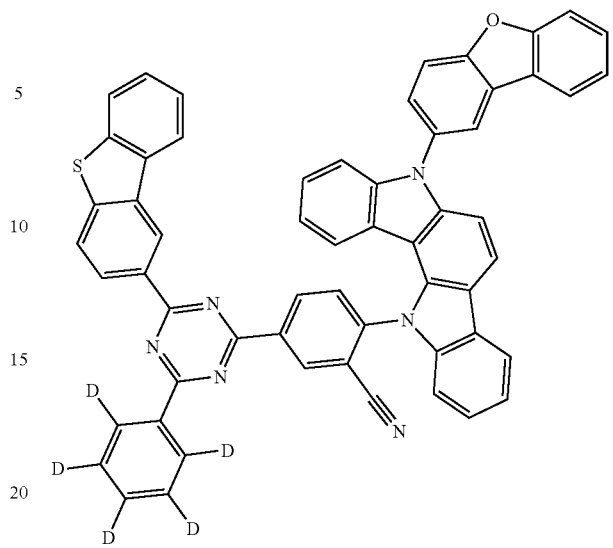
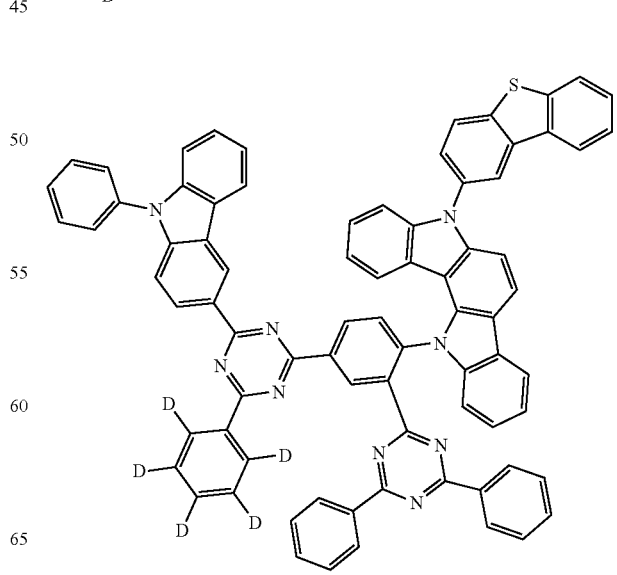

201
-continued
202
-continued
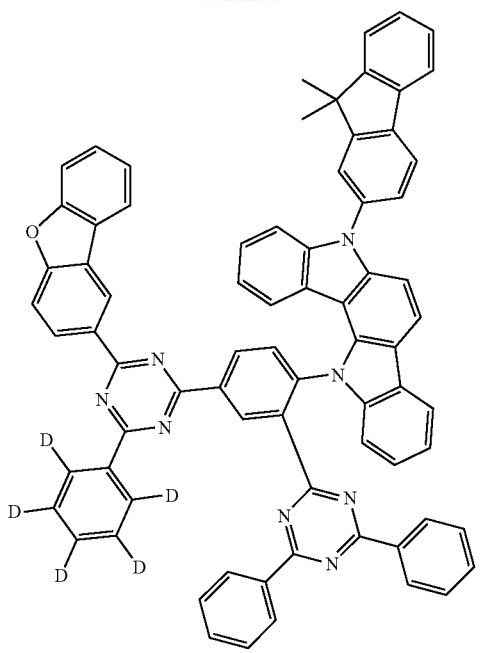
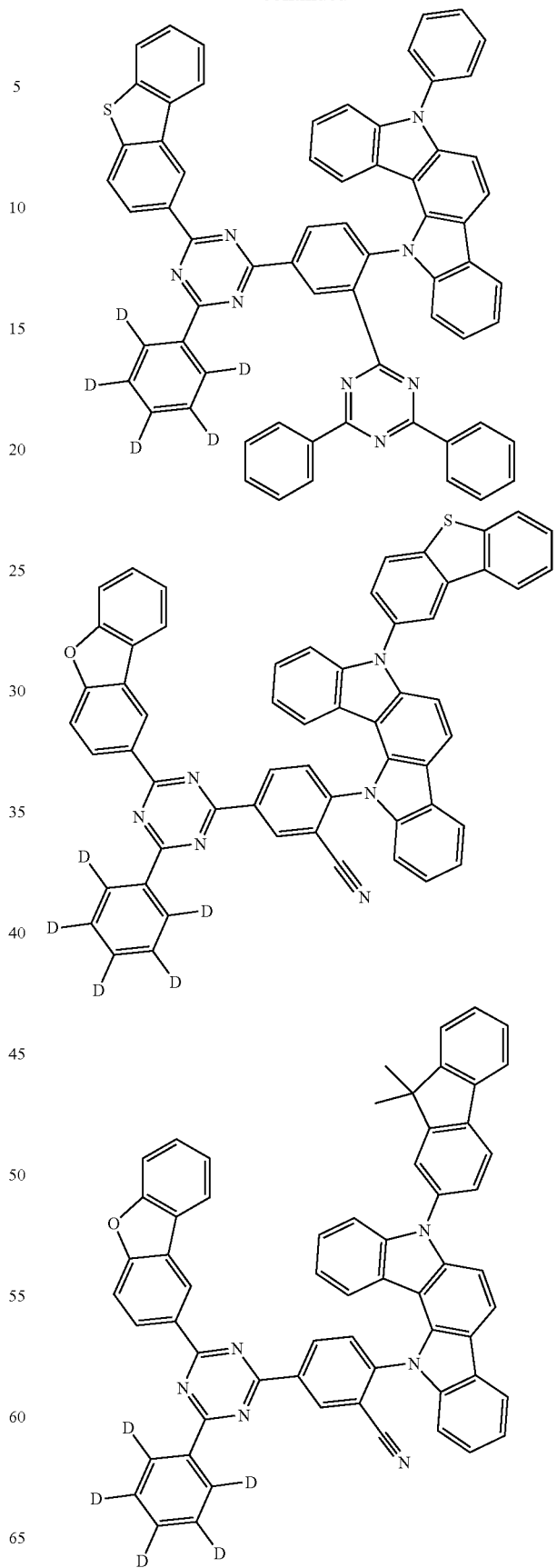

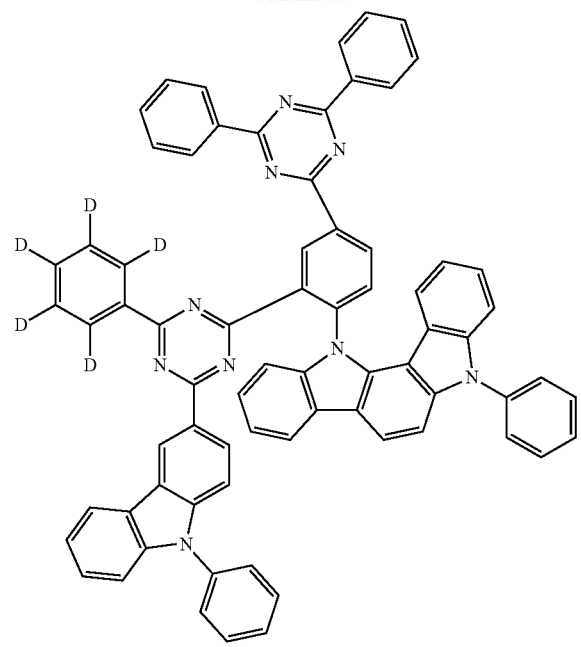
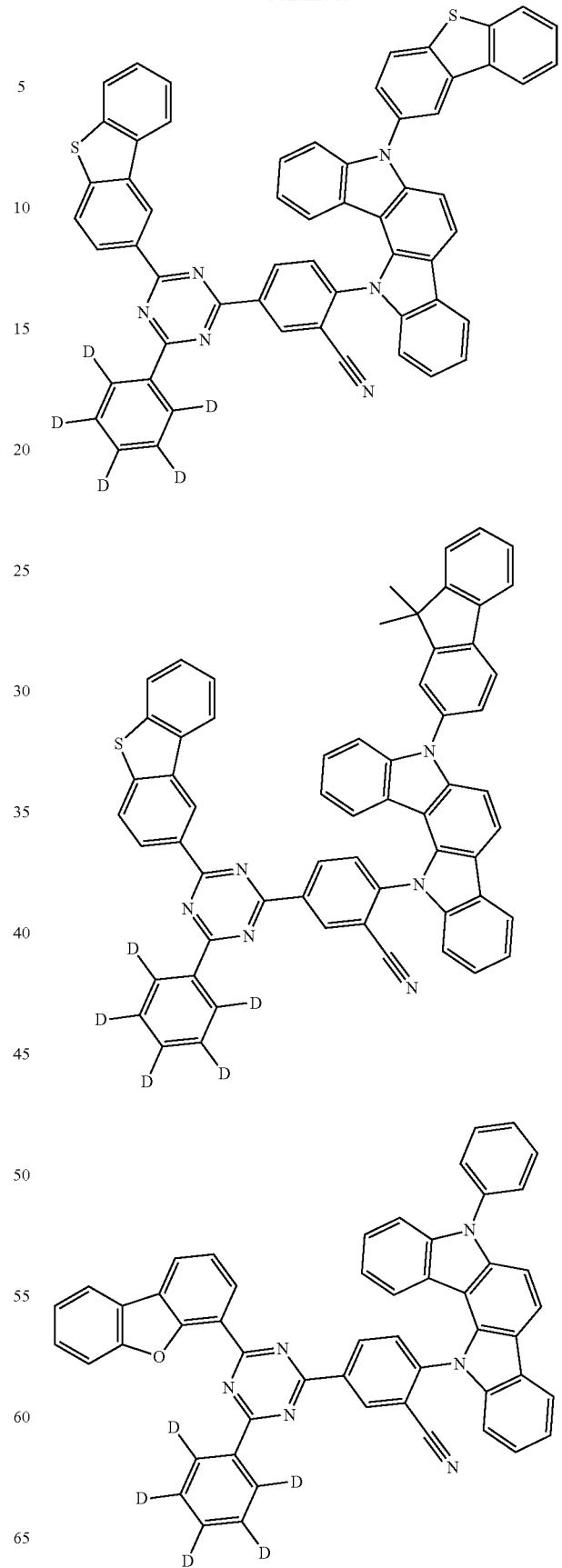

205
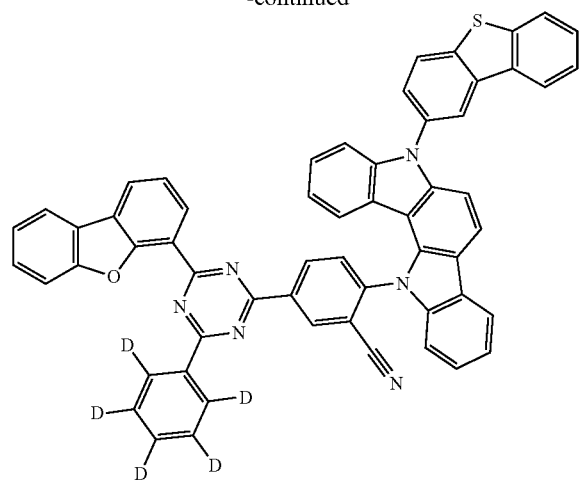
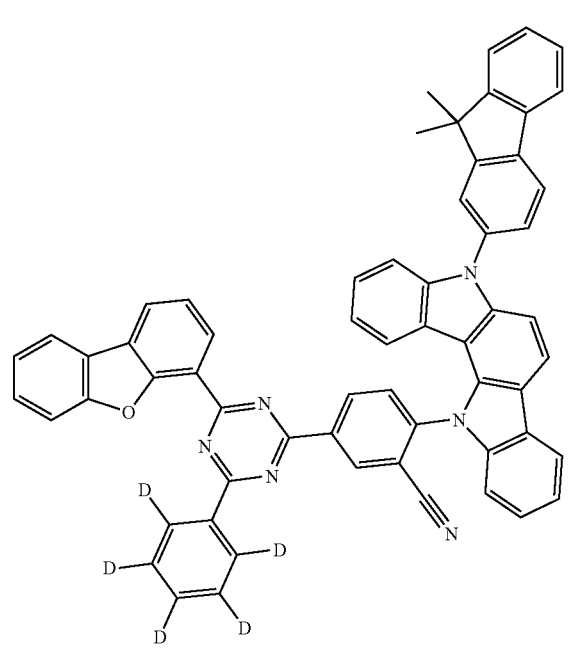
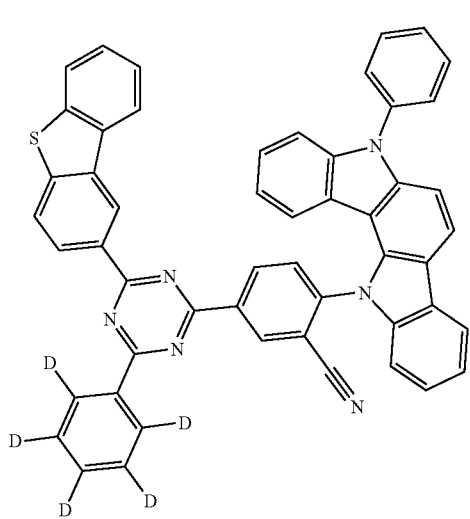
206
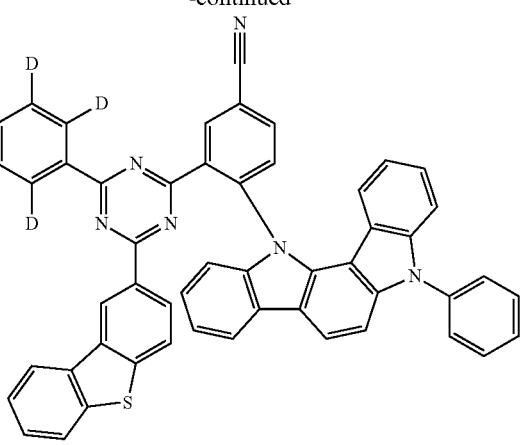
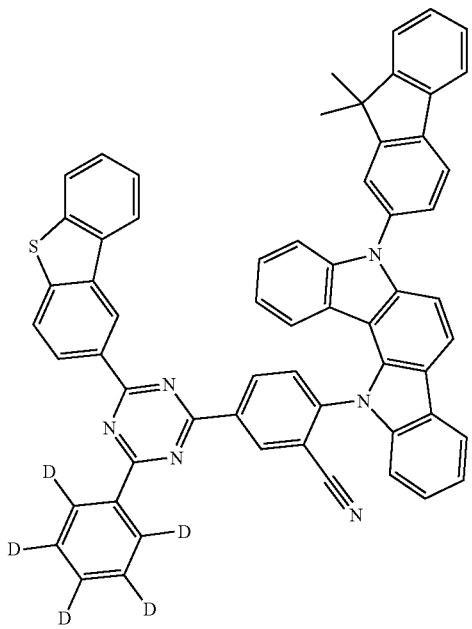
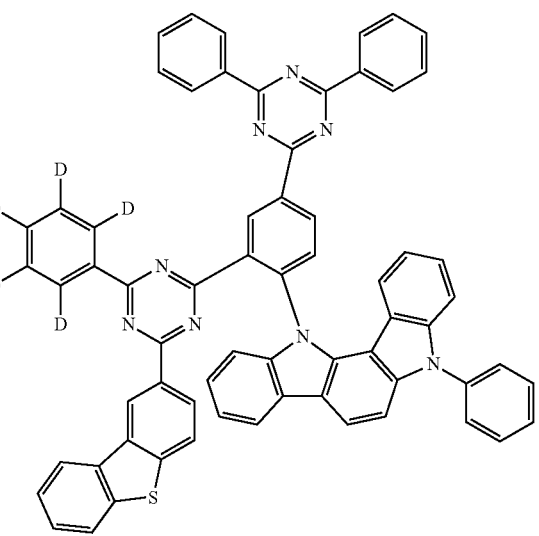

207
-continued
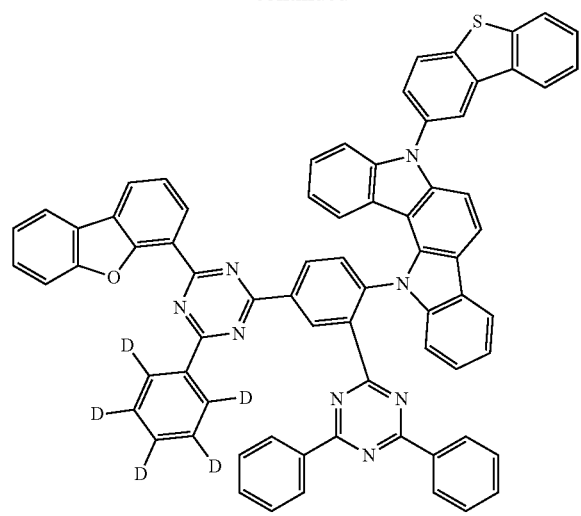
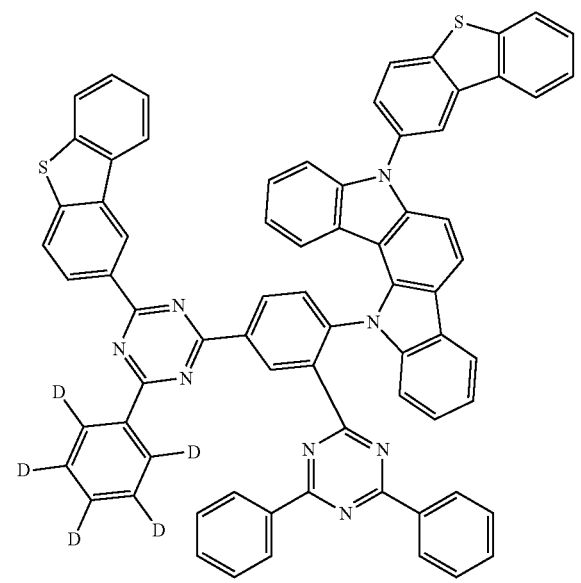
208
-continued
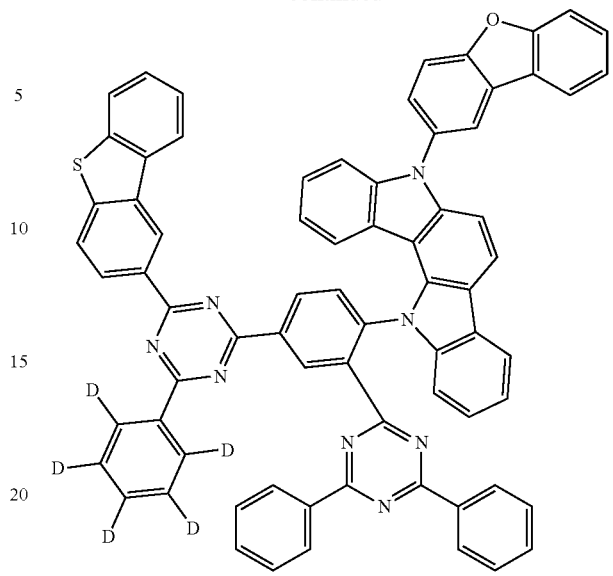
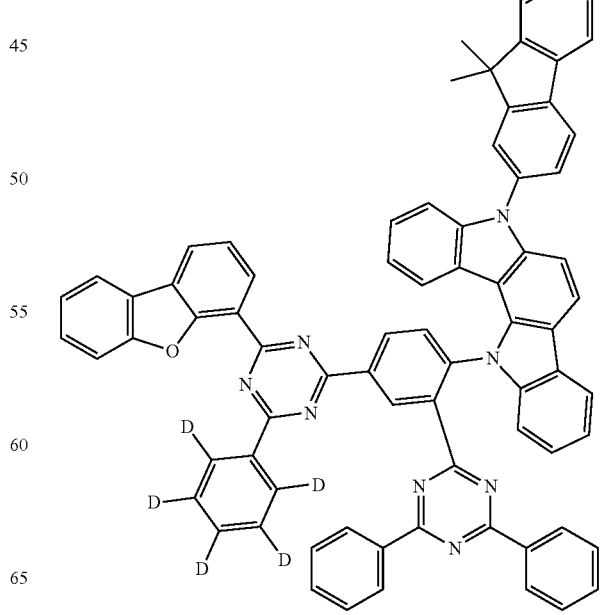

209
-continued
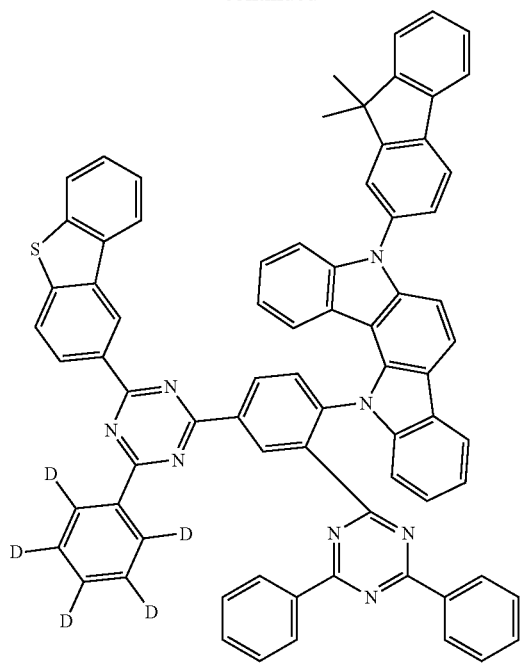
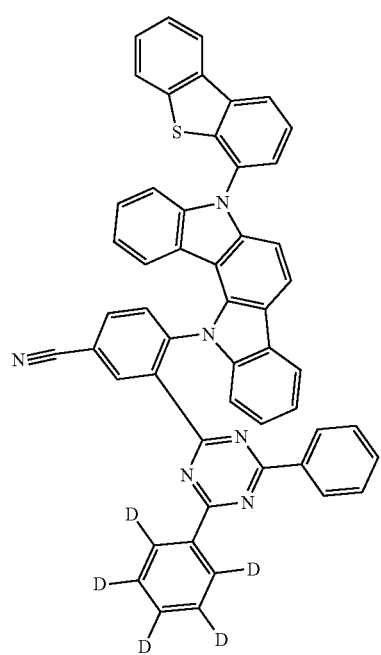
210
-continued
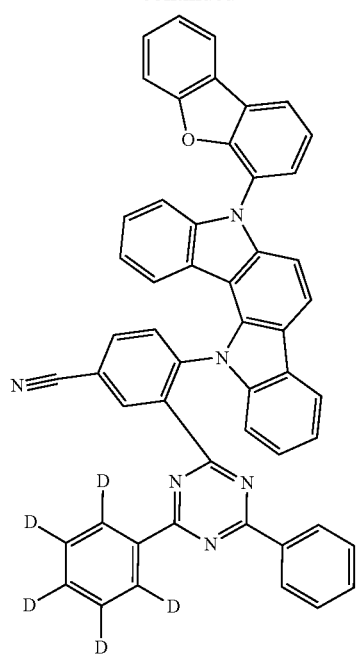
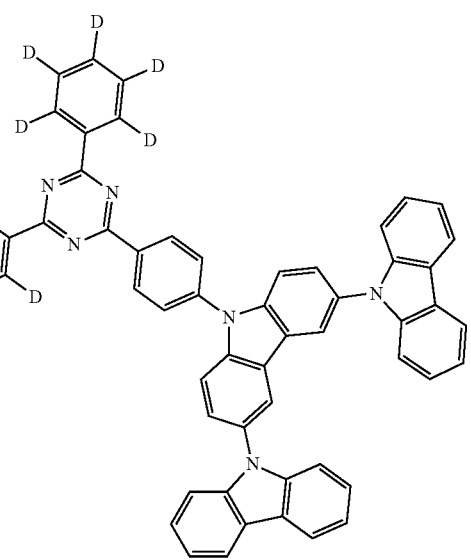

211
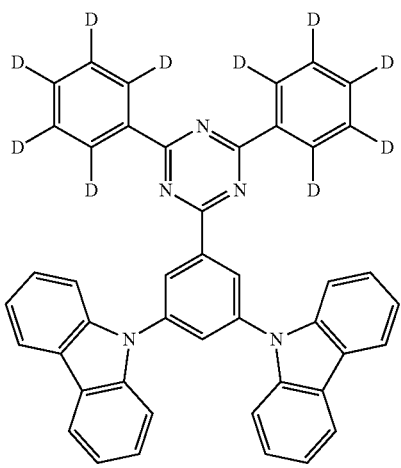
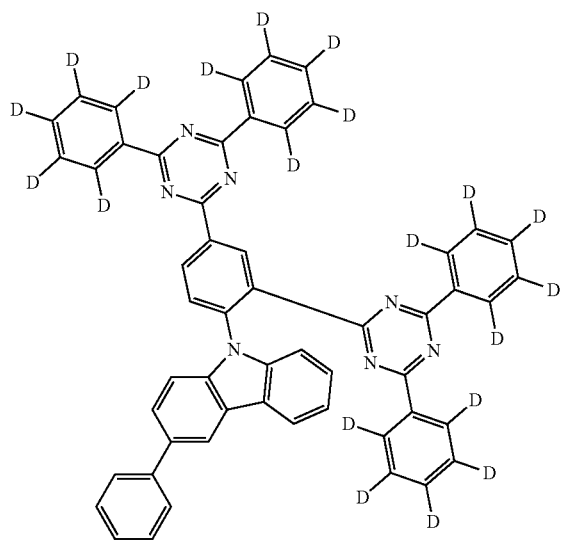
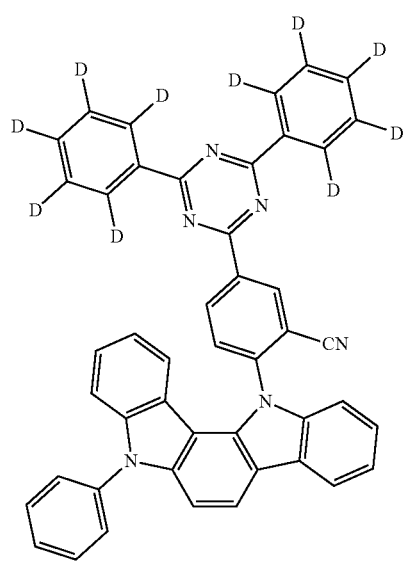
212
-continued
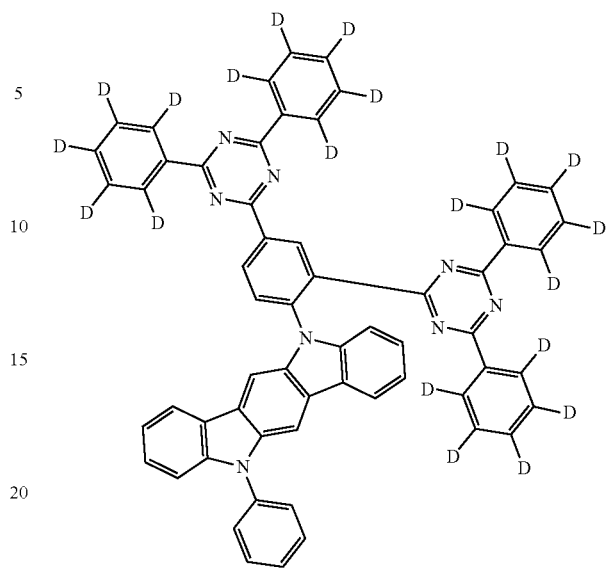
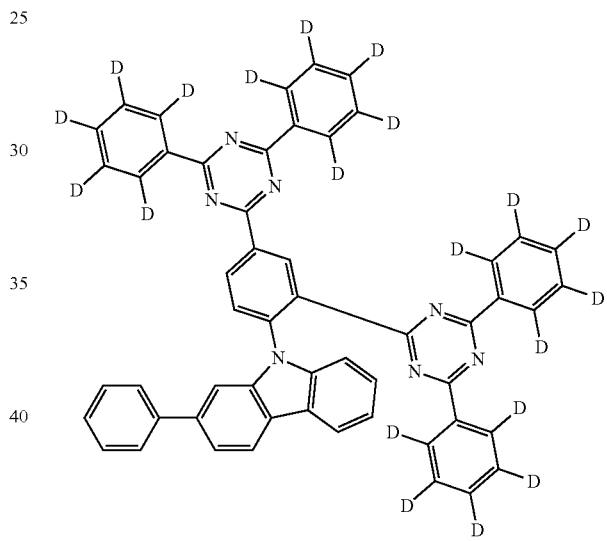

-continued
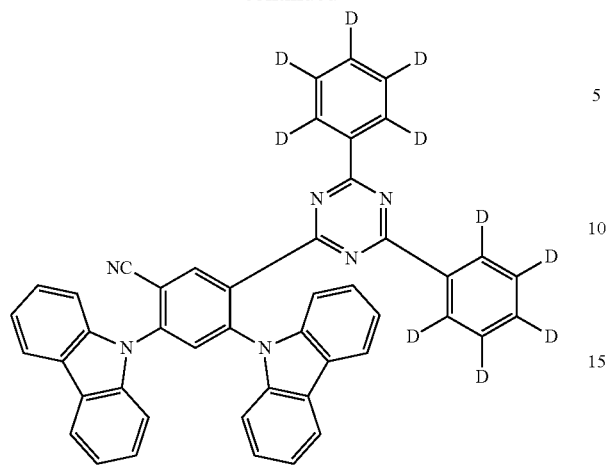
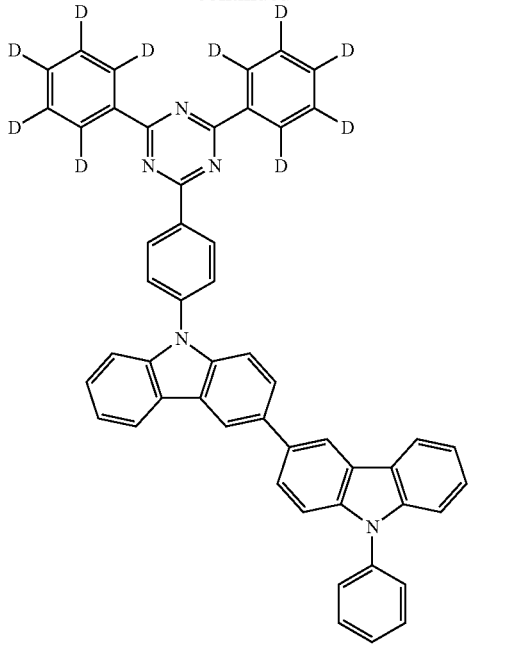
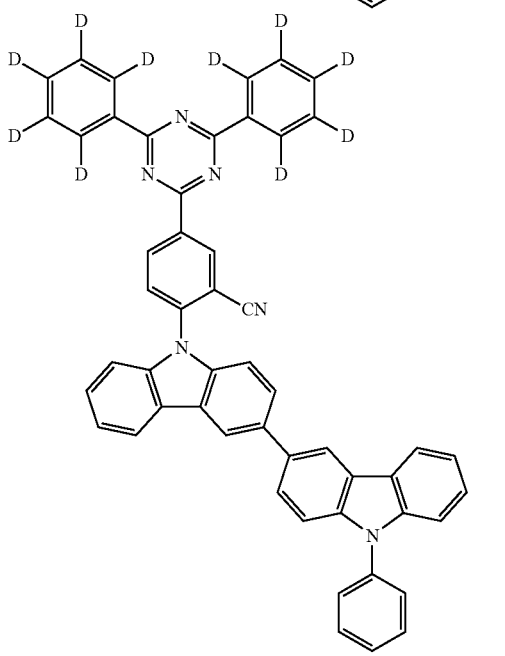
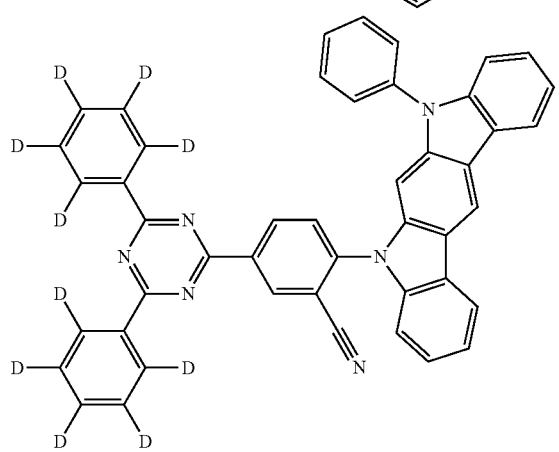

215
-continued
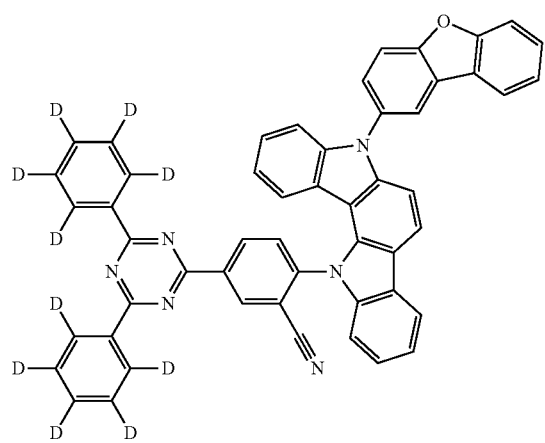
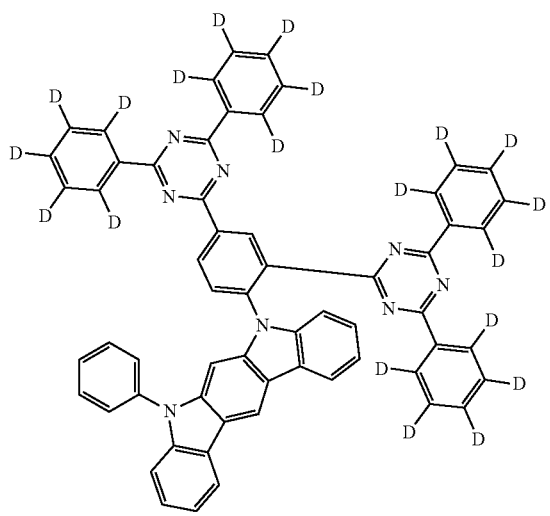
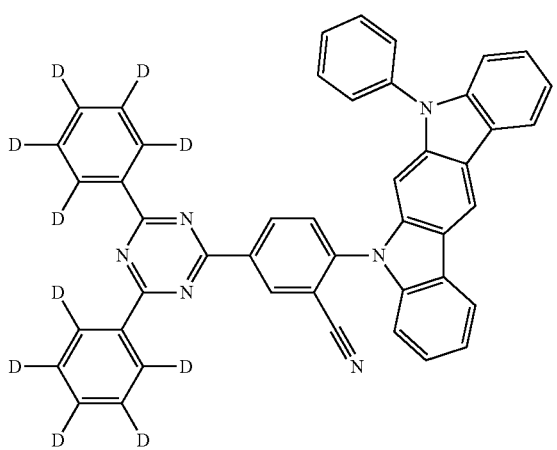
216
-continued
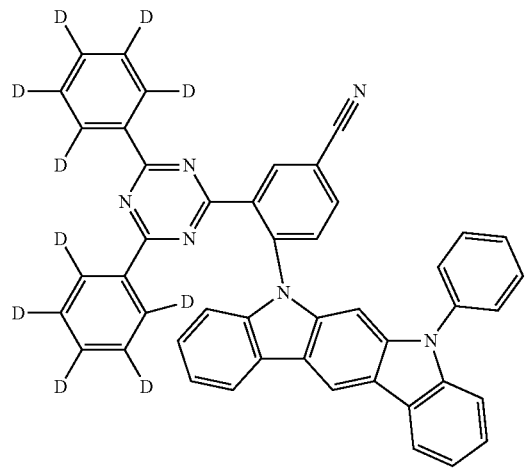
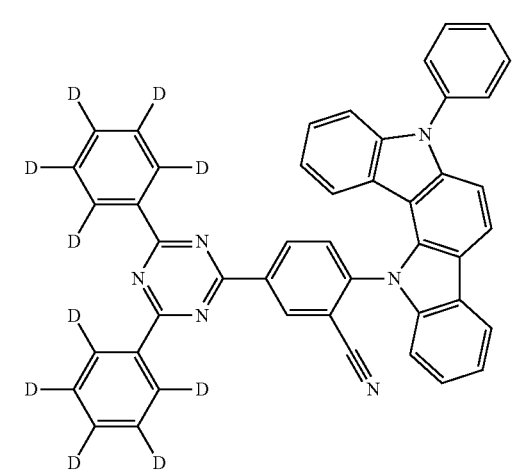
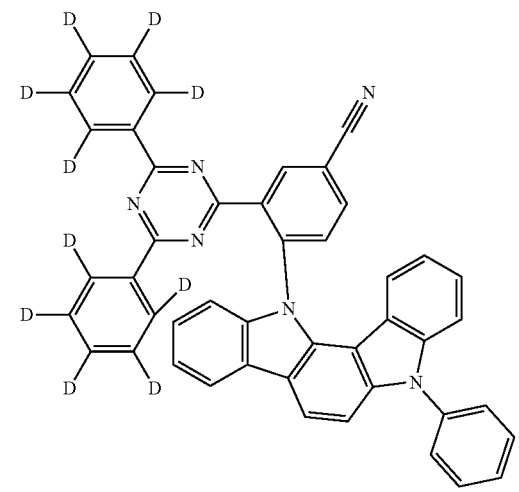

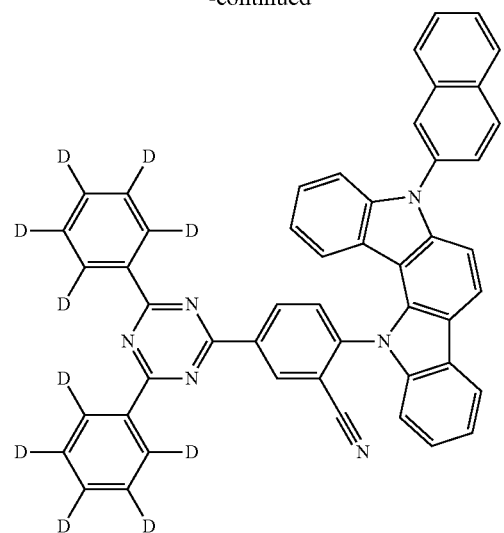
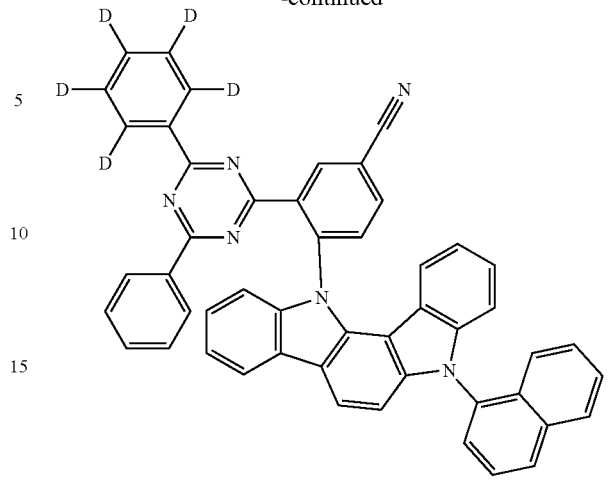
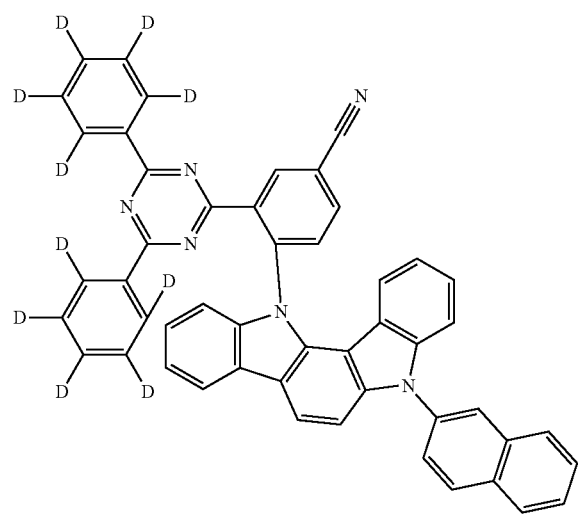
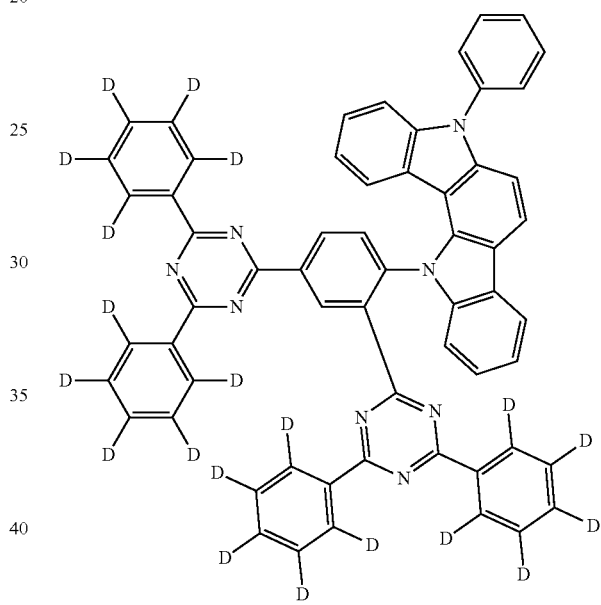
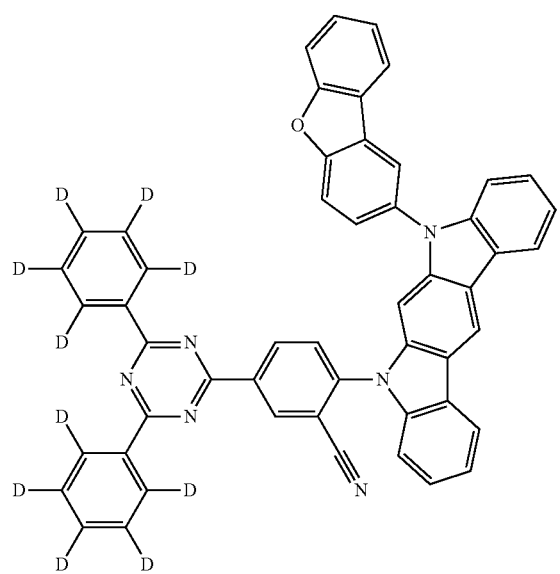
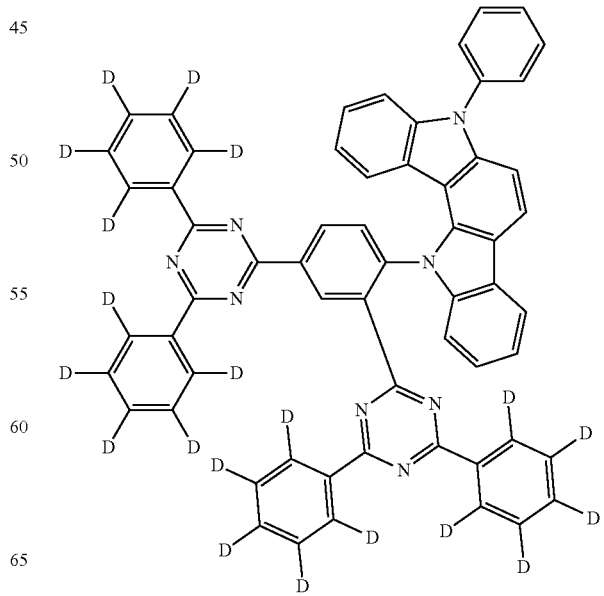

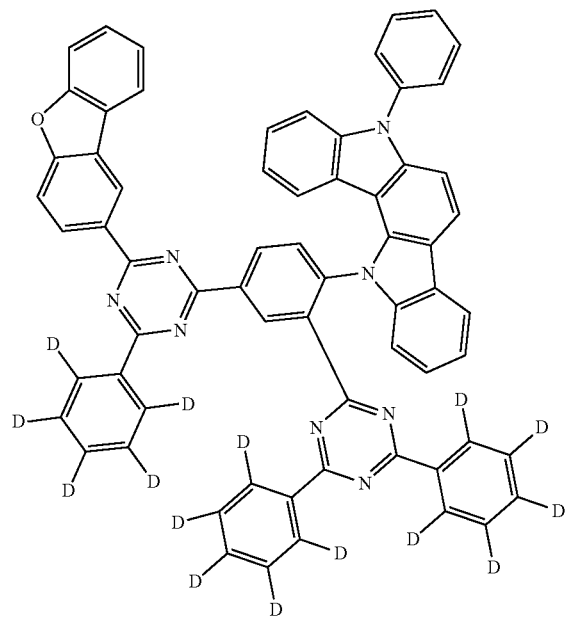
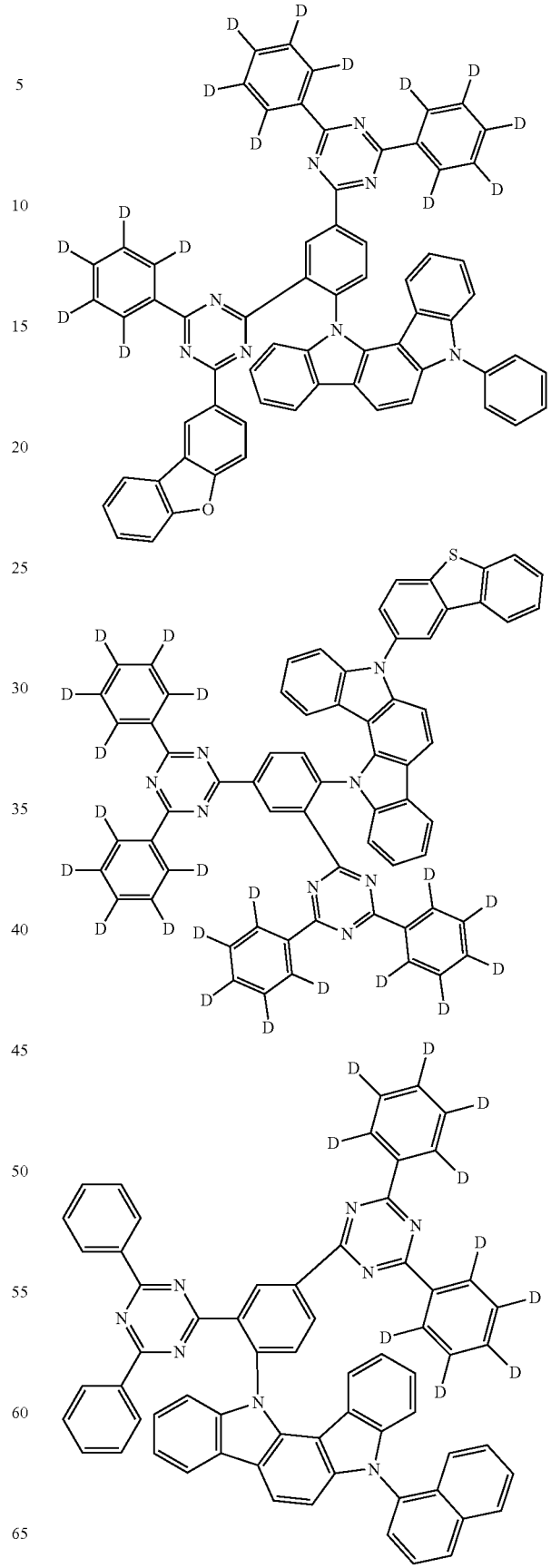

221
-continued
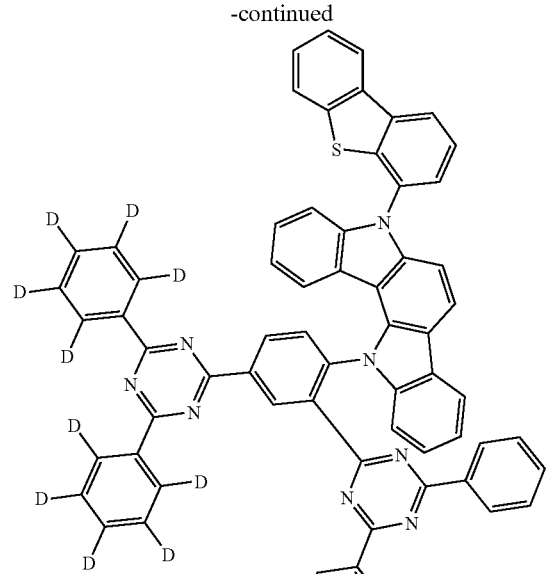
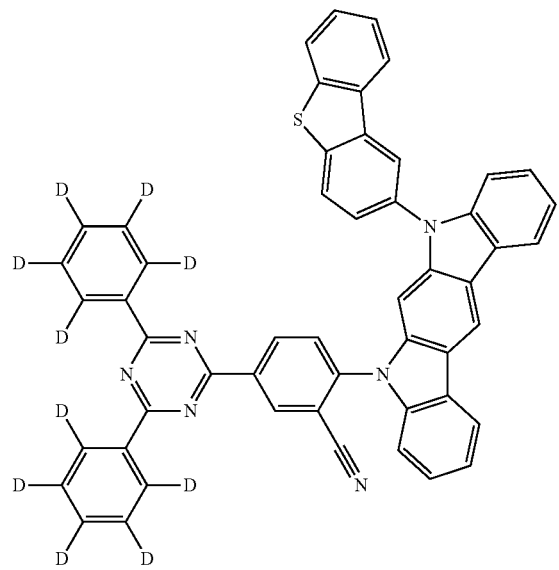
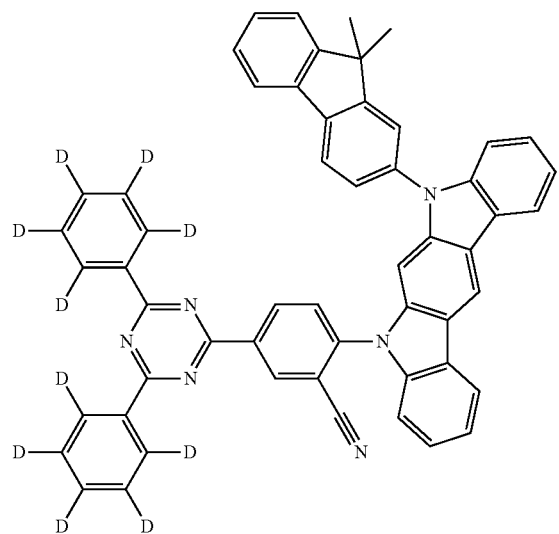
222
-continued
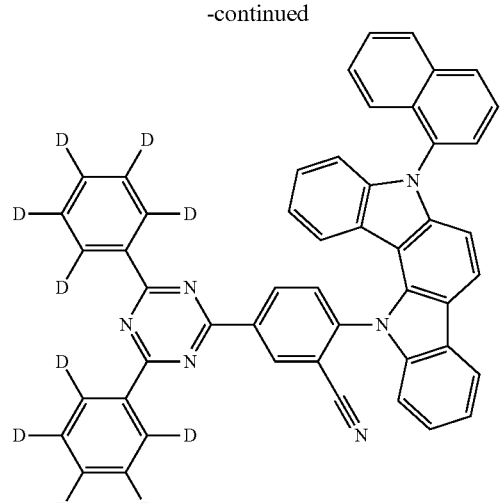
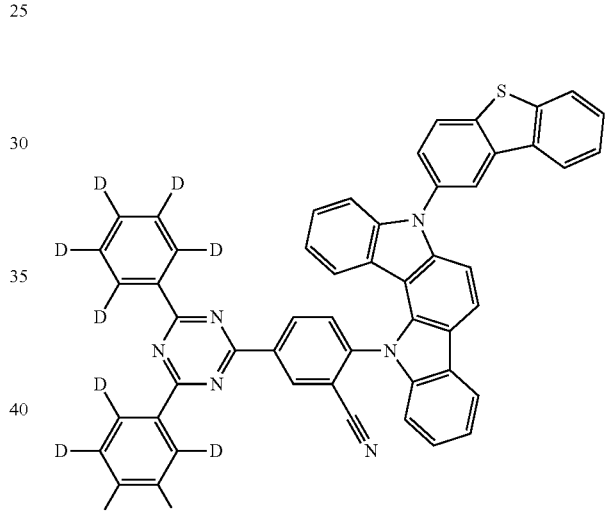
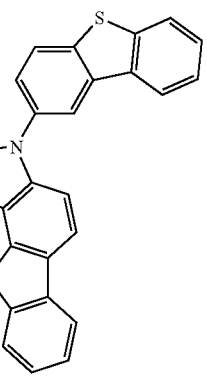

223
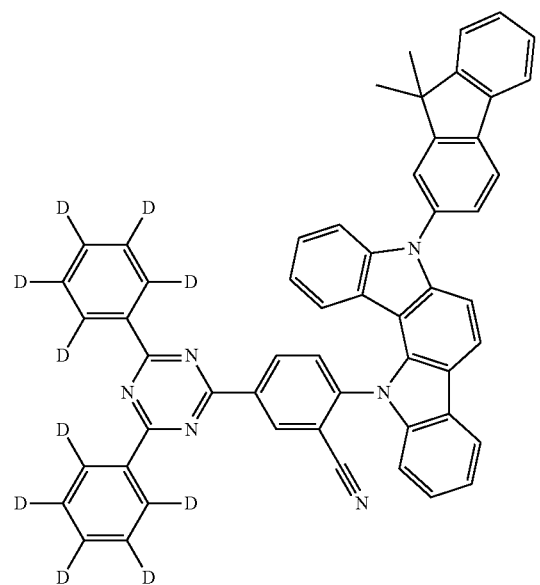
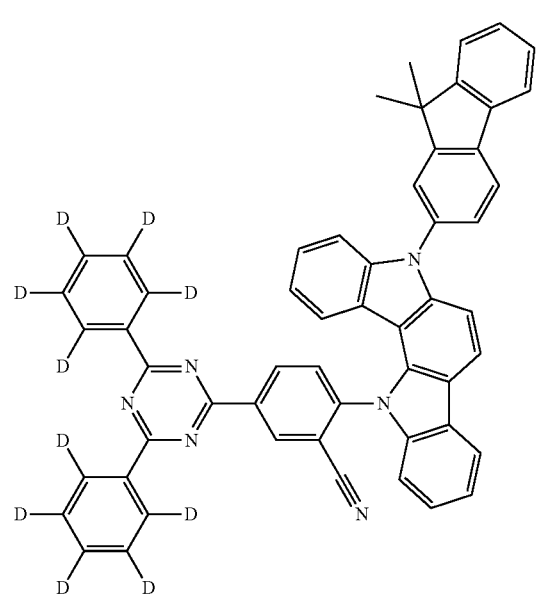
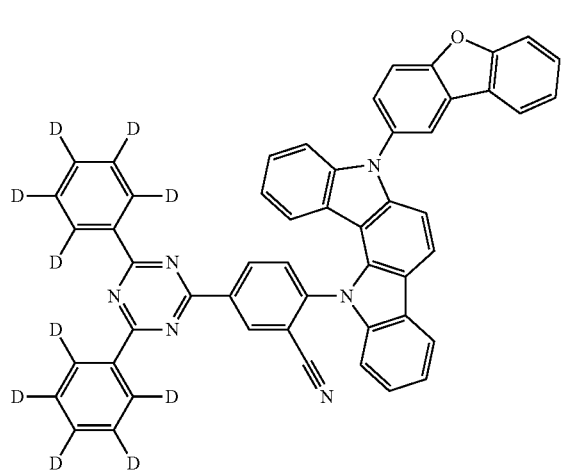
224
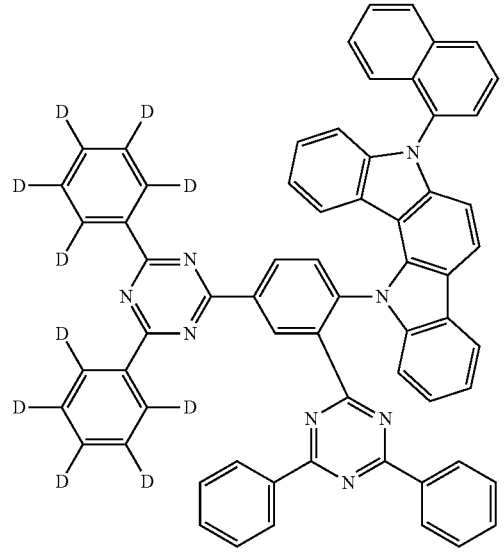
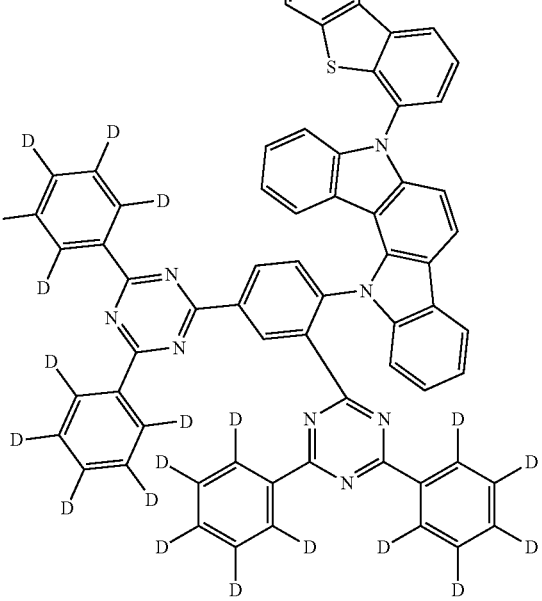

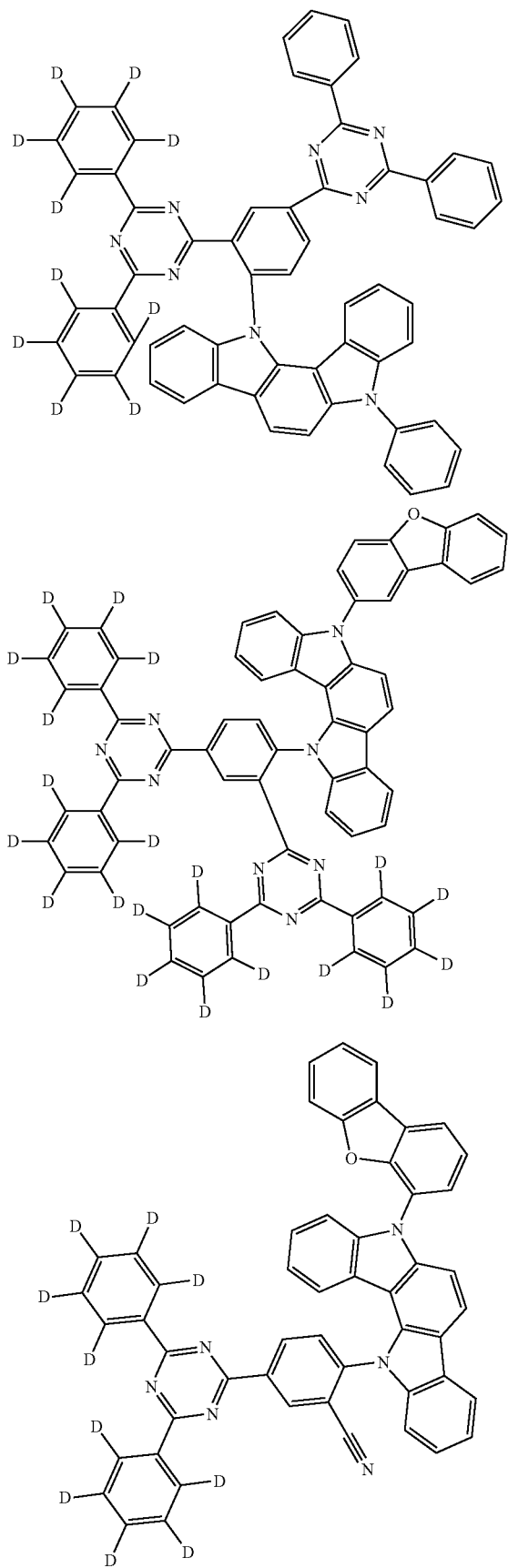
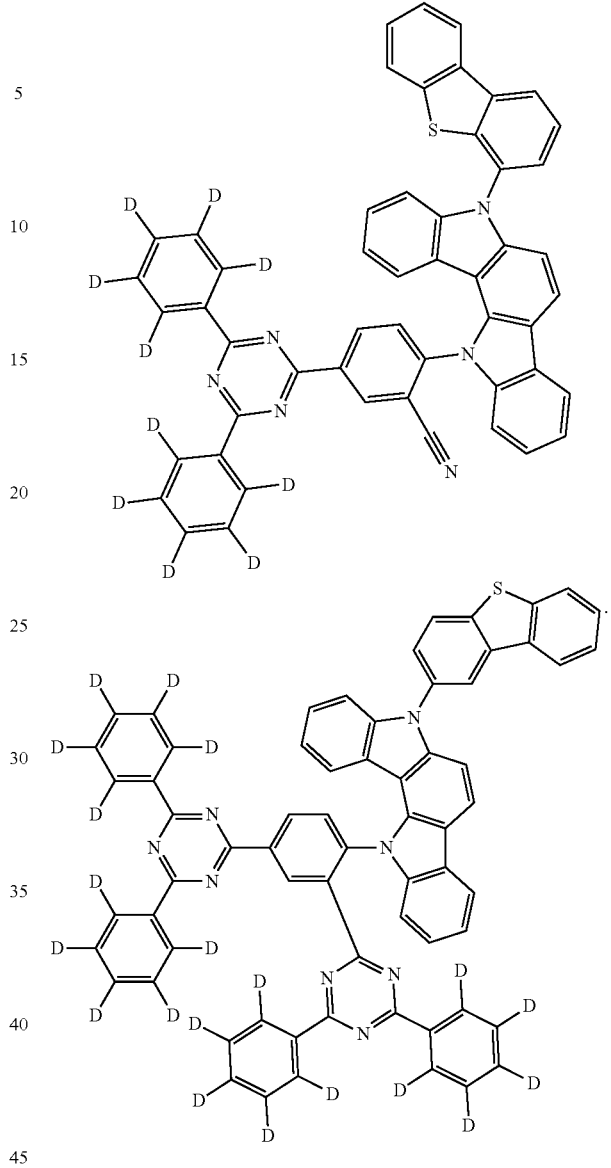

7. The compound of claim 1, wherein a difference ($\Delta ST_D$) between the singlet energy level ($S1_D$) and the triplet energy level ($T1_D$) of the compound represented by Formula 1 is 0 eV to 0.3 eV.

8. An organic light emitting device comprising:
   a first electrode;
   a second electrode provided to face the first electrode; and
   a light emitting layer provided between the first electrode and the second electrode,
   wherein the light emitting layer comprises the compound according to claim 1.

9. The organic light emitting device of claim 8, wherein the light emitting layer further comprises a host, and the triplet energy level ($T1_H$) of the host is higher than the triplet energy level ($T1_D$) of the compound represented by Formula 1.

10. The organic light emitting device of claim 8, wherein the light emitting layer further comprises a host, and the singlet energy level ($S1_H$) of the host is higher than the singlet energy level ($S1_D$) of the compound represented by Formula 1.

\* \* \* \* \*